(12) United States Patent
Vikkula

(10) Patent No.: US 7,700,748 B2
(45) Date of Patent: Apr. 20, 2010

(54) VMGLOM GENE AND ITS MUTATIONS CAUSING DISORDERS WITH A VASCULAR COMPONENT

(75) Inventor: Miikka Vikkula, Kraainem (BE)

(73) Assignee: Universite Catholique de Louvain, Louvain-la-Neuve (BE)

( * ) Notice: Subject to any disclaimer, the term of this patent is extended or adjusted under 35 U.S.C. 154(b) by 936 days.

(21) Appl. No.: 10/204,254

(22) PCT Filed: Feb. 16, 2001

(86) PCT No.: PCT/EP01/01760

§ 371 (c)(1),
(2), (4) Date: Aug. 27, 2002

(87) PCT Pub. No.: WO01/60856

PCT Pub. Date: Aug. 23, 2001

(65) Prior Publication Data

US 2003/0176649 A1     Sep. 18, 2003

Related U.S. Application Data

(60) Provisional application No. 60/195,577, filed on Apr. 6, 2000.

(30) Foreign Application Priority Data

Feb. 16, 2000  (EP)  .................................. 00870022
Dec. 22, 2000  (EP)  .................................. 00870320

(51) Int. Cl.
*C07H 21/02*   (2006.01)
*C12Q 1/68*    (2006.01)
*C07K 14/00*   (2006.01)

(52) U.S. Cl. ........................... 536/23.1; 435/6; 530/350
(58) Field of Classification Search ...................... None
See application file for complete search history.

(56) References Cited

OTHER PUBLICATIONS

Meyer et al. Review, Cell Mol Biol, 2001, 47: 1277-1294.*
Fisher et al., Review, Cell Mol Biol, 2001, 47: 1269-1275.*
Gardlik et al., Review, Med Sci Monit, 2005, 11: RA110-121).*
Chambraud et5 al., J. Biol. Chem., 1996, 271: 32923-32929).*
Tille et al., Arterioscl. Thromb. Vasc. Biol., 2004, 24: 1578-1590.*
Tire I., proceeding of the Nutrition Society, 2002, 61: 457-463.*
Gault et al., Neurosurgery, 2004, 55: 1-17.*
Huang et al., Genomics, 1995, 30: 293-298.*
GENBANK accession No. R58066.*
Sequence alignment.*
Boon. L M . et al (1999) *A Gene for Inherited Cutaneous Venous Anomalies ("Glomangiomas") Localizes to Chromosome 1p21-22.* Am. J. Hum Genet 65 125-133.
Chambraud, B.. et al. (1996) FAP48. A New protein That Forms Specific Complexes with Both Immunophilins FKBP59 and FKBP12 J Bio Chem 271(51). 32923-32929.

* cited by examiner

*Primary Examiner*—Ileana Popa
(74) *Attorney, Agent, or Firm*—Knobbe, Martens, Olson & Bear, LLP

(57) ABSTRACT

The present invention relates to genes responsible for disorders with a vascular component, the identification of mutations in said genes and the detection of their sequences as well as methods for detection and treatment for disorders with a vascular component. This invention further relates to proteins encoded by said genes and their applications.

6 Claims, 84 Drawing Sheets

Figure 1:
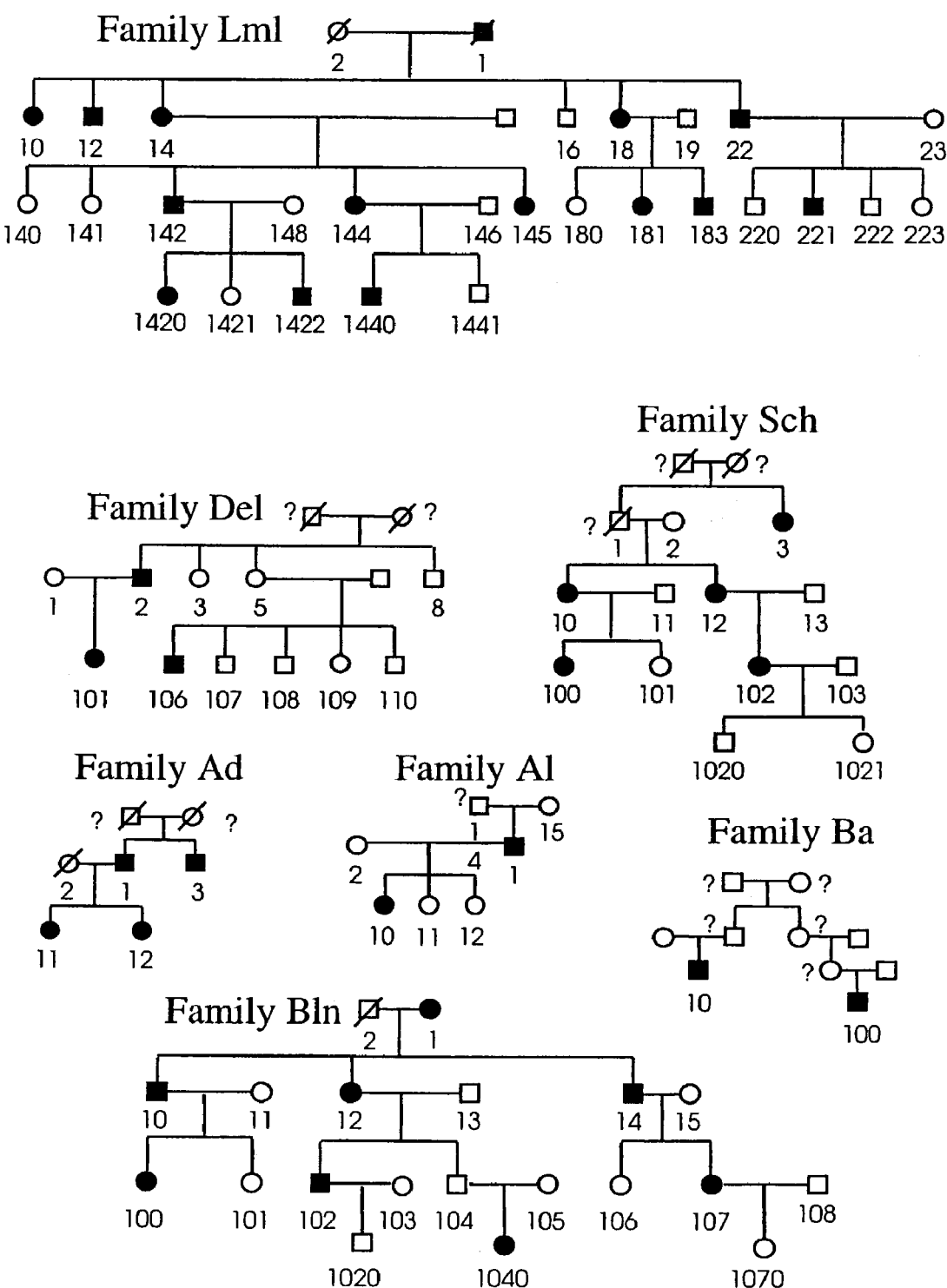

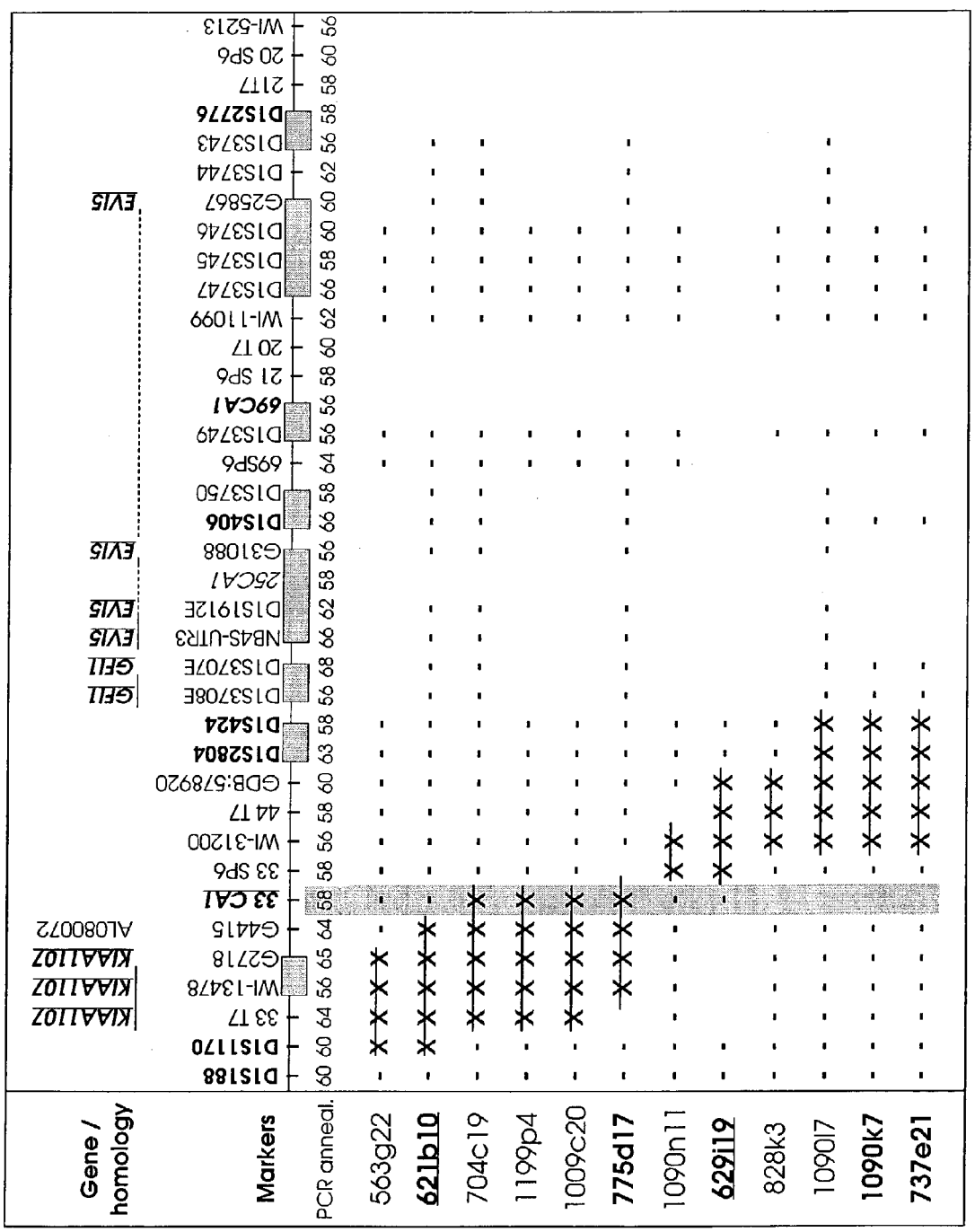
FIGURE 3 (part 1)

FIGURE 3 (part 2)

FIGURE 3 (part 3)

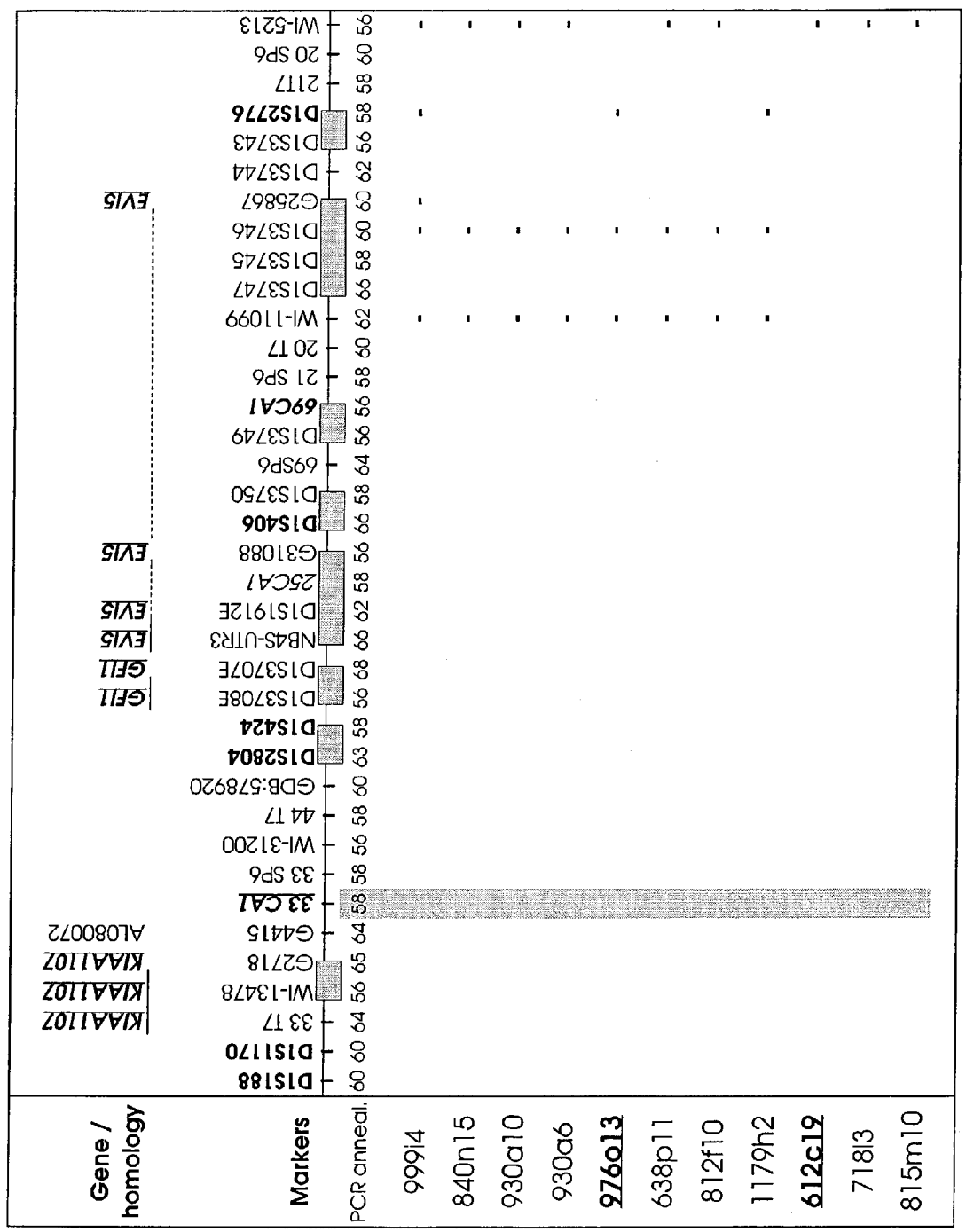
FIGURE 3 (part 4)

FIGURE 3 (part 5)

| Gene / homology | Markers | PCR anneal. | 563g22 | 621b10 | 704c19 | 1199p4 | 1009c20 | 775d17 | 1090n11 | 629i19 | 828k3 | 1090i7 | 1090k7 | 737e21 |
|---|---|---|---|---|---|---|---|---|---|---|---|---|---|---|
| | 50CA1 | 64 | | | | | | | | | | | | |
| RPL5 | G35847 | 88 | | | | | | | | | | | | |
| RPL5 | WI-1423 | 62 | | | | | | | | | | | | |
| RPL5 | D1S187OE | 82 | | | | | | · | | · | | | | |
| | D1S2868 | 56 | · | · | · | · | · | · | · | · | · | · | | |
| | 75 SP6 | 65 | | | | | | | | | | | | |
| | 70 17 | 63 | | | | | | | | | | | | |
| | 47 SP6 | 64 | | | | | | | | | | | | · |
| | 75CA2 | 58 | | | | | | | | | | | | |
| | 17/55 17 | 64 | | | | | | | | | | | | |
| | 16 17 | 64 | | | | | | | | | | | | |
| | 75CA1 | 64 | | | | | | | | | | | | |
| | 15 17 | 58 | | | | | | | | | | | | |
| | 65 17 | 54 | | | | | | | | | | | | |
| | 52/53 17 | 60 | | | | | | | | | | | | |
| | D1S2849 | 64 | | | | | | | | | | | | |
| | 57 17 | 64 | | | | | | | | | | | | |
| | 54 17 | 58 | | | | | | | | | | | | |
| | G3468 | 60 | | | | | | | | | | | | |
| | G13221 | 56 | | | | | | | | | | | | |
| | 70 SP6 | 62 | | | | | | | | | | | | |
| | 56CA3 | 62 | | | | | | | | | | | | |
| AF086050 | 56CA2 | 60 | | | | | | | | | | | | |
| | D1S1887E | 56 | | | | | | | | | | | | |
| | G10303 | 56 | | | | | | | | | | | | |
| AL080084.1 | GDB:191074 | 56 | | | | | | | | | | | | |
| AL080084.1 | G29243 | 56 | | | | | | | | | | | | |
| AL080084.1 | WI-20561 | 56 | | | | | | | | | | | | |
| AF151858.1 | G35002 | 58 | | | | | | | | | | | | |
| | 53 SP6 | 58 | | | | | | | | | | | | |
| | 56CA1 | 62 | | | | | | | | | | | | |
| | 54 SP6 | 58 | | | | | | | | | | | | |
| | D1S2779 | 56 | | | | | | | | | | | | |
| | G32495FS | 56 | | | | | | | | | | | | |

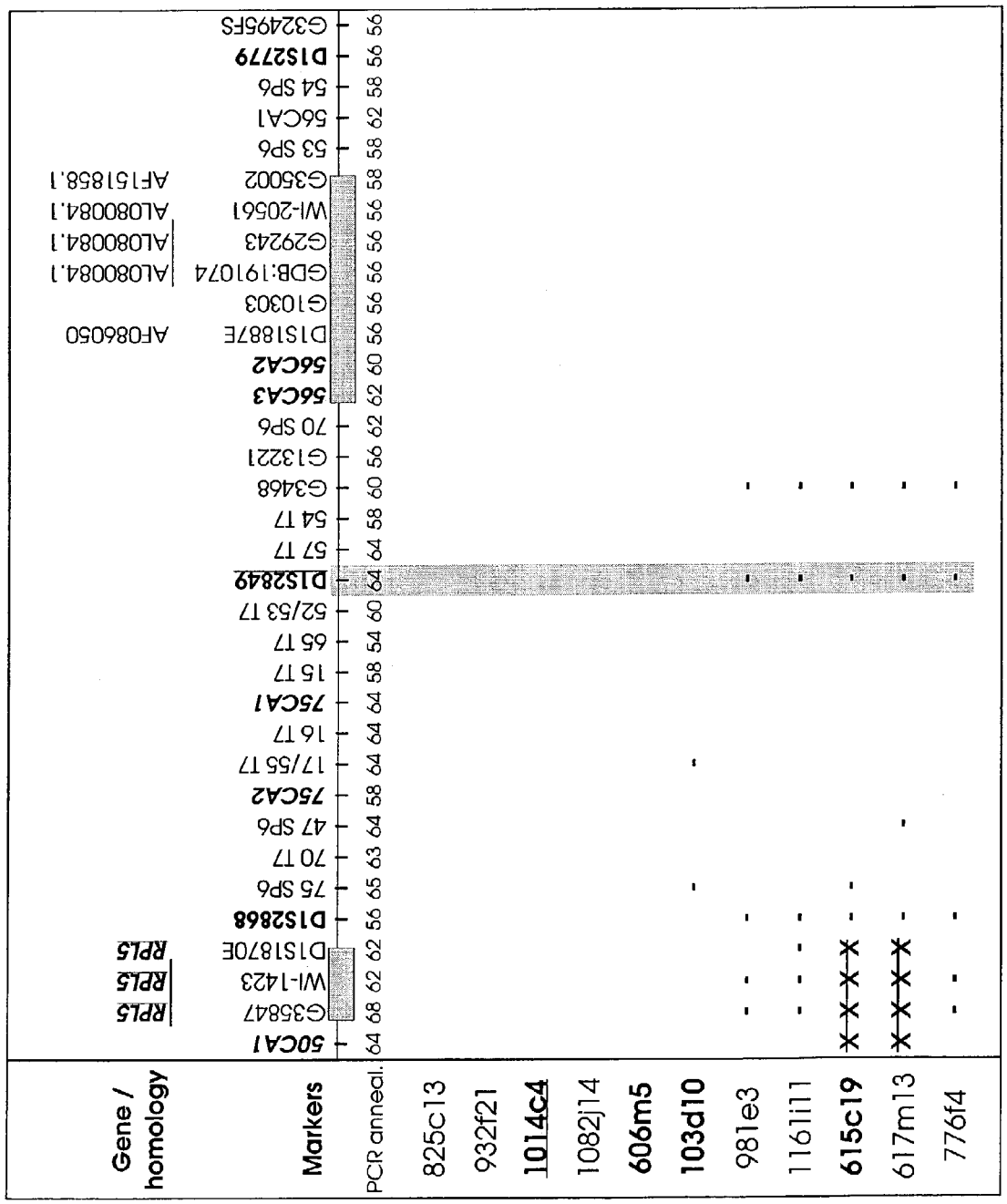
FIGURE 3 (part 6)

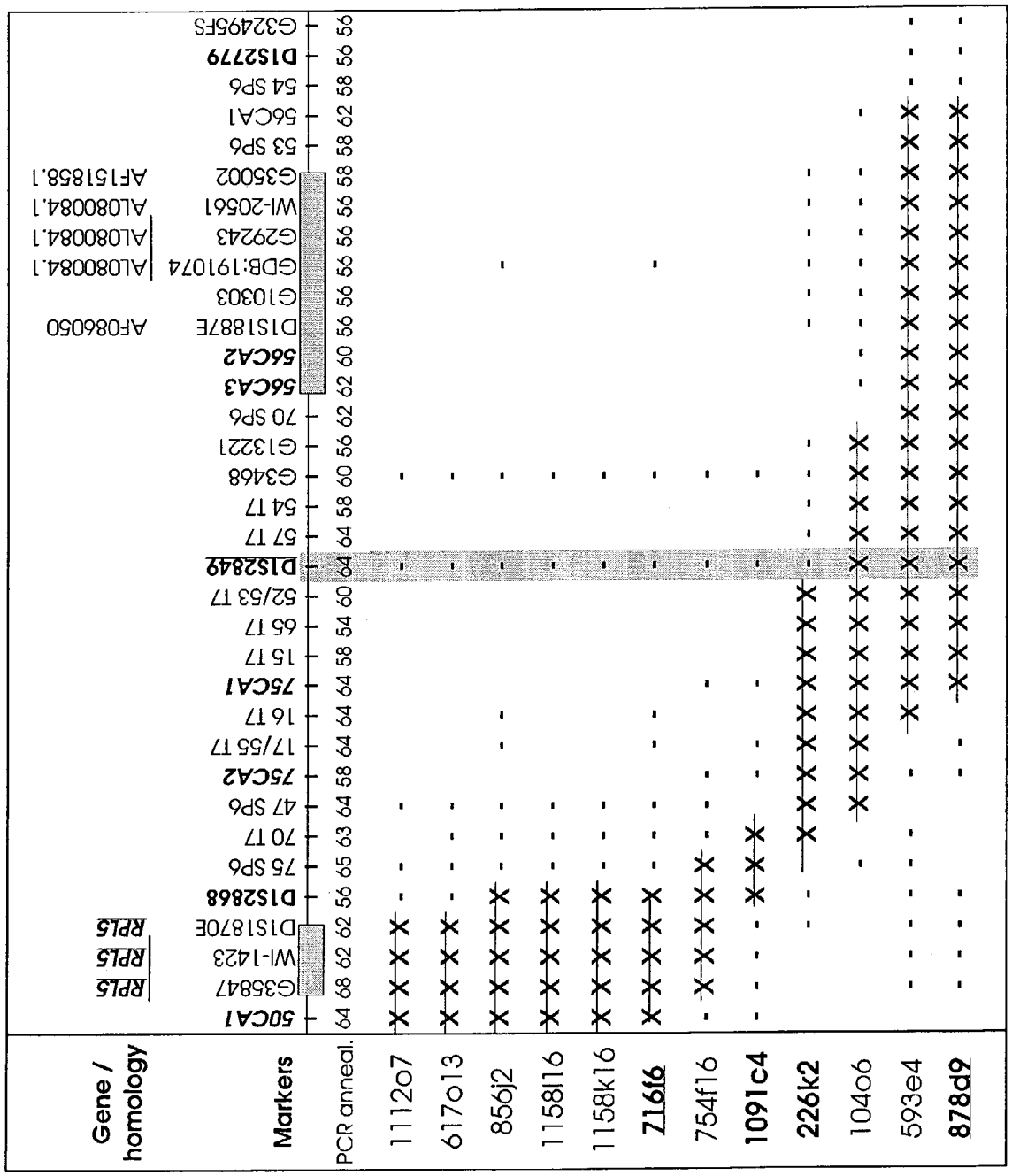
FIGURE 3 (part 7)

FIGURE 3 (part 8)

FIGURE 5

DNA_SEQUENCE : human VMGLOM cDNA "long form"
VMGLOM_1.seq  Length: 1849  December 16, 1999 13:25  Type: N  Check: 5787 ..

```
   1  TCTGGCCGAT TTTAGCATCG AAACTAGGAG AAATAAGAAT GGCTGTAGAG
  51  GAACTTCAGT CTATAATAAA GAGATGTCAA ATCCTAGAAG AGCAAGACTT
 101  TAAAGAAGAG GATTTTGGCC TATTTCAGTT AGCTGGGCAA AGATGCATAG
 151  AAGAAGGGCA CACAGACCAG CTATTAGAAA TTATTCAAAA TGAAAAGAAT
 201  AAGGTCATCA TCAAGAATAT GGGCTGGAAT CTCGTTGGTC CTGTTGTTCG
 251  ATGCCTTTTG TGTAAAGATA AGAGGATAG TAAAAGAAAA GTTTATTTTT
 301  TGATCTTTGA TTTATTGGTA AAGTTATGCA ATCCAAAGCA ATTATTGTTG
 351  GGTTTGCTTG AACTGATTGA AGAGCCCTCT GGAAAACAGA TATCCCAAAG
 401  TATTCTTCTT TTGCTTCAGC CATTACAAAC AGTGATTCAG AAACTTCATA
 451  ACAAGGCATA TTCAATTGGA TTAGCATTGT CTACCCTTTG GAATCAGCTA
 501  TCTCTTCTTC CTGTTCCATA CTCAAAAGAA CAAATACAAA TGGATGACTA
 551  TGGCCTTTGT CAGTGTTGCA AGGCCTTAAT AGAGTTCACT AAGCCTTTTG
 601  TGGAAGAAGT CATTGATAAC AAAGAAAACT CACTGGAAAA TGAAAAGTTA
 651  AAGGATGAAT TACTGAAATT TTGTTTCAAA AGCTTGAAAT GCCCTTTGCT
 701  GACAGCACAA TTCTTTGAAC AGTCTGAAGA AGGTGGAAAT GATCCTTTCA
 751  GGTATTTTGC ATCAGAAATA ATAGGTTTTT TATCAGCAAT TGGACACCCT
 801  TTCCCCAAAA TGATTTTTAA TCATGGAAGG AAAAAGAGAA CTTGGAATTA
 851  CCTTGAATTT GAAGAAGAAG AAAATAAACA GTTAGCAGAC TCAATGGCTT
 901  CTCTGGCATA TCTAGTATTT GTACAGGGCA TCCATATTGA TCAGCTTCCA
 951  ATGGTCTTAA GCCCATTGTA CCTTTTGCAG TTTAATATGG GGCACATTGA
1001  AGTCTTTTTG CAAAGAACAG AAGAGTCTGT TATCTCCAAA GGATTGGAGC
1051  TGCTGGAGAA TAGTTTATTG AGAATAGAAG ACAATAGTCT ACTTTACCAG
1101  TACTTAGAAA TCAAGAGTTT TCTTACTGTA CCTCAGGGCT TAGTGAAAGT
1151  AATGACACTT TGCCCCATTG AGACACTGAG GAAAAGAGT TTAGCTATGC
1201  TTCAGCTGTA TATTAACAAG TTGGATTCAC AAGGCAAATA TACATTATTT
1251  AGGTGCTTAT TGAATACAAG TAATCACTCA GGTGTGGAGG CTTTTATTAT
```

FIGURE 5 (CONTINUED)

```
1301   TCAAAATATC   AAAAATCAAA   TTGACATGTC   ATTAAAGAGA   ACACGTAACA
1351   ACAAATGGTT   TACAGGACCA   CAGTTGATTT   CCCTTCTTGA   TTTGGTACTT
1401   TTTCTCCCAG   AGGGTGCAGA   AACAGATTTA   CTGCAAAACT   CAGATAGGAT
1451   TATGGCTTCA   TTAAATTTAT   TGAGGTATTT   GGTTATCAAA   GATAATGAAA
1501   ATGACAATCA   AACTGGATTA   TGGACAGAAC   TTGGAAATAT   TGAGAATAAT
1551   TTCTTAAAGC   CACTTCATAT   AGGACTTAAT   ATGTCAAAAG   CACATTATGA
1601   AGCAGAAATT   AAAAATAGCC   AAGAGGCCCA   GAAATCTAAA   GATCTTTGTT
1651   CTATAACTGT   AAGTGGAGAA   GAGATCCCTA   ATATGCCTCC   TGAAATGCAG
1701   CTTAAGGTCC   TGCATTCAGC   TCTTTTCACA   TTTGATTTGA   TTGAAAGTGT
1751   TCTAGCTCGA   GTGGAAGAAC   TCATTGAAAT   AAAAACAAAG   TCTACCTCTG
1801   AAGAAAATAT   TGGGATAAAG   TGAAGTTCC   ATTTCCTAAA   TAAAAACTA
```

FIGURE 6
AA_SEQUENCE : human VMGLOM predicted amino acid sequence "long form"
TRANSLATE of: vmglom_1.seq check: 5787 from: 39 to: 1823
generated symbols 1 to: 595.

VMGLOM_1.pep  Length: 595  December 16, 1999 13:40  Type: P  Check: 7856  ..

1  MAVEELQSII KRCQILEEQD FKEEDFGLFQ LAGQRCIEEG HTDQLLEIIQ

51  NEKNKVIIKN MGWNLVGPVV RCLLCKDKED SKRKVYFLIF DLLVKLCNPK

101  ELLLGLLELI EEPSGKQISQ SILLLLQPLQ TVIQKLHNKA YSIGLALSTL

151  WNQLSLLPVP YSKEQIQMDD YGLCQCCKAL IEFTKPFVEE VIDNKENSLE

201  NEKLKDELLK FCFKSLKCPL LTAQFFEQSE EGGNDPFRYF ASEIIGFLSA

251  IGHPFPKMIF NHGRKKRTWN YLEFEEEENK QLADSMASLA YLVFVQGIHI

301  DQLPMVLSPL YLLQFNMGHI EVFLQRTEES VISKGLELLE NSLLRIEDNS

351  LLYQYLEIKS FLTVPQGLVK VMTLCPIETL RKKSLAMLQL YINKLDSQGK

401  YTLFRCLLNT SNHSGVEAFI IQNIKNQIDM SLKRTRNNKW FTGPQLISLL

451  DLVLFLPEGA ETDLLQNSDR IMASLNLLRY LVIKDNENDN QTGLWTELGN

501  IENNFLKPLH IGLNMSKAHY EAEIKNSQEA QKSKDLCSIT VSGEEIPNMP

551  PEMQLKVLHS ALFTFDLIES VLARVEELIE IKTKSTSEEN IGIK*

FIGURE 7

Human VMGLOM cDNA sequence "short form"

```
   1  TCTGGCCGAT TTTAGCATCG AAACTAGGAG AAATAAGAAT GGCTGTAGAG
  51  GAACTTCAGT CTATAATAAA GAGATGTCAA ATCCTAGAAG AGCAAGACTT
 101  TAAAGAAGAG GATTTTGGCC TATTTCAGTT AGCTGGGCAA AGATGCATAG
 151  AAGAAGGGCA CACAGACCAG CTATTAGAAA TTATTCAAAA TGAAAAGAAT
 201  AAGGTCATCA TCAAGAATAT GGGCTGGAAT CTCGTTGGTC CTGTTGTTCG
 251  ATGCCTTTTG TGTAAAGATA AGAGGATAG TAAAAGAAAA GTTTATTTTT
 301  TGATCTTTGA TTTATTGGTA AAGgttcaat tgtgaatatt tttatagTTA
 351  TGCAATCCAA AGGAATTATT GTTGGGTTTG CTTGAACTGA TTGAAGAGCC
 401  CTCTGGAAAA CAGATATCCC AAAGTATTCT TCTTTTGCTT CAGCCATTAC
 451  AAACAGTGAT TCAGAAACTT CATAACAAGG CATATTCAAT GGATTAGCA
 501  TTGTCTACCC TTTGGAATCA GCTATCTCTT CTTCCTGTTC CATACTCAAA
 551  AGAACAAATA CAAATGGATG ACTATGGCCT TTGTCAGTGT TGCAAGGCCT
 601  TAATAGAGTT CACTAAGCCT TTTGTGGAAG AAGTCATTGA TAACAAAGAA
 651  AACTCACTGG AAAATGAAAA GTTAAAGGAT GAATTACTGA AATTTGTTT
 701  CAAAAGCTTG AAATGCCCTT TGCTGACAGC ACAATTCTTT GAACAGTCTG
 751  AAGAAGGTGG AAATGATCCT TTCAGGTATT TTGCATCAGA ATAATAGGT
 801  TTTTTATCAG CAATTGGACA CCCTTTCCCC AAAATGATTT TTAATCATGG
 851  AAGGAAAAAG AGAACTTGGA ATTACCTTGA ATTTGAAGAA GAAGAAAATA
 901  AACAGTTAGC AGACTCAATG GCTTCTCTGG CATATCTAGT ATTTGTACAG
 951  GGCATCCATA TTGATCAGCT TCCAATGGTC TTAAGCCCAT TGTACCTTTT
1001  GCAGTTTAAT ATGGGGCACA TTGAAGTCTT TTTGCAAAGA ACAGAAGAGT
1051  CTGTTATCTC CAAAGGATTG GAGCTGCTGG AGAATAGTTT ATTGAGAATA
1101  GAAGACAATA GTCTACTTTA CCAGTACTTA GAAATCAAGA GTTTTCTTAC
1151  TGTACCTCAG GGCTTAGTGA AAGTAATGAC ACTTTGCCCC ATTGAGACAC
1201  TGAGGAAAAA GAGTTTAGCT ATGCTTCAGC TGTATATTAA CAAGTTGGAT
```

FIGURE 7 (CONTINUED)

```
1251   TCACAAGGCA AATATACATT ATTTAGGTGC TTATTGAATA CAAGTAATCA

1301   CTCAGGTGTG GAGGCTTTTA TTATTCAAAA TATCAAAAAT CAAATTGACA

1351   TGTCATTAAA GAGAACACGT AACAACAAAT GGTTTACAGG ACCACAGTTG

1401   ATTTCCCTTC TTGATTTGGT ACTTTTCTC CCAGAGGGTG CAGAAACAGA

1451   TTTACTGCAA AACTCAGATA GGATTATGGC TTCATTAAAT TTATTGAGGT

1501   ATTTGGTTAT CAAAGATAAT GAAAATGACA ATCAAACTGG ATTATGGACA

1551   GAACTTGGAA ATATTGAGAA TAATTTCTTA AAGCCACTTC ATATAGGACT

1601   TAATATGTCA AAAGCACATT ATGAAGCAGA AATTAAAAAT AGCCAAGAGG

1651   CCCAGAAATC TAAAGATCTT TGTTCTATAA CTGTAAGTGG AGAAGAGATC

1701   CCTAATATGC CTCCTGAAAT GCAGCTTAAG GTCCTGCATT CAGCTCTTTT

1751   CACATTTGAT TTGATTGAAA GTGTTCTAGC TCGAGTGGAA GAACTCATTG

1801   AAATAAAAAC AAAGTCTACC TCTGAAGAAA ATATTGGGAT AAAGTGAAAG

1851   TTCCATTTCC TAAATAAAAA CTA
```

FIGURE 8

AA_SEQUENCE : human VMGLOM predicted amino acid sequence "short form"
TRANSLATE of: vmglom.seq check: 9452 from: 39 to: 1847
generated symbols 1 to: 603.

VMGLOM.pep  Length: 99  December 16, 1999 14:18  Type: P  Check: 717  ..

1  MAVEELQSII KRCQILEEQD FKEEDFGLFQ LAGQRCIEEG HTDQLLEIIQ

51  NEKNKVIIKN MGWNLVGPVV RCLLCKDKED SKRKVYFLIF DLLVKVQL⁻

FIGURE 9

DNA_MULTIPLE_ALIGNMENT

December 16, 1999 13:27  Check: 6647 ..

Name: VMGLOM       : human VMGLOM "short form"
Name: VMGLOM_1     : human VMGLOM "long form"
Name: U73704       : human FAP-48

```
                    1                                                  50
      VMGLOM    ~~~~~~~~~~ ~~~~~~~~~~ ~~~~~~~~~~ ~~~~~~~~~~ ~~~~~~~~~~
    VMGLOM_1    ~~~~~~~~~~ ~~~~~~~~~~ ~~~~~~~~~~ ~~~~~~~~~~ ~~~~~~~~~~
      U73704    AGAAGAGCGG GCTAAGACGC CGGAGGAGGT GGCGGCGGCT GGGAGAGGCG 51                                                 100
      VMGLOM    ~~~~~TCTGG CCGATTTTAG CATCGAAACT AGGAGAAATA AGAATGGCTG
    VMGLOM_1    ~~~~~TCTGG CCGATTTTAG CATCGAAACT AGGAGAAATA AGAATGGCTG
      U73704    AGGGTTCTGG CCGATTTTAG CATCGAAACT AGGAGAAATA AGAATGGCTG 101                                                 150
      VMGLOM    TAGAGGAACT TCAGTCTATA ATAAAGAGAT GTCAAATCCT AGAAGAGCAA
    VMGLOM_1    TAGAGGAACT TCAGTCTATA ATAAAGAGAT GTCAAATCCT AGAAGAGCAA
      U73704    TAGAGGAACT TCAGTCTATA ATAAAGAGAT GTCAAATCCT AGAAGAGCAA 151                                                 200
      VMGLOM    GACTTTAAAG AAGAGGATTT TGGCCTATTT CAGTTAGCTG GGCAAAGATG
    VMGLOM_1    GACTTTAAAG AAGAGGATTT TGGCCTATTT CAGTTAGCTG GGCAAAGATG
      U73704    GACTTTAAAG AAGAGGATTT TGGCCTATTT CAGTTAGCTG GGCAAAGATG 201                                                 250
      VMGLOM    CATAGAAGAA GGGCACACAG ACCAGCTATT AGAAATTATT CAAAATGAAA
    VMGLOM_1    CATAGAAGAA GGGCACACAG ACCAGCTATT AGAAATTATT CAAAATGAAA
      U73704    CATAGAAGAA GGGCACACAG ACCAGCTATT AGAAATTATT CAAAATGAAA 251                                                 300
      VMGLOM    AGAATAAGGT CATCATCAAG AATATGGGCT GGAATCTCGT TGGTCCTGTT
    VMGLOM_1    AGAATAAGGT CATCATCAAG AATATGGGCT GGAATCTCGT TGGTCCTGTT
      U73704    AGAATAAGGT CATCATCAAG AATATGGGCT GGAATCTCGT TGGTCCTGTT 301                                                 350
      VMGLOM    GTTCGATGCC TTTTGTGTAA AGATAAAGAG GATAGTAAAA GAAAAGTTTA
    VMGLOM_1    GTTCGATGCC TTTTGTGTAA AGATAAAGAG GATAGTAAAA GAAAAGTTTA
      U73704    GTTCGATGCC TTTTGTGTAA AGATAAAGAG GATAGTAAAA GAAAAGTTTA 351                                                 400
      VMGLOM    TTTTTTGATC TTTGATTTAT TGGTAAAGgt tcaattgtga atatttttat
    VMGLOM_1    TTTTTTGATC TTTGATTTAT TGGTAA.... .......... ..........
      U73704    TTTTTTGATC TTTGATTTAT TGGTAA.... .......... ..........

401                                                 450
      VMGLOM    agTTATGCAA TCCAAAGGAA TTATTGTTGG GTTTGCTTGA ACTGATTGAA
    VMGLOM_1    AGTTATGCAA TCCAAAGGAA TTATTGTTGG GTTTGCTTGA ACTGATTGAA
      U73704    AGTTATGCAA TCCAAAGGAA TTATTGTTGG GTTTGCTTGA ACTGATTGAA 451                                                 500
      VMGLOM    GAGCCCTCTG GAAAACAGAT ATCCCAAAGT ATTCTTCTTT TGCTTCAGCC
```

FIGURE 9 (CONTINUED)

```
         VMGLOM_1   GAGCCCTCTG GAAAACAGAT ATCCCAAAGT ATTCTTCTTT TGCTTCAGCC
            U73704  GAGCCCTCTG GAAAACAGAT ATCCCAAAGT ATTCTTCTTT TGCTTCAGCC 501                                                550
           VMGLOM   ATTACAAACA GTGATTCAGA AACTTCATAA CAAGGCATAT TCAATTGGAT
         VMGLOM_1   ATTACAAACA GTGATTCAGA AACTTCATAA CAAGGCATAT TCAATTGGAT
            U73704  ATTACAAACA GTGATTCAGA AACTTCATAA CAAGGCATAT TCAATTGGAT 551                                                600
           VMGLOM   TAGCATTGTC TACCCTTTGG AATCAGCTAT CTCTTCTTCC TGTTCCATAC
         VMGLOM_1   TAGCATTGTC TACCCTTTGG AATCAGCTAT CTCTTCTTCC TGTTCCATAC
            U73704  TAGCATTGTC TACCCTTTGG AATCAGCTAT CTCTTCTTCC TGTTCCATAC 601                                                650
           VMGLOM   TCAAAAGAAC AAATACAAAT GGATGACTAT GGCCTTTGTC AGTGTTGCAA
         VMGLOM_1   TCAAAAGAAC AAATACAAAT GGATGACTAT GGCCTTTGTC AGTGTTGCAA
            U73704  TCAAAAGAAC AAATACAAAT GGATGACTAT GGCCTTTGTC AGTGTTGCAA 651                                                700
           VMGLOM   GGCCTTAATA GAGTTCACTA AGCCTTTTGT GGAAGAAGTC ATTGATAACA
         VMGLOM_1   GGCCTTAATA GAGTTCACTA AGCCTTTTGT GGAAGAAGTC ATTGATAACA
            U73704  GGCCTTAATA GAGTTCACTA AGCCTTTTGT GGAAGAAGTC ATTGATAACA 701                                                750
           VMGLOM   AAGAAAACTC ACTGGAAAAT GAAAAGTTAA AGGATGAATT ACTGAAATTT
         VMGLOM_1   AAGAAAACTC ACTGGAAAAT GAAAAGTTAA AGGATGAATT ACTGAAATTT
            U73704  AAGAAAACTC ACTGGAAAAT GAAAAGTTAA AGGATGAATT ACTGAAATTT 751                                                800
           VMGLOM   TGTTTCAAAA GCTTGAAATG CCCTTTGCTG ACAGCACAAT TCTTTGAACA
         VMGLOM_1   TGTTTCAAAA GCTTGAAATG CCCTTTGCTG ACAGCACAAT TCTTTGAACA
            U73704  TGTTTCAAAA GCTTGAAATG CCCTTTGCTG ACAGCACAAT TCTTTGAACA 801                                                850
           VMGLOM   GTCTGAAGAA GGTGGAAATG ATCCTTTCAG GTATTTTGCA TCAGAAATAA
         VMGLOM_1   GTCTGAAGAA GGTGGAAATG ATCCTTTCAG GTATTTTGCA TCAGAAATAA
            U73704  GTCTGAAGAA GGTGGAAATG ATCCTTTCAG GTATTTTGCA TCAGAAATAA 851                                                900
           VMGLOM   TAGGTTTTTT ATCAGCAATT GGACACCCTT TCCCCAAAAT GATTTTTAAT
         VMGLOM_1   TAGGTTTTTT ATCAGCAATT GGACACCCTT TCCCCAAAAT GATTTTTAAT
            U73704  TAGGTTTTTT ATCAGCAATT GGACACCCTT TCCCCAAAAT GATTTTTAAT 901                                                950
           VMGLOM   CATGGAAGGA AAAAGAGAAC TTGGAATTAC CTTGAATTTG AAGAAGAAGA
         VMGLOM_1   CATGGAAGGA AAAAGAGAAC TTGGAATTAC CTTGAATTTG AAGAAGAAGA
            U73704  CATGGAAGGA AAAAGAGAAC TTGGAATTAC CTTGAATTTG AAGAAGAAGA 951                                               1000
           VMGLOM   AAATAAACAG TTAGCAGACT CAATGGCTTC TCTGGCATAT CTAGTATTTG
         VMGLOM_1   AAATAAACAG TTAGCAGACT CAATGGCTTC TCTGGCATAT CTAGTATTTG
            U73704  AAATAAACAG TTAGCAGACT CAATGGCTTC TCTGGCATAT CTAGTATTTG 1001                                              1050
           VMGLOM   TACAGGGCAT CCATATTGAT CAGCTTCCAA TGGTCTTAAG CCCATTGTAC
```

FIGURE 9 (CONTINUED)

```
    VMGLOM_1  TACAGGGCAT CCATATTGAT CAGCTTCCAA TGGTCTTAAG CCCATTGTAC
       U73704  TACAGGGCAT CCATATTGAT CAGCTTCCAA TGGTCTTAAG CCCATTGTAC 1051                                                 1100
       VMGLOM  CTTTTGCAGT TTAATATGGG GCACATTGAA GTCTTTTTGC AAAGAACAGA
    VMGLOM_1  CTTTTGCAGT TTAATATGGG GCACATTGAA GTCTTTTTGC AAAGAACAGA
       U73704  CTTTTGCAGT TTAATATGGG GCACATTGAA GTCTTTTTGC AAAGAACAGA 1101                                                 1150
       VMGLOM  AGAGTCTGTT ATCTCCAAAG GATTGGAGCT GCTGGAGAAT AGTTTATTGA
    VMGLOM_1  AGAGTCTGTT ATCTCCAAAG GATTGGAGCT GCTGGAGAAT AGTTTATTGA
       U73704  AGAGTCTGTT ATCTCCAAAG GATTGGAGCT GCTGGAGAAT AGTTTATTGA 1151                                                 1200
       VMGLOM  GAATAGAAGA CAATAGTCTA CTTTACCAGT ACTTAGAAAT CAAGAGTTTT
    VMGLOM_1  GAATAGAAGA CAATAGTCTA CTTTACCAGT ACTTAGAAAT CAAGAGTTTT
       U73704  GAATAGAAGA CAATAGTCTA CTTTACCAGT ACTTAGAAAT CAAGAGTTTT 1201                                                 1250
       VMGLOM  CTTACTGTAC CTCAGGGCTT AGTGAAAGTA ATGACACTTT GCCCCATTGA
    VMGLOM_1  CTTACTGTAC CTCAGGGCTT AGTGAAAGTA ATGACACTTT GCCCCATTGA
       U73704  CTTACTGTAC CTCAGGGCTT AGTGAAAGTA ATGACACTTT GCCCCATTGA 1251                                                 1300
       VMGLOM  GACACTGAGG AAAAAGAGTT TAGCTATGCT TCAGCTGTAT ATTAACAAGT
    VMGLOM_1  GACACTGAGG AAAAAGAGTT TAGCTATGCT TCAGCTGTAT ATTAACAAGT
       U73704  GACACTGAGG AAAAAGAGTT TAGCTATGCT TCAGCTGTAT ATTAACAAGT 1301                                                 1350
       VMGLOM  TGGATTCACA AGGCAAATAT ACATTATTTA GGTGCTTATT GAATACAAGT
    VMGLOM_1  TGGATTCACA AGGCAAATAT ACATTATTTA GGTGCTTATT GAATACAAGT
       U73704  TGGATTCACA AGGCAAATAT ACATTATTT. .......... ..........

1351                                                 1400
       VMGLOM  AATCACTCAG GTGTGGAGGC TTTTATTATT CAAAATATCA AAAATCAAAT
    VMGLOM_1  AATCACTCAG GTGTGGAGGC TTTTATTATT CAAAATATCA AAAATCAAAT
       U73704  .......... .......... .......... .......... ..........

1401                                                 1450
       VMGLOM  TGACATGTCA TTAAAGAGAA CACGTAACAA CAAATGGTTT ACAGGACCAC
    VMGLOM_1  TGACATGTCA TTAAAGAGAA CACGTAACAA CAAATGGTTT ACAGGACCAC
       U73704  .......... ....AGAGAA CACGTAACAA CAAATGGTTT ACAGGACCAC 1451                                                 1500
       VMGLOM  AGTTGATTTC CCTTCTTGAT TTGGTACTTT TTCTCCCAGA GGGTGCAGAA
    VMGLOM_1  AGTTGATTTC CCTTCTTGAT TTGGTACTTT TTCTCCCAGA GGGTGCAGAA
       U73704  AGTTGATTTC CCTTCTTGAT TTGGTACTTT TTCTCCCAGA GGGTGCAGAA 1501                                                 1550
       VMGLOM  ACAGATTTAC TGCAAAACTC AGATAGGATT ATGGCTTCAT TAAATTTATT
    VMGLOM_1  ACAGATTTAC TGCAAAACTC AGATAGGATT ATGGCTTCAT TAAATTTATT
       U73704  ACAGATTTAC TGCAAAACTC AGATAGGATT ATGGCTTCAT TAAATTTATT 1551                                                 1600
       VMGLOM  GAGGTATTTG GTTATCAAAG ATAATGAAAA TGACAATCAA ACTGGATTAT
```

FIGURE 9 (CONTINUED)

```
VMGLOM_1    GAGGTATTTG GTTATCAAAG ATAATGAAAA TGACAATCAA ACTGGATTAT
   U73704   GAGGTATTTG GTTATCAAAG ATAATGAAAA TGACAATCAA ACTGGATTAT 1601                                                 1650
    VMGLOM   GGACAGAACT TGGAAATATT GAGAATAATT TCTTAAAGCC ACTTCATATA
  VMGLOM_1   GGACAGAACT TGGAAATATT GAGAATAATT TCTTAAAGCC ACTTCATATA
    U73704   GGACAGAACT TGGAAATATT GAGAATAATT TCTTAAAGCC ACTTCATATA 1651                                                 1700
    VMGLOM   GGACTTAATA TGTCAAAAGC ACATTATGAA .GCAGAAATT AAAAATAGCC
  VMGLOM_1   GGACTTAATA TGTCAAAAGC ACATTATGAA .GCAGAAATT AAAAATAGCC
    U73704   GGACTTAATA TGTCAAAAGC ACATTATGAA GGCAGAAATT AAAAATAGCC 1701                                                 1750
    VMGLOM   AAGAGGCCCA GAAATCTAAA GATCTTTGTT CTATAACTGT AAGTGGAGAA
  VMGLOM_1   AAGAGGCCCA GAAATCTAAA GATCTTTGTT CTATAACTGT AAGTGGAGAA
    U73704   AAGAGGCCCA GAAATCTAAA GATCTTTGTT CTATAACTGT AAGTGGAGAA 1751                                                 1800
    VMGLOM   GAGATCCCTA ATATGCCTCC TGAAATGCAG CTTAAGGTCC TGCATTCAGC
  VMGLOM_1   GAGATCCCTA ATATGCCTCC TGAAATGCAG CTTAAGGTCC TGCATTCAGC
    U73704   GAGATCCCTA ATATGCCTCC TGAAATGCAG CTTAAGGTCC TGCATTCAGC 1801                                                 1850
    VMGLOM   TCTTTTCACA TTTGATTTGA TTGAAAGTGT TCTAGCTCGA GTGGAAGAAC
  VMGLOM_1   TCTTTTCACA TTTGATTTGA TTGAAAGTGT TCTAGCTCGA GTGGAAGAAC
    U73704   TCTTTTCACA TTTGATTTGA TTGAAAGTGT TCTAGCTCGA GTGGAAGAAC 1851                                                 1900
    VMGLOM   TCATTGAAAT AAAAACAAAG TCTACCTCTG AAGAAAATAT TGGGATAAAG
  VMGLOM_1   TCATTGAAAT AAAAACAAAG TCTACCTCTG AAGAAAATAT TGGGATAAAG
    U73704   TCATTGAAAT AAAAACAAAG TCTACCTCTG AAGAAAATAT TGGGATAAAG 1901                                                 1946
    VMGLOM   TGAAAGTTCC ATTTCCTAAA TAAAAACTA~ ~~~~~~~~~~ ~~~~~~
  VMGLOM_1   TGAAAGTTCC ATTTCCTAAA TAAAAACTA~ ~~~~~~~~~~ ~~~~~~
    U73704   TGAAAGTTCC ATTTCCTAAA TAAAAACTAA TAAATATAG TACCTC
```

FIGURE 10

AA_MULTIPLE_ALIGNMENT

December 16, 1999 14:19  Check: 753 ..

Name: VMGLOM_1 : human predicted amino acid VMGLOM "long form"
Name: u73704   : human predicted amino acid FAP48
Name: VMGLOM   : human predicted amino acid VMGLOM "short form"
//

```
                   1                                                      50
VMGLOM_1    MAVEELQSII KRCQILEEQD FKEEDFGLFQ LAGQRCIEEG HTDQLLEIIQ
   u73704   MAVEELQSII KRCQILEEQD FKEEDFGLFQ LAGQRCIEEG HTDQLLEIIQ
VMGLOM      MAVEELQSII KRCQILEEQD FKEEDFGLFQ LAGQRCIEEG HTDQLLEIIQ 51                                                     100
VMGLOM_1    NEKNKVIIKN MGWNLVGPVV RCLLCKDKED SKRKVYFLIF DLLVKLCNPK
   u73704   NEKNKVIIKN MGWNLVGPVV RCLLCKDKED SKRKVYFLIF DLLVKLCNPK
VMGLOM      NEKNKVIIKN MGWNLVGPVV RCLLCKDKED SKRKVYFLIF DLLVKVQL*~

101                                                     150
VMGLOM_1    ELLLGLLELI EEPSGKQISQ SILLLLQPLQ TVIQKLHNKA YSIGLALSTL
   u73704   ELLLGLLELI EEPSGKQISQ SILLLLQPLQ TVIQKLHNKA YSIGLALSTL
VMGLOM      ~~~~~~~~~~ ~~~~~~~~~~ ~~~~~~~~~~ ~~~~~~~~~~ ~~~~~~~~~~

151                                                     200
VMGLOM_1    WNQLSLLPVP YSKEQIQMDD YGLCQCCKAL IEFTKPFVEE VIDNKENSLE
   u73704   WNQLSLLPVP YSKEQIQMDD YGLCQCCKAL IEFTKPFVEE VIDNKENSLE
VMGLOM      ~~~~~~~~~~ ~~~~~~~~~~ ~~~~~~~~~~ ~~~~~~~~~~ ~~~~~~~~~~

201                                                     250
VMGLOM_1    NEKLKDELLK FCFKSLKCPL LTAQFFEQSE EGGNDPFRYF ASEIIGFLSA
   u73704   NEKLKDELLK FCFKSLKCPL LTAQFFEQSE EGGNDPFRYF ASEIIGFLSA
VMGLOM      ~~~~~~~~~~ ~~~~~~~~~~ ~~~~~~~~~~ ~~~~~~~~~~ ~~~~~~~~~~

251                                                     300
VMGLOM_1    IGHPFPKMIF NHGRKKRTWN YLEFEEEENK QLADSMASLA YLVFVQGIHI
   u73704   IGHPFPKMIF NHGRKKRTWN YLEFEEEENK QLADSMASLA YLVFVQGIHI
VMGLOM      ~~~~~~~~~~ ~~~~~~~~~~ ~~~~~~~~~~ ~~~~~~~~~~ ~~~~~~~~~~

301                                                     350
VMGLOM_1    DQLPMVLSPL YLLQFNMGHI EVFLQRTEES VISKGLELLE NSLLRIEDNS
   u73704   DQLPMVLSPL YLLQFNMGHI EVFLQRTEES VISKGLELLE NSLLRIEDNS
VMGLOM      ~~~~~~~~~~ ~~~~~~~~~~ ~~~~~~~~~~ ~~~~~~~~~~ ~~~~~~~~~~

351                                                     400
VMGLOM_1    LLYQYLEIKS FLTVPQGLVK VMTLCPIETL RKKSLAMLQL YINKLDSQGK
   u73704   LLYQYLEIKS FLTVPQGLVK VMTLCPIETL RKKSLAMLQL YINKLDSQGK
VMGLOM      ~~~~~~~~~~ ~~~~~~~~~~ ~~~~~~~~~~ ~~~~~~~~~~ ~~~~~~~~~~

401                                                     450
VMGLOM_1    YTLFRCLLNT S...NHSGVE AFIIQNIKNQ IDMSLKRTRN NKWFTGPQLI
   u73704   YTLFREHVTT NGLQDHS~~~ ~~~~~~~~~~ ~~~~~~~~~~ ~~~~~~~~~~
VMGLOM      ~~~~~~~~~~ ~~~~~~~~~~ ~~~~~~~~~~ ~~~~~~~~~~ ~~~~~~~~~~

451                                                     500
```

FIGURE 10 (CONTINUED)

```
VMGLOM_1   SLLDLVLFLP  EGAETDLLQN  SDRIMASLNL  LRYLVIKDNE  NDNQTGLWTE
   u73704  ~~~~~~~~~~  ~~~~~~~~~~  ~~~~~~~~~~  ~~~~~~~~~~  ~~~~~~~~~~
   VMGLOM  ~~~~~~~~~~  ~~~~~~~~~~  ~~~~~~~~~~  ~~~~~~~~~~  ~~~~~~~~~~

501                                                    550
VMGLOM_1   LGNIENNFLK  PLHIGLNMSK  AHYEAEIKNS  QEAQKSKDLC  SITVSGEEIP
   u73704  ~~~~~~~~~~  ~~~~~~~~~~  ~~~~~~~~~~  ~~~~~~~~~~  ~~~~~~~~~~
   VMGLOM  ~~~~~~~~~~  ~~~~~~~~~~  ~~~~~~~~~~  ~~~~~~~~~~  ~~~~~~~~~~

551                                                    598
VMGLOM_1   NMPPEMQLKV  LHSALFTFDL  IESVLARVEE  LIEIKTKSTS  EENIGIK*
   u73704  ~~~~~~~~~~  ~~~~~~~~~~  ~~~~~~~~~~  ~~~~~~~~~~  ~~~~~~~~
   VMGLOM  ~~~~~~~~~~  ~~~~~~~~~~  ~~~~~~~~~~  ~~~~~~~~~~  ~~~~~~~~
```

FIGURE 11

DNA_SEQUENCE : mouse VMGLOM "long form"
mVMGLOM.seq  Length: 1719  December 16, 1999 13:59  Type: N  Check: 6256  ..

```
   1  ATGGCTGTGG AGGAACTTCA GAGCATAATA AAAAGATGTC AAATCCTAGA
  51  AGAGCATGAT TTTAAAGAAG AAGATTTTGG CCTCTTTCAG TTAGCAGGTC
 101  AAAGATGCAT TGAAGATGGT TATATAAACC AGCTGCTAGA GATTATTCAA
 151  GATGAAAAGA ACAAGACCAT CATTAAGTCT ATGGGGTGGA ATCTTGTTGG
 201  TCCAGTTGTT CGATGCCTCC TGAGGGGCAG AGAAGAGGAT AAAAGAGAAG
 251  AGTGTTTTCT GATATTTGAT TTGCTGGTGA AGTTATGTAA TCCAAAGGAA
 301  TTGTTGTTGG GTTTGCTTGA ACTCATTGAA GAGCCCTCCG GAAAACAGAT
 351  TTCCCAAATT ATTCTTCTTT TACTGCAACC ATTACAAACA GTTATTCAGA
 401  AACTTCCTAA CAACAAGGCA TACTCCGTTG ACTAGCATT GTCAACACTT
 451  TGGAGTCAGC TGTCTCTTCT TCCTGTTCCA CACTCAGAAG AACAAATTCA
 501  GGCAGATGAT TATGGCCTCT GTCAGTGTTG TAAGGCCTTG ATAGAGTTCA
 551  CGAAACCTTT TGTGGAAGAA GTAATAAGTG ATAAAGAAAA CAAAGAAAAT
 601  GCAAAACTAA AAGATGAATT ACTGAAATTT TGTTTCAAAG GCTTGAAATG
 651  CCCTTTGCTG ACAGCACAAT TCCTCGAACA GTCAGAAGAC GTTGGAAATG
 701  ACCCTTTTCG GTGTTTTGCA TCTGAAATAA TAGGATTTTT ATCAAAAATT
 751  GGACACCCTG TCCCCCAAAT TATTCTTAAT CATGGAAGGA AAAAAAGGAC
 801  TTGGGATTAC CTTGAATTTG AAGAAGAAGA AGACAAACAA CTGGCAGAGT
 851  CTGTGGCTTC TCTGACATAT CTAGTATTTG TTCAGGGCAT CGGTATTGAT
 901  CAGCTGCCCA TGGTCTTAAG CCCATCGTAC CTTCTGCAGT TGAACATGGA
 951  GCATATTGAA GTGTTTCTGC AAAGAACAGA ACAGTCTATT TACTCCAAAG
1001  GATTGGAACT TCTGGAGACT AGCTTATTGA GATTAGAAGA CAACAGCCTA
1051  TGTTATCAGT ACTTAGAAAT CAAGAGTTTT CTTGCTGTGC CTCAGGGCTT
1101  AGTCAAAGTT ATGACACTTT GCCCCATTGA CATTGAGG AAAAAAGGTT
1151  TATCTATGCT TCAGCTGTTT ATTGACAAGT TGGATTCACA AGGCAAATAT
1201  ACATTATTTA GGTGCTTACT AAATACAAGT AATCACTCAG GAGTGGAAGC
1251  CTTTGTAATT CAAAACATCA AAAATCAGAT TGATTTATCA TTTAAGAAAA
```

FIGURE 11 (CONTINUED)

```
1301  CATATAACAA ATGGTTTGCA GGAGCACAGC TGATCTCTCT GTTAGACCTG
1351  GTCCTGTCTC TCCCTGAGGG CGCTGAGACA GACTTACTGC AGAACTCAGA
1401  CAGGATTATG GCTTCATTAA ATTTATTGAG GTATTTGGTT ATCAAAGATA
1451  ATGAAGATGA CAATCAAACT GGATTATGGA CAGAACTTGG AAAAATTGAA
1501  AATAACTTTC TAAAGCCACT TCATATAGGA CTTAATATGT CAAAAGCACA
1551  TTATGAAGCA GAAATTAAAA ACAGCCAACA AAATAACCAA GTAGCCTCAA
1601  TGTGTAAAGG TGTTTGTTCC GTGACTGTAG GTGGAGAAGA AATCCCTTCT
1651  ATGCCTCCTG AAATGCAGCT TAAGGTCTTA CATTCCGCTC TCTTCACATT
1701  TGACTTGATT GAAAGTGTT
```

FIGURE 12

AA_SEQUENCE : mouse VMGLOM predicted amino acid sequence "long form"
TRANSLATE of: mvmglomb.seq check: 6256 from: 1 to: 1719
generated symbols 1 to: 573.

mVMGLOMb.pep  Length: 573  December 16, 1999 14:00  Type: P  Check: 1800  ..

```
  1  MAVEELQSII KRCQILEEHD FKEEDFGLFQ LAGQRCIEDG YINQLLEIIQ
 51  DEKNKTIIKS MGWNLVGPVV RCLLRGREED KREECFLIFD LLVKLCNPKE
101  LLLGLLELIE EPSGKQISQI ILLLLQPLQT VIQKLPNNKA YSVGLALSTL
151  WSQLSLLPVP HSEEQIQADD YGLCQCCKAL IEFTKPFVEE VISDKENKEN
201  AKLKDELLKF CFKGLKCPLL TAQFLEQSED VGNDPFRCFA SEIIGFLSKI
251  GHPVPQIILN HGRKKRTWDY LEFEEEEDKQ LAESVASLTY LVFVQGIGID
301  QLPMVLSPSY LLQLNMEHIE VFLQRTEQSI YSKGLELLET SLLRLEDNSL
351  CYQYLEIKSF LAVPQGLVKV MTLCPIETLR KKGLSMLQLF IDKLDSQGKY
401  TLFRCLLNTS NHSGVEAFVI QNIKNQIDLS FKKTYNKWFA GAQLISLLDL
451  VLSLPEGAET DLLQNSDRIM ASLNLLRYLV IKDNEDDNQT GLWTELGKIE
501  NNFLKPLHIG LNMSKAHYEA EIKNSQQNNQ VASMCKGVCS VTVGGEEIPS
551  MPPEMQLKVL HSALFTFDLI ESV
```

FIGURE 13 mouse VMGLOM " short form " cDNA_SEQUENCE
Length: 1743  December 16, 1999 13:54

```
   1  ATGGCTGTGG AGGAACTTCA GAGCATAATA AAAAGATGTC AAATCCTAGA
  51  AGAGCATGAT TTTAAAGAAG AAGATTTTGG CCTCTTTCAG TTAGCAGGTC
 101  AAAGATGCAT TGAAGATGGT TATATAAACC AGCTGCTAGA GATTATTCAA
 151  GATGAAAAGA ACAAGACCAT CATTAAGTCT ATGGGGTGGA ATCTTGTTGG
 201  TCCAGTTGTT CGATGCCTCC TGAGGGGCAG AGAAGAGGAT AAAAGAGAAG
 251  AGTGTTTTCT GATATTTGAT TTGCTGGTGA AGttcaatt gtgaatattt
 301  ttatagTTAT GTAATCCAAA GGAATTGTTG TTGGGTTTGC TTGAACTCAT
 351  TGAAGAGCCC TCCGGAAAAC AGATTTCCCA AATTATTCTT CTTTTACTGC
 401  AACCATTACA ACAGTTATT CAGAAACTTC CTAACAACAA GGCATACTCC
 451  GTTGGACTAG CATTGTCAAC ACTTTGGAGT CAGCTGTCTC TTCTTCCTGT
 501  TCCACACTCA GAAGAACAAA TTCAGGCAGA TGATTATGGC CTCTGTCAGT
 551  GTTGTAAGGC CTTGATAGAG TTCACGAAAC CTTTTGTGGA AGAAGTAATA
 601  AGTGATAAAG AAAACAAAGA AAATGCAAAA CTAAAAGATG AATTACTGAA
 651  ATTTTGTTTC AAAGGCTTGA ATGCCCTTT GCTGACAGCA CAATTCCTCG
 701  AACAGTCAGA AGACGTTGGA ATGACCCTT TCGGTGTTT TGCATCTGAA
 751  ATAATAGGAT TTTTATCAAA AATTGGACAC CCTGTCCCCC AAATTATTCT
 801  TAATCATGGA AGGAAAAAAA GGACTTGGGA TTACCTTGAA TTTGAAGAAG
 851  AAGAAGACAA ACAACTGGCA GAGTCTGTGG CTTCTCTGAC ATATCTAGTA
 901  TTTGTTCAGG GCATCGGTAT TGATCAGCTG CCCATGGTCT TAAGCCCATC
 951  GTACCTTCTG CAGTTGAACA TGGAGCATAT TGAAGTGTTT CTGCAAAGAA
1001  CAGAACAGTC TATTTACTCC AAAGGATTGG AACTTCTGGA GACTAGCTTA
1051  TTGAGATTAG AAGACAACAG CCTATGTTAT CAGTACTTAG AAATCAAGAG
1101  TTTTCTTGCT GTGCCTCAGG GCTTAGTCAA AGTTATGACA CTTTGCCCCA
1151  TTGAGACATT GAGGAAAAAA GGTTTATCTA TGCTTCAGCT GTTTATTGAC
1201  AAGTTGGATT CACAAGGCAA ATATACATTA TTTAGGTGCT TACTAAATAC
1251  AAGTAATCAC TCAGGAGTGG AAGCCTTTGT AATTCAAAAC ATCAAAAATC
```

FIGURE 13 (CONTINUED)

```
1301  AGATTGATTT ATCATTTAAG AAAACATATA ACAAATGGTT TGCAGGAGCA
1351  CAGCTGATCT CTCTGTTAGA CCTGGTCCTG TCTCTCCCTG AGGGCGCTGA
1401  GACAGACTTA CTGCAGAACT CAGACAGGAT TATGGCTTCA TTAAATTTAT
1451  TGAGGTATTT GGTTATCAAA GATAATGAAG ATGACAATCA AACTGGATTA
1501  TGGACAGAAC TTGGAAAAAT TGAAAATAAC TTTCTAAAGC CACTTCATAT
1551  AGGACTTAAT ATGTCAAAAG CACATTATGA AGCAGAAATT AAAAACAGCC
1601  AACAAAATAA CCAAGTAGCC TCAATGTGTA AAGGTGTTTG TTCCGTGACT
1651  GTAGGTGGAG AAGAAATCCC TTCTATGCCT CCTGAAATGC AGCTTAAGGT
1701  CTTACATTCC GCTCTCTTCA CATTTGACTT GATTGAAAGT GTT
```

FIGURE 14

AA_SEQUENCE : mouse VMGLOM "short form" predicted amino acid sequence

TRANSLATE of: mvmglom.seq check: 8617 from: 1 to: 1743
generated symbols 1 to: 581.

mVMGLOM.pep  Length: 98  December 16, 1999 14:27  Type: P  Check: 6328  ..

1  MAVEELQSII KRCQILEEHD FKEEDFGLFQ LAGQRCIEDG YINQLLEIIQ

51  DEKNKTIIKS MGWNLVGPVV RCLLRGREED KREECFLIFD LLVKVQL*

Figure 18:
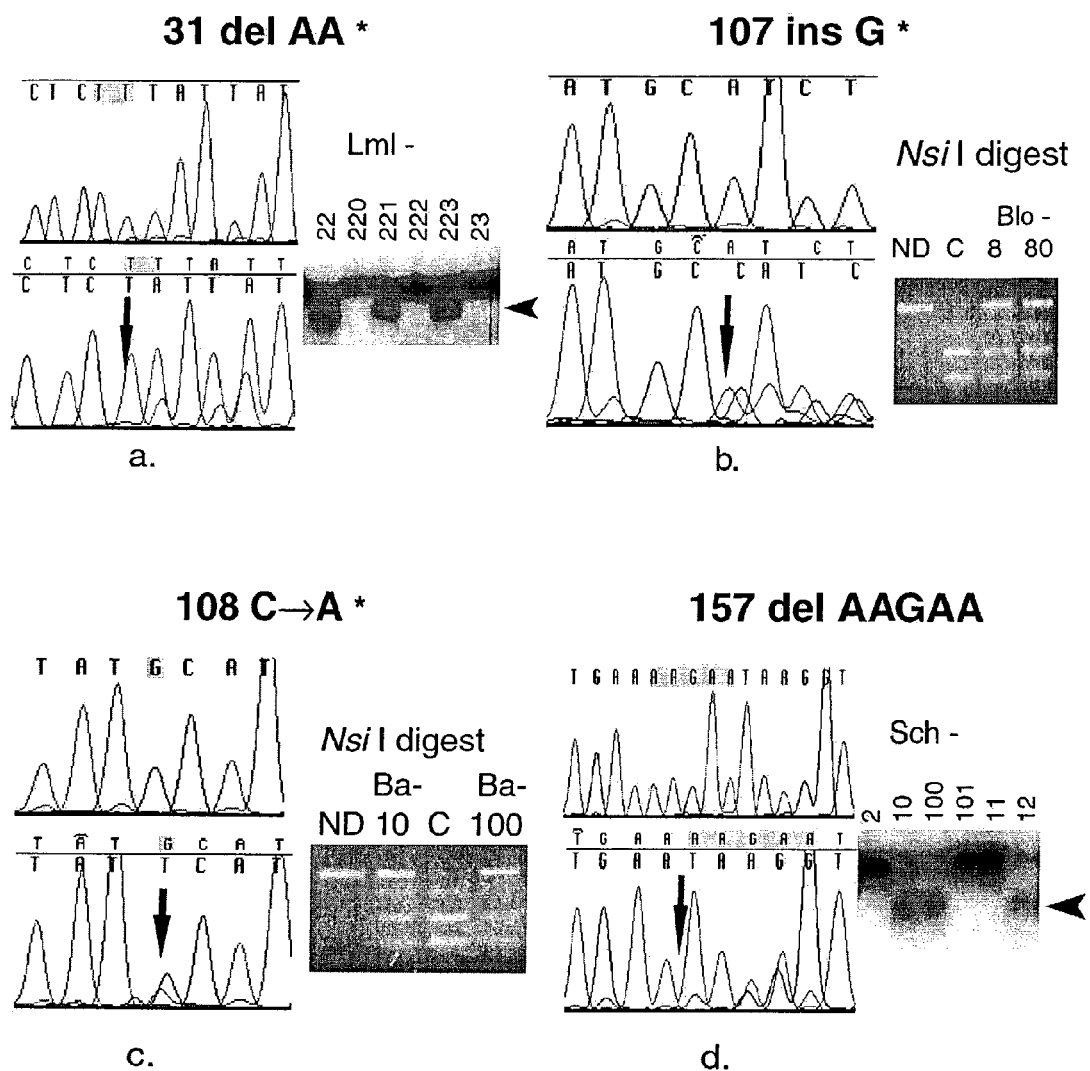
Figure 18:
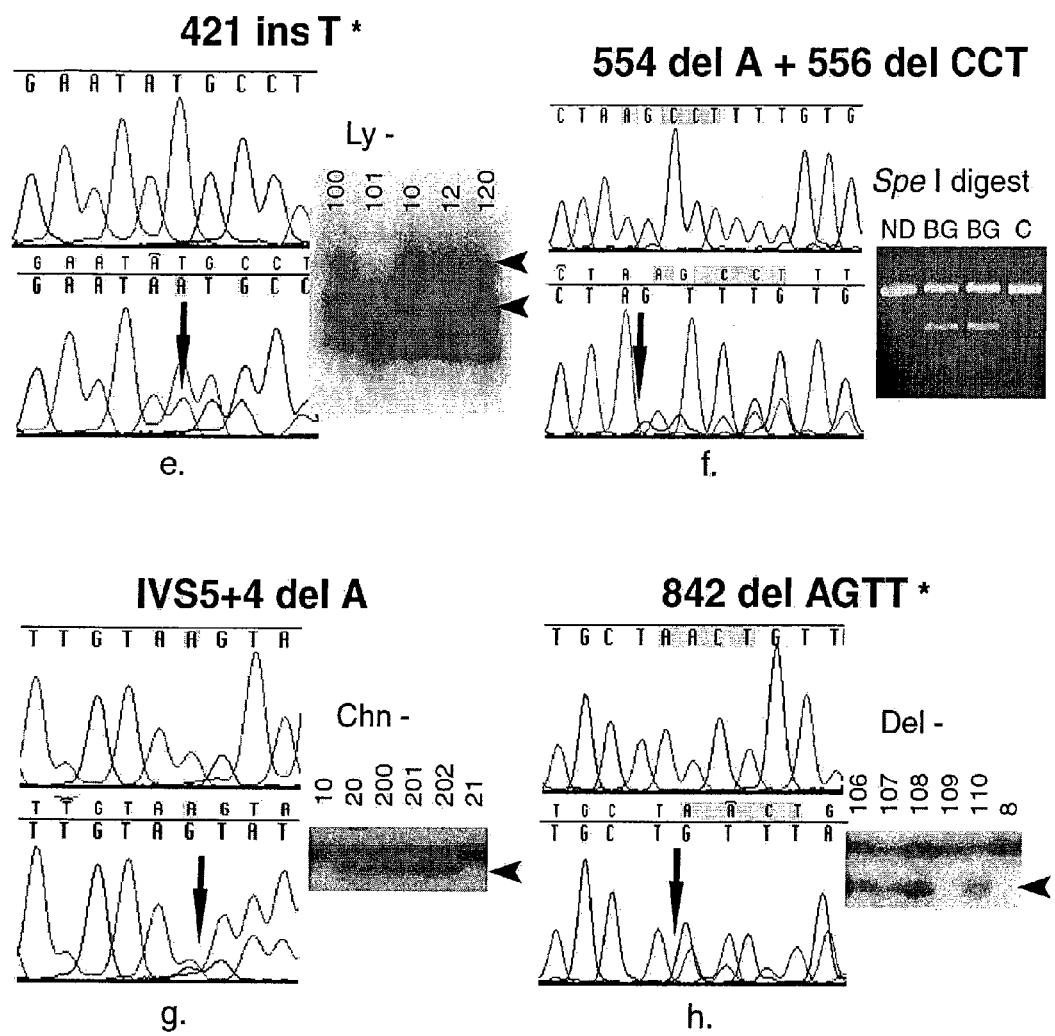

1180 del CAA
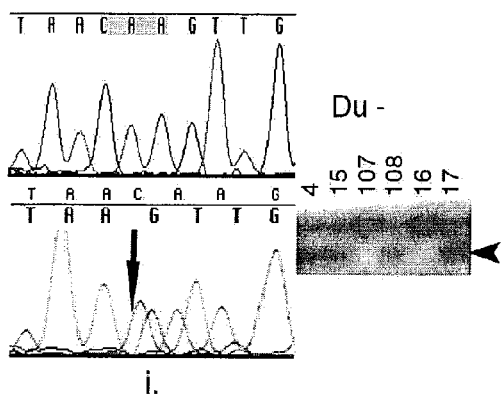
i.
1355 del T
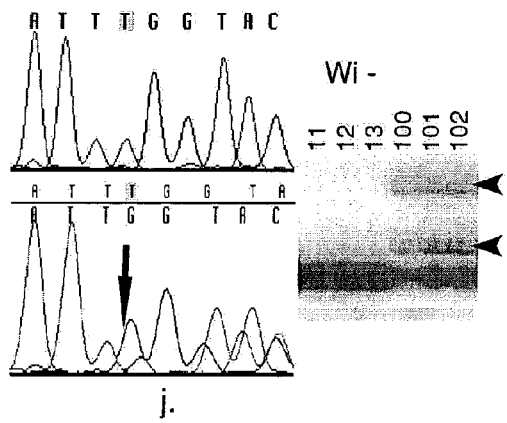
j.
1470 del TCAA
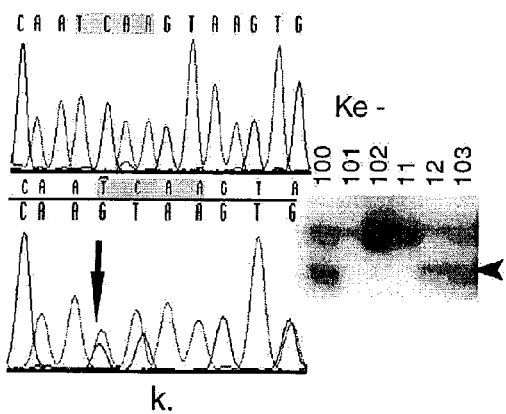
k.
1547 C→G
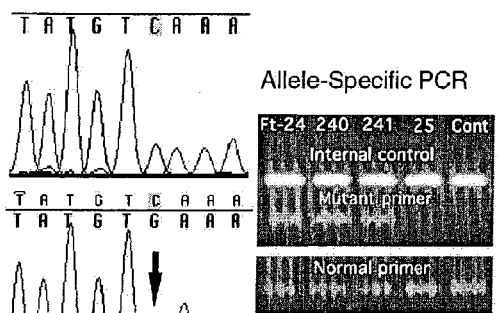
l.
1711 del GT
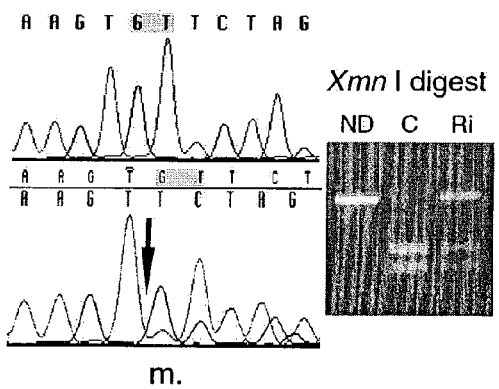
m.
Figure 18 c

FIGURE 19

DNA-sequence : human glomulin (VMGLOM) genomic sequence (SEQ ID NO 142), exons 1 and 2 (underlined) and intron 1 and partially intron 2

```
   1   gattttagca tcgaaactag gagaaataag aatggctgta gaggaacttc
  51   agtctataat aaagagatgt gtwwktatta atttttgtaa aattaaatac
 101   ctttcaaaat atgggaaggg cacagattgt ttttaattat atttgtkgtc
 151   actcaaattg tttatcttct ttaatccttg cttttttga cctgtaaaga
 201   gcatgagtgg gggaggcaga ttggattatt tctccaggtg acatacttat
 251   ctaaataacc ttttacattt taatcctgat cctttcata gatttcactg
 301   gtacrgtaga tttcaaggtc acttattaaa gtatttatta gtggtaatcc
 351   taattttgat acgtgtgtta tttacgttac atttatctag aatttaaaca
 401   gatttccttt tttcatagat aaatcaagaa gttattgtat ttaattttta
 451   tttgcatata ctttttttg tttgtttttt gggttttttt tttttttgcc
 501   agcaaatcct agaagagcaa gactttaaag aagaggattt tggcctattt
 551   cagttagctg ggcaaagatg catagaagaa gggcacacag accagctatt
 601   agaaattatt caaaatgaaa agaataaggt gcgtacaatc ttggtgttta
 651   cttttcagtc ttgggaagag aataatcaca tgatgctatt catccagtca
 701   tttatccatc aaacatttaa gaatctactt aaattttcac agtagggaac
 751   tgaaaacaaa aaagaatta gaaatattta ggccaggcgc agtggctcac
 801   gttcgtaatc acagcgttat gggaggccaa ggcaggcaga tcacttgagc
 851   ccaggagttt gagrccagcc tgggcaacag agtaagaccc tgtctcagaa
 901   aaaaaaaaaa aaaaagara agakacagtc atatacttga aggkttttta
 951   ccatctggtc amacataaac aatgtwaacm actwacaata ttgaggcaaa
1001   wtaatatwtk gctatagttg arkaaagagk ttttagrara acagaatwct
1051   tctggttwgg gggccaaa
```

FIGURE 20

DNA-sequence : human glomulin (VMGLOM) genomic sequence SEQ ID NO 143), exons 3, 4 and 5 (underlined) and introns 3 and 4, and partially introns 2 and 5

```
   1  ctggggtggc cgaatcmcgg ggtmaggraa acagrgccmw cmswggctwa
  51  cawkgggaaa ccccytctct rctaaaawaa aaaaaaaaaa aaggcaaaaa
 101  attagccagg catggtggcg grtgcctgta gccccagcta cttgggggc
 151  tgagacagga gaatgacatg aacccatgga agcaggagct tgcagtgagc
 201  tgggacagcg ccactgcact ccagcctggg cgacagagcg agactcagtt
 251  tcaaaataaa taaataaata agaatgtatt taactttaaa aaacagagac
 301  agggtctcac taggttgccc aggctggtct caaactcctg ggctcaagtg
 351  atcctcctgc ctcagcctcc taaggtgctg ggattagaga catgagccac
 401  tgcacccagc caaccaccgt gcttttaaag aaggactcta gaatgtaaac
 451  tctaggaggg tagtgatctt atccagtgtg ttcctcactt tayatttcta
 501  acctctcaga atattcatag tgtaggcttg cgtaaatmac tgatgagtta
 551  aaatacaaag caggccagag caagtggaat acattgttga tcctttgaga
 601  attagtggtt ttgataatga atgtgaatta gtcattataa agataaactt
 651  ttacttgtat ggtaagcatt ctgaaatatc tttgaacata gaagccactt
 701  gtatgtagga gagaaaatta atgaagttgt atcccttctt tttttataa
 751  attacaagga ttatatttag agactccaag aactttaaaa ggtacatgag
 801  cattggctgg atttctttat gaataagggg agcaaaattg tctgtggaag
 851  ttaagtacct gtattaagca aattaactct tttgttggaa atagaggcac
 901  tatttaaatc ttgggaaaca ccaacttgcc tgataaaaag taaagaccct
 951  tttgcctttc ctcagggaac atattaaaaa ctatttaaaa atgttgatgt
1001  ctgttagtag ccaaccctgg aaagtctctg gtgaaatgtc ataggcttca
1051  cttgtctcat cttcctattt cagaaacaat tctgagctct tccaagatag
1101  gaaagcacac tgcgagagtc ytatagatgg cagtgtttgc tttactctga
```

FIGURE 20 (CONTINUED)

```
1151  aaatgttttt acaggtcatc atcaagaata tgggctggaa tctcgttggt
1201  cctgttgttc gatgccttt gtgtaaagat aagaggata gtaaaagaaa
1251  agtttatttt ttgatctttg atttattggt aaaggtaagt taacaaaaca
1301  aggttctctt tatcataaca cacagcagta ttttactaat tcccctttaa
1351  tgtttattgg tttggtaaga wagcttttgg ttcatgaaag tacatgcaga
1401  aaggaactcg ttggagaaaa gacccagtct tattgattgg ataggcaatt
1451  ccatttcagg atttcccaaa ttttctggat aaaagaatt gtctaacctc
1501  atattaacct catatcggac ccattgattc agcatctcca gggagagacc
1551  tgggaagcta tatcttaaca agtagcctta tcgtatagat gtggaataca
1601  agctttagag aggtagttca aggtcacatt tatcttttgg caacattgga
1651  actagattaa aatctcagtc ctctttcctt tgtggtatgt tccctaaaag
1701  aaaatggaag gcctagaata caagtgatta aaattgaagt aggaataggg
1751  tagaacacag atcagttgtg actaacaacc ttagaaagtg accctgggta
1801  aaagggctag tagagtttac agtcaatatt tgatggccaa gaaagataaa
1851  ttctgaagga aaagtatatt ataagaaact gtttagtgat cagtgcaaat
1901  atacccaaat atatattgga aggagagctc catctgtatg agttattgac
1951  tatgggagct gggagctttt aaaaaaccag tcaagtgaga tgataagata
2001  tggccagtca gaaagcaatg caaagtttta cctgttcaaa aaatacaaaa
2051  gagattccag actagtctaa ataggcttgc agcatgggat tgaaaggtcc
2101  cacctgctgg agcccctgag aatctgttaa ggcaatttca gagtggacag
2151  gtgaagctca aaggaaacct gagcctaaag atccattgac ttcttgcttt
2201  ttagttttat agttacttga ccatcacaga ttctgtgttt ttgctcatgc
2251  atatttttc aacaattgta taaataattt taatrttaag caaaaacata
2301  attgtatwaa taktttgkcg rtatatgcct tcttaaaaat agtaataatg
2351  tggctttaaa tacaacttgk wttaaacagg ttcaattgtg aatattttta
2401  tagttatgca atccaaagga attattgttg ggtttgcttg aactgattga
```

FIGURE 20 (CONTINUED)

```
2451  agagccctct ggaaaacaga tatcccaaag tattcttctt ttgcttcagc
2501  cattacaaac aggtaatgrg aawtttgata tcagagtact tcttgttgta
2551  tctctaaatg ccttgatggk tacctcaaaa tgtcaatact acaccaaagt
2601  aaagtttaca gctaattagt gagtactctg ctyaaaccaa taatagcaat
2651  gccaatgtga atactgctgc tcatagaaag attatagtat ctggccagag
2701  tgggtaccca gtaaatattc tgttgaatgt catactattt ttcatgtgct
2751  atattgaaaa ctatacettt ttgcctaacc ttcctatctg ctgcttaaat
2801  ctagaatttt ctctctaaac atgtttcaag ggttacctct gtggtgtctg
2851  cagtrctaaa tctgatagca ttatggtagt ctggaagagt atcaggcaag
2901  gcattgctca gcctctgctt tgggaggttg gattgggyat agcaaagcta
2951  ctactgaaga atgaaacgag gagatatggg atgataaggc tccrtggctg
3001  agtgcagtaa cagtattggt aggtaatggg tcttagcaac caaggcagac
3051  agtatccata ggaagaggtt attttcatt ttaggaaatt cgtttatctc
3101  acartctgat agagggacct agaatcagaa attaaatttg ttttaaatat
3151  gaatgcctgc cagcttcata ctacctgtaa tattcagtct tctagggaaa
3201  aaaaatctaa taataccacc tcctatttgt gtagtgcttt atagtttaca
3251  atacacttat attttgygct tataacaacc caaaaacatg gaaagaacat
3301  gtttctgtct taagtacata gcctgttaca catagtctgt tataaacata
3351  acctaaacag catttcatgg caagatgctg tattatttta tgcacaacta
3401  agaagaaaaa aacactgcca attagactgt gatgtgtcat cttgattcaa
3451  gagttgttaa aatgtgggag gaggaagtkt cwtawaattc cacatttgcc
3501  gaatttcttg tcccatgttt agcatacttg atgagcgaca atttgatctc
3551  tgtttttgtg attcagaaac ttcataacaa ggcatattca attggattag
3601  cattgtctac cctttggaat cagctatctc ttcttcctgt tccatactca
3651  aaagaacaaa tacaaatgga tgactatggc ctttgtcagt gttgcaaggc
3701  cttaatagag ttcactaagc cttttgtgga agaagtcatt gataacaaag
```

FIGURE 20 (CONTINUED)

```
3751  aaaactcact ggaaaatgaa aagttaaagg atgaattact gaaattgtat
3801  agtataattt gtanagcaac atctcacagt ggnacttaag taatnngata
3851  gttcagtgna ttttatgttc tcttcacttg tgtttgacat gtaaatanga
3901  aatctagttt catgatttct gaatttatnn aagaatgtgg ggtnncagtn
3951  tgatacagnc atgggaactt gnagacatct atattttaaa aaattatagg
4001  ccgggtgtag tggctcacac atgtaatccc atncactgtg ggatgactga
4051  agtgagagga ttgcttgggg ccaggagttc tgaa
```

FIGURE 21

DNA-sequence : human glomulin (VMGLOM) genomic sequence (SEQ ID NO 144), exon 6 (underlined) and partially introns 5 and 6

```
  1   aaaagtgggc tgaacttgcc cttttataac agcattaatc tcatccgtga
 51   gagtggagcc cccttggcct aattcccacc tccttatggc agttaaattt
101   caacatgagt tttggagagc agagtcattc aaaccatagc agtgcttatg
151   ttatttttca agtaaaatta acttatattt caagacctag ggattttata
201   cttggaagtg ttcatttcat agttacctat ttcttatgcc ttagttgttt
251   caaaagcttg aaatgccctt tgctgacagc acaattcttt gaacagtctg
301   aagaaggtgg aaatgatcct ttcaggtatt ttgcatcaga aataatagta
351   agtacagcta atttaatctg ctataatctt aaatgtnatc ccactatatt
401   ctcagtactg cacatgtnaa tngcatacat tcattaatnn ngnnntgtgt
451   atttnnngtn gaacacacat aaacannnga tggnnaa
```

FIGURE 22

DNA-sequence : human glomulin (VMGLOM) genomic sequence (SEQ ID NO 145), exon 7 (underlined) and partially introns 6 and 7

```
  1  aggagtgatt acacctcccc ttggtgagaa tgtggagtnt gaatacacgg
 51  ggtgggggc atntnagagt cagagagcta tggtttccnn nnnnatccat
101  ntcataggt tttttatcag caattggaca ccctttcccc aaaatgattt
151  ttaatcatgg aaggaaaaag agaacttgga attaccttga atttgaagaa
201  gaagaaaata aacagttagc agactcaatg gcttctctgg catatctagt
251  atttgtacag ggcatccata ttgatcagct tccaatggtc ttaaggtaag
301  agttagtgtt tggtttattc atgtattcta aaaggaattt cataaaattc
351  tcatttatct aatgtccaat atatgcatat taacacacta atacatttta
401  aataaatagt aaaggctatt tttaataaga atgatcccag ctataatctg
451  ttaaagatag cagtagacaa gtaatgaaag tggggagtgt tgaaataggt
501  gtaagggaat ggtggggaca agaatcagaa gatgataaac agggcttggt
551  tttgaagctt ttgagaccac cctggaacta gccaggtacc cagggggtatc
601  atcatctttt cactggatta ctgctgtaat cctgagtgga tttatatatc
651  tacttttact tccttttaat ttaacacatt ctcaacatac cagaaagcga
701  agcgcttaaa agaagtccct tactgtacct cagggctt
```

FIGURE 23

DNA-sequence : human glomulin (VMGLOM) genomic sequence (SEQ ID NO 146), exon 8 (underlined) and partially introns 7 and 8

```
   1  tgaaataaca gaaatagttt gtctcatagt tctggatgct ccttctgagg
  51  gttgtgaagg agaatcttct ccatgcctct ctcctggctt ctggtgattt
 101  gctcacaatc tttgatggtc tttggcttgt agatgcatta tcctgttctc
 151  tgccttcatg ttcgtatgct gttctccctg tgtgcttgct gtctgtctcc
 201  aaactttcct tttacataag gacaacagtc atattggatt agggcccacc
 251  ctaataatct cattttaaat tgattacctc cataaccctc tctccaaata
 301  aggtcaaatt ctgaggtact agaggttagg actccaacat atcttttttg
 351  ggggagatac aattcaaccc ataacaatat gtatgtgtgt acatatctct
 401  gtgtgtgtgt ataatatgta tatttgtttt gtttctattt tagcccattg
 451  taccttttgc agtttaatat ggggcacatt gaagtctttt tgcaaaggta
 501  agatcgttta tgatggtatc tcaaaatgaa atagtatgtt aaaatagtcc
 551  ttgttaagat cagcggagac tgccttttct ttgctaagct ctaattaatt
 601  aattggttat tttataaaac agcgaggcaa ataattcacg agagagacag
 651  aaatgagtca aggaggtttt acaccaaagt ctgtttatt  ttaaacttaa
 701  gacagtatta agattttgtc ttaagggctt ttacagtcat ctgtttctaa
 751  ggtttcttct cttattccaa aagttggtaa attaaaacac ctctacccca
 801  ctgcatcctn ccttccatnc ttaaggaagg gcagtcaata aaagaagtnn
 851  cttccgtatt ttttcctnna tggacacagt cctgtgaatt gcatctaaag
 901  gaaggagngt gtcttgnact ttccatcctt nttnataant ttannnatnt
 951  atnngnatcn nnnngnatng tccantttc  anaatgtgag ccaagcntnn
1001  ttttgcgtgc anntnnnttg nangagnnnn nctnannagt cagtncacng
1051  nnncntnttc tgantnnnta gaanctgcag catctcgtct aaanaagtcc
1101  nngngnncan tncggnttag ngnnnntaca tatnngnncn ccnnngagtn
1151  nataagttgn tctcntncn
```

FIGURE 24

DNA-sequence : human glomulin (VMGLOM) genomic sequence (SEQ ID NO 147), exons 9, 10, 11 and 12 (underlined) and introns 9, 10, 11 and partially introns 8 and 12

```
   1  tgntctatca tctnnggagc gatcgtgtcg cgatcggttn gacgtgtata
  51  tngtatgnga nagagttaga tnanatcata cattgttngt atancgnata
 101  tagtatgtct gattagtcta atctgagann naactgnnag tcannagtct
 151  tttnngnata taaagaattg gaaagatttt acagaataat caactggaat
 201  atatagcatt ggttatatca ggtttagtta gtgtcttagc acttgctgtt
 251  gaagatctat tgttttgaag ttaggaaata atccctgagt agatttattt
 301  tggtcagatt tagtggcctt agccaaaccg aaagacagat caaagatgga
 351  ttaaaacttt tgatcaagtt cttctnacag aatttctcct taatgatatg
 401  cattttaaca agtgttaaaa tttcagtttt tgctgtattt ttcataagat
 451  gtaagtatca ttctaaaata gtttaccaaa ttcatgnata aatttgtcaa
 501  tattattttt ctagtaacag aagagtctgt tatctccaaa ggattggtna
 551  gcatgtttgt tcccattata acttaaatac atagttatgt caacgacaat
 601  aacagctgtt gacttcacta tcatagtatc tgcatatatt ttaatctgta
 651  ggagctgctg gagaatagtt tattgagaat agaagacaat agtctacttt
 701  accagtactt agaaatcaag agttttctta ctgtacctca ggtaaataaa
 751  atatgtattc taatattgaa aatagcccct tgcctgttct gaacttaaag
 801  taaggtcttt tctgattcct ttcccactct tttctctgca acctttgaaa
 851  actctggtgt aatgctgtcc agtagaactt tgacaatatg aaagccacta
 901  gccaaactga acacttgaaa tgtgactaag gaactatttt ttttttttg
 951  aggtgtagtc ttgctgtktc gcccaggttg kagtgcagtg gtgctatctc
1001  agctcactgc aagctccacc ycctgggttc attccattct cctgcctcag
1051  cctcccgwgt agctgggact acaggygccc gycaccacac ccagctaata
1101  ttttgtatt tatagtagag acggwgtttc actgtgttag ccaggatggt
```

FIGURE 24 (CONTINUED)

```
1151  ctcgatctcc tgacttcgtg atcagcctgc ctcagccccc caaagtgctg
1201  ggattacagg tgtgagccac cacacccagc cggaactaag tttcaaattt
1251  aaatttaat  ttatttaaac acgaatagct attagaggcc accattattg
1301  atagcacagc atccagtaga aaagcataac tttcttcttc taacacttta
1351  tttctgtagg gatcttggwa aatgaagctt ctttatgttt ctcataactc
1401  aagttctcag gwctccatct aaggyatcca ctgactcatt accagaaaga
1451  ctaatacaca ttgtgttttt ccctcctatg gtttattttk yccaawcctc
1501  tttgttagtt atgwtatcca aggwaatcct tagatttcag tgtgggaact
1551  ggttttccta atatttaaat agaaaaacat gkttttttgtt aacatattgt
1601  ttgattgttt tttaattaat aaattatatt tctgtagatt tgatttcatt
1651  ttcttgccac tgtagacata attgaaaatt atcgtttgct tttaaaagta
1701  cactgtgtga cactctactc aatatcactt aaaaaatcaa ttgtagttag
1751  ctttctggaa tggaaggctt agggaaaaat taatttactt cacttttaaa
1801  tctcctaccc tcacttctct gaattttag  tatcctattg atgtattata
1851  gttgtttgtt tgcagtcagt ataatctgtt tacatctgaa ttttacattt
1901  ttttatttcc agggcttagt gaaagtaatg acactttgcc ccattgagac
1951  actggtatgt aaatatttgg tgactaaaga ataatgagtt acagtgagaa
2001  aatttgacaa ataatttaat tttcttttta aaaattttaa tttgtgaaat
2051  ttttatttag gaggtacaag tgtggatgta ttacatgcat aaaatggata
2101  gtgatgaagt ctgggtaagc tttattcatt ttatataata atattgtttg
2151  ttccattta  gaggaaaaag agtttagcta tgcttcagct gtatattaac
2201  aagttggatt cacaaggcaa atatacatta tttaggtatg tatcaagcat
2251  ggctaattgc taagtgtgtg gttgattaaa aagtcatgtt aatgccatgt
2301  aattgtttta gggcatagta tgtcggtatg ttttacatgt aattcaactc
2351  tggttggaac ccatattata aattctcagt gatggctaga gaaagggtta
2401  atcaaatatt tcagacatac tatatatatg tctatatttt gtatgactaa
```

FIGURE 24 (CONTINUED)

```
2451  tagtatatat tgcagttcaa tcaattggga tactctaaat ttgaaataga
2501  cttaaaaaat aattaaactg agattgatga tgctcctgct ggaaatttat
2551  gtatgtcact aatctccatt actcacagtt caaattgatg gctctggaat
2601  taaaactttg ataggctatg aactatgtta atagtaagag cttactaata
2651  ctgctctttg aggtggataa gattctagaa actctctaag ttaaagattg
2701  gtaaactttc taattaattt tctgtgaaga gcaaatagta aatataggtt
2751  ttatgggcta tacagtctct gttgcaagtg ctcaaacttt gactttgtat
2801  tggggatggg tgtgttccac gtaaactcta ttgataaaat tagggcaatc
2851  aggctggatt tgctaaaatt gtcttacctg gggattggcc aatattagaa
2901  ctgttctttt ttggcgggtg aaaaggtgtg atcatggctc actgaagcct
2951  tcaccttggc cccccagctt aaggtgatac acc
```

FIGURE 25

DNA-sequence : human glomulin (VMGLOM) genomic sequence (SEQ ID NO 148), exons 13, 14 and 15 (underlined) and introns 13, 14, and partially introns 12 and 15

```
   1  taactgggac tacagggcat gccatcatgc ccagctaatt tgtttgtgga
  51  gatggggttt tcccatgttg cacaaggctt gtctcaaaca ccttggctca
 101  agcgattcac ccacttcagc ctcccaaagt gttgagatga cacgcatgag
 151  ccatcatgcc cagccaacac tcttgattct atcttttctt gttttctatt
 201  gatagtaaga gcaagtttat gaaatctcaa ttcttaggta ttataccggc
 251  tttcctgttc tgttctatgt gtatctctac caataaatcc ccttttttt
 301  cttaagctag tcatatctag tttttgttt ttttttgca attaagctac
 351  tctagcactg gactactttc acaggaaata atttggggat tttttagacc
 401  attatgttag tgccctttct tgccatgtta aattattgta actatgttca
 451  taaaaatatt caaattttgg tttgatagaa atggcttgtt ggaagatcca
 501  gttataaata agtatttacc ggccgggtgt ggtggctcat gcctgtaatc
 551  ccagcacttt gggaggctga ggcaggcgga tcacgaggtc aggagtttga
 601  gacaagcctg gccaacatgg tgaaaccctg tttctactac aaatacaaaa
 651  aattagccag gcacggtggc gggcgcctgt aatcacagct actcaggagg
 701  ctgaggcagg agaatcgctt gaacccggga ggcggaggtt gcagtgagcc
 751  aaaattgtgc cactgcactc cagcctgggc gacagggcga gactctgtct
 801  aaaaaagtaa aataaataa ataagaattt accatttagt gagagcaata
 851  actattacag gtgactttgt aattggttga tgaccttgct aattaccatt
 901  actgtggggt ttttattcct agaagtaaca catggcctct ttgaatttgt
 951  aaaactttta tcaccattta attctaatgc tgtccaggat aatttcacat
1001  ctattgtaat tttgctttca aggtgcttat tgaatacaag taatcactca
1051  ggtgtggagg cttttattat tcaaaatatc aaaaatcaaa ttgacatgtc
1101  attaaggta agaacatagc caagtgtca attaccaatt tatttcgtag
```

FIGURE 25 (CONTINUED)

```
1151  ggtatattta ttcatatgta gaatacatta atgtgagtta ttgctctatc
1201  tctagtatta ctattactta aatattatta aggcatattt ttccccctat
1251  ttctactatg ttttaaaaac tctgaatttg gaaatttagt taactataag
1301  tttaaattgt attctttgag gttttggttt ttgttttttgt ttttttttgag
1351  acagggtttc acgcctgtca cccagcttgg agtgcagtgg catgatctca
1401  gctcactgca gcctccacct cctgggctca agcagttctc ccaactcagc
1451  ctcccgagta attgggacta caggtgtcca ccagtgcgcc tggctgaatt
1501  ttgattttgt agagatggag tttcactgtg ttgcccaggc tcgtcttgaa
1551  ctcctgagct caagtgatcc acccaccttg gcctcccaaa atgctgggat
1601  tacaggtgtg agtcatcact ctgggcctct ttgagctgat attgtggctt
1651  attttttgctt tgttatatgc ttctcaaaaa tgaatggaaa cttaagtctc
1701  ttctgtttct gagtgctcag taattctaaa tggaaaacag agtgaccagt
1751  gttctcaaac tggcagggtt cattcctggt gtctggaaag tgaatgaaag
1801  tacggaaatt aaagttaaaa actgtatttt aaatgtgcaa ttcttcrttt
1851  ttgtagtgtc aaggtattag aaaaacacat kaattacatg aattataaag
1901  ctttctcaat ttttcgtttg cttttcagag aacacgtaac aacaaatggt
1951  ttacaggacc acagttgatt tcccttcttg atttggtact ttttctccca
2001  gagggtgcag aaacagattt actgcaaaac tcagataggt kkaggtgacc
2051  attaccaaag ttcacatagt aaattcagaa taaaatgtga acatctgcc
2101  ttagggaacc taaagtaata aaatgtcttt tcctgtgatt ttatgatcta
2151  tggctaattc attaagttac ataaagattt ttcatattta agtgatttga
2201  taatgtgtag aaacaaaatt aaaacctcct ctttctagat gaatgaccag
2251  cactatgatt tgatagcttt tatgtaccca gcattccata gaaatttgca
2301  atgacagcac ttgtgactta aaactaaaaa tctgtgtatg taatttatgt
2351  gtttaggttt tgttgttttta ttgttttttcc aggtcatttt ttttttccat
2401  ataraacata taatttcagt tttacagtat actgngaatg gatattgara
```

FIGURE 25 (CONTINUED)

```
2451  aatggttnta aagcatttaa aaagtaatct taaaattcag aaagcaagag
2501  atgatgctct caaatattaa agataacaag gctttcttta aacaaggatg
2551  ataatttyca caattgtatg atttaaacaa atggaaaaca gtgataagtk
2601  atyactactc aaaagatat taatgsaaat agtttctatt ggcaaaccta
2651  attataaaaa tatgaccaaa gttttagctt attgagattg ctgttgacta
2701  tataaaacca tactgtagta acatatattt ttaattaaca gattatggct
2751  tcattaaatt tattgaggta tttggttatc aaagataatg aaaatgacaa
2801  tcaagtaagt gaagtatttg aaaagaaact gtgagtatat tcaaaaggca
2851  taaggaatgt ttcagatatt cagtacctaa agccaatatt taatatctta
2901  cccagatata aaggccggga agagtgccaa caattattct gaaacctgaa
2951  gttaattccc aggagcattt accacccac atccagcttt cctttccctt
3001  tccatttcct attgtacgtc tgctttcttg ctgaaagcac ttagtccgt
3051  tgggtggata agttgcaggt cctaagtcaa ctaaccttgn tggagctcaa
3101  cgtacatatg gtgtcttgtt cagtttcctc cacctatagc tcatgagctg
3151  tataaaatca tctgatattt taatattgcc tcatcagaca tgacaaattg
3201  aagcatt
```

FIGURE 26

DNA-sequence : human glomulin (VMGLOM) genomic sequence (SEQ ID NO 149), exons 16, 17 and 18 (underlined) and introns 16 and 17, and partially introns 15 and 18

```
   1  atcttcacct actttggtca ccagggaggt tcaaattagc cgggtattag
  51  aaaagtttcc atcagtagga aagggaaagc atcctctaga actagatccg
 101  tggtgtggat atcaattgaa aggccatact tgggatgaag gcataaataa
 151  ggtagagtca ttgtggagat ggctcataga ggaagagacg tctgtgaatt
 201  tatcctcaaa taattttctc ataaataaaa cttaacaagt taatagatct
 251  caaaacctgg agctatccaa atggtgcagt gataagcgta gtgcccaag
 301  tacatttttc ttttaattgg tattcacata actagctata gtaataatta
 351  ttaaatagtg aagtccattg tgaaaagcaa gggccatgtt tcatttattt
 401  ttgtttttg agcttttatc gcgtttaata gtaggcaatc aatcattgtt
 451  gaactaaata actcatcttt cattcttaac agactggatt atggacagaa
 501  cttggaaata ttgagaataa tttcttaaag ccacttcata taggacttaa
 551  tatgtcaaaa gcacattatg aagcagaaat taaaaatagc caaggttggt
 601  aatgtgcaat tttgttttca attaggtcta aaaagtagtc taattttgga
 651  actgtcatat tcaaatttaa gaactttta aaaatcttgt actttagaag
 701  accataacag ctaagccatt ttatttatag ttaaaattct tagcagatct
 751  ataagctaat ttacctaaaa tcgggttaat gaagacttaa accaaatatt
 801  acattgtama ggccttcaag gtctgattaa gaatctgtat tacagctatt
 851  tccgtttggg taccattcct ttggtattgc tgggtccact ctccatctca
 901  ctctcaagta aatccataca aattatgaaa agwatcttag atccagaatt
 951  tttttaagtc aataattcta taataatcgt gtgatctctt ccgtatatct
1001  gtggtggtgc ttttataggc attaccggaa attttgtttt tagtataatg
1051  gctataattc tgattatata ctgaagaaaa cagtttcatg aatcctatac
1101  atgccaaaat aatgctattt atctaaagaa gcattaattt acatgttgca
```

FIGURE 26 (CONTINUED)

```
1151  gaattttgat  atttcattct  gtttgcttat  agcttaagta  taccctgagc
1201  tgttaaacaa  tggacttaat  aatttataca  ataactgac   atgttttaag
1251  ttagtgaatg  aaagtagctt  atacctttgt  tattgaaatc  tgagagttaa
1301  gtgtcacaca  tgatttgttt  ctcttatcag  aggcccagaa  atctaaagat
1351  ctttgttcta  taactgtaag  tggagaagag  atccctaata  tgcctcctga
1401  aatgcagctt  aaggtgatct  gaaattttct  tctttccttt  ttcttcttta
1451  gaaacggggt  cttgctatct  gcccaagct   ggagtgcagt  ggcatgattg
1501  tggctcactg  cagcttcaac  tccctgggct  caagtgatcc  acccacctca
1551  gattcctgat  tagccaggac  tgcaggtgca  caccaccatg  cctggctaat
1601  ttttagtaga  datagggtct  cactatgttg  ctcaggctgg  tctccaactc
1651  ctggcctcta  gtaatcctct  cagctcagcc  tcccaaagca  caggaattac
1701  aggtgcaaac  cactgtacct  ggtcttaaat  attcctaagc  tacctccagc
1751  tgaaatcttt  tctatgtttt  gctttgtttt  gctttaaagg  cagcattaat
1801  aacattactt  tttcttggca  ttgcaggtcc  tgcattcagc  tcttttcaca
1851  tttgatttga  ttgaaagtgt  tctagctcga  gtggaagaac  tcattgaaat
1901  aaaaacaaag  tctacctctg  aagaaaatat  tgggataaag  tgaaagttcc
1951  atttcctaaa  taaaaacta
```

FIGURE 27

Human genomic sequence : partial promoter, exon -1, intron -1, exon 1 and the beginning of intron 1. The exons are underlined. (SEQ ID NO 150)

```
LOCUS       around E(-1)-E1   2000 bp
DEFINITION around E(-1)-E1, 2000 bases, 9298 checksum.
ORIGIN
    1 cacattaggt acaagataga ttcctacaca aataacaaac tgtagaccac
   51 cttttcttct tttccacata ttttatgtcc aatcgtgtgt aaatcaaaat
  101 gaaataggaa gggagagcaa tttgtttttg caaattgatt actgtctaat
  151 ttttcttggt taaaatgtat ctctttgggg attgaatttt cttctgtatc
  201 atagttgctt aattaaccac tcctgaaaat ctgagatctg ggtactttta
  251 ggggaaacct ctctccgtct gccaaacgtc ctctctgggg gaagagggga
  301 gtccggcacc ttaaagaact gggcacccaa gcaatctgga aaggaggacc
  351 ggtcctaggt tcaaggccag ctgccaacgc tgccctagtc acttgccccg
  401 aaacccgggg accccaggcc tgggttcccg gggcctccac tgtcctttgt
  451 ctcagaggct ggggccacag tccgcgtgag ggaaatcttg aacactggc
  501 gtaaagdggt gaggggcggc caggaaatct ttcccaggag gtgcggacgg
  551 cggtgggaag ctttcggcct actctacctg ggagaacccc tcccctgaag
  601 cagcctttca ggagcgcccg cgcgctgcgg tctataactc gagatcgggg
  651 cccagctttc agggtccaaa agtgggaaga gatccttgct cctacctgcg
  701 gcttttcgag agcagcgggg agcccggcc ttgcggccgg cagaagacgg
  751 cccagcgaag tccgccatgg gggagagtag tctgccggac ggggacacgc
  801 tccggcgtct cgccccgagg ccccgcctcc ctacgcgtag cgcggggcgg
  851 ggccagaaga gcgggctaag acgccggagg aggtggcggc ggctgggaga
  901 ggcgagggtt ctggccggta agtggagttg tggagaggtt cagggtggcc
  951 agggctcgcg gttggccgtg agccgcggcg gacttggtgc tgcgggccga
 1001 ctaggccacg cgaggtggtg gagcctgccc acctaggcga gcaggaatcg
 1051 gaagacatgg cttcctctga tgcagcccgc acgcgcgctg gggtgttcac
 1101 tcgccttcca gcgcgctgcc ctgaggaccg ggctgactcg cgccctact
 1151 gagggcttgg ggccgagcct tgccgccagg agaagcgatg gtctcctcct
 1201 gaaggccgcc gttgtcttgt ctccgtgtga tacagtgatt tcactagctg
 1251 gattgatcac tttggggact gcaactccta gagagaaatg aatggaggg
 1301 catctgaatc ttcaccccct atagataagc ttgtgttgca ccccaatttt
 1351 tgtgaggtga gacattaaaa atgaaaaatc cctgatgat tagaattttg
 1401 atttcaggtc cacctttgg aaatttttt tcagaaaaga agtgctttgc
 1451 tttttaaaag ccctttagtt cgtatatgcc tcgcctcttg ggagtgctcg
 1501 agaggttttt tttgttttt tttccttcaa agtagctttc aaaactatgc
 1551 tcctagaaaa cttaaaacat gcaataaggg cttctaaaaa aacactttat
 1601 tttcttaggc aaacatacta agattcagta ataacatttc aactttaaaa
 1651 ctttacattt tctcctagca tgctattgga ccaaaaaaca caacaacaaa
 1701 aactttccat tttctttatt gtatttacta ataatttatc acactgaaac
 1751 ataacttttg aatacttaag tgtaatatca cggatagtta acagtgtgtt
 1801 ttgtatttgt agatttagc atcgaaacta ggagaaataa gaATGgctgt
 1851 agaggaactt cagtctataa taaagagatg tgtaagtatt aattttgta
 1901 aaattaaata cctttcaaaa tatgggaagg gcacagattg ttttaatta
 1951 tatttgtggt cactcaaatt gtttatcttc tttaatcctt gcttttttg
//
```

FIGURE 28

Mouse genomic sequence : promoter, exon -1, intron -1, exon 1, intron 1, exon 2 and partial intron 2. The exons are underlined.(SEQ ID NO 151)

```
Contig[0064]
Contig[0064]  Length: 10934  Mar 27 juin 2000  10:48  Check: 5143  ..
    1 ggatccactc acagtcttct gtactcctcc aaagggcttg gktcatttct
   51 ccagctctgc actctgtagc acatactgct tgccttcagg ctggctctac
  101 tccactgctg ttgctgtccc atggtagtct tcccacagta ctggcatctc
  151 tgaaacactg gggtcttcta ctgcaactga gatgcacttt caccaatagt
  201 ccctcatggc tctcttcctc aacttctttg catgatcctt tcagtcttgg
  251 gctgcacctt caccgatggc ttttcctggc atcgcacagt gccaaacctc
  301 agctgttctt catgatccct tcatgtcttc aaaagcagta ccacctgggt
  351 gactctggct gccagtacaa ggtacaacca tggtcaccta tggaacacag
  401 cttccctgtg ctctcaggaa acacttccca gaagatttt atctcaataa
  451 tgttggtctc ttcttgatca ctgctaattt ctcagctcca gctgaccagc
  501 atcaagtatc ccagcaaagc aaaggcttca atttagtagt tctgagctct
  551 tgttaaatca cagctggttc tttagcccca cctaaccgga accacagaat
  601 cttaatccaa aatagcaaac ggccagagtc ttaaaacttc acaagccagg
  651 cctcactgtc tgcactgttt tcaacactct tatcttccaa gctcccaaag
  701 atcatccact gagctctcag ctctcaatgg ctttttctag cccaaagttc
  751 caaagtcctt ccacaatcct ccccaaacca tgtctgccat agcaaataca
  801 ccactatggc atcagcttgt ctatttttgt tagtcagggt tatcagttct
  851 gtgatgaaac accgtggcta aaaagcaaac tgggaagaaa atggtttatt
  901 ctgcttgtac ttycacattg ttgatcatca cmaraggaag tcatgacagg
  951 aagtcaagca gggctggaac ttggaggcag gagctgatgc agaggccatg
 1001 gaggagtgct gcttactggc ttgcttcccc tggcttgctt ccctggctt
 1051 gctcagcctg cttttttgta gaacccagga ctagagccca gggatggagc
 1101 cacccactgt gggctgggtc ctctgcatgg aggcgtgtcc tcagctgagg
 1151 cttttttcctt ttcttctttg acttacctgt tctgtttcct ctggtccttt
 1201 gtctgtcaag tcaacaaaca aaatcagcaa gtacaatact catatacaca
 1251 aataaatctt taaatatata tattctatt taaatctggt agtctgacca
 1301 ttgaacacgt acacactcct tcaggaattc ttctgtgatg ttctcctcta
 1351 agagctgctc tacgatgcgc acagctttcc tttcaaactc caccttcctt
 1401 tgtatagcag cttccagttc tgcttgcctg aaatttttaat gagaaagtta
 1451 acccaattca agacttctcc taccttcaac actccatgct ttaaaagcca
 1501 cctagtggcc tactattttg ccaataaatg agcttttaac tctccacctc
 1551 tgatccaata cttttttggtc ttcccagtgt gtacatggaa gctggccacg
 1601 aggacttact tctaggctca gagaacaagg aaacacttat agactccagt
 1651 agaggagggc tgggcaggac atggtggtac atgccacagt tacacacttg
 1701 ggaggaggca gtgggaagat tcagagtcta aggcaagtgt gaactacata
 1751 aaatgaagtt atattttaa aaagagtat atatataaat tttataacaa
 1801 aatttatata tataaattt ccttttgtag ttttgccata catagtaaaa
 1851 aaaatttttt tctctgtcac ataagtaaac agaatgaagg gtgaagagat
 1901 gatttctact ttctttcac tcaaaaaatt gtcaacagcc tagttgtggt
 1951 agctcagctt actagaacag ttatgtctga aaagaagagc agcatttct
 2001 caccttcatt ataaagtcct actaaataac tatcctgata tgtgaaatgc
 2051 agtcgaggaa cccttgccat agccaccacg ggtcccatca gtgctctgtc
 2101 cccccccactc ccccaacaca cacacacaca cggaaggcaa aaatcgaagc
 2151 tatctcagga aacagcctca ctgagctgca caccaagaac agacaccatg
 2201 cccaggtccc acaacaggcc cagtcaacca gaataggaca gaagcacaga
 2251 aggagattc actgtcacgc tcaggataca gtgctgtggt gacttactcg
 2301 ctcttcttct aggttgggac ctaccagaac tacctctgtt ggtcaccagg
 2351 tcttacccctt ctctctcaca tctggaacct agaaactttc atgtgttcac
```

FIGURE 28 (CONTINUED)

```
2401  gtgaaggtag gaaccttcat taacttttga gactttagac tctcgttctt
2451  tgcctagagc aatatgtccc ctcccaaccc ccataacttg ggactctggt
2501  acagattcac caacaattct tttttgcaaa atacatgaaa gtgagaagtt
2551  tgcaaccaaa cacctatttt tatcccatca agatcatttt attgttactt
2601  taagataccg gggctagaac ccagggcctc gtacatgcta agcaagcact
2651  ctactactga gctataacca ctaactccat aaagaccact tttgtatcaa
2701  agaaagtaaa aagatatgaa cacagattac attacaggtc tttatattaa
2751  atacgaaaag cttcatgaaa ataattttt ctcactttat gcccatcaat
2801  aaaggtgata tcatgtacta agatttatat acaatttgct ggctccaatt
2851  atcaagcaca ctgactgttt aaccattctc ctgactgaca gatatctaca
2901  gtaccttact atgttctctg tctgtcacaa atgatgcag tcaataatgt
2951  tgtcctggca gttttacatc aaactgacac acactaatgt cactggagag
3001  gagggaacct taagaatgcc tctatgagag ctcatgtctt tagctgcata
3051  tatagcagaa gatgtcctag tcagccatca ttgggcaaag aggccccttg
3101  gtcttgcaaa ctttatattc cccagtacag gggaatgcca gggccaagaa
3151  gtgggagtgg gtgggtaggg gagcagggtg gggggagggt atagagaact
3201  ttcgggatag gatttgaaat gtaaataaag aaaatattta attaaaaaaa
3251  aaaaaaagaa tgcctctatg agttctagct acaggcaagc taaagagca
3301  ttttcttagt gattgatggg aaggacccag cccatttgtg gatgatgtta
3351  tcctaggggc ttatgctgta tgaaagcagg ctgagcaagc catgctcaac
3401  aagcccgtaa ggagcactcc tccatggtat ctgcatcggc tcctgcccca
3451  aggttcctgc cctgcgtgag ttcctgacct gactgtcctt ccgtgatgag
3501  cagtgatacg gaagtggaag ctcagttctt gtgagcaaaa ccgacttgtt
3551  caacaacaca tcctaagggc ctaactcaaa tacagacgat cttgtatttg
3601  gaaattatct tgcaagaaga gtcggtgagt cctgaagtga tgaatgttag
3651  tctcttcaga tgagtttgc tctagctatc tcctctgtga cacgagaggc
3701  catgactttt tggaagctct aaactgtaaa ggatgctttt ggttggtttg
3751  tttttaagtt cctatttaac gttacaaaga agacaaaaac aaaataaaag
3801  aaaacaaaaa aacgggcagt ggtggagaac ggttttaatc ccagcacttg
3851  ggaggcagag gcaggcggat ttctgagttt gaggccagcc tggtctacag
3901  agtgagttcc aggacagcca gggctataca gagaaaccct gtctcgaaaa
3951  accaaggggg ggggggggag gggaaagaaa gaaggaagg aagaaggaaa
4001  gaaagaaaag aaagaaaaaa gaaagaaaa acaaaacaac aacagaacaa
4051  aaaacccaga agacaaaagg tgccttgaag tgataaagaa agaacctgct
4101  tcagcgagct tggcacatac aacagtaata gtgtacctga agaaatggga
4151  aagattggtt aattcaggaa ctatgtcccc agaacttct acaggtgttc
4201  atgatagttt ccaacagcct aagcctccac attggttttc ctacagctga
4251  aggacagagc agtcttacgt gagaatcgac agtgcttcct gagtcttcag
4301  tattttctca agaaaggtat gcactatgct tttaaactat ttgggctgga
4351  gtatagctcg gtaaattaga caaagagctt cattagaatg tacaaagtct
4401  ttaagttcaa ttcccagatt gcaaaaacag aaaacagaac atcaaaacaa
4451  aaaaaccaaa accaaaaaga aaaagaaaa aaaaaaaaa aagaaaaaa
4501  aaaaagaaa agaaaaaaaa aaccaaatca gattgaatta atgagataaa
4551  agcaaagtga aatgcagatg cccacgtggt tctacctttt agatgcatct
4601  cctcgtttca gggctcgggt ctgtttagta cctacaattg aagagagaaa
4651  agtcaagtgc caatgcattt gatgtagcag agtagtcccc aaatatcaca
4701  ctgtaggcac catttccttt tctctcacac atctcatttc caacttcgat
4751  gtgtacaaaa aaagaaaaac aaccccccccc cagaaaaaca aaaacaaaag
4801  gggggctaa acaggaagca aattcaattg tttctgtaaa ttaattacat
4851  tttacatttt catgacggca gttcttcgag gactcttct catataccgg
4901  atgcgcttta atcaagtgct tttaaaacac tctctaaact gggttccttt
4951  agaataaaca ttgctcagtc tcccaaatgt tgttcccttt gcctaaagag
5001  aggagtctga gacctcagag accagatatc aaagcaatcc aaggttcaag
5051  gcaactgacc accacctgcc ttggccactt gttcccacgt acgggtagat
5101  cctaaaaccc ctgtgtaaga gtgtgggatt cctcccccga aggcactagg
```

FIGURE 28 (CONTINUED)

```
5151  acagcctgcg ttgggaagct ctgggcctca tccacccgga gttctcgctc
5201  tccccggcgc agcctcagaa agaggtccgc gcgtgcgtgg tactcaaacc
5251  aaggtctcag ggtcccagcc tgggacggtg gctcttgttc gtaccggtag
5301  catctcggtg ggtgctggaa gcccgggtac ttgggcctag agagcaaggt
5351  acggcagagt cagccatggg gaaatgcggt cagaagaggg ggtcgggaca
5401  gcacatctac ctcctcacgc ttcgcccgga accgtgtggg ggcgggccca
5451  gggagggcgg ggcgagcggc ggaggggggcg ggcccagggc ggggcggggc
5501  gagcggcgga gggggagggt ccggtccggg ggcggggcca ggagtgcggc
5551  ctgcgctacc tgaagtggag aaggaggagg aggtcaagag gcaggcgcgt
5601  ggatcggcgg gtaggtagac atgctaggtc gggcggatcg ggctcgccga
5651  acaggacctg cgccgcacgc ggctctcctg ctcggcctct ggaggtgctg
5701  gagcctggac accctgccct gcaggagcag ggagaaatgg cctcccttcg
5751  cctcagccag gcgcggtagg gtgtgatttt cctgttcgcg cctgcgggc
5801  aaggaccttc gctgctggcc tccttttcgt gatactcggt gatctcactg
5851  acgattgttt atgtgaggag ggagatcctg tggagaatgg ggtgggcggc
5901  atcggaatct tcaacttctt tgggtgactt aattatgttg gattccagtt
5951  tttgtcaatg ggacatttaa aaaaattact taatgattag atttttcatt
6001  ccaggtccac aatttggatt tttgttttcc ttttaaacaa aggcttttct
6051  agtagttctt tctagggctc tttttatttt tttactcgtc attctttaaa
6101  aattacttc tttaggcatt atatcagggg cttttaaaaa tgcttcatta
6151  ggctaacaca gtaacgttca gtaatagcag ttaacctata aaactttaca
6201  ttgtgtttgt tgtcttgtct aataattcag aatgaaacgg tttatgaaac
6251  ataatttaca tggtatcaca caattaactg ggttttttg tattagttca
6301  ttacagcatc aaaattagga aaataattag gaatggctgt ggaggaactt
6351  cagagcataa taaaaagatg tgtaagtact tctccgaaaa cacctttaaa
6401  tatatgggaa gggcatagag tatctttact ttgtggtcac tcatgttatt
6451  tatcttaact aaattctgct tcttcttttt tgacttgtaa atatcaaaaa
6501  atcaggaaag tagattagat gataatgatg atggtggtgg tgactttcaa
6551  tcctagtact tttgggaggc aaaggcagag gggtctctga ttttgaggct
6601  ggcctggttt acatggtaaa tttccaggac agctcgggct atgaagagag
6651  agagacctct ctcacaaaag gggcataagg ggctagagag atggttcagt
6701  ggttaagagc acttgttctt gcggaggacc tgggttcatt tctcaaaacc
6751  caggccctgt tctggcccac aatgggcatc aggcacatgc atatgtatga
6801  aggtaaacgt tagtaaattg tatttaaaag catattaaat catgtacatg
6851  tctgtttatg tgtgttggta gggggtatat atgagtataa gtgcctggca
6901  tggaagccgt agcgttagga ccactcagag ctggagttac aggtggttgt
6951  gagccacctg atctgggtgc tgggaattga actcaggtcc tctgcaagga
7001  tagtatttgc tcttatctac caaaccactt ctctagtccc agtagtcttt
7051  aattttaaat ttcttattgt tttcataagt ttctctggta cagtaggttc
7101  aagatcactc cctaagccat actgattcat gcttatagac agcagtcagg
7151  agctgtgaca agaggacctg aaatttccag gtcagcctaa gcctcctcat
7201  gagagcccgt ctcaaaagcc aaaatgaata aagccaatca ttaaaatatt
7251  aggataattc taattttat ctgtgtctta gtcagggttt ctattcctgc
7301  acaaacatca tgaccaagaa acaagttggg gaggaaaggg tttattcggc
7351  ttatacttcc atactgcagt tcatcaccaa ggaagtcagg actggaagtc
7401  aagcaggtca gaaagcagga gctgatgcag aagccatgga gggatgttct
7451  ttactggctt ccccctggctt gctcagcctg ctctcttata gaaccaagac
7501  taccagccca gagatggtcc cactcacaag gggcctttcc cccttgatca
7551  ctaattgaga aaatgcctta cagttggatc tcatggaggc atttcctcaa
7601  ctgaagttcc tttctctgtg ataactccgc tgtgtcaagt tgacacaacg
7651  agccagtaca attgacccct tgtcaacttg acacacaaac acatcactag
7701  taagcctcaa cccttgcatt cttattcatc cccaaggtct aaataacttt
7751  aaacgtctca aagtctttac atattcttaa aatttcaatc tcttttaagat
7801  atccatctct tttaaaatcc aaagtctttt tacaattaaa agtctcttaa
7851  ctgtgggctc cactaaaata gtttcttcct ttaagaggga aaatatcagg
```

FIGURE 28 (CONTINUED)

```
7901  gcacagtcac agtcaaaaac aaaaatcaat ctccaaccat ccaatgtctg
7951  ggatccaact caagatcttc tgggctcctc caagggcttg ggtcacttct
8001  ccagccatgc cctttgaagc acacgcgtca tcctctaggc tccagatgcc
8051  tgtactccac tgctgctgct cttggtggtc atctcatggt actggcatct
8101  ccaaaacact gcatgacccc ttcagtcctg ggccgtcaat tgcaactgag
8151  gctgcacctt caccaatggc cttccatggc ctctcacagt gccacgcctc
8201  agctgctctg tgtgacccct tcatgccttc aaaaccagta ccacctgggt
8251  gacccttaca tattaccaag tcccgctgca gcaggagtac aaccttggcc
8301  atcttctgga ccacagcatc tttgtgcttt cagaaaacac ttcccagaag
8351  atgtcacctc aaagatgctg gtctctttt aatcactgct aatttcttag
8401  ctccagctaa ccagcattaa tagtcccagt aatgcaaagt ttttgcttta
8451  gtagttctgg tatcttgtta atcacagctg attcttcagc cccagctaac
8501  cagaactaca gaatcttcac aatcaaaaac agcagtggcc ctgaaaagag
8551  gctttaattt tccctctgaa atttcacaag ccagacctac atcttctgca
8601  ctgttctcaa cattatcttc caagctccta cacaacatct gacagagctc
8651  ttaacaacga atggatcttc aagcccaaag ttccaaagtc cttccacagt
8701  cctccccaaa acaaggtcag gttgtcacag gaatacccca ctatgttggt
8751  accaatttgt cttagtcagg gtttctattc ctgcacaaac atcatgacca
8801  agaagcaagt tggggaggaa agggtttatt cagcttataa ttccatactg
8851  ctgtttatca ccaaggaagt caggactgga actcaaacag gtcaggaagc
8901  aggagctgat gcagaggcca tggagggatg ttctttactg gcttgcttcc
8951  cctggcttgc tcagcctgct ctcttataga accaagacta cctaccagcc
9001  cagagatggt cccacccaca aggggccttt ccccttgat cactaattga
9051  gaaatgcct tacagttgta tctcatgggc atttccttaa tggaagctcc
9101  tttctctgtg ataactccag ctgtgtcaag ttgacacaaa actagccagt
9151  acaatctctg taacatgttc atttttgcta caatttaaga tttcagtttt
9201  tttcctagag ataaaatcag gaagtcattt atattaaatc tatatttgca
9251  tctgtgtgaa ttttttattg tttacagcaa atcctagaag agcatgattt
9301  taaagaagaa gattttggcc tctttcagtt agcaggtcaa agatgcattg
9351  aagatggtta tataaaccag ctgctagaga ttattcaaga tgaaaagaac
9401  aaggtaagcc caggctctgt gtccactctt cagtctttga gaaggaaata
9451  atacattgtt gttattactc atttggaagg ggaataatac attgttgtta
9501  ttacttattt gggaagggat aatacattga taatactcat ttgagaaggg
9551  aataatagat tgttgttgtt aaccatttat ccatcctctt agttactatt
9601  ctactgctgc agtgcgggag tatgaccatg tctcagcctt ccttagagaa
9651  ggaacagttc attggggctt tcagggtcag aggatgaggt catggaggtc
9701  actcctgaga accatcaacc tagtgattac ctggtccttg aggctgggtg
9751  tctcagcagt cagcccagtc tacaatggct gtccccactg ggcagggct
9801  ggatgtctca gtggtcctgt ttgaacccag acatctaaaa tggctgtaga
9851  gctgccgatc ctaggtcaca atgaaagctt agaaactggt tctcatagca
9901  gggaaggagg tggcggcagc agcaccagct ggactgctat taaccaacca
9951  cacactgcag gagggaaggc caaggaacaa aggtgcagtc ttccttctcc
10001 cgtgcccttc ctacctgtac tgctacaaca atcaaagcag ttaggatccc
10051 agctgatgtt aagatcaact ataatatact cttatggcct ccaatacagt
10101 cagtttttgtg gggttttttga ggcagagtct tagcccatgc tgtcctggag
10151 ttcttaaact tactatgtgt ttttcgttgt ttgtgtgtgt gcgggtggag
10201 gagggaaggg agggagaggc gtgcttttgt gagtgtatat gcaggtgcat
10251 gccaaggcca ggggttgatg ttgattgtcc tcaatcactc ccatcttttt
10301 gaaacaaggt ccctcatttg aacctgggac tcacacattc atctaggctg
10351 ggtggccaac aaattctaag cgacgtgcca tgatncttt ctagatgatt
10401 ttttaanagg nttctacctt tgaaaattag ctttgtgccc acaaggtntc
10451 tcggcctaaa tntaaaattc cnaaagatg gtggaatcaa caccctttct
10501 cctatttngg caacctaaaa atttaaaatt nggtaagttt gtgtggttcg
10551 atgttgcaaa aattttcaac ccttgagaag gaaaatttt aaaattggaa
10601 aaacgtaaaa actcatttn ttaaaaagt ttatttant gngattncaa
```

FIGURE 28 (CONTINUED)

```
10651  agtgtaaaaa aaaatccttg gttattttta cacgttaggg gggggtttaa
10701  aacattttgg gttttntttt aaaacccccc ttctttttt gngaaatttt
10751  tttctcttca caaacngccc ccgcgttttc tcctttgtcc ctcccaaaaa
10801  aatcctaatt tttccacttt cccttanttc aaaaagggaa gaaatttaaa
10851  tatatgncan agttcctgta ggataaatan natcgctatc tttattttta
10901  tatttttgt cgtgatgnaa ataaatacaa ataa
```

FIGURE 29

Mouse genomic sequence : exon 3, intron 3, exon 4, intron 4, exon exon 5, intron 5, exon 6, intron 6 and exon 7. The exons are underlined.(SEQ ID NO 152)

```
Contig[0046]
Contig[0046]  Length: 8427  Jeu 22 juin 2000  14:23  Check: 3740 ..
   1 accatcatta agtctatggg gtggaatctt gttggtccag ttgttcgatg
  51 cctcctgagg ggcagagaag aggataaaag agaagagtgt tttctgatat
 101 ttgatttgct ggtgaaggta agtcaggaaa gcttgttctg tctgtcatgc
 151 acacagcagc tccacaattc ccttccactt ttaattcttg ttcttcggta
 201 agaaaatttt agtccaggaa attattccta gataatgccc agttgtactt
 251 gactggatga gtgggcagct ccagctgagc atcatcaaca tttctagata
 301 taagaattac ccagtctgag accctaact cagtttccag taagaaagct
 351 acaaggtgat ttaacaagtg ttctcattat ataggcgaag tcacttttag
 401 agaacttta atgccatgct gacccttgtg tagcattaga gccagaatca
 451 aataccagat atgaaagtta agagagactg aggggtggc agatcaacaa
 501 taacaactct tgtttgaaaa tgccatagta aaatctaata taggaagatt
 551 ttgggatatt ggagattgtt gggatataca cagatgagta ctgggatgag
 601 aaagctcctc ccgggtaaca gcacttgatc atgaggactt ttaaagaggg
 651 aggcagtggc tggggatgca gctctggtag aggcactgag aaagttaagc
 701 agattgaggc tttaagctga gaaagaaatt agggaaacaa cacccttctc
 751 aatagtcaca aataatataa aataccttgg cgtgactcta actaaggaag
 801 tgaaagatct gtatgataag aacttcaagt ctctaaagaa agaaattaaa
 851 gaagatctca gaagatggaa agatctccca tgctcatgga ttggcaggat
 901 caacattgta aaaatggcta ttttgccaaa agcaatctac agattcaatg
 951 caatccccat caaaattcca actcaattct tcaacgaatt agaaagggca
1001 atcggcagat tcatctggaa taacaaaaaa ccgaggatag caaaaactct
1051 tctcaaggat aaaagaactt ctggtggaat caccatgccg gacctaaaac
1101 tgtactacag agcaattgtg atcaaaactg catggtactg gtatactgac
1151 agacaagtag accaatggaa cagaattgaa gacccagaga tgaatccaca
1201 cacctatggt cacttgatct tcgacaaggg agctaaaacc atccagtgga
1251 aaaagacag cattttcaac aaatggtgct ggcacaactg gttgttatca
1301 tgtagaagaa tgcgaattga tccatttcca tctccttgta ctaaggtcaa
1351 atctaagtgg attaaggaac tccacataaa accagagaca ctgaaactta
1401 tagaggagaa agtggggaaa agccttgaag atatgggtac aggggaaaaa
1451 ttcctgaata aacagcaat ggcttgtgct gtaagatcaa gaatcaataa
1501 atgggacctc ataaaattgc aaagcttctg caaagcaaaa gacaccgtca
1551 ataagacaaa aaggccacca acagattggg aaaggatctt acctatccc
1601 aaatcagata ggggactaat atccaatata tataaagaac tcaagaaggt
1651 ggactccaga aaatcaaata accccattaa aaaatggggc tcagagctga
1701 acaaagaatt ctcacctgag gaataccgaa tggcagagaa gcacctgaaa
1751 aaatgttcaa catccttaat catcagggaa atgcaaatca aaacaacact
1801 gagattccac ttcactccag tcagaatggc taagatcaaa gactcaggtg
1851 acagcagatg ctggcaagga tgtggagaag ggggaacact cctccattgt
1901 tggtgggatt gcaagcttgt acaaccactc tggaaatcag tctggcggtt
1951 cctcagaaaa ttggacatag tactaccgga agatcccgca atacctctcc
2001 tgggcatata tccagaagat gtcccaaccg gtaagaagaa cacatgctcc
2051 actatgttca tagcagcctt gtttataata gccagaagct ggaaagaacc
2101 cagatgcccc tcaacagagg aatggataca gaaatggtgt acatttac
2151 acaatggagt actactcagc tattaaaaaa atgaatttat gaattccta
2201 ggcaaatgga tggacctgga gggtatcatc ctgggtgaag taacccaatc
2251 acaaaggarc tcgcacaata tgtactcact gataagtgga tattagccca
2301 gaacttagg atacccaaga tataagatac aacttgccaa acgcatgaaa
2351 ttcaagaaga acgaagaccc aaagtgtgga cactttaccc tttcttagaa
```

FIGURE 29 (CONTINUED)

```
2401  atgggaacaa aacacccata gaaggagtta cagagacaaa atttggagct
2451  gtgacgaaag gatggaccat ctagtgattg ccatatgcag ggatccatcc
2501  cataatcagc ttccaaatgc tgacaccatt gcataaacta gcaagatttt
2551  gctgaaagga cccagatata gctctctctt gtgagactat gccggggcct
2601  agcaaacaca gaagtggatg atcacggtca gctattggat gggtcacacg
2651  gcccccaatg gaggagctag agaaattacc caaggagcta agggaactg
2701  caaccctata ggtggaacaa caatatgaac taaccagtac cccggagctc
2751  ttgtctttag ctgcatatgt atcaaaagat ggcctagtcg gccatcactg
2801  caaagagagg cccattggac ttgcaaactt tatatgcccc agtacagggg
2851  aacgccatgg ccaaaaaggg ggagtgggtg ggtaggggat tgggggggtg
2901  ggtatgggaa aactttggga tagcattgaa aatgtaaatg aggaaaatac
2951  ctaataaaaa aaaaagatat ggcagtcagg acacactata gagcatctgt
3001  tgagaaaaca caagagacca gtggtgtcgc gtcagggcct tgcatggaga
3051  gtctgcagtc tacagtgaag aagcctgagt tctgaaaagc cttaacaact
3101  gaatagggca ttttacagtt agcaaataga actgtatttt ctcggtatgt
3151  cttctttaaa atagtaatca tgtggcttta aatgcaactt gtattaaaca
3201  ggttcaattg tgaatatttt tatagttatg taatccaaag gaattgttgt
3251  tgggtttgct tgaactcatt gaagagccct ccggaaaaca gatttcccaa
3301  attattcttc ttttactgca accattacaa acaggtaatg agcattttga
3351  tatccaagta tttcttgttc tatttgcatt agtgtcttga tgtttaccct
3401  aagtatgaac tgtcaccaaa gtaaagtttg tgataagtta ctgcatgctc
3451  agcttttagg ctgtcccagc agcgccagtg tggatgctgc aggatgcctg
3501  gaagattggc tgctcagtaa atcccttgtt gtatgtcata ctgtttgcgt
3551  gtgtgtagct ctttggttag cttctttttt gcatatatgt gtgttttgtc
3601  tgcatgcatg tttgtacatc acttgcatgc ctggtacctt atcagatccc
3651  ctggagtttg agctgccata tgggttctgg gaactgaatc tgggtcctct
3701  gggagcagcc agtgctctta gccactgagc cgtctctctc tagcctccta
3751  gtaagcttct tatccacagc tatagttaga atttcccctc taagcatgtt
3801  tagtggctca gctgtggtac ctgcagcact cagtctaaca gcagtgtggt
3851  cgtcctgtag tttggttaag aaggatatga gacagggtgt tactcggcct
3901  ttgaattggg aggttggagt taaaaggttc aaccagaatg aaatgaggca
3951  tgaaaagaga gaaagcttca cagttcaata ttggcaaata atggctctca
4001  gcaaccaaca tagacacttt ccatgaaaga agctatttac tgtttgtgtg
4051  tatgtagcac atatatatgc ttcagaatat gatagacact tcttaaatat
4101  tcaaagtttt ctaaggacac aaaaagcttt taatactct tgtacactta
4151  tatggtgctt tgcaattttc cattcatatt ttgtgcttat aatcaaaaat
4201  aagggaaaga tgtaaccagt tataaaaata ctgtatttgt tggttttctt
4251  attgctgggc ctaagtgcct gacaactggc aatttaaaga agaactgttc
4301  atctggttag gatccgcagt ccaccatggt ggcgaggcat ggtggaagta
4351  gggtggcgaa gtacctggtc acattgtaat gacagtcaca gtagtgaggt
4401  caggctctac cgcctcagag cccacctcta gtgaccactt cctttagcaa
4451  ggctccacct gctaaggatc cagagcctctg tcccatgtga agaagttctg
4501  tgtcacaggg tgacacagtt aactgtcacg cataagcaca ggtgaccact
4551  taagaggcga acacaggtga cagctcatac actgagcaca gtaaccactt
4601  atgcggtgag cagagggagt aactgcttgg tctctgttgc agttattcag
4651  aaacttccta caacaaggc atactccgtt ggactagcat tgtcaacact
4701  ttggagtcag ctgtctcttc ttcctgttcc acactcagaa gaacaaattc
4751  aggcagatga ttatggcctc tgtcagtgtt gtaaggcctt gatagagttc
4801  acgaaacctt ttgtggaaga agtaataagt gataaagaaa acaaagaaaa
4851  tgcaaaacta aaagatgaat tactgaaatt gtaagtatac cttgaggaac
4901  atttcaccgt ggagtgagta attagcagct cagttacctt atgtttctta
4951  tttgtacata caaatctagt ttcatatttt gaattttaga cgtagatgtt
5001  tggctgacac agcgtggtcg ttttctgagg cactgacagt acaaaaccaa
5051  ccttcactta attcactttc acccatcaca gcaagcaaac actgaaagtg
5101  ggggcagggg atgtactcaa ctcaagggac ttattactct gtctcgggga
```

FIGURE 29 (CONTINUED)

```
5151  actcgtacct gaaaatagag accactagag agttgggctt ccaccctgac
5201  tgcagactca gcaaagtgct catccactct ctcacaccgt gggttctaac
5251  caaacatcca ccagtggtta gggtggctgc cgatccctaa gtatatggat
5301  ggtccaaact gaggtgctct cagtatgaca cagcctccgg acttgatggc
5351  tctcagtatg acacaggatt gtaagatcaa agctagagcc tcgattatag
5401  aataagttgt cccaaaaacc aaatcaacac aaaacctcca aaataaagga
5451  caaaataaag gaatttgtgt taaatttctc ttggacagta ctgaattttt
5501  ttttttttaa aatttgggag actaatgcca ttcttacctt ttctattttt
5551  ctgggttaag gcatttaaag ttgttttaa aaacaaaaaa aattgttttg
5601  aaaaaaacg tcctaaagaa ctagaaaagg cttagttaca gaataaagtt
5651  agagtttaaa aaaatgcaac tctatgaaaa acatgactat attgtcctga
5701  attytccttg gaccagtgay ggtgacctct tggactagct ggccctcagg
5751  agacattcag catcaattgt aacactctag agattcaatt gaatctgagc
5801  tatgcagtct agcaaggcct tctcatgctt tcccagtact gtcacgagtg
5851  aggarggatt cagcctgtgt taccgtgctt gccttaggtc acgtctgtga
5901  catagtaaag tatcagrtga tttgtaatca aggcattgtg gcttgcagtt
5951  ctaggagttc tcaggctgga ctgaggctca ggttcgctga gctcatactt
6001  tgagaacagc atcttctttc ccatgagagt gaacccacct ttcaaaggtc
6051  tcacttgtta tactgtttta gcctgagttg aggggctgca ctcagttctc
6101  atgaaaagcc aggtatgaag aactacaggt gtcgtgcctt gggagtgttg
6151  actgcaaagt tacccatwtc ttatgccgta gttgtttcaa aggcttgaaa
6201  tgccctttgc tgacagcaca attcctcgaa cagtcagaag acgttggaaa
6251  tgacccttt cggtgttttg catctgaaat aatagtaagt acagccgatc
6301  taatctctaa tacttataac tttaaattta tcctgctata ttgtgatata
6351  tgaccagtta aactgttaat ttattaatag ggcagtatat agttttttag
6401  aatacagata aacaacagga tggaaactaa gtagcagtaa tattatccaa
6451  agccttctaa atgtttctaa atgctaataa ataagaaaat gtatacatac
6501  atatacggtc ttgaaaatgt gtatattttc cattggtatt aatttcatat
6551  tattttttt agagagagag aatgtgtgtg agtgagtgtt gtgtgtatgt
6601  gttcatgtgt atctgacctg aatttatttg caccacatgc atgcagtacc
6651  tgtggaaacc agaagagacc atcagatctt agttgtcagc aacatgtgg
6701  atgctaggaa ttgaatttgg actctctaga agagcagcca gccccatct
6751  taagcatttt aaagtacagc attaagtgtg tttccattgc tgtgcaatca
6801  ccagcgctgc catctcaaga acatttcttt ctacctgaat tctctacttg
6851  ctaagcgctg ccccagcacc ctccccacac cctgtcctgt cactaactgg
6901  ctaagtgtgc atacatacac acacacaccc acacacacac acacacacac
6951  actgtcctgt cattgcctga ctaagcactc ctcccaggcc cctgcctgtc
7001  ctgtcactgc ctggcagctg ccacactgta ttggaaagca cttctattgt
7051  ttccatgctg aaatggtttt tctctttta tttcggtatt ttgaagacaa
7101  ggtctctcta catagatctg gctattctgg aactctcttt gcagttcagg
7151  ctggccttga actcacagtg atccacttgt gtctgtctcc caaaatggtg
7201  ggattaaagg tgtgcccagc ttcatttgtg tttaaaactt actcatttta
7251  ttttatcaca gtgggtttgt gcatcacatg tgtatagtgg ccaaggagac
7301  cagaagaggg tattggatcc cttggaattg gagttgtaga tggttgtgag
7351  ctgccatgag ggtggtgaga accaaacctg ggtcttctgc aagagcagca
7401  agtactctta actgctaagt catctcttca gcccctgaaa tgacctgtct
7451  tagtttactc taaagccctc cctccagcaa ttgggtagtt tagctatcag
7501  caaaaactca atgtatgtgt gtgtgtgtat atgttgtgtc atgtgtgcgt
7551  gcacatgcgc ctttaattat gattttgagc gagatcatat caaggaagga
7601  aggaaggaaa gcagaaaccc tgcctgaata ggtaaggccc atccagtaat
7651  cttgaataac tcaaaatcaa ttgattcaag acctgcatta caccagcaga
7701  cttcctccgt ggcttagtca gtgtgctgtt gctatgcaga gacactgtga
7751  ctacagcaac tcttaggaaa ggaagtactg aattgggct tgcttacagt
7801  ttcagaagtt tggttcatta tctccatggt ggagagcatg cagcacaca
7851  ggaagacatg gtgctggaga aacagttgag tttccattca aacccacagg
```

FIGURE 29 (CONTINUED)

```
7901  cagcaggaag agagagtctg ggtctggctt gggcttttga aacctcagag
7951  cccaccccca ctgacatact tttaacaagg ccacacctcc tattccttct
8001  caagtagtgc cactccctgc cgaccaagca ttcaagtgtg tgatcccata
8051  gggccattct tattcagagc actgcattca cctttgccat ttaagagggc
8101  ctaacaatgg gggtgacatt caaagcaagt gccacaaatt gtatataccc
8151  tcaaagagaa gggatatgga cagagtatgg acatggaata agtgggtgat
8201  gtatgccaac agcttccttt ttaaaaaccc atttcacagg gatttttatc
8251  aaaaattgga caccctgtcc cccaaattat tcttaatcat ggaaggaaaa
8301  aaaggacttg ggattacctt gaatttgaag aagaagaaga caaacaactg
8351  gcagagtctg tggcttctct gacatatcta gtatttgttc agggcatcgg
8401  tattgatcag ctgcccatgg tcttaag
```

FIGURE 30

Human MTE dot blot glomulin hybridization results

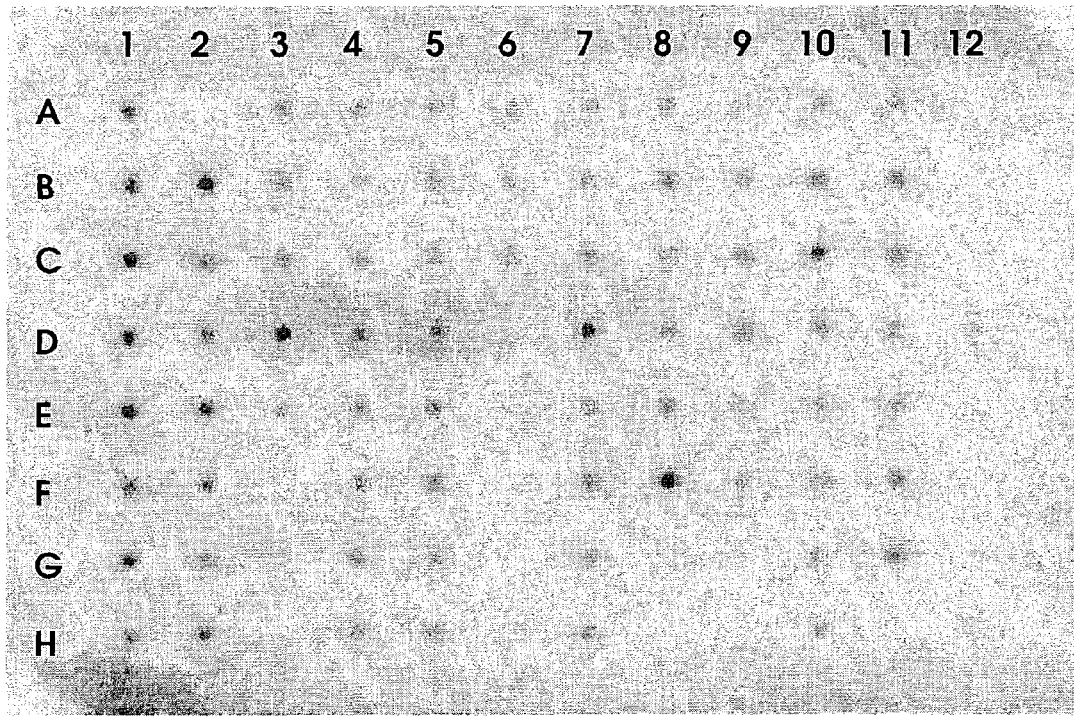

|   | 1 | 2 | 3 | 4 | 5 | 6 | 7 | 8 | 9 | 10 | 11 | 12 |
|---|---|---|---|---|---|---|---|---|---|---|---|---|
| A | whole brain | Empty | substantia nigra | heart | esophagus | colon, transverse | kidney | lung | liver | leukemia, HL-60 | fetal brain | yeast total RNA |
| B | cerebral cortex | cerebellum, right | nucleus accumbens | aorta | stomach | colon, descending | skeletal muscle | placenta | pancreas | HeLa S3 | fetal heart | yeast tRNA |
| C | frontal lobe | corpus callosum | thalamus | atrium, left | duodenum | rectum | spleen | bladder | adrenal gland | leukemia, K-562 | fetal kidney | E. coli rRNA |
| D | parietal lobe | amygdala | pituitary gland | atrium, right | jejunum | | thymus | uterus | thyroid gland | leukemia, MOLT-4 | fetal liver | E. coli DNA |
| E | occipital lobe | caudate nucleus | spinal cord | ventricle, left | ileum | | peripheral blood leukocyte | prostate | salivary gland | Burkitt's lymphoma, Raji | fetal spleen | poly r(A) |
| F | temporal lobe | hippo-campus | | ventricle, right | ileocecum | | lymph node | testis | mammary gland | Burkitt's lymphoma, Daudi | fetal thymus | human $C_0t$ .1 DNA |
| G | p.g.* of cerebral cortex | medulla oblongata | | inter-ventricular septum | appendix | | bone marrow | ovary | | colorectal adeno-carcinoma, SW480 | fetal lung | human DNA 100 ng |
| H | pons | putamen | | apex of the heart | colon, ascending | | trachea | | | lung carcinoma, A549 | | human DNA 500 ng |

* paracentral gyrus

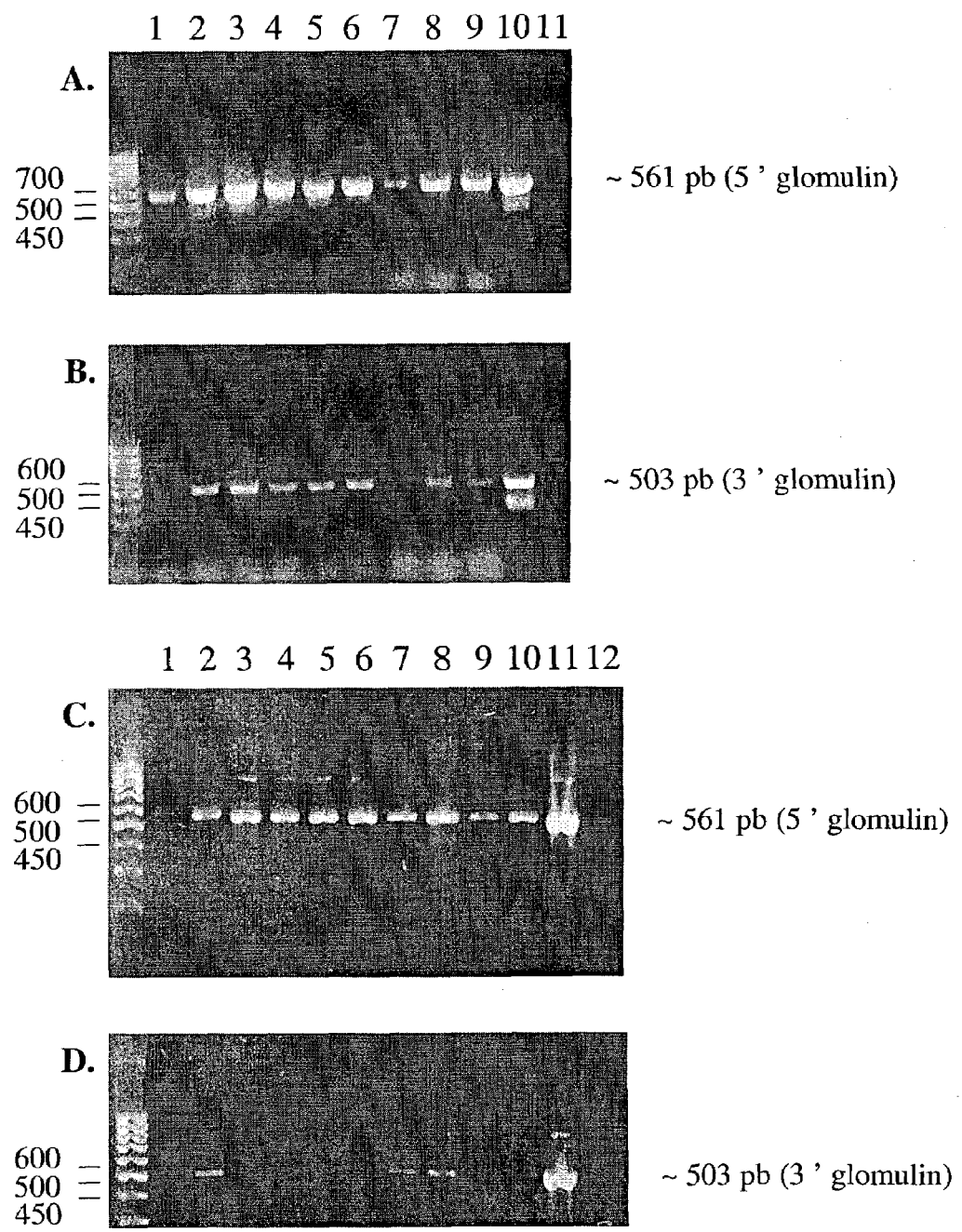
FIGURE 31 - Glomulin RT-PCR: results

FIGURE 32 (SEQ ID NO 153)

*Glomulin* protein sequence

MAVEELQSIIKRCQILEEQDFKEEDFGLFQLAGQRCIEEGHTDQLLEIIQNEKNKVIIKNMG
WNLVGPVVRCLLCKDKEDSKRKVYFLIFDLLVKLCNPKELLLGLLELIEEPSGKQISQSILL
LLQPLQTVIQKLHNKAYSIGLALSTLWNQLSLLVPYSKEQIQMDDYGLCQCCKALIEFT   207
KPFVEEVIDNKENSLENEKLKDELLKFCFKSLKCPLLTAQFFEQSEEGGNDPFRYFASEIIG (SEQ ID
FLSAIGHPFPKMIFNHGRKKRTWNYLEFEEEENKQLADSMASLAYLVFVQGIHIDQLPMV NO 138)
LSPLYLLQFNMGHIEVFLQRTEESVISKGLELLENSLLRIEDNSLLYQYLEIKSFLTVPQGL
VKVMTLCPIETLRKKSLAMLQLYINKLDSQGKYTLFRCLLNTSNHSGVEAFIIQNIKNQID
MSLKRTRNNKWFTGPQLISLLDLVLFLPEGAETDLLQNSDRIMASLNLLRYLVIKDNEND
NQTGLWTELGNIENNFLKPLHIGLNMSKAHYEAEIKNSQEAQKSKDLCSITVSGEEIPNMP
PEMQLKVLHSALFTFDLIESVLARVEELIEIKTKSTSEENIGIK*   208
(SEQ ID
NO 139)

FIGURE 33

ANTIGEN : 208
RABBIT CODE : SB455
ELISA results :

| DILUTION | | PEPTIDE | | | | | | | | CARRIER | | | |
|---|---|---|---|---|---|---|---|---|---|---|---|---|---|
| | | PPI (preimmune) | | | PP (1st test sample) | | | GP (2nd test sample) | | | PPI | PP | GP |
| | | 1 | 2 | 3 | 4 | 5 | 6 | 7 | 8 | 9 | 10 | 11 | 12 |
| 100 | A | 0,042 | 0,04 | 0,04 | 1,457 | 1˚,39 | 1,511 | 1,788 | 1,766 | 1,616 | 0,034 | 2,408 | 4 | |
| 300 | B | 0,041 | 0,041 | 0,039 | 0,516 | 0,578 | 0,583 | 1,171 | 1˚,1831˚ | ,1690 | 0,039 | 0,946 | 3,536 | |
| 900 | C | 0,046 | 0,042 | 0,043 | 0,191 | 0,222 | 0,195 | 0,465 | 0,491 | 0,487 | 0,042 | 0,618 | 2,456 | |
| 2700 | D | 0,043 | 0,042 | 0,046 | 0,161 | 0,097 | 0,097 | 0,197 | 0,191 | 0,193 | 0,043 | 0,325 | 1,164 | |
| 8100 | E | 0,041 | 0,043 | 0,06 | 0,057 | 0,061 | 0,055 | 0,092 | 0,094 | 0,094 | 0,04 | 0,308 | 0,604 | |
| 24300 | F | 0,039 | 0,039 | 0,039 | 0,045 | 0,047 | 0,045 | 0,062 | 0,064 | 0,059 | 0,036 | 0,213 | 0,272 | |
| 72900 | G | 0,044 | 0,043 | 0,043 | 0,047 | 0,044 | 0,046 | 0,048 | 0,052 | 0,053 | 0,042 | 0,042 | 0,044 | – contr. |
| 218700 | H | 0,038 | 0,041 | 0,04 | 0,038 | 0,035 | 0,037 | 0,047 | 0,046 | 0,044 | 1,699 | 1,593 | 1,6 | + contr. |

A.
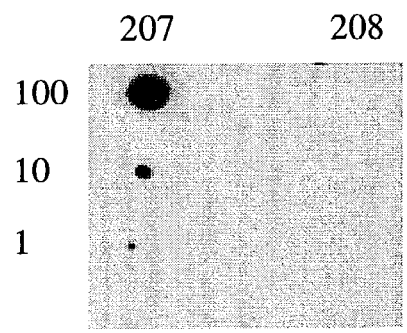
452
1:500
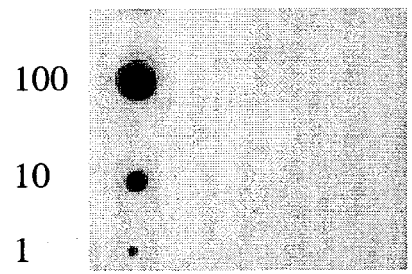
453
1:500
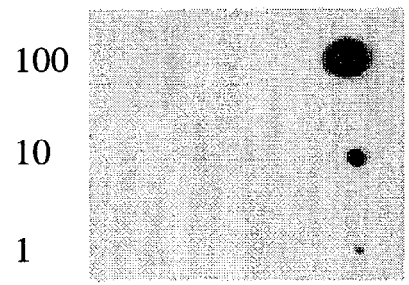
454
1:500
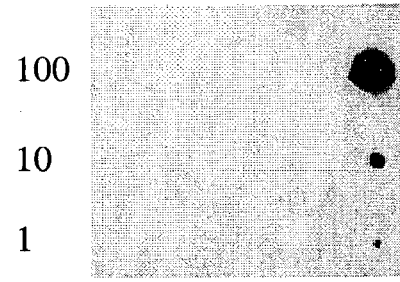
455
1:500
B.
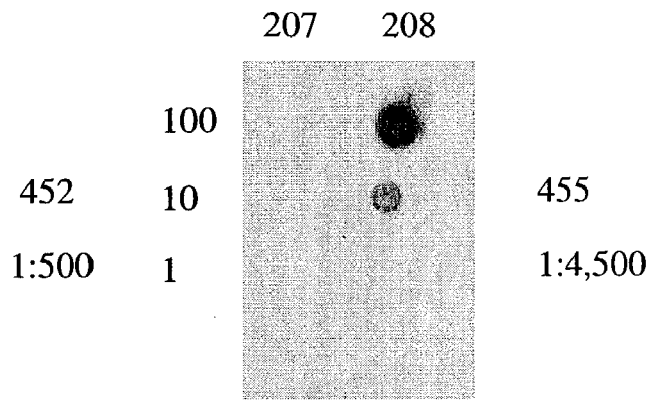
455
1:4,500
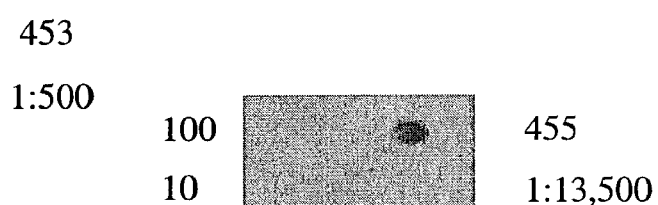
455
1:13,500
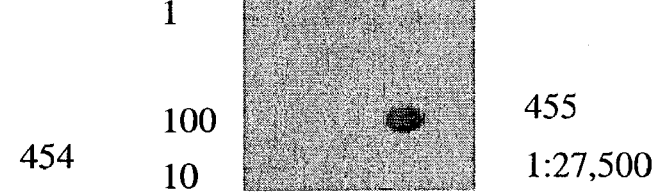
455
1:27,500
FIGURE 34

FIGURE 35
Prokaryotic expression vectors
pET-15b - glomulin
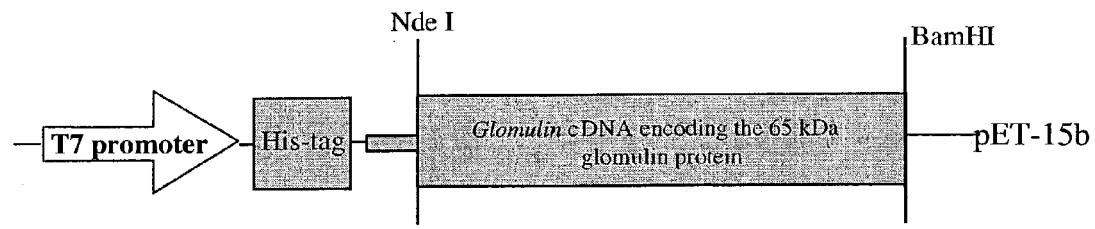
pET-3a - glomulin
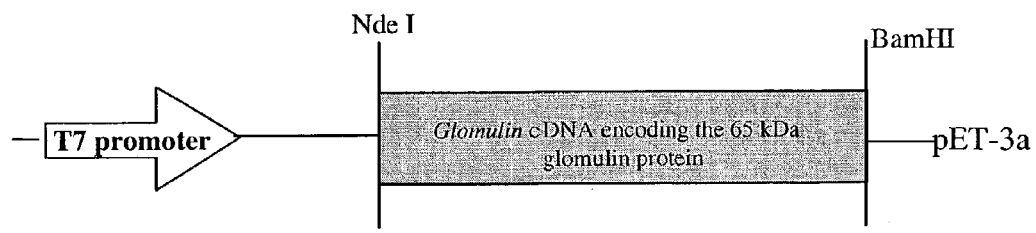

FIGURE 36
A. lacZ knock-out construct
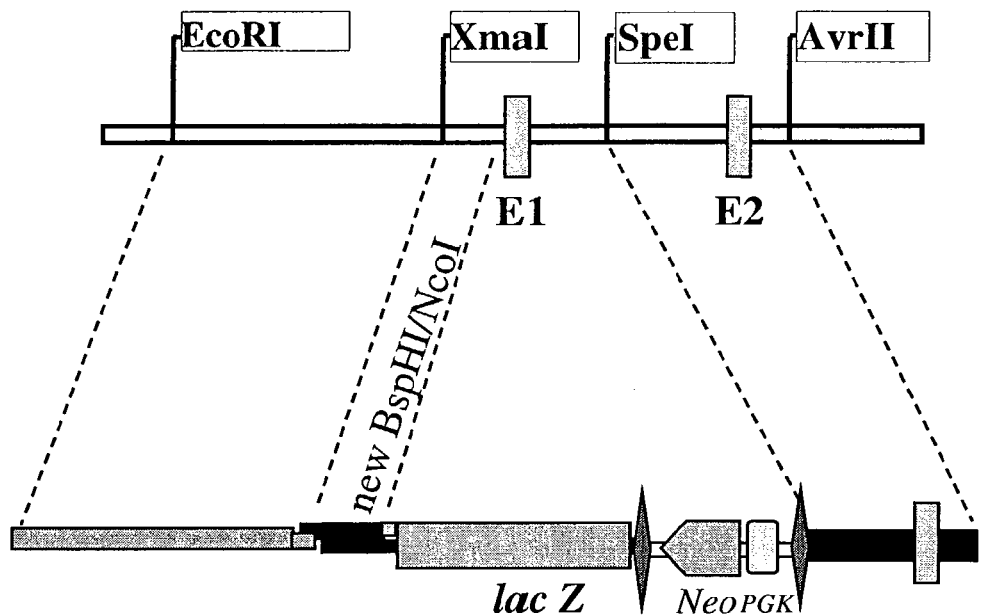
B. Conditional knock-out construct
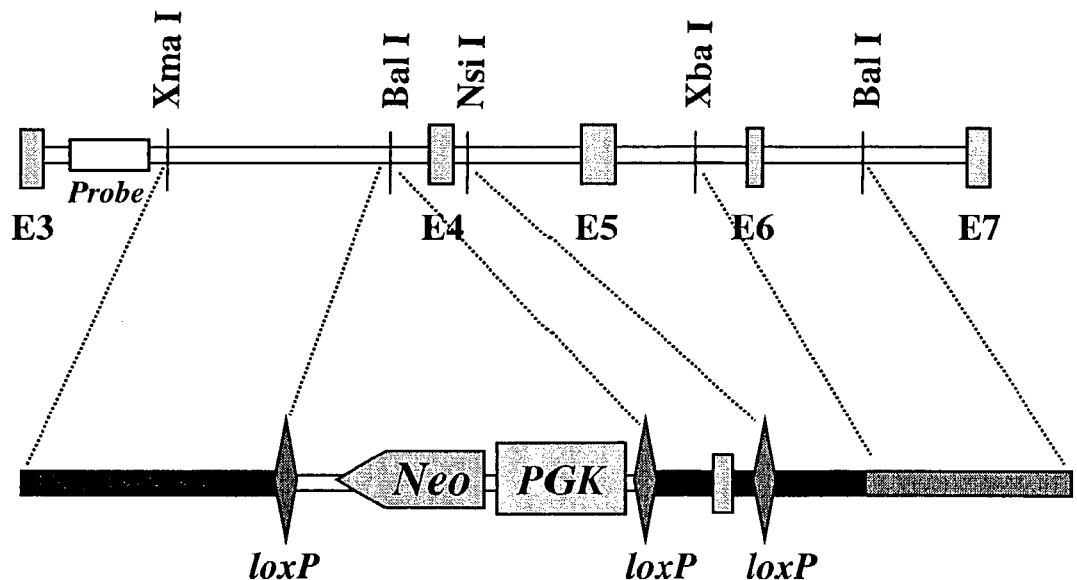

FIGURE 42
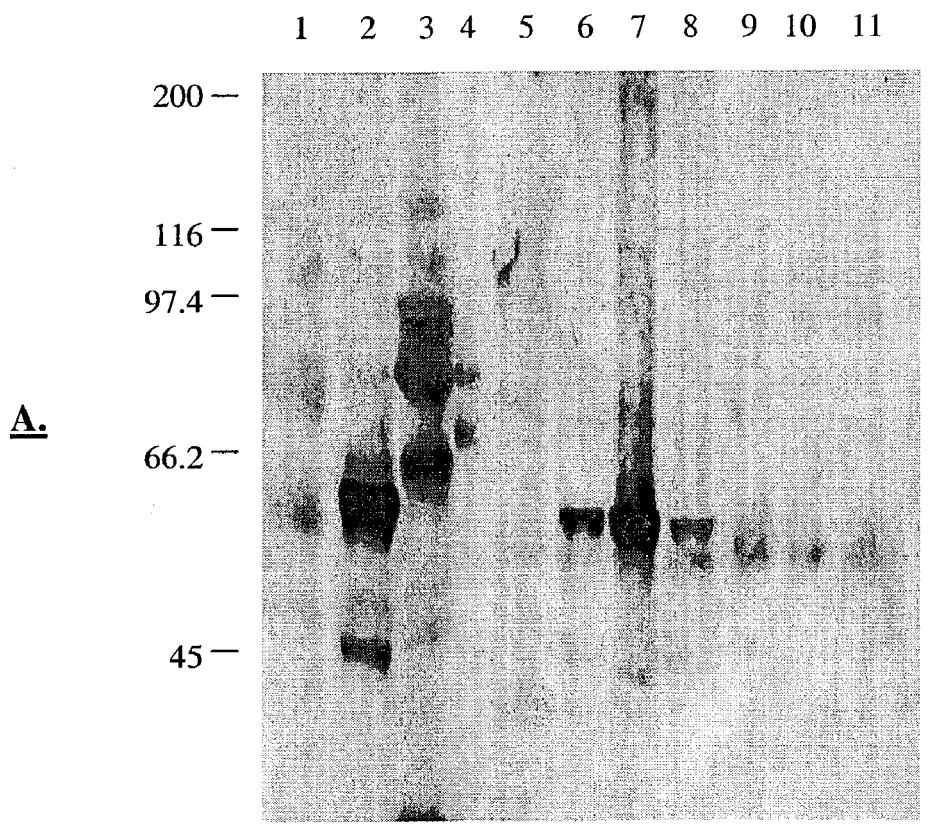
A.
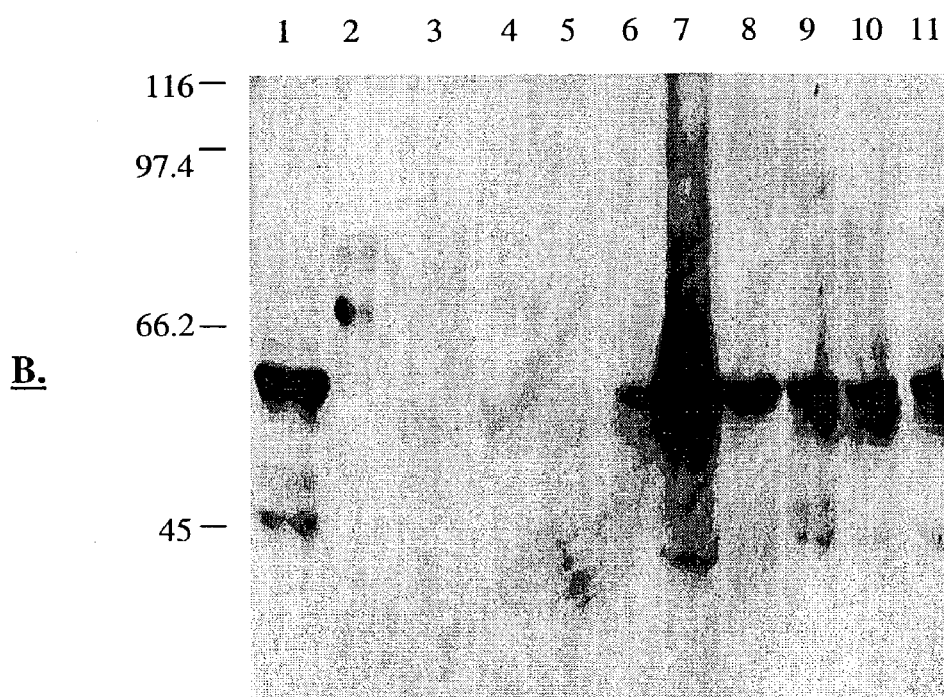
B.

TABLE 1A

| | BI USA | Bt Bel | Sh USA | F Sco | T Ita | Bln Fra | Sch Ger | n/N fam. | n/N con. | P |
|---|---|---|---|---|---|---|---|---|---|---|
| HAPLOTYPE A | | | | | | | | | | |
| A205XD5 | 241 | 239/R | 241/245 | 245/R | 241 | 241 | 245 | - | - | - |
| D1S435 | 175 | 157 | 161 | 175 | 175 | 157 | 157 | 5/12 | 25/60 | 1.000 |
| B337XE1 | 263 | 263 | 267 | 281 | 259 | 263 | 267 | 4/12 | 24/54 | 0.481 |
| D1S188 | 162 | 168 | 166 | 166 | 166 | 168 | 166 | 3/12 | 6/54 | 0.205 |
| D1S1170+ | 118 | 118 | 118 | 118 | 122 | 118 | 118 | 10/12 | 30/60 | 0.034 |
| 33CA1 | 156 | 156 | 156 | 156 | 152 | 156 | 156 | 9/12 | 18/62 | 0.002 * |
| D1S2804 | 179 | 179 | 179 | 179 | 179 | 179 | 179 | 7/12 | 10/62 | 0.001 * |
| D1S424 | 223 | 225 | 223 | 223 | 223 | 225 | 223 | 5/12 | 9/62 | 0.033 |
| D1S406+ | 200 | 200 | 200 | 204 | 200 | 196 | 200 | 5/12 | 6/64 | 0.003 * |
| 69CA1 | 171 | 169/171 | 171 | 171 | 171 | 171 | 171 | 9/12 | 15/60 | 0.001 * |
| D1S2776 | 206 | 206 | 206 | 206 | 206 | 206 | 206 | 8/12 | 8/62 | 0.000 * |
| 50CA1 | 127 | 125/127 | 129 | 127 | 127 | 127 | 127 | 7/12 | 2/48 | 0.000 * |
| D1S2868 | 146 | 146 | 146 | 146 | 146 | 146 | 146 | 7/12 | 14/62 | 0.012 |
| 75CA1 | 171/173 | 171/173 | 173 | 173 | 171 | 173 | 173 | 6/12 | 5/54 | 0.001 * |
| D1S2849 | 179 | 179 | 179 | 179 | 179 | 179 | 179 | 8/12 | 17/64 | 0.007 * |
| D1S2779 | 229 | 231 | 233 | 231 | 241 | 231 | 231 | 4/12 | 21/62 | 0.971 |
| D1S236 | 194 | 210 | 194 | 190 | 212 | 190/R | 190/R | 3/12 | 37/62 | 0.027 |
| D1S2775 | 201/R | 199/201 | 201 | 201 | 201 | 195/R | 201/R | - | - | - |

TABLE 1B

| | HAPLOTYPE B | | | | | | | |
|---|---|---|---|---|---|---|---|---|
| | Al USA | Ba Yug | Del Bel | Ad Fra | n/N fam. | n/N con. | P | Lml Fra |
| A205XD5 | 241 | 241 | 241 | 241 | - | - | - | 241/R |
| D1S435 | 157/161 | 161 | 175 | 157/161 | - | - | - | 161/R |
| B337XE1 | 259 | 259/267 | 259 | 259 | 5/12 | 14/54 | 0.276 | 263/R |
| D1S188 | 154 | 160 | 154 | 152 | 2/12 | 6/54 | 0.594 | 168 |
| D1S1170+ | 118 | 118/122 | 118/122 | 122 | 10/12 | 30/60 | 0.034 | 118 |
| 33CA1 | 156 | 156 | 156 | 152 | 9/12 | 18/62 | 0.002 * | 142 |
| D1S2804 | 185 | 185 | 183 | 185 | 3/12 | 13/62 | 0.756 | 191 |
| D1S424 | 209 | 209 | 209 | 209 | 4/12 | 28/60 | 0.396 | 225 |
| D1S406+ | 208 | 204/208 | 208 | 208 | 5/12 | 17/64 | 0.290 | 208 |
| 69CA1 | 169 | 169 | 171 | 169/171 | 4/12 | 30/60 | 0.291 | 173 |
| D1S2776 | 198 | 198 | 198 | 198 | 4/12 | 11/62 | 0.219 | 206 |
| 50CA1 | 125 | 125 | 125 | 127 | 5/12 | 27/48 | 0.365 | 125 |
| D1S2868 | 148 | 148 | 148 | 148 | 4/12 | 25/62 | 0.650 | 144 |
| 75CA1 | 171 | 171 | 171 | 175 | 7/12 | 36/54 | 0.584 | 171 |
| D1S2849 | 181 | 179 | 181 | 183 | 2/12 | 10/64 | 0.928 | 176 |
| D1S2779 | 235 | 233 | 235 | 241 | 2/12 | 3/62 | 0.135 | 229 |
| D1S236 | 194 | 212 | 210 | 212 | - | - | - | 212 |
| D1S2775 | 201 | 201 | 199/201 | 199/201 | - | - | - | 199 |

TABLE 4

PCR primer sequences for the 22 new end-of-clone STSs

| SEQ ID NO | Name | PAC | Primer 1 | Primer 2 | Size (bp) | SEQ ID NO | Annealing (°C) |
|---|---|---|---|---|---|---|---|
| 13 | 15 T7 | 999i4 | AGC AAA CTT ACT GGC AGT GC | GCT ACT TGG AGC TGA GCA G | 217 | 14 | 58 |
| 15 | 16 T7 | 878d9 | AGG AGA ATG GCG TGA ACC C | TCA AAG ATT CTT CCT TCC TGC | 146 | 16 | 64 |
| 17 | 17 T7* | 593e4 | ACT CAG GAA TGG AGT CAT GG | CAT GCT CAC AGG GTA GAT AC | 191 | 18 | 64 |
| 19 | 20 SP6 | 1161i11 | TCT AAA GTC TTG TCA CAG TGC | GTC TAT ATG GCA TGT TTC TCC | 196 | 20 | 60 |
| 21 | 20 T7 | 1161i11 | AGC AGG TAT GTC ACA CAG TG | TAT GGC TTG GAT CTC CCT TC | 218 | 22 | 60 |
| 23 | 21 SP6* | 981e3 | TAT CTT CAA TGA AAT CCC AAT AC | GTT TTG ACA AAG TAT CAG ATT GC | 168 | 24 | 58 |
| 25 | 21 T7 | 981e3 | ACT GCC CTC ATA CTA CCA TG | CTG AAC CAA CCA TGC ATC AC | 238 | 26 | 58 |
| 27 | 33 SP6 | 775d17 | GCC ACT TGT ATG TAG GAG AG | TGG CTA CTA ACA GAC ATC AAC | 320 | 28 | 58 |
| 29 | 33 T7 | 775d17 | GAC GTC CTA TCC AGT AGA AG | TTT CAC TGG ACC TTC CTG AG | 246 | 30 | 64 |
| 31 | 44 T7 | 1090n11 | CTC TAG AGA GTA TGC GTC TC | ACA CTG ACT ACT ATG GAA CTG | 231 | 32 | 58 |
| 33 | 47 SP6 | 1091c4 | ATG GAG AAC TCC AGT GAG AG | TAA GTT CTG ATT GCA TGG GTC | 205 | 34 | 64 |
| 35 | 52/53 T7 | 930a6/ 930a10 | AGA CTG ATA ATT CTG AGC TAT C | ATG CAT GCA GGC CAC ATA TG | 266 | 36 | 60 |
| 37 | 53 SP6 | 930a10 | TAC TCT GGA TCT CTC ACA GG | TAG CTT GTC CTC TCT TGC TG | 258 | 38 | 58 |
| 39 | 54 SP6 | 812f10 | AGC AGT TAT TTC TGG TGG TAG | TGG AGA TTT AGA CAG TTT ATA AC | 168 | 40 | 58 |
| 41 | 54 T7 | 812f10 | CCA GGG TGG TCT CAA ACT C | TAA GTC TAT GAT CCA TTT CGA G | 166 | 42 | 58 |
| 43 | 57 T7 | 638p11 | GAG AGT GAG ACC CTG TCT G | AAA GGA CAG AGA ATC AAC CTG | 167 | 44 | 64 |
| 45 | 65 T7 | 840n15 | GTG ACA GGA GCC AAT GAA TG | GGG ATG TCT AGA CAG AAG TG | 240 | 46 | 54 |
| 47 | 69 SP6 | 103d10 | GGG TTA GGG GTA AAG GGT GG | CGA AGA ACC TGG TAT GCA GG | 122 | 48 | 58 |
| 49 | 69SP6 bis* | 103d10 | TCC TGC ATA CCA GGT TCT TC | TGT TCT GCT GGT AGT AGT CC | 265 | 50 | 64 |
| 51 | 70 SP6 | 104o6 | TGA GCC ACC ACG CCC AAC | TGC GCA CGT TCT TGT GCT G | 165 | 52 | 62 |
| 53 | 70 T7 | 104o6 | ATA TCT GAC ATC TCA GAG TGG | CTG GCC TGA ATT TCA GAG TC | 258 | 54 | 63 |
| 55 | 75 SP6 | 226k2 | CTC TGC ATA GAG TCA GCA AG | CCA CCA TGC CCA GTT TCT C | 188 | 56 | 65 |

* = used as probe. 20 bp overlap between 69SP6 and 69SP6 bis, as primer 1 of 69SP6 bis is complementary to primer 2 of 69SP6

TABLE 5

PCR pri,er sequences for novel CA-repeats

| Name | PAC | SEQ ID NO | Forward | Reverse | Approx. size (bp) | SEQ ID NO. | mapping | Het. in controls | Alleles identified |
|---|---|---|---|---|---|---|---|---|---|
| 25CA1 | 606m5 | 57 | GAG GTC AGG AGT TCG AGA | GTA GGA GTG CAT CAC CAT GC | 139 | 58 | PCR not | specific | - |
| 33CA1 | 775d17 | 59 | TCT GAC TTT GAC GTT GTA ACC | CAG TCA CTT CTC TTT CAT CAG | 157 | 60 | 55 | 12/16 | 7 |
| 50CA1 | 617o13 | 61 | TGT AAA GAG CTG CTG CAC TC | AGC AAA GTG ACA TCT GAC TTC | 129 | 62 | 64 | 15/16 | 6 |
| 56CA1* | 612c19 | 63 | CTT GAA GCC AGG AGT TTG AG | CAG CCT CCC AAG TAG CTA G | 141 | 64 | 55 | 0/16 | 1 |
| 56CA2 | 612c19 | 65 | ATG TTG TTC AGC GCA ACC TC | AGC CTG GAT GAC AGA ATG AC | 181 | 66 | 55 | 7/16 | 4 |
| 56CA3 | 612c19 | 67 | GGT ATG GTG AAT GAA GCA TTC | TGA GCT CCT GAA TTA CAC ATC | 148 | 68 | 58 | 6/16 | 2 |
| 69CA1 | 103d10 | 69 | TTT TTA AAT CCC ATA ACT TGC | C GCA GTG GTG AGA GAG TGG | 175 | 70 | 58 | 11/16 | 6 |
| 75CA1 | 226k2 | 71 | CAA CAG GTT GAG AAG GCA A | GGG TGA CAG AGT GAG ACT G | 169 | 72 | 58 | 11/16 | 5 |
| 75CA2 | 226k2 | 73 | CAA CAT AGA TCC TGG GAA C | GAG AAT CTG ACC TTG AAG GC | 195 | 74 | 58 | 10/16 | 5 |

*not polymorphic

TABLE 6

| | SEQ ID NO | Forward Primer | Reverse Primer | SEQ ID NO |
|---|---|---|---|---|
| Exon 1 | 75 | CAT CGA AAC TAG GAG AAA TAA G | CCA CTC ATG CTC TTT ACA GG | 76 |
| Exon 2 | 77 | CAT AGA TAA ATC AAG AAG TTA TTG | ATG TGA TTA TTC TCT TCC CAA G | 78 |
| Exon 3 | 79 | TGC GAG AGT CCT ATA GAT GG | TGC TGT GTG TTA TGA TAA AGA G | 80 |
| Exon 4 | 81 | ATA TTT TGT CGA TAT ATG CCT TC | GTG TAG TAT TGA CAT TTT GAG G | 82 |
| Exon 5 | 83 | TTG ATG AGC GAC AAC TTG ATC | TAA GTC CAC TGT GAG ATG TTC | 84 |
| Exon 6 | 85 | CTT GGA AGT GTT CAT TTC ATA G | GCA GTA CTG AGA ATA TAG TGG | 86 |
| Exon 7 | 87 | GTC AGA GAG CTA TGG TTT CC | GTG TTA ATA TGC ATA TAT TGG AC | 88 |
| Exon 8 | 89 | CTA GAG GTT AGG ACT CCA AC | CAG TCT CCG CTG ATC TTA AC | 90 |
| Exon 9 | 91 | AGA ATT TCT CCT TAA TGA TAT GC | TGA TAG TGA AGT CAA CAG CTG | 92 |
| Exon 10 | 93 | ACT TAA ATA CAT AGT TAT GTC AAC | TAA GTT CAG AAC AGG CAA AGG | 94 |
| Exon 11 | 95 | TCA GTA TAA TCT GTT TAC ATC TG | TGT AAT ACA TCC ACA CTT GTA C | 96 |
| Exon 12 | 97 | GTG ATG AAG TCT GGG TAA GC | AAC AAT TAC ATG GCA TTA ACA TG | 98 |
| Exon 13 | 99 | ATC ACC ATT TAA TTC TAA TGC TG | TAG AGA TAG AGC AAT AAC TCA C | 100 |
| Exon 14 | 101 | TTT TTG TAG TGT CAA GGT ATT AG | TTT ATT ACT TTA GGT TCC CTA AG | 102 |
| Exon 15 | 103 | TAG CTT ATT GAG ATT GCT GTT G | TAT CTG AAA CAT TCC TTA TGC C | 104 |
| Exon 16 | 105 | AGT AGG CAA TCA ATC ATT GTT G | AAT GGC TTA GCT GTT ATG GTC | 106 |
| Exon 17 | 107 | GAG AGT TAA GTG TCA CAC ATG | AGC TTG GGC AAG ATA GCA AG | 108 |
| Exon 18 | 109 | AGC TAC CTC CAG CTG AAA TC | TAG TTT TTA TTT AGG AAA TGG AAC | 110 |

TABLE 7

| | EXON size | Average Intron size |
|---|---|---|
| Exon 1 | > 62 bp | 432 bp |
| Exon 2 | 126 | 6 kbp |
| Exon 3 | 120 | 1.3 kbp |
| Exon 4 | (24)+109 | 1.2 kbp |
| Exon 5 | 238 | 2.5 kbp |
| Exon 6 | 104 | 20 kbp |
| Exon 7 | 187 | < 3 kbp |
| Exon 8 | 54 | < 3 kbp |
| Exon 9 | 31 | 115 bp |
| Exon 10 | 90 | 1.2 kbp |
| Exon 11 | 42 | 207 bp |
| Exon 12 | 74 | 1.6 kbp |
| Exon 13 | 85 | 823 bp |
| Exon 14 | 110 | 710 bp |
| Exon 15 | 64 | 14 kbp |
| Exon 16 | 112 | 740 bp |
| Exon 17 | 83 | 473 bp |
| Exon 18 | > 143 | - |

| Mutation | Description |
|---|---|
| VMGLOM$^{\Delta AA31,32}$ | deletion of 2 nucleotides, positions 31-32 (exon 1) |
| VMGLOM$^{insG107}$ | insertion of a G, position 107 (exon 2) |
| VMGLOM$^{C>A108}$ | substitution of a C by an A, position 108 (exon 2) |
| VMGLOM$^{\Delta AAGAA157-161}$ | deletion of 5 nucleotides, positions 157-161 (exon 2) |
| VMGLOM$^{insA423}$ | insertion of an A, position 423 (exon 5) |
| VMGLOM$^{\Delta A554+\Delta CCT556-558}$ | deletion of 4 nucleotides, positions 554+556-558 (exon 5) |
| VMGLOM$^{\Delta A+4intr5\Delta G\text{-}Sintr5}$ | <u>deletion of the 4$^{th}$ nucleotide (A) in the splice site consensus in intron 5</u><s>deletion of the 5$^{th}$ nucleotide (G) in the splice site consensus in intron 5</s> (5' end of intron) |
| VMGLOM$^{\Delta AGTT842-845}$ | deletion of 4 nucleotides, positions 842-845 (exon 7) |
| VMGLOM$^{\Delta CAA1179-1181\text{-}1180\text{-}1182}$ | deletion of 3 nucleotides, positions <s>1203-1205</s><u>1179-1181</u> corresponding to one Asn deletion (exon 12) |
| VMGLOM$^{\Delta T1355}$ | deletion of a T, position 1355 (exon 14) |
| VMGLOM$^{\Delta TCAA1470-1473}$ | deletion of 4 nucleotides, positions 1470-1473 (exon 15) |
| VMGLOM$^{C>G1547}$ | substitution of a C by a G, position 1547 (exon 16) |
| VMGLOM$^{\Delta GT1711,1712}$ | deletion of GT, positions 1711-1712 (exon 18) |

Table 8.

SEQUENCE LISTING

<160> NUMBER OF SEQ ID NOS: 154

<210> SEQ ID NO 1
<211> LENGTH: 1849
<212> TYPE: DNA
<213> ORGANISM: Homo sapiens

<400> SEQUENCE: 1

```
tctggccgat tttagcatcg aaactaggag aaataagaat ggctgtagag gaacttcagt      60
ctataataaa gagatgtcaa atcctagaag agcaagactt taaagaagag gattttggcc     120
tatttcagtt agctgggcaa agatgcatag aagaagggca cacagaccag ctattagaaa     180
ttattcaaaa tgaaaagaat aaggtcatca tcaagaatat gggctggaat ctcgttggtc     240
ctgttgttcg atgcctttg tgtaaagata aagaggatag taaagaaaaa gtttatttt       300 tgatctttga tttattggta aagttatgca atccaaagga attattgttg ggtttgcttg     360
aactgattga agagccctct ggaaaacaga tatcccaaag tattcttctt ttgcttcagc     420
cattacaaac agtgattcag aaacttcata acaaggcata ttcaattgga ttagcattgt     480 ctacccttg gaatcagcta tctcttcttc ctgttccata ctcaaaagaa caaatacaaa      540
tggatgacta tggcctttgt cagtgttgca aggccttaat agagttcact aagcctttg     600 tggaagaagt cattgataac aaagaaaact cactggaaaa tgaaagtta aaggatgaat      660 tactgaaatt ttgtttcaaa agcttgaaat gccctttgct gacagcacaa ttctttgaac     720
agtctgaaga aggtggaaat gatcctttca ggtattttgc atcagaaata ataggttttt    780
tatcagcaat tggacaccct ttccccaaaa tgatttttaa tcatggaagg aaaaagagaa     840
cttggaatta ccttgaattt gaagaagaag aaaataaaca gttagcagac tcaatggctt    900
ctctggcata tctagtattt gtacagggca tccatattga tcagcttcca atggtcttaa    960
gcccattgta cctttttgcag tttaatatgg ggcacattga agtctttttg caaagaacag   1020
aagagtctgt tatctccaaa ggattggagc tgctggagaa tagtttattg agaatagaag    1080
acaatagtct actttaccag tacttagaaa tcaagagttt tcttactgta cctcagggct    1140
tagtgaaagt aatgacactt tgccccattg agacactgag gaaaaagagt ttagctatgc    1200
ttcagctgta tattaacaag ttggattcac aaggcaaata tacattattt aggtgcttat    1260
tgaatacaag taatcactca ggtgtggagg cttttattat tcaaaatatc aaaaatcaaa    1320
ttgacatgtc attaaagaga acacgtaaca acaaatggtt tacaggacca cagttgatt    1380
```

```
ccccttcttga tttggtactt tttctcccag agggtgcaga aacagattta ctgcaaaact    1440
cagataggat tatggcttca ttaaatttat tgaggtattt ggttatcaaa gataatgaaa    1500
atgacaatca aactggatta tggacagaac ttggaaatat tgagaataat ttccttaaagc   1560 cacttcatat aggacttaat atgtcaaaag cacattatga agcagaaatt aaaaatagcc    1620
aagaggccca gaaatctaaa gatctttgtt ctataactgt aagtggagaa gagatcccta    1680
atatgcctcc tgaaatgcag cttaaggtcc tgcattcagc tctttttcaca tttgatttga   1740 ttgaaagtgt tctagctcga gtggaagaac tcattgaaat aaaaacaaag tctacctctg    1800
aagaaaatat tgggataaag tgaaagttcc atttcctaaa taaaaacta               1849
```

<210> SEQ ID NO 2
<211> LENGTH: 594
<212> TYPE: PRT
<213> ORGANISM: Homo sapiens

<400> SEQUENCE: 2

```
Met Ala Val Glu Glu Leu Gln Ser Ile Ile Lys Arg Cys Gln Ile Leu
1               5                   10                  15

Glu Glu Gln Asp Phe Lys Glu Asp Phe Gly Leu Phe Gln Leu Ala
            20                  25                  30

Gly Gln Arg Cys Ile Glu Glu Gly His Thr Asp Gln Leu Leu Glu Ile
        35                  40                  45

Ile Gln Asn Glu Lys Asn Lys Val Ile Ile Lys Asn Met Gly Trp Asn
    50                  55                  60

Leu Val Gly Pro Val Arg Cys Leu Leu Cys Lys Asp Lys Glu Asp
65                  70                  75                  80

Ser Lys Arg Lys Val Tyr Phe Leu Ile Phe Asp Leu Leu Val Lys Leu
                85                  90                  95

Cys Asn Pro Lys Glu Leu Leu Leu Gly Leu Leu Glu Leu Ile Glu Glu
            100                 105                 110

Pro Ser Gly Lys Gln Ile Ser Gln Ser Ile Leu Leu Leu Gln Pro
        115                 120                 125

Leu Gln Thr Val Ile Gln Lys Leu His Asn Lys Ala Tyr Ser Ile Gly
    130                 135                 140

Leu Ala Leu Ser Thr Leu Trp Asn Gln Leu Ser Leu Leu Pro Val Pro
145                 150                 155                 160

Tyr Ser Lys Glu Gln Ile Gln Met Asp Asp Tyr Gly Leu Cys Gln Cys
                165                 170                 175

Cys Lys Ala Leu Ile Glu Phe Thr Lys Pro Phe Val Glu Val Ile
            180                 185                 190

Asp Asn Lys Glu Asn Ser Leu Glu Asn Glu Lys Leu Lys Asp Glu Leu
        195                 200                 205

Leu Lys Phe Cys Phe Lys Ser Leu Lys Cys Pro Leu Leu Thr Ala Gln
    210                 215                 220

Phe Phe Glu Gln Ser Glu Glu Gly Gly Asn Asp Pro Phe Arg Tyr Phe
225                 230                 235                 240

Ala Ser Glu Ile Ile Gly Phe Leu Ser Ala Ile Gly His Pro Phe Pro
                245                 250                 255

Lys Met Ile Phe Asn His Gly Arg Lys Lys Arg Thr Trp Asn Tyr Leu
            260                 265                 270

Glu Phe Glu Glu Glu Glu Asn Lys Gln Leu Ala Asp Ser Met Ala Ser
        275                 280                 285
```

-continued

```
Leu Ala Tyr Leu Val Phe Val Gln Gly Ile His Ile Asp Gln Leu Pro
    290                 295                 300
Met Val Leu Ser Pro Leu Tyr Leu Leu Gln Phe Asn Met Gly His Ile
305                 310                 315                 320
Glu Val Phe Leu Gln Arg Thr Glu Glu Ser Val Ile Ser Lys Gly Leu
                325                 330                 335
Glu Leu Leu Glu Asn Ser Leu Leu Arg Ile Glu Asp Asn Ser Leu Leu
            340                 345                 350
Tyr Gln Tyr Leu Glu Ile Lys Ser Phe Leu Thr Val Pro Gln Gly Leu
        355                 360                 365
Val Lys Val Met Thr Leu Cys Pro Ile Glu Thr Leu Arg Lys Lys Ser
    370                 375                 380
Leu Ala Met Leu Gln Leu Tyr Ile Asn Lys Leu Asp Ser Gln Gly Lys
385                 390                 395                 400
Tyr Thr Leu Phe Arg Cys Leu Leu Asn Thr Ser Asn His Ser Gly Val
                405                 410                 415
Glu Ala Phe Ile Ile Gln Asn Ile Lys Asn Gln Ile Asp Met Ser Leu
            420                 425                 430
Lys Arg Thr Arg Asn Asn Lys Trp Phe Thr Gly Pro Gln Leu Ile Ser
        435                 440                 445
Leu Leu Asp Leu Val Leu Phe Leu Pro Glu Gly Ala Glu Thr Asp Leu
    450                 455                 460
Leu Gln Asn Ser Asp Arg Ile Met Ala Ser Leu Asn Leu Leu Arg Tyr
465                 470                 475                 480
Leu Val Ile Lys Asp Asn Glu Asn Asp Asn Gln Thr Gly Leu Trp Thr
                485                 490                 495
Glu Leu Gly Asn Ile Glu Asn Asn Phe Leu Lys Pro Leu His Ile Gly
            500                 505                 510
Leu Asn Met Ser Lys Ala His Tyr Glu Ala Glu Ile Lys Asn Ser Gln
        515                 520                 525
Glu Ala Gln Lys Ser Lys Asp Leu Cys Ser Ile Thr Val Ser Gly Glu
    530                 535                 540
Glu Ile Pro Asn Met Pro Pro Glu Met Gln Leu Lys Val Leu His Ser
545                 550                 555                 560
Ala Leu Phe Thr Phe Asp Leu Ile Glu Ser Val Leu Ala Arg Val Glu
                565                 570                 575
Glu Leu Ile Glu Ile Lys Thr Lys Ser Thr Ser Glu Glu Asn Ile Gly
            580                 585                 590
Ile Lys

<210> SEQ ID NO 3
<211> LENGTH: 1873
<212> TYPE: DNA
<213> ORGANISM: Homo sapiens

<400> SEQUENCE: 3
tctggccgat tttagcatcg aaactaggag aaataagaat ggctgtagag gaacttcagt     60
ctataataaa gagatgtcaa atcctagaag agcaagactt taaagaagag gattttggcc    120
tatttcagtt agctgggcaa agatgcatag aagaagggca cacagaccag ctattagaaa    180
ttattcaaaa tgaaaagaat aaggtcatca tcaagaatat gggctggaat ctcgttggtc    240
ctgttgttcg atgcctttg tgtaaagata aagaggatag taaagaaaa gtttatttt       300 tgatctttga tttattggta aaggttcaat tgtgaatatt tttatagtta tgcaatccaa    360
```

-continued

```
aggaattatt gttgggtttg cttgaactga ttgaagagcc ctctggaaaa cagatatccc    420
aaagtattct tcttttgctt cagccattac aaacagtgat tcagaaactt cataacaagg    480
catattcaat tggattagca ttgtctaccc tttggaatca gctatctctt cttcctgttc    540
catactcaaa agaacaaata caaatggatg actatggcct tgtcagtgt tgcaaggcct     600 taatagagtt cactaagcct tttgtggaag aagtcattga taacaaagaa aactcactgg    660
aaaatgaaaa gttaaaggat gaattactga aattttgttt caaaagcttg aaatgccctt    720
tgctgacagc acaattcttt gaacagtctg aagaaggtgg aaatgatcct ttcaggtatt    780
ttgcatcaga ataataggt ttttatcag caattggaca cccttcccc aaaatgattt       840 ttaatcatgg aaggaaaaag agaacttgga attaccttga atttgaagaa gagaaaata    900 aacagttagc agactcaatg gcttctctgg catatctagt atttgtacag ggcatccata    960
ttgatcagct tccaatggtc ttaagcccat tgtacctttt gcagtttaat atggggcaca    1020
ttgaagtctt tttgcaaaga acagaagagt ctgttatctc caaggattg gagctgctgg     1080 agaatagttt attgagaata aagacaata gtctacttta ccagtactta gaaatcaaga    1140
gttttcttac tgtacctcag ggcttagtga aagtaatgac actttgcccc attgagacac    1200
tgaggaaaaa gagtttagct atgcttcagc tgtatattaa caagttggat tcacaaggca    1260
aatatacatt atttaggtgc ttattgaata caagtaatca ctcaggtgtg gaggcttta    1320 ttattcaaaa tatcaaaaat caaattgaca tgtcattaaa gagaacacgt aacaacaaat    1380
ggtttacagg accacagttg atttcccttc ttgatttggt acttttctc ccagagggtg    1440 cagaaacaga tttactgcaa aactcagata ggattatggc ttcattaaat ttattgaggt    1500
atttggttat caaagataat gaaaatgaca atcaaactgg attatggaca gaacttggaa    1560
atattgagaa taattctta aagccacttc atataggact aatatgtca aaagcacatt      1620 atgaagcaga aattaaaaat agccaagagg cccagaaatc taaagatctt tgttctataa    1680
ctgtaagtgg agaagagatc cctaatatgc ctcctgaaat gcagcttaag gtcctgcatt    1740
cagctctttt cacatttgat ttgattgaaa gtgttctagc tcgagtggaa gaactcattg    1800
aaataaaaac aaagtctacc tctgaagaaa atattgggat aaagtgaaag ttccatttcc    1860
taaataaaaa cta                                                       1873
```

<210> SEQ ID NO 4
<211> LENGTH: 98
<212> TYPE: PRT
<213> ORGANISM: Homo sapiens

<400> SEQUENCE: 4

```
Met Ala Val Glu Glu Leu Gln Ser Ile Ile Lys Arg Cys Gln Ile Leu
1               5                   10                  15

Glu Glu Gln Asp Phe Lys Glu Asp Phe Gly Leu Phe Gln Leu Ala
            20                  25                  30

Gly Gln Arg Cys Ile Glu Glu Gly His Thr Asp Gln Leu Leu Glu Ile
        35                  40                  45

Ile Gln Asn Glu Lys Asn Lys Val Ile Ile Lys Asn Met Gly Trp Asn
    50                  55                  60

Leu Val Gly Pro Val Val Arg Cys Leu Leu Cys Lys Asp Lys Glu Asp
65                  70                  75                  80

Ser Lys Arg Lys Val Tyr Phe Leu Ile Phe Asp Leu Leu Val Lys Val
                85                  90                  95

Gln Leu
```

<210> SEQ ID NO 5
<211> LENGTH: 1719
<212> TYPE: DNA
<213> ORGANISM: Mus musculus

<400> SEQUENCE: 5

```
atggctgtgg aggaacttca gagcataata aaaagatgtc aaatcctaga agagcatgat      60
tttaaagaag aagattttgg cctctttcag ttagcaggtc aaagatgcat tgaagatggt     120
tatataaacc agctgctaga gattattcaa gatgaaaaga caagaccat cattaagtct      180
atggggtgga atcttgttgg tccagttgtt cgatgcctcc tgaggggcag agaagaggat     240
aaaagagaag agtgttttct gatatttgat ttgctggtga agttatgtaa tccaaaggaa     300
ttgttgttgg gtttgcttga actcattgaa gagccctccg aaaacagat tcccaaatt      360
attcttcttt tactgcaacc attacaaaca gttattcaga aacttcctaa caacaaggca     420
tactccgttg gactagcatt gtcaacactt tggagtcagc tgtctcttct tcctgttcca     480
cactcagaag aacaaattca ggcagatgat tatggcctct gtcagtgttg taaggccttg     540
atagagttca cgaaaccttt tgtggaagaa gtaataagtg ataaagaaaa caagaaaat     600
gcaaaactaa aagatgaatt actgaaattt tgtttcaaag cttgaaatg cccttttgctg     660
acagcacaat tcctcgaaca gtcagaagac gttggaaatg acccttttcg gtgttttgca     720
tctgaaataa taggatttt atcaaaaatt ggacaccctg tcccccaaat tattcttaat     780
catggaagga aaaaaaggac ttgggattac cttgaatttg aagaagaaga agacaaacaa     840
ctggcagagt ctgtggcttc tctgacatat ctagtaattg ttcagggcat cggtattgat     900
cagctgccca tggtcttaag cccatcgtac cttctgcagt gaacatgga gcatattgaa      960
gtgtttctgc aaagaacaga acagtctatt tactccaaag gattgaaact tctggagact    1020
agcttattga gattagaaga caacagccta tgttatcagt acttagaaat caagagtttt    1080
cttgctgtgc ctcagggctt agtcaaagtt atgacacttt gccccattga cattgagg      1140
aaaaaaggtt tatctatgct tcagctgttt attgacaagt tggattcaca aggcaaatat    1200
acattattta ggtgcttact aaatacaagt aatcactcag gagtggaagc ctttgtaatt    1260
caaaacatca aaaatcagat tgatttatca tttaagaaaa catataacaa atggtttgca    1320
ggagcacagc tgatctctct gttagacctg gtcctgtctc tccctgaggg cgctgagaca    1380
gacttactgc agaactcaga caggattatg gcttcattaa atttattgag gtatttggtt    1440
atcaaagata tgaagatga caatcaaact ggattatgga cagaacttgg aaaaattgaa    1500
aataactttc taaagccact tcatatagga cttaatatgt caaaagcaca ttatgaagca    1560
gaaattaaaa acagccaaca aaataaccaa gtagcctcaa tgtgtaaagg tgtttgttcc    1620
gtgactgtag gtggagaaga atccccttct atgcctcctg aaatgcagct taaggtctta    1680
cattccgctc tcttcacatt tgacttgatt gaaagtgtt                          1719
```

<210> SEQ ID NO 6
<211> LENGTH: 573
<212> TYPE: PRT
<213> ORGANISM: Mus musculus

<400> SEQUENCE: 6

```
Met Ala Val Glu Glu Leu Gln Ser Ile Ile Lys Arg Cys Gln Ile Leu
 1               5                  10                  15
Glu Glu His Asp Phe Lys Glu Glu Asp Phe Gly Leu Phe Gln Leu Ala
            20                  25                  30
```

```
Gly Gln Arg Cys Ile Glu Asp Gly Tyr Ile Asn Gln Leu Leu Glu Ile
            35                  40                  45

Ile Gln Asp Glu Lys Asn Lys Thr Ile Ile Lys Ser Met Gly Trp Asn
 50                  55                  60

Leu Val Gly Pro Val Val Arg Cys Leu Leu Arg Gly Arg Glu Glu Asp
 65                  70                  75                  80

Lys Arg Glu Glu Cys Phe Leu Ile Phe Asp Leu Leu Val Lys Leu Cys
                     85                  90                  95

Asn Pro Lys Glu Leu Leu Leu Gly Leu Leu Glu Leu Ile Glu Glu Pro
                100                 105                 110

Ser Gly Lys Gln Ile Ser Gln Ile Ile Leu Leu Leu Gln Pro Leu
            115                 120                 125

Gln Thr Val Ile Gln Lys Leu Pro Asn Asn Lys Ala Tyr Ser Val Gly
130                 135                 140

Leu Ala Leu Ser Thr Leu Trp Ser Gln Leu Ser Leu Leu Pro Val Pro
145                 150                 155                 160

His Ser Glu Glu Gln Ile Gln Ala Asp Asp Tyr Gly Leu Cys Gln Cys
                165                 170                 175

Cys Lys Ala Leu Ile Glu Phe Thr Lys Pro Phe Val Glu Glu Val Ile
                180                 185                 190

Ser Asp Lys Glu Asn Lys Glu Asn Ala Lys Leu Lys Asp Glu Leu Leu
            195                 200                 205

Lys Phe Cys Phe Lys Gly Leu Lys Cys Pro Leu Leu Thr Ala Gln Phe
            210                 215                 220

Leu Glu Gln Ser Glu Asp Val Gly Asn Asp Pro Phe Arg Cys Phe Ala
225                 230                 235                 240

Ser Glu Ile Ile Gly Phe Leu Ser Lys Ile Gly His Pro Val Pro Gln
                245                 250                 255

Ile Ile Leu Asn His Gly Arg Lys Lys Arg Thr Trp Asp Tyr Leu Glu
                260                 265                 270

Phe Glu Glu Glu Asp Lys Gln Leu Ala Glu Ser Val Ala Ser Leu
            275                 280                 285

Thr Tyr Leu Val Phe Val Gln Gly Ile Gly Ile Asp Gln Leu Pro Met
290                 295                 300

Val Leu Ser Pro Ser Tyr Leu Leu Gln Leu Asn Met Glu His Ile Glu
305                 310                 315                 320

Val Phe Leu Gln Arg Thr Glu Gln Ser Ile Tyr Ser Lys Gly Leu Glu
                325                 330                 335

Leu Leu Glu Thr Ser Leu Leu Arg Leu Glu Asp Asn Ser Leu Cys Tyr
            340                 345                 350

Gln Tyr Leu Glu Ile Lys Ser Phe Leu Ala Val Pro Gln Gly Leu Val
            355                 360                 365

Lys Val Met Thr Leu Cys Pro Ile Glu Thr Leu Arg Lys Lys Gly Leu
            370                 375                 380

Ser Met Leu Gln Leu Phe Ile Asp Lys Leu Asp Ser Gln Gly Lys Tyr
385                 390                 395                 400

Thr Leu Phe Arg Cys Leu Leu Asn Thr Ser Asn His Ser Gly Val Glu
                405                 410                 415

Ala Phe Val Ile Gln Asn Ile Lys Asn Gln Ile Asp Leu Ser Phe Lys
                420                 425                 430

Lys Thr Tyr Asn Lys Trp Phe Ala Gly Ala Gln Leu Ile Ser Leu Leu
            435                 440                 445
```

```
Asp Leu Val Leu Ser Leu Pro Glu Gly Ala Glu Thr Asp Leu Leu Gln
    450                 455                 460

Asn Ser Asp Arg Ile Met Ala Ser Leu Asn Leu Leu Arg Tyr Leu Val
465                 470                 475                 480

Ile Lys Asp Asn Glu Asp Asn Gln Thr Gly Leu Trp Thr Glu Leu
                485                 490                 495

Gly Lys Ile Glu Asn Asn Phe Leu Lys Pro Leu His Ile Gly Leu Asn
            500                 505                 510

Met Ser Lys Ala His Tyr Glu Ala Glu Ile Lys Asn Ser Gln Gln Asn
        515                 520                 525

Asn Gln Val Ala Ser Met Cys Lys Gly Val Cys Ser Val Thr Val Gly
    530                 535                 540

Gly Glu Glu Ile Pro Ser Met Pro Pro Glu Met Gln Leu Lys Val Leu
545                 550                 555                 560

His Ser Ala Leu Phe Thr Phe Asp Leu Ile Glu Ser Val
                565                 570
```

```
<210> SEQ ID NO 7
<211> LENGTH: 1743
<212> TYPE: DNA
<213> ORGANISM: Mus musculus

<400> SEQUENCE: 7
atggctgtgg aggaacttca gagcataata aaaagatgtc aaatcctaga agagcatgat      60
tttaaagaag aagattttgg cctctttcag ttagcaggtc aaagatgcat tgaagatggt     120
tatataaacc agctgctaga gattattcaa gatgaaaaga caagaccat cattaagtct      180 atggggtgga tcttgttggt ccagttgtt cgatgcctcc tgaggggcag agaagaggat      240
aaaagagaag agtgttttct gatatttgat ttgctggtga aggttcaatt gtgaatattt     300
ttatagttat gtaatccaaa ggaattgttg ttgggtttgc ttgaactcat tgaagagccc     360
tccggaaaac agatttccca aattattctt ctttttactgc aaccattaca aacagttatt     420
cagaaacttc ctaacaacaa ggcatactcc gttggactag cattgtcaac actttggagt     480
cagctgtctc ttcttcctgt tccacactca gaagaacaaa ttcaggcaga tgattatggc     540
ctctgtcagt gttgtaaggc cttgatagag ttcacgaaac cttttgtgga agaagtaata     600
agtgataaag aaaacaaaga aatgcaaaa ctaaaagatg aattactgaa attttgtttc      660
aaaggcttga atgcccttt gctgacagca caattcctcg aacagtcaga agacgttgga     720
aatgaccctt ttcggtgttt tgcatctgaa ataataggat tttatcaaa aattggacac      780 cctgtccccc aaattattct taatcatgga aggaaaaaaa ggacttggga ttaccttgaa     840
tttgaagaag aagaagacaa acaactggca gagtctgtgg cttctctgac atatctagta     900
tttgttcagg gcatcggtat tgatcagctg cccatggtct taagcccatc gtaccttctg     960
cagttgaaca tggagcatat tgaagtgttt ctgcaaagaa cagaacagtc tatttactcc    1020
aaaggattgg aacttctgga gactagctta ttgagattag aagacaacag cctatgttat    1080
cagtacttag aaatcaagag ttttcttgct gtgcctcagg gcttagtcaa agttatgaca    1140 cttttgcccca ttgagacatt gaggaaaaaa ggtttatcta tgcttcagct gtttattgac    1200
aagttggatt cacaaggcaa atatacatta tttaggtgct tactaaatac aagtaatcac    1260
tcaggagtgg aagcctttgt aattcaaaac atcaaaaatc agattgattt atcatttaag    1320
aaaacatata acaaatggtt tgcaggagca cagctgatct ctctgttaga cctggtcctg    1380
tctctccctg agggcgctga gacagactta ctgcagaact cagacaggat tatggcttca    1440
```

```
ttaaatttat tgaggtattt ggttatcaaa gataatgaag atgacaatca aactggatta    1500
tggacagaac ttggaaaaat tgaaaataac tttctaaagc cacttcatat aggacttaat    1560
atgtcaaaag cacattatga agcagaaatt aaaaacagcc aacaaaataa ccaagtagcc    1620
tcaatgtgta aaggtgtttg ttccgtgact gtaggtggag aagaaatccc ttctatgcct    1680
cctgaaatgc agcttaaggt cttacattcc gctctcttca catttgactt gattgaaagt    1740
gtt                                                                 1743
```

<210> SEQ ID NO 8
<211> LENGTH: 97
<212> TYPE: PRT
<213> ORGANISM: Mus musculus

<400> SEQUENCE: 8

```
Met Ala Val Glu Glu Leu Gln Ser Ile Ile Lys Arg Cys Gln Ile Leu
1               5                   10                  15

Glu Glu His Asp Phe Lys Glu Glu Asp Phe Gly Leu Phe Gln Leu Ala
            20                  25                  30

Gly Gln Arg Cys Ile Glu Asp Gly Tyr Ile Asn Gln Leu Leu Glu Ile
        35                  40                  45

Ile Gln Asp Glu Lys Asn Lys Thr Ile Ile Lys Ser Met Gly Trp Asn
    50                  55                  60

Leu Val Gly Pro Val Val Arg Cys Leu Leu Arg Gly Arg Glu Glu Asp
65                  70                  75                  80

Lys Arg Glu Glu Cys Phe Leu Ile Phe Asp Leu Leu Val Lys Val Gln
                85                  90                  95

Leu
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9

```
tctggccgat tttagcatcg                                                 20
```

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10

```
tagttttat ttaggaaatg gaac                                             24
```

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11

```
aatggctgtg gaggaacttc                                                 20
```

```
<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
gcattttgtt ggtttttatt tatg                                        24

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
agcaaactta ctggcagtgc                                             20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
gctacttgga gctgagcag                                              19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
aggagaatgg cgtgaaccc                                              19

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
tcaaagattc ttccttcctg c                                           21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
actcaggaat ggagtcatgg                                             20
```

```
<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
catgctcaca gggtagatac                                                  20

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
tctaaagtct tgtcacagtg c                                                21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
gtctatatgg catgtttctc c                                                21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
agcaggtatg tcacacagtg                                                  20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
tatggcttgg atctcccttc                                                  20

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
tatcttcaat gaaatcccaa tac                                              23
```

```
<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
gttttgacaa agtatcagat tgc                                          23

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25
actgccctca tactaccatg                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26
ctgaaccaac catgcatcac                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
gccacttgta tgtaggagag                                              20

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
tggctactaa cagacatcaa c                                            21

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
gacgtcctat ccagtagaag                                              20
```

```
<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
tttcactgga ccttcctgag                                              20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
ctctagagag tatgcgtctc                                              20

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 32
acactgacta ctatggaact g                                            21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
atggagaact ccagtgagag                                              20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
taagttctga atgcatgggt c                                            21

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35
agactgataa ttctgagcta tc                                           22
```

```
<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 36
atgcatgcag gccacatatg                                                   20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 37
tactctggat ctctcacagg                                                   20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 38
tagcttgtcc tctcttgctg                                                   20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 39
agcagttatt tctggtggta g                                                 21

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 40
tggagattta gacagtttat aac                                               23

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 41
ccagggtggt ctcaaactc                                                    19
```

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 42
taagtctatg atccatttcg ag                                              22

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 43
gagagtgaga ccctgtctg                                                  19

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 44
aaaggacaga gaatcaacct g                                               21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 45
gtgacaggag ccaatgaatg                                                 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 46
gggatgtcta gacagaagtg                                                 20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 47
gggttagggg taaagggtgg                                                 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 48
cgaagaacct ggtatgcagg                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 49
tcctgcatac caggttcttc                                              20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 50
tgttctgctg gtagtagtcc                                              20

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 51
tgagccacca cgcccaac                                                18

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 52
tgcgcacgtt cttgtgctg                                               19

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 53
atatctgaca tctcagagtg g                                            21

```
<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 54
ctggcctgaa tttcagagtc                                               20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 55
ctctgcatag agtcagcaag                                               20

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 56
ccaccatgcc cagtttctc                                                19

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 57
gaggtcagga gttcgagac                                                19

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 58
gtaggagtgc atcaccatgc                                               20

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 59
tctgactttg acgttgtaac c                                             21
```

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 60
cagtcacttc tctttcatca g                                              21

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 61
tgtaaagagc tgctgcactc                                                20

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 62
agcaaagtga catctgactt c                                              21

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 63
cttgaagcca ggagtttgag                                                20

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 64
cagcctccca agtagctag                                                 19

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 65
atgttgttca gcgcaacctc                                                20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 66
agcctggatg acagaatgag                                              20

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 67
ggtatggtga atgaagcatt c                                            21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 68
tgagctcctg aattacacat c                                            21

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 69
tttttaaatc ccataacttg cc                                           22

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 70
gcagtggtga gagagtgg                                                18

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 71
caacaggttg agaaggcaag                                              20

```
<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 72
gggtgacaga gtgagactg                                             19

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 73
caacatagat cctgggaacg                                            20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 74
gagaatctga ccttgaaggc                                            20

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 75
catcgaaact aggagaaata ag                                         22

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 76
ccactcatgc tctttacagg                                            20

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 77
catagataaa tcaagaagtt attg                                       24
```

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 78
atgtgattat tctcttccca ag                                           22

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 79
tgcgagagtc ctatagatgg                                              20

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 80
tgctgtgtgt tatgataaag ag                                           22

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 81
atattttgtc gatatatgcc ttc                                          23

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 82
gtgtagtatt gacattttga gg                                           22

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 83
ttgatgagcg acaacttgat c                                            21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 84
taagtccact gtgagatgtt c                                              21

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 85
cttggaagtg ttcatttcat ag                                             22

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 86
gcagtactga gaatatagtg g                                              21

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 87
gtcagagagc tatggtttcc                                                20

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 88
gtgttaatat gcatatattg gac                                            23

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 89
ctagaggtta ggactccaac                                                20

```
<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 90
cagtctccgc tgatcttaac                                              20

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 91
agaatttctc cttaatgata tgc                                          23

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 92
tgatagtgaa gtcaacagct g                                            21

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 93
acttaaatac atagttatgt caac                                         24

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 94
taagttcaga acaggcaaag g                                            21

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 95
tcagtataat ctgtttacat ctg                                          23
```

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 96
tgtaatacat ccacacttgt ac                                          22

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 97
gtgatgaagt ctgggtaagc                                             20

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 98
aacaattaca tggcattaac atg                                         23

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 99
atcaccattt aattctaatg ctg                                         23

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 100
tagagataga gcaataactc ac                                          22

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 101
tttttgtagt gtcaaggtat tag                                         23

```
<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 102
tttattactt taggttccct aag                                           23

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 103
tagcttattg agattgctgt tg                                            22

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 104
tatctgaaac attccttatg cc                                            22

<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 105
agtaggcaat caatcattgt tg                                            22

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 106
aatggcttag ctgttatggt c                                             21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 107
gagagttaag tgtcacacat g                                             21
```

```
<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 108
agcttgggca agatagcaag                                              20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 109
agctacctcc agctgaaatc                                              20

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 110
tagtttttat ttaggaaatg gaac                                         24

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 111
taatacgact cactataggg                                              20

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 112
catttaggtg acactatag                                               19

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 113
tctggccgat tttagcatcg                                              20
```

```
<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 114
tagtttttat ttaggaaatg gaac                                           24

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 115
gctgattcca aagggtagac                                                20

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 116
tgggatatct gttttccaga g                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 117
ctatcctctt tatctttaca c                                              21

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 118
tctggccgat tttagcatcg                                                20

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 119
tagtttttat ttaggaaatg gaac                                           24
```

```
<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 120
gcacacagac cagctattag                                             20

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 121
tcaaagaatt gtgctgtcag c                                           21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 122
agtttagcta tgcttcagct g                                           21

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 123
ggaggcatat tagggatctc                                             20

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 124
ttggtatcgt ggaagtactc a                                           21

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 125
tgtcatcata tttggcaggt tt                                          22
```

```
<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 126
atcgaccact acctgggcaa                                                   20

<210> SEQ ID NO 127
<211> LENGTH: 19
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 127
ttctgcatca cgtcccgga                                                    19

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 128
aatggctgtg gaggaacttc                                                   20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 129
catcgaacaa ctggaccaac                                                   20

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 130
ttggtatcgt ggaagtactc a                                                 21

<210> SEQ ID NO 131
<211> LENGTH: 22
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 131
tgtcatcata tttggcaggt tt                                                22
```

```
<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 132
tacctgcggc ttttcgagag                                              20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 133
accctgaacc tctccacaac                                              20

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 134
cttaagtgta atatcacgga tag                                          23

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 135
ctgcttcata atgtgctttt                                              20

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 136
agtaggcaat caatcattgt tg                                           22

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence:
      oligionucleotide: probe or primer

<400> SEQUENCE: 137
aatggcttag ctgttatggt c                                            21
```

<210> SEQ ID NO 138
<211> LENGTH: 16
<212> TYPE: PRT
<213> ORGANISM: Human

<400> SEQUENCE: 138

Cys Val Pro Tyr Ser Lys Glu Gln Ile Gln Met Asp Asp Tyr Gly Leu
1               5                   10                  15

<210> SEQ ID NO 139
<211> LENGTH: 16
<212> TYPE: PRT
<213> ORGANISM: Human

<400> SEQUENCE: 139

Cys Glu Ile Lys Thr Lys Ser Thr Ser Glu Glu Asn Ile Gly Ile Lys
1               5                   10                  15

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 140
ggagaaatac atatggctgt ag                                              22

<210> SEQ ID NO 141
<211> LENGTH: 26
<212> TYPE: DNA
<213> ORGANISM: Artificial Sequence
<220> FEATURE:
<223> OTHER INFORMATION: Description of Artificial Sequence:
      oligonucleotide: probe or primer

<400> SEQUENCE: 141
aaccctattt cactttcacc taggac                                          26

<210> SEQ ID NO 142
<211> LENGTH: 1068
<212> TYPE: DNA
<213> ORGANISM: Human

<400> SEQUENCE: 142
gattttagca tcgaaactag gagaaataag aatggctgta gaggaacttc agtctataat      60
aaagagatgt gtwwktatta atttttgtaa aattaaatac ctttcaaaat atgggaaggg     120
cacagattgt ttttaattat atttgtkgtc actcaaattg tttatcttct ttaatccttg     180 cttttttttga cctgtaaaga gcatgagtgg gggaggcaga ttggattatt tctccaggtg    240
acatacttat ctaaataacc ttttacattt taatcctgat ccttttcata gatttcactg     300
gtacrgtaga tttcaaggtc acttattaaa gtatttatta gtggtaatcc taattttgat    360
acgtgtgtta tttacgttac atttatctag aatttaaaca gatttccttt tttcatagat    420
aaatcaagaa gttattgtat ttaattttta tttgcatata ctttttttg tttgtttttt     480 gggtttttt ttttttttgcc agcaaatcct agaagagcaa gacttaaag aagaggattt     540 tggcctattt cagttagctg ggcaaagatg catagaagaa gggcacacag accagctatt    600
agaaattatt caaaatgaaa agaataaggt gcgtacaatc ttggtgttta cttttcagtc    660
ttgggaagag aataatcaca tgatgctatt catccagtca tttatccatc aaacatttaa    720

```
gaatctactt aaattttcac agtagggaac tgaaaacaaa aaaagaatta gaaatattta    780
ggccaggcgc agtggctcac gttcgtaatc acagcgttat gggaggccaa ggcaggcaga    840
tcacttgagc ccaggagttt gagrccagcc tgggcaacag agtaagaccc tgtctcagaa    900
aaaaaaaaaa aaaaaagara agakacagtc atatacttga aggkttttta ccatctggtc    960
amacataaac aatgtwaacm actwacaata ttgaggcaaa wtaatatwtk gctatagttg   1020
arkaaagagk ttttagrara acagaatwct tctggttwgg gggccaaa              1068
```

```
<210> SEQ ID NO 143
<211> LENGTH: 4084
<212> TYPE: DNA
<213> ORGANISM: Human
<220> FEATURE:
<221> NAME/KEY: misc_feature
<222> LOCATION: (3814)..(3814)
<223> OTHER INFORMATION: N = any nucleic acid
<220> FEATURE:
<221> NAME/KEY: misc_feature
<222> LOCATION: (3833)..(3833)
<223> OTHER INFORMATION: N = any nucleic acid
<220> FEATURE:
<221> NAME/KEY: misc_feature
<222> LOCATION: (3845)..(3846)
<223> OTHER INFORMATION: N = any nucleic acid
<220> FEATURE:
<221> NAME/KEY: misc_feature
<222> LOCATION: (3859)..(3859)
<223> OTHER INFORMATION: N = any nucleic acid
<220> FEATURE:
<221> NAME/KEY: misc_feature
<222> LOCATION: (3898)..(3898)
<223> OTHER INFORMATION: N = any nucleic acid
<220> FEATURE:
<221> NAME/KEY: misc_feature
<222> LOCATION: (3929)..(3930)
<223> OTHER INFORMATION: N = any nucleic acid
<220> FEATURE:
<221> NAME/KEY: misc_feature
<222> LOCATION: (3944)..(3945)
<223> OTHER INFORMATION: N = any nucleic acid
<220> FEATURE:
<221> NAME/KEY: misc_feature
<222> LOCATION: (3950)..(3950)
<223> OTHER INFORMATION: N = any nucleic acid
<220> FEATURE:
<221> NAME/KEY: misc_feature
<222> LOCATION: (3959)..(3959)
<223> OTHER INFORMATION: N = any nucleic acid
<220> FEATURE:
<221> NAME/KEY: misc_feature
<222> LOCATION: (3972)..(3972)
<223> OTHER INFORMATION: N = any nucleic acid
<220> FEATURE:
<221> NAME/KEY: misc_feature
<222> LOCATION: (4033)..(4033)
<223> OTHER INFORMATION: N = any nucleic acid

<400> SEQUENCE: 143
ctggggtggc cgaatcmcgg ggtmaggraa acagrgccmw cmswggctwa cawkgggaaa     60
ccccytctct rctaaaawaa aaaaaaaaaa aaggcaaaaa attagccagg catggtggcg    120
grtgcctgta gccccagcta cttggggggc tgagacagga gaatgacatg aacccatgga    180
agcaggagct tgcagtgagc tgggacagcg ccactgcact ccagcctggg cgacagagcg    240
agactcagtt tcaaaataaa taataaata agaatgtatt taactttaaa aaacagagac    300
agggtctcac taggttgccc aggctggtct caaactcctg ggctcaagtg atcctcctgc    360
ctcagcctcc taaggtgctg ggattagaga catgagccac tgcacccagc caaccaccgt    420
gcttttaaag aaggactcta gaatgtaaac tctaggaggg tagtgatctt atccagtgtg    480
```

```
ttcctcactt tayatttcta acctctcaga atattcatag tgtaggcttg cgtaaatmac    540
tgatgagtta aaatacaaag caggccagag caagtggaat acattgttga tccttcgaga   600
attagtggtt ttgataatga atgtgaatta gtcattataa agataaactt ttacttgtat   660
ggtaagcatt ctgaaatatc tttgaacata gaagccactt gtatgtagga gagaaaatta  720
atgaagttgt atcccttctt ttttttataa attacaagga ttatatttag agactccaag   780
aactttaaaa ggtacatgag cattggctgg atttctttat gaataagggg agcaaaattg   840
tctgtggaag ttaagtacct gtattaagca aattaactct tttgttggaa atagaggcac   900
tatttaaatc ttgggaaaca ccaacttgcc tgataaaaag taaagaccct tttgcctttc   960
ctcagggaac atattaaaaa ctatttaaaa atgttgatgt ctgttagtag ccaaccctgg  1020
aaagtctctg gtgaaatgtc ataggcttca cttgtctcat cttcctattt cagaaacaat  1080
tctgagctct tccaagatag gaaagcacac tgcgagagtc ytatagatgg cagtgtttgc  1140
tttactctga aaatgttttt acaggtcatc atcaagaata tgggctggaa tctcgttggt  1200
cctgttgttc gatgcctttt gtgtaaagat aaagaggata gtaaaagaaa agtttatttt  1260
ttgatctttg atttattggt aaaggtaagt taacaaaaca aggttctctt tatcataaca  1320
cacagcagta ttttactaat tcccctttaa tgtttattgg tttggtaaga wagcttttgg  1380
ttcatgaaag tacatgcaga aaggaactcg ttggagaaaa gacccagtct tattgattgg  1440
ataggcaatt ccatttcagg atttcccaaa ttttctggat aaaaagaatt gtctaacctc  1500
atattaacct catatcggac ccattgattc agcatctcca gggagagacc tgggaagcta  1560
tatcttaaca agtagcctta tcgtatagat gtggaataca agctttagag aggtagttca  1620
aggtcacatt tatctttggg caacattgga actagattaa aatctcagtc ctctttcctt  1680
tgtggtatgt tccctaaaag aaaatggaag gcctagaata caagtgatta aaattgaagt  1740
aggaataggg tagaacacag atcagttgtg actaacaacc ttagaaagtg accctgggta  1800
aaagggctag tagagtttac agtcaatatt tgatggccaa gaaagataaa ttctgaagga  1860
aaagtatatt ataagaaact gtttagtgat cagtgcaaat atacccaaat atatattgga  1920
aggagagctc catctgtatg agttattgac tatgggagct gggagctttt aaaaaaccag  1980
tcaagtgaga tgataagata tggccagtca gaaagcaatg caaagttta cctgttcaaa  2040
aaatacaaaa gagattccag actagtctaa ataggcttgc agcatgggat tgaaaggtcc  2100
cacctgctgg agccctgag aatctgttaa ggcaatttca gagtggacag gtgaagctca  2160
aaggaaacct gagcctaaag atccattgac ttcttgcttt ttagttttat agttacttga  2220
ccatcacaga ttctgtgttt ttgctcatgc atattttttc aacaattgta taaataattt  2280
taatrttaag caaaaacata attgtatwaa taktttgkcg rtatatgcct tcttaaaaat  2340
agtaataatg tggctttaaa tacaacttgk wttaaacagg ttcaattgtg aatattttta  2400
tagttatgca atccaaagga attattgttg ggtttgcttg aactgattga agagccctct  2460
ggaaaacaga tatcccaaag tattcttctt ttgcttcagc cattacaaac aggtaatgrg  2520
aawtttgata tcagagtact tcttgttgta tctctaaatg ccttgatggk tacctcaaaa  2580
tgtcaatact acaccaaagt aaagtttaca gctaattagt gagtactctg ctyaaaccaa  2640
taatagcaat gccaatgtga atactgctgc tcatagaaag attatagtat ctggccagag  2700
tgggtaccca gtaaatattc tgttgaatgt catactattt ttcatgtgct atattgaaaa  2760
ctatacctt ttgcctaacc ttcctatctg ctgcttaaat ctagaatttt ctctctaaac  2820
atgtttcaag ggttacctct gtggtgtctg cagtrctaaa tctgatagca ttatggtagt  2880
```

```
ctggaagagt atcaggcaag gcattgctca gcctctgctt tgggaggttg gattgggyat    2940
agcaaagcta ctactgaaga atgaaacgag gagatatggg atgataaggc tccrtggctg    3000
agtgcagtaa cagtattggt aggtaatggg tcttagcaac caaggcagac agtatccata    3060
ggaagaggtt atttttcatt ttaggaaatt cgtttatctc acartctgat agagggacct    3120
agaatcagaa attaaatttg ttttaaatat gaatgcctgc cagcttcata ctacctgtaa    3180
tattcagtct tctagggaaa aaaaatctaa taataccacc tcctatttgt gtagtgcttt    3240
atagtttaca atacacttat attttgygct tataacaacc caaaaacatg gaagaacat     3300 gtttctgtct taagtacata gcctgttaca catagtctgt tataaacata acctaaacag    3360
catttcatgg caagatgctg tattatttta tgcacaacta agaagaaaaa aacactgcca    3420
attagactgt gatgtgtcat cttgattcaa gagttgttaa aatgtgggag gaggaagtkt    3480
cwtawaattc cacatttgcc gaatttcttg tcccatgttt agcatacttg atgagcgaca    3540
atttgatctc tgtttttgtg attcagaaac ttcataacaa ggcatattca attggattag    3600
cattgtctac cctttggaat cagctatctc ttcttcctgt tccatactca aaagaacaaa    3660
tacaaatgga tgactatggc ctttgtcagt gttgcaaggc cttaatagag ttcactaagc    3720
cttttgtgga agaagtcatt gataacaaag aaaactcact ggaaaatgaa aagttaaagg    3780
atgaattact gaaattgtat agtataattt gtanagcaac atctcacagt ggnacttaag    3840
taatnngata gttcagtgna ttttatgttc tcttcacttg tgtttgacat gtaaatanga    3900
aatctagttt catgatttct gaatttatnn aagaatgtgg ggtnncagtn tgatacagnc    3960
atgggaactt gnagacatct atattttaaa aaattatagg ccgggtgtag tggctcacac    4020
atgtaatccc atncactgtg ggatgactga agtgagagga ttgcttgggg ccaggagttc    4080
tgaa                                                                 4084
```

```
<210> SEQ ID NO 144
<211> LENGTH: 487
<212> TYPE: DNA
<213> ORGANISM: Human
<220> FEATURE:
<221> NAME/KEY: misc_feature
<222> LOCATION: (387)..(387)
<223> OTHER INFORMATION: N = any nucleic acid
<220> FEATURE:
<221> NAME/KEY: misc_feature
<222> LOCATION: (418)..(418)
<223> OTHER INFORMATION: N = any nucleic acid
<220> FEATURE:
<221> NAME/KEY: misc_feature
<222> LOCATION: (422)..(422)
<223> OTHER INFORMATION: N = any nucleic acid
<220> FEATURE:
<221> NAME/KEY: misc_feature
<222> LOCATION: (439)..(441)
<223> OTHER INFORMATION: N = any nucleic acid
<220> FEATURE:
<221> NAME/KEY: misc_feature
<222> LOCATION: (443)..(445)
<223> OTHER INFORMATION: N = any nucleic acid
<220> FEATURE:
<221> NAME/KEY: misc_feature
<222> LOCATION: (455)..(457)
<223> OTHER INFORMATION: N = any nucleic acid
<220> FEATURE:
<221> NAME/KEY: misc_feature
<222> LOCATION: (460)..(460)
<223> OTHER INFORMATION: N = any nucleic acid
<220> FEATURE:
<221> NAME/KEY: misc_feature
<222> LOCATION: (476)..(478)
<223> OTHER INFORMATION: N = any nucleic acid
```

```
<220> FEATURE:
<221> NAME/KEY: misc_feature
<222> LOCATION: (484)..(485)
<223> OTHER INFORMATION: N = any nucleic acid

<400> SEQUENCE: 144
aaaagtgggc tgaacttgcc cttttataac agcattaatc tcatccgtga gagtggagcc    60
cccttggcct aattcccacc tccttatggc agttaaattt caacatgagt tttggagagc   120
agagtcattc aaaccatagc agtgcttatg ttatttttca agtaaaatta acttatattt   180
caagacctag ggattttata cttggaagtg ttcatttcat agttacctat ttcttatgcc   240
ttagttgttt caaaagcttg aaatgccctt tgctgacagc acaattcttt gaacagtctg   300
aagaaggtgg aaatgatcct ttcaggtatt ttgcatcaga ataatagta agtacagcta    360 atttaatctg ctataatctt aaatgtnatc ccactatatt ctcagtactg cacatgtnaa   420
tngcatacat tcattaatnn ngnnntgtgt atttnnngtn gaacacacat aaacannnga   480 tggnnaa                                                             487

<210> SEQ ID NO 145
<211> LENGTH: 738
<212> TYPE: DNA
<213> ORGANISM: Human
<220> FEATURE:
<221> NAME/KEY: misc_feature
<222> LOCATION: (39)..(39)
<223> OTHER INFORMATION: N = any nucleic acid
<220> FEATURE:
<221> NAME/KEY: misc_feature
<222> LOCATION: (63)..(63)
<223> OTHER INFORMATION: N = any nucleic acid
<220> FEATURE:
<221> NAME/KEY: misc_feature
<222> LOCATION: (65)..(65)
<223> OTHER INFORMATION: N = any nucleic acid
<220> FEATURE:
<221> NAME/KEY: misc_feature
<222> LOCATION: (89)..(94)
<223> OTHER INFORMATION: N = any nucleic acid
<220> FEATURE:
<221> NAME/KEY: misc_feature
<222> LOCATION: (101)..(101)
<223> OTHER INFORMATION: N = any nucleic acid

<400> SEQUENCE: 145
aggagtgatt acacctcccc ttggtgagaa tgtggagtnt gaatacacgg ggtgggggc    60 atntnagagt cagagagcta tggtttccnn nnnnatccat ntcataggt tttttatcag   120 caattggaca cccttcccc aaaatgattt ttaatcatgg aaggaaaaag agaacttgga   180
attaccttga atttgaagaa gaagaaaata aacagttagc agactcaatg gcttctctgg   240
catatctagt atttgtacag ggcatccata ttgatcagct tccaatggtc ttaaggtaag   300
agttagtgtt tggtttattc atgtattcta aaaggaattt cataaaattc tcatttatct   360
aatgtccaat atatgcatat taacacacta atacatttta aataaatagt aaaggctatt   420
tttaataaga atgatcccag ctataatctg ttaaagatag cagtagacaa gtaatgaaag   480
tggggagtgt tgaaataggt gtaagggaat ggtggggaca agaatcagaa gatgataaac   540
agggcttggt tttgaagctt tgagaccac cctggaacta gccaggtacc cagggtatc    600 atcatctttt cactggatta ctgctgtaat cctgagtgga tttatatatc tacttttact   660 tcctttaat ttaacacatt ctcaacatac cagaaagcga agcgcttaaa agaagtccct   720
tactgtacct cagggctt                                                 738
```

```
<210> SEQ ID NO 146
<211> LENGTH: 1169
<212> TYPE: DNA
<213> ORGANISM: Human
<220> FEATURE:
<221> NAME/KEY: misc_feature
<222> LOCATION: (810)..(810)
<223> OTHER INFORMATION: N = any nucleic acid
<220> FEATURE:
<221> NAME/KEY: misc_feature
<222> LOCATION: (819)..(819)
<223> OTHER INFORMATION: N = any nucleic acid
<220> FEATURE:
<221> NAME/KEY: misc_feature
<222> LOCATION: (849)..(850)
<223> OTHER INFORMATION: N = any nucleic acid
<220> FEATURE:
<221> NAME/KEY: misc_feature
<222> LOCATION: (868)..(869)
<223> OTHER INFORMATION: N = any nucleic acid
<220> FEATURE:
<221> NAME/KEY: misc_feature
<222> LOCATION: (908)..(908)
<223> OTHER INFORMATION: N = any nucleic acid
<220> FEATURE:
<221> NAME/KEY: misc_feature
<222> LOCATION: (917)..(917)
<223> OTHER INFORMATION: N = any nucleic acid
<220> FEATURE:
<221> NAME/KEY: misc_feature
<222> LOCATION: (931)..(931)
<223> OTHER INFORMATION: N = any nucleic acid
<220> FEATURE:
<221> NAME/KEY: misc_feature
<222> LOCATION: (934)..(934)
<223> OTHER INFORMATION: N = any nucleic acid
<220> FEATURE:
<221> NAME/KEY: misc_feature
<222> LOCATION: (939)..(939)
<223> OTHER INFORMATION: N = any nucleic acid
<220> FEATURE:
<221> NAME/KEY: misc_feature
<222> LOCATION: (944)..(946)
<223> OTHER INFORMATION: N = any nucleic acid
<220> FEATURE:
<221> NAME/KEY: misc_feature
<222> LOCATION: (953)..(954)
<223> OTHER INFORMATION: N = any nucleic acid
<220> FEATURE:
<221> NAME/KEY: misc_feature
<222> LOCATION: (949)..(949)
<223> OTHER INFORMATION: N = any nucleic acid
<220> FEATURE:
<221> NAME/KEY: misc_feature
<222> LOCATION: (983)..(954)
<223> OTHER INFORMATION: N = any nucleic acid
<220> FEATURE:
<221> NAME/KEY: misc_feature
<222> LOCATION: (956)..(956)
<223> OTHER INFORMATION: N = any nucleic acid
<220> FEATURE:
<221> NAME/KEY: misc_feature
<222> LOCATION: (960)..(964)
<223> OTHER INFORMATION: N = any nucleic acid
<220> FEATURE:
<221> NAME/KEY: misc_feature
<222> LOCATION: (966)..(966)
<223> OTHER INFORMATION: N = any nucleic acid
<220> FEATURE:
<221> NAME/KEY: misc_feature
<222> LOCATION: (969)..(969)
<223> OTHER INFORMATION: N = any nucleic acid
<220> FEATURE:
<221> NAME/KEY: misc_feature
<222> LOCATION: (975)..(975)
<223> OTHER INFORMATION: N = any nucleic acid
```

```
<220> FEATURE:
<221> NAME/KEY: misc_feature
<222> LOCATION: (982)..(982)
<223> OTHER INFORMATION: N = any nucleic acid
<220> FEATURE:
<221> NAME/KEY: misc_feature
<222> LOCATION: (997)..(997)
<223> OTHER INFORMATION: N = any nucleic acid
<220> FEATURE:
<221> NAME/KEY: misc_feature
<222> LOCATION: (999)..(1000)
<223> OTHER INFORMATION: N = any nucleic acid
<220> FEATURE:
<221> NAME/KEY: misc_feature
<222> LOCATION: (1012)..(1013)
<223> OTHER INFORMATION: N = any nucleic acid
<220> FEATURE:
<221> NAME/KEY: misc_feature
<222> LOCATION: (1015)..(1017)
<223> OTHER INFORMATION: N = any nucleic acid
<220> FEATURE:
<221> NAME/KEY: misc_feature
<222> LOCATION: (1021)..(1021)
<223> OTHER INFORMATION: N = any nucleic acid
<220> FEATURE:
<221> NAME/KEY: misc_feature
<222> LOCATION: (1023)..(1023)
<223> OTHER INFORMATION: N = any nucleic acid
<220> FEATURE:
<221> NAME/KEY: misc_feature
<222> LOCATION: (1027)..(1031)
<223> OTHER INFORMATION: N = any nucleic acid
<220> FEATURE:
<221> NAME/KEY: misc_feature
<222> LOCATION: (1034)..(1034)
<223> OTHER INFORMATION: N = any nucleic acid
<220> FEATURE:
<221> NAME/KEY: misc_feature
<222> LOCATION: (1036)..(1037)
<223> OTHER INFORMATION: N = any nucleic acid
<220> FEATURE:
<221> NAME/KEY: misc_feature
<222> LOCATION: (1045)..(1045)
<223> OTHER INFORMATION: N = any nucleic acid
<220> FEATURE:
<221> NAME/KEY: misc_feature
<222> LOCATION: (1049)..(1049)
<223> OTHER INFORMATION: N = any nucleic acid
<220> FEATURE:
<221> NAME/KEY: misc_feature
<222> LOCATION: (1051)..(1053)
<223> OTHER INFORMATION: N = any nucleic acid
<220> FEATURE:
<221> NAME/KEY: misc_feature
<222> LOCATION: (1055)..(1055)
<223> OTHER INFORMATION: N = any nucleic acid
<220> FEATURE:
<221> NAME/KEY: misc_feature
<222> LOCATION: (1057)..(1057)
<223> OTHER INFORMATION: N = any nucleic acid
<220> FEATURE:
<221> NAME/KEY: misc_feature
<222> LOCATION: (1064)..(1064)
<223> OTHER INFORMATION: N = any nucleic acid
<220> FEATURE:
<221> NAME/KEY: misc_feature
<222> LOCATION: (1066)..(1068)
<223> OTHER INFORMATION: N = any nucleic acid
<220> FEATURE:
<221> NAME/KEY: misc_feature
<222> LOCATION: (1074)..(1074)
<223> OTHER INFORMATION: N = any nucleic acid
<220> FEATURE:
<221> NAME/KEY: misc_feature
<222> LOCATION: (1094)..(1094)
<223> OTHER INFORMATION: N = any nucleic acid
```

```
<220> FEATURE:
<221> NAME/KEY: misc_feature
<222> LOCATION: (1101)..(1102)
<223> OTHER INFORMATION: N = any nucleic acid
<220> FEATURE:
<221> NAME/KEY: misc_feature
<222> LOCATION: (1104)..(1104)
<223> OTHER INFORMATION: N = any nucleic acid
<220> FEATURE:
<221> NAME/KEY: misc_feature
<222> LOCATION: (1106)..(1107)
<223> OTHER INFORMATION: N = any nucleic acid
<220> FEATURE:
<221> NAME/KEY: misc_feature
<222> LOCATION: (1110)..(1110)
<223> OTHER INFORMATION: N = any nucleic acid
<220> FEATURE:
<221> NAME/KEY: misc_feature
<222> LOCATION: (1112)..(1112)
<223> OTHER INFORMATION: N = any nucleic acid
<220> FEATURE:
<221> NAME/KEY: misc_feature
<222> LOCATION: (1116)..(1116)
<223> OTHER INFORMATION: N = any nucleic acid
<220> FEATURE:
<221> NAME/KEY: misc_feature
<222> LOCATION: (1121)..(1121)
<223> OTHER INFORMATION: N = any nucleic acid
<220> FEATURE:
<221> NAME/KEY: misc_feature
<222> LOCATION: (1123)..(1126)
<223> OTHER INFORMATION: N = any nucleic acid
<220> FEATURE:
<221> NAME/KEY: misc_feature
<222> LOCATION: (1134)..(1135)
<223> OTHER INFORMATION: N = any nucleic acid
<220> FEATURE:
<221> NAME/KEY: misc_feature
<222> LOCATION: (1137)..(1138)
<223> OTHER INFORMATION: N = any nucleic acid
<220> FEATURE:
<221> NAME/KEY: misc_feature
<222> LOCATION: (1140)..(1140)
<223> OTHER INFORMATION: N = any nucleic acid
<220> FEATURE:
<221> NAME/KEY: misc_feature
<222> LOCATION: (1143)..(1145)
<223> OTHER INFORMATION: N = any nucleic acid
<220> FEATURE:
<221> NAME/KEY: misc_feature
<222> LOCATION: (1150)..(1151)
<223> OTHER INFORMATION: N = any nucleic acid
<220> FEATURE:
<221> NAME/KEY: misc_feature
<222> LOCATION: (1160)..(1160)
<223> OTHER INFORMATION: N = any nucleic acid
<220> FEATURE:
<221> NAME/KEY: misc_feature
<222> LOCATION: (1165)..(1165)
<223> OTHER INFORMATION: N = any nucleic acid
<220> FEATURE:
<221> NAME/KEY: misc_feature
<222> LOCATION: (1167)..(1167)
<223> OTHER INFORMATION: N = any nucleic acid
<220> FEATURE:
<221> NAME/KEY: misc_feature
<222> LOCATION: (1169)..(1169)
<223> OTHER INFORMATION: N = any nucleic acid

<400> SEQUENCE: 146
tgaaataaca gaaatagttt gtctcatagt tctggatgct ccttctgagg gttgtgaagg      60
agaatcttct ccatgcctct ctcctggctt ctggtgattt gctcacaatc tttgatggtc     120
tttggcttgt agatgcatta tcctgttctc tgccttcatg ttcgtatgct gttctccctg     180
tgtgcttgct gtctgtctcc aaactttcct tttacataag gacaacagtc atattggatt     240
```

| | |
|---|---|
| agggcccacc ctaataatct cattttaaat tgattacctc cataaccta tctccaaata | 300 |
| aggtcaaatt ctgaggtact agaggttagg actccaacat atctttttg ggggagatac | 360 |
| aattcaaccc ataacaatat gtatgtgtgt acatatctct gtgtgtgtgt ataatatgta | 420 |
| tatttgtttt gtttctattt tagcccattg taccttttgc agtttaatat ggggcacatt | 480 |
| gaagtcttt tgcaaaggta agatcgttta tgatggtatc tcaaaatgaa atagtatgtt | 540 |
| aaaatagtcc ttgttaagat cagcggagac tgccttttct ttgctaagct ctaattaatt | 600 |
| aattggttat tttataaaac agcgaggcaa ataattcacg agagagacag aaatgagtca | 660 |
| aggaggtttt acaccaaagt ctgttttatt ttaaacttaa dacagtatta agattttgtc | 720 |
| ttaagggctt ttacagtcat ctgtttctaa ggtttcttct cttattccaa aagttggtaa | 780 |
| attaaaacac ctctaccca ctgcatcctn ccttccatnc ttaaggaagg gcagtcaata | 840 |
| aaagaagtnn cttccgtatt ttttcctnna tggacacagt cctgtgaatt gcatctaaag | 900 |
| gaaggagngt gtcttgnact ttccatcctt nttnataant ttannnatnt atnngnatcn | 960 |
| nnnngnatng tccantttc anaatgtgag ccaagcntnn ttttgcgtgc anntnnnttg | 1020 |
| nangagnnnn nctnannagt cagtncacng nnncntnttc tgantnnnta gaanctgcag | 1080 |
| catctcgtct aaanaagtcc nngngnncan tncggnttag ngnnnntaca tatnngnncn | 1140 |
| ccnnngagtn nataagttgn tctcntncn | 1169 |

```
<210> SEQ ID NO 147
<211> LENGTH: 2983
<212> TYPE: DNA
<213> ORGANISM: Human
<220> FEATURE:
<221> NAME/KEY: misc_feature
<222> LOCATION: (3)..(3)
<223> OTHER INFORMATION: N = any nucleic acid
<220> FEATURE:
<221> NAME/KEY: misc_feature
<222> LOCATION: (14)..(15)
<223> OTHER INFORMATION: N = any nucleic acid
<220> FEATURE:
<221> NAME/KEY: misc_feature
<222> LOCATION: (40)..(40)
<223> OTHER INFORMATION: N = any nucleic acid
<220> FEATURE:
<221> NAME/KEY: misc_feature
<222> LOCATION: (52)..(52)
<223> OTHER INFORMATION: N = any nucleic acid
<220> FEATURE:
<221> NAME/KEY: misc_feature
<222> LOCATION: (58)..(58)
<223> OTHER INFORMATION: N = any nucleic acid
<220> FEATURE:
<221> NAME/KEY: misc_feature
<222> LOCATION: (61)..(61)
<223> OTHER INFORMATION: N = any nucleic acid
<220> FEATURE:
<221> NAME/KEY: misc_feature
<222> LOCATION: (72)..(72)
<223> OTHER INFORMATION: N = any nucleic acid
<220> FEATURE:
<221> NAME/KEY: misc_feature
<222> LOCATION: (74)..(74)
<223> OTHER INFORMATION: N = any nucleic acid
<220> FEATURE:
<221> NAME/KEY: misc_feature
<222> LOCATION: (88)..(88)
<223> OTHER INFORMATION: N = any nucleic acid
<220> FEATURE:
<221> NAME/KEY: misc_feature
<222> LOCATION: (94)..(94)
<223> OTHER INFORMATION: N = any nucleic acid
```

```
<220> FEATURE:
<221> NAME/KEY: misc_feature
<222> LOCATION: (97)..(97)
<223> OTHER INFORMATION: N = any nucleic acid
<220> FEATURE:
<221> NAME/KEY: misc_feature
<222> LOCATION: (129)..(131)
<223> OTHER INFORMATION: N = any nucleic acid
<220> FEATURE:
<221> NAME/KEY: misc_feature
<222> LOCATION: (137)..(138)
<223> OTHER INFORMATION: N = any nucleic acid
<220> FEATURE:
<221> NAME/KEY: misc_feature
<222> LOCATION: (144)..(145)
<223> OTHER INFORMATION: N = any nucleic acid
<220> FEATURE:
<221> NAME/KEY: misc_feature
<222> LOCATION: (154)..(155)
<223> OTHER INFORMATION: N = any nucleic acid
<220> FEATURE:
<221> NAME/KEY: misc_feature
<222> LOCATION: (157)..(157)
<223> OTHER INFORMATION: N = any nucleic acid
<220> FEATURE:
<221> NAME/KEY: misc_feature
<222> LOCATION: (376)..(376)
<223> OTHER INFORMATION: N = any nucleic acid
<220> FEATURE:
<221> NAME/KEY: misc_feature
<222> LOCATION: (487)..(487)
<223> OTHER INFORMATION: N = any nucleic acid
<220> FEATURE:
<221> NAME/KEY: misc_feature
<222> LOCATION: (549)..(549)
<223> OTHER INFORMATION: N = any nucleic acid

<400> SEQUENCE: 147
```

| | | | | | |
|---|---|---|---|---|---|
| tgntctatca | tctnnggagc | gatcgtgtcg | cgatcggttn | gacgtgtata | tngtatgnga | 60 |
| nagagttaga | tnanatcata | cattgttngt | atancgnata | tagtatgtct | gattagtcta | 120 |
| atctgagann | naactgnnag | tcannagtct | tttnngnata | taaagaattg | gaaagatttt | 180 |
| acagaataat | caactggaat | atatagcatt | ggttatatca | ggtttagtta | gtgtcttagc | 240 |
| acttgctgtt | gaagatctat | tgttttgaag | ttaggaaata | atccctgagt | agatttattt | 300 |
| tggtcagatt | tagtggcctt | agccaaaccg | aaagacagat | caaagatgga | ttaaaacttt | 360 |
| tgatcaagtt | cttctacag | aatttctcct | taatgatatg | cattttaaca | agtgttaaaa | 420 |
| tttcagtttt | tgctgtattt | ttcataagat | gtaagtatca | ttctaaaata | gtttaccaaa | 480 |
| ttcatgnata | aatttgtcaa | tattattttt | ctagtaacag | aagagtctgt | tatctccaaa | 540 |
| ggattggtna | gcatgtttgt | tcccattata | acttaaatac | atagttatgt | caacgacaat | 600 |
| aacagctgtt | gacttcacta | tcatagtatc | tgcatatatt | ttaatctgta | ggagctgctg | 660 |
| gagaatagtt | tattgagaat | agaagacaat | agtctacttt | accagtactt | agaaatcaag | 720 |
| agttttctta | ctgtacctca | ggtaaataaa | atatgtattc | taatattgaa | atagcccctt | 780 |
| tgcctgttct | gaacttaaag | taaggtcttt | tctgattcct | ttcccactct | tttctctgca | 840 |
| acctttgaaa | actctggtgt | aatgctgtcc | agtagaactt | tgacaatatg | aaagccacta | 900 |
| gccaaactga | acacttgaaa | tgtgactaag | gaactatttt | tttttttttg | aggtgtagtc | 960 |
| ttgctgtktc | gcccaggttg | kagtgcagtg | gtgctatctc | agctcactgc | aagctccacc | 1020 |
| ycctgggttc | attccattct | cctgcctcag | cctcccgwgt | agctgggact | acaggygccc | 1080 |
| gycaccacac | ccagctaata | ttttttgtatt | tatagtagag | acggwgtttc | actgtgttag | 1140 |
| ccaggatggt | ctcgatctcc | tgacttcgtg | atcagcctgc | ctcagccccc | caaagtgctg | 1200 |

```
ggattacagg tgtgagccac cacacccagc cggaactaag tttcaaattt aaattttaat    1260
ttatttaaac acgaatagct attagaggcc accattattg atagcacagc atccagtaga    1320
aaagcataac tttcttcttc taacacttta tttctgtagg gatcttggwa aatgaagctt    1380
ctttatgttt ctcataactc aagttctcag gwctccatct aaggyatcca ctgactcatt    1440
accagaaaga ctaatacaca ttgtgttttt ccctcctatg gtttatttk yccaawcctc    1500 tttgttagtt atgwtatcca aggwaatcct tagatttcag tgtgggaact ggttttccta    1560
atatttaaat agaaaaacat gkttttgtt aacatattgt ttgattgttt tttaattaat    1620
aaattatatt tctgtagatt tgatttcatt ttcttgccac tgtagacata attgaaaatt    1680
atcgtttgct tttaaaagta cactgtgtga cactctactc aatatcactt aaaaaatcaa    1740
ttgtagttag ctttctggaa tggaaggctt agggaaaaat taatttactt cactttaaa    1800 tctcctaccc tcacttctct gaattttag tatcctattg atgtattata gttgtttgtt    1860
tgcagtcagt ataatctgtt tacatctgaa ttttacattt ttttattcc agggcttagt    1920 gaaagtaatg acactttgcc ccattgagac actggtatgt aaatatttgg tgactaaaga    1980
ataatgagtt acagtgagaa aatttgacaa ataatttaat tttctttta aaaattttaa    2040 tttgtgaaat ttttatttag gaggtacaag tgtggatgta ttacatgcat aaaatggata    2100
gtgatgaagt ctgggtaagc tttattcatt ttatataata atattgtttg ttccatttta    2160
gaggaaaaag agtttagcta tgcttcagct gtatattaac aagttggatt cacaaggcaa    2220
atatacatta tttaggtatg tatcaagcat ggctaattgc taagtgtgtg gttgattaaa    2280
aagtcatgtt aatgccatgt aattgtttta gggcatagta tgtcggtatg ttttacatgt    2340
aattcaactc tggttggaac ccatattata aattctcagt gatggctaga gaaagggtta    2400
atcaaatatt tcagacatac tatatatatg tctatatttt gtatgactaa tagtatatat    2460
tgcagttcaa tcaattggga tactctaaat ttgaaataga cttaaaaaat aattaaactg    2520
agattgatga tgctcctgct ggaaatttat gtatgtcact aatctccatt actcacagtt    2580
caaattgatg gctctggaat taaaactttg ataggctatg aactatgtta atagtaagag    2640
cttactaata ctgctctttg aggtggataa gattctagaa actctctaag ttaaagattg    2700
gtaaactttc taattaattt tctgtgaaga gcaaatagta aatataggtt ttatgggcta    2760
tacagtctct gttgcaagtg ctcaaacttt gactttgtat tggggatggg tgtgttccac    2820
gtaaactcta ttgataaaat tagggcaatc aggctggatt tgctaaaatt gtcttacctg    2880
gggattggcc aatattagaa ctgttctttt ttggcgggtg aaaaggtgtg atcatggctc    2940
actgaagcct tcaccttggc cccccagctt aaggtgatac acc                       2983
```

<210> SEQ ID NO 148
<211> LENGTH: 3207
<212> TYPE: DNA
<213> ORGANISM: Human
<220> FEATURE:
<221> NAME/KEY: misc_feature
<222> LOCATION: (2435)..(2435)
<223> OTHER INFORMATION: N = any nucleic acid
<220> FEATURE:
<221> NAME/KEY: misc_feature
<222> LOCATION: (2458)..(2458)
<223> OTHER INFORMATION: N = any nucleic acid
<220> FEATURE:
<221> NAME/KEY: misc_feature
<222> LOCATION: (3090)..(3090)
<223> OTHER INFORMATION: N = any nucleic acid

<400> SEQUENCE: 148

```
taactgggac tacagggcat gccatcatgc ccagctaatt tgtttgtgga gatggggttt      60
tcccatgttg cacaaggctt gtctcaaaca ccttggctca agcgattcac ccacttcagc     120
ctcccaaagt gttgagatga cacgcatgag ccatcatgcc cagccaacac tcttgattct     180
atcttttctt gttttctatt gatagtaaga gcaagtttat gaaatctcaa ttcttaggta     240
ttataccggc tttcctgttc tgttctatgt gtatctctac caataaatcc cctttttttt     300
cttaagctag tcatatctag ttttttgttt ttttttttgca attaagctac tctagcactg    360
gactactttc acaggaaata atttgggat ttttttagacc attatgttag tgcccttttct   420
tgccatgtta aattattgta actatgttca taaaaatatt caaattttgg tttgatagaa     480
atggcttgtt ggaagatcca gttataaata agtatttacc ggccgggtgt ggtggctcat     540
gcctgtaatc ccagcacttt gggaggctga ggcaggcgga tcacgaggtc aggagtttga     600
gacaagcctg gccaacatgg tgaaaccctg tttctactac aaatacaaaa aattagccag     660
gcacggtggc gggcgcctgt aatcacagct actcaggagg ctgaggcagg agaatcgctt     720
gaacccggga ggcggaggtt gcagtgagcc aaaattgtgc cactgcactc cagcctgggc     780
gacagggcga gactctgtct aaaaaagtaa aataaaataa ataagaattt accatttagt     840
gagagcaata actattacag gtgactttgt aattggttga tgaccttgct aattaccatt     900
actgtggggt tttattcct agaagtaaca catggcctct ttgaatttgt aaaactttta     960
tcaccattta attctaatgc tgtccaggat aatttcacat ctattgtaat tttgctttca    1020
aggtgcttat tgaatacaag taatcactca ggtgtggagg cttttattat tcaaaatatc    1080
aaaaatcaaa ttgacatgtc attaaaggta agaacatagc caaagtgtca attaccaatt    1140
tatttcgtag ggtatattta ttcatatgta gaatacatta atgtgagtta ttgctctatc    1200
tctagtatta ctattactta aatattatta aggcatattt tttcccctat ttctactatg    1260
ttttaaaaac tctgaatttg gaaatttagt taactataag tttaaattgt attctttgag    1320
gttttggttt ttgttttttgt tttttttgag acagggtttc acgcctgtca cccagcttgg    1380
agtgcagtgg catgatctca gctcactgca gcctccacct cctgggctca agcagttctc    1440
ccaactcagc ctcccgagta attgggacta caggtgtcca ccagtgcgcc tggctgaatt    1500
ttgattttgt agagatggag tttcactgtg ttgcccaggc tcgtcttgaa ctcctgagct    1560
caagtgatcc acccaccttg gcctcccaaa atgctgggat tacaggtgtg agtcatcact    1620
ctgggcctct ttgagctgat attgtggctt attttttgctt tgttatatgc ttctcaaaaa    1680
tgaatggaaa cttaagtctc ttctgttttct gagtgctcag taattctaaa tggaaaacag    1740
agtgaccagt gttctcaaac tggcagggtt cattcctggt gtctggaaag tgaatgaaag    1800
tacggaaatt aaagttaaaa actgtatttt aaatgtgcaa ttcttcrttt tgtagtgtc     1860
aaggtattag aaaaacacat kaattacatg aattataaag ctttctcaat ttttcgtttg    1920
cttttcagag aacacgtaac aacaaatggt ttacaggacc acagttgatt tcccttcttg    1980
atttggtact ttttctccca gagggtgcag aaacagattt actgcaaaac tcagataggt    2040
kkaggtgacc attaccaaag ttcacatagt aaattcagaa taaaatgtga acatctgcc     2100
ttagggaacc taaagtaata aaatgtcttt tcctgtgatt ttatgatcta tggctaattc    2160
attaagttac ataaagattt ttcatattta agtgatttga taatgtgtag aaacaaaatt    2220
aaaacctcct ctttctagat gaatgaccag cactatgatt tgatagcttt tatgtaccca    2280
gcattccata gaaatttgca atgacagcac ttgtgactta aaactaaaaa tctgtgtatg    2340
```

```
taatttatgt gtttaggttt tgttgtttta ttgttttttcc aggtcatttt ttttttccat    2400
ataraacata taatttcagt tttacagtat actgngaatg atattgara aatggttnta    2460 aagcatttaa aaagtaatct taaaattcag aaagcaagag atgatgctct caaatattaa    2520
agataacaag gctttcttta acaaggatg ataatttyca caattgtatg atttaaacaa    2580
atggaaaaca gtgataagtk atyactactc aaaaagatat taatgsaaat agtttctatt    2640
ggcaaaccta attataaaaa tatgaccaaa gttttagctt attgagattg ctgttgacta    2700
tataaaacca tactgtagta acatatattt ttaattaaca gattatggct tcattaaatt    2760
tattgaggta tttggttatc aaagataatg aaaatgacaa tcaagtaagt gaagtatttg    2820
aaaagaaact gtgagtatat tcaaaaggca taaggaatgt ttcagatatt cagtacctaa    2880
agccaatatt taatatctta cccagatata aaggccggga agagtgccaa caattattct    2940
gaaacctgaa gttaattccc aggagcattt accaccccac atccagcttt cctttcccttt    3000 tccatttcct attgtacgtc tgcttttcttg ctgaaagcac ttagtcccgt tgggtggata    3060
agttgcaggt cctaagtcaa ctaaccttgn tggagctcaa cgtacatatg gtgtcttgtt    3120
cagtttcctc cacctatagc tcatgagctg tataaaatca tctgatattt taatattgcc    3180
tcatcagaca tgacaaattg aagcatt                                       3207
```

<210> SEQ ID NO 149
<211> LENGTH: 1969
<212> TYPE: DNA
<213> ORGANISM: Human

<400> SEQUENCE: 149

```
atcttcacct actttggtca ccagggaggt tcaaattagc cgggtattag aaaagtttcc      60
atcagtagga aagggaaagc atcctctaga actagatccg tggtgtggat atcaattgaa     120
aggccatact tgggatgaag gcataaataa ggtagagtca ttgtggagat ggctcataga     180
ggaagagacg tctgtgaatt tatcctcaaa taattttctc ataaataaaa cttaacaagt     240
taatagatct caaaacctgg agctatccaa atggtgcagt gataagcgta gtgccccaag     300
tacatttttc tttttaattgg tattcacata actagctata gtaataatta ttaaatagtg     360
aagtccattg tgaaaagcaa gggccatgtt tcatttattt ttgttttttg agcttttatc     420
gcgtttaata gtaggcaatc aatcattgtt gaactaaata actcatcttt cattcttaac     480
agactggatt atggacagaa cttggaaata ttgagaataa tttcttaaag ccacttcata     540
taggacttaa tatgtcaaaa gcacattatg aagcagaaat taaaaatagc caaggttggt     600
aatgtgcaat tttgttttca attaggtcta aaaagtagtc taattttgga actgtcatat     660
tcaaatttaa gaactttta aaaatcttgt actttagaag accataacag ctaagccatt     720
ttatttatag ttaaaattct tagcagatct ataagctaat ttacctaaaa tcgggttaat     780
gaagacttaa accaaatatt acattgtama ggccttcaag gtctgattaa gaatctgtat     840
tacagctatt tccgtttggg taccattcct ttggtattgc tgggtccact ctccatctca     900
ctctcaagta aatccataca aattatgaaa agwatcttag atccagaatt tttttaagtc     960
aataattcta taataatcgt gtgatctctt ccgtatatct gtggtggtgc ttttataggc    1020
attaccggaa attttgtttt tagtataatg gctataattc tgattatata ctgaagaaaa    1080
cagtttcatg aatcctatac atgccaaaat aatgctattt atctaaagaa gcattaattt    1140
acatgttgca gaatttgat atttcattct gtttgcttat agcttaagta tacccctgagc    1200 tgttaaacaa tggacttaat aatttataca aataactgac atgtttaag ttagtgaatg     1260
```

| | |
|---|---|
| aaagtagctt ataccttttgt tattgaaatc tgagagttaa gtgtcacaca tgattttttt | 1320 |
| ctcttatcag aggcccagaa atctaaagat ctttgttcta taactgtaag tggagaagag | 1380 |
| atccctaata tgcctcctga aatgcagctt aaggtgatct gaaattttct tctttccttt | 1440 |
| ttcttcttta gaaacggggt cttgctatct tgcccaagct ggagtgcagt ggcatgattg | 1500 |
| tggctcactg cagcttcaac tccctgggct caagtgatcc acccacctca gattcctgat | 1560 |
| tagccaggac tgcaggtgca caccaccatg cctggctaat ttttagtaga gatagggtct | 1620 |
| cactatgttg ctcaggctgg tctccaactc ctggcctcta gtaatcctct cagctcagcc | 1680 |
| tcccaaagca caggaattac aggtgcaaac cactgtacct ggtcttaaat attcctaagc | 1740 |
| tacctccagc tgaaatcttt tctatgtttt gctttgtttt gctttaaagg cagcattaat | 1800 |
| aacattactt tttcttggca ttgcaggtcc tgcattcagc tcttttcaca tttgatttga | 1860 |
| ttgaaagtgt tctagctcga gtggaagaac tcattgaaat aaaaacaaag tctacctctg | 1920 |
| aagaaaatat tgggataaag tgaaagttcc atttcctaaa taaaaacta | 1969 |

<210> SEQ ID NO 150
<211> LENGTH: 2000
<212> TYPE: DNA
<213> ORGANISM: Human

<400> SEQUENCE: 150

| | |
|---|---|
| cacattaggt acaagataga ttcctacaca aataacaaac tgtagaccac cttttcttct | 60 |
| tttccacata tttatgtcc aatcgtgtgt aaatcaaaat gaataggaa gggagagcaa | 120 |
| tttgttttg caaattgatt actgtctaat ttttcttggt taaaatgtat ctctttgggg | 180 |
| attgaatttt cttctgtatc atagttgctt aattaaccac tcctgaaaat ctgagatctg | 240 |
| ggtactttta ggggaaacct ctctccgtct gccaaacgtc ctctctgggg gaagagggga | 300 |
| gtccggcacc ttaaagaact gggcacccaa gcaatctgga aaggaggacc ggtcctaggt | 360 |
| tcaaggccag ctgccaacgc tgccctagtc acttgccccg aaacccgggg accccaggcc | 420 |
| tgggttcccg gggcctccac tgtcctttgt ctcagaggct ggggccacag tccgcgtgag | 480 |
| ggaaatcttg gaacactggc gtaaaggggt gaggggcggc caggaaatct ttcccaggag | 540 |
| gtgcggacgg cggtgggaag cttctcggcct actctacctg ggagaacccc tcccctgaag | 600 |
| cagcctttca ggagcgcccg cgcgctgcgg tctataactc gagatcgggg cccagctttc | 660 |
| agggtccaaa agtgggaaga gatccttgct cctacctgcg gcttttcgag agcagcgggg | 720 |
| agccccggcc ttgcggccgg cagaagacgg cccagcgaag tccgccatgg gggagagtag | 780 |
| tctgccggac ggggacacgc tccggcgtct cgccccgagg cccgcctcc ctacgcgtag | 840 |
| cgcggggcgg ggccagaaga gcgggctaag acgccggagg aggtggcggc ggctgggaga | 900 |
| ggcgagggtt ctggccggta agtggagttg tggagaggtt cagggtggcc agggctcgcg | 960 |
| gttggccgtg agccgcggcg gacttggtgc tgcgggccga ctaggccacg cgaggtggtg | 1020 |
| gagcctgccc acctaggcga gcaggaatcg gaagacatgg cttcctctga tgcagcccgc | 1080 |
| acgcgcgctg gggtgttcac tcgccttcca gcgcgctgcc ctgaggaccg ggctgactcg | 1140 |
| cgcccctact gagggcttgg ggccgagcct tgccgccagg agaagcgatg gtctcctcct | 1200 |
| gaaggccgcc gttgtcttgt ctccgtgtga tacagtgatt tcactagctg gattgatcac | 1260 |
| tttggggact gcaactccta gagagaaatg gaatggaggg catctgaatc ttcaccccct | 1320 |
| atagataagc ttgtgttgca ccccaatttt tgtgaggtga acattaaaaa atgaaaaatc | 1380 |
| ccctgatgat tagaattttg atttcaggtc cacctttttgg aaattttttt tcagaaaaga | 1440 |

-continued

| | |
|---|---|
| agtgctttgc tttttaaaag ccctttagtt cgtatatgcc tcgcctcttg ggagtgctcg | 1500 |
| agaggttttt tttgtttttt tttccttcaa agtagctttc aaaactatgc tcctagaaaa | 1560 |
| cttaaaacat gcaataaggg cttctaaaaa aacactttat tttcttaggc aaacatacta | 1620 |
| agattcagta ataacatttc aactttaaaa ctttacattt tctcctagca tgctattgga | 1680 |
| ccaaaaaaca caacaacaaa aactttccat tttctttatt gtatttacta ataatttatc | 1740 |
| acactgaaac ataactttg aatacttaag tgtaatatca cggatagtta acagtgtgtt | 1800 |
| ttgtatttgt agattttagc atcgaaacta ggagaaataa gaatggctgt agaggaactt | 1860 |
| cagtctataa taaagagatg tgtaagtatt aattttgta aaattaaata cctttcaaaa | 1920 |
| tatgggaagg gcacagattg ttttaatta tatttgtggt cactcaaatt gtttatcttc | 1980 |
| tttaatcctt gctttttttg | 2000 |

```
<210> SEQ ID NO 151
<211> LENGTH: 10934
<212> TYPE: DNA
<213> ORGANISM: Mus musculus
<220> FEATURE:
<221> NAME/KEY: misc_feature
<222> LOCATION: (10385)..(10385)
<223> OTHER INFORMATION: N = any nucleic acid
<220> FEATURE:
<221> NAME/KEY: misc_feature
<222> LOCATION: (10407)..(10407)
<223> OTHER INFORMATION: N = any nucleic acid
<220> FEATURE:
<221> NAME/KEY: misc_feature
<222> LOCATION: (10411)..(10411)
<223> OTHER INFORMATION: N = any nucleic acid
<220> FEATURE:
<221> NAME/KEY: misc_feature
<222> LOCATION: (10448)..(10448)
<223> OTHER INFORMATION: N = any nucleic acid
<220> FEATURE:
<221> NAME/KEY: misc_feature
<222> LOCATION: (10462)..(10462)
<223> OTHER INFORMATION: N = any nucleic acid
<220> FEATURE:
<221> NAME/KEY: misc_feature
<222> LOCATION: (10472)..(10472)
<223> OTHER INFORMATION: N = any nucleic acid
<220> FEATURE:
<221> NAME/KEY: misc_feature
<222> LOCATION: (10508)..(10508)
<223> OTHER INFORMATION: N = any nucleic acid
<220> FEATURE:
<221> NAME/KEY: misc_feature
<222> LOCATION: (10531)..(10531)
<223> OTHER INFORMATION: N = any nucleic acid
<220> FEATURE:
<221> NAME/KEY: misc_feature
<222> LOCATION: (10620)..(10620)
<223> OTHER INFORMATION: N = any nucleic acid
<220> FEATURE:
<221> NAME/KEY: misc_feature
<222> LOCATION: (10639)..(10639)
<223> OTHER INFORMATION: N = any nucleic acid
<220> FEATURE:
<221> NAME/KEY: misc_feature
<222> LOCATION: (10642)..(10642)
<223> OTHER INFORMATION: N = any nucleic acid
<220> FEATURE:
<221> NAME/KEY: misc_feature
<222> LOCATION: (10647)..(10647)
<223> OTHER INFORMATION: N = any nucleic acid
<220> FEATURE:
<221> NAME/KEY: misc_feature
<222> LOCATION: (10717)..(10717)
<223> OTHER INFORMATION: N = any nucleic acid
```

```
<220> FEATURE:
<221> NAME/KEY: misc_feature
<222> LOCATION: (10742)..(10742)
<223> OTHER INFORMATION: N = any nucleic acid
<220> FEATURE:
<221> NAME/KEY: misc_feature
<222> LOCATION: (10766)..(10766)
<223> OTHER INFORMATION: N = any nucleic acid
<220> FEATURE:
<221> NAME/KEY: misc_feature
<222> LOCATION: (10827)..(10827)
<223> OTHER INFORMATION: N = any nucleic acid
<220> FEATURE:
<221> NAME/KEY: misc_feature
<222> LOCATION: (10857)..(10857)
<223> OTHER INFORMATION: N = any nucleic acid
<220> FEATURE:
<221> NAME/KEY: misc_feature
<222> LOCATION: (10860)..(10860)
<223> OTHER INFORMATION: N = any nucleic acid
<220> FEATURE:
<221> NAME/KEY: misc_feature
<222> LOCATION: (10880)..(10881)
<223> OTHER INFORMATION: N = any nucleic acid
<220> FEATURE:
<221> NAME/KEY: misc_feature
<222> LOCATION: (10918)..(10918)
<223> OTHER INFORMATION: N = any nucleic acid

<400> SEQUENCE: 151
ggatccactc acagtcttct gtactcctcc aaagggcttg gktcatttct ccagctctgc    60
actctgtagc acatactgct tgccttcagg ctggctctac tccactgctg ttgctgtccc   120
atggtagtct tcccacagta ctggcatctc tgaaacactg gggtcttcta ctgcaactga   180
gatgcacttt caccaatagt ccctcatggc tctcttcctc aacttctttg catgatcctt   240
tcagtcttgg gctgcacctt caccgatggc ttttcctggc atcgcacagt gccaaacctc   300
agctgttctt catgatccct tcatgtcttc aaaagcagta ccacctgggt gactctggct   360
gccagtacaa ggtacaacca tggtcaccta tggaacacag cttccctgtg ctctcaggaa   420
acacttccca gaagattttt atctcaataa tgttggtctc ttcttgatca ctgctaattt   480
ctcagctcca gctgaccagc atcaagtatc ccagcaaagc aaaggcttca atttagtagt   540
tctgagctct tgttaaatca cagctggttc tttagcccca cctaaccgga accacagaat   600
cttaatccaa aatagcaaac ggccagagtc ttaaaacttc acaagccagg cctcactgtc   660
tgcactgttt tcaacactct tatcttccaa gctcccaaag atcatccact gagctctcag   720
ctctcaatgg cttttttctag cccaaagttc caaagtcctt ccacaatcct ccccaaacca   780
tgtctgccat agcaaataca ccactatggc atcagcttgt ctattttttgt tagtcagggt   840 tatcagttct gtgatgaaac accgtggcta aaaagcaaac tgggaagaaa atggtttatt   900
ctgcttgtac ttycacattg ttgatcatca cmaraggaag tcatgacagg aagtcaagca   960
gggctggaac ttggaggcag gagctgatgc agaggccatg gaggagtgct gcttactggc  1020
ttgcttcccc tggcttgctt ccctggctt gctcagcctg ctttttttgta gaacccagga  1080 ctagagccca gggatggagc cacccactgt gggctgggtc ctctgcatgg aggcgtgtcc  1140
tcagctgagg ctttttcctt ttcttctttg acttacctgt tctgtttcct ctggtccttt  1200
gtctgtcaag tcaacaaaca aaatcagcaa gtacaatact catatacaca aataaatctt  1260
taaatatata tattctattt taaatctggt agtctgacca ttgaacacgt acacactcct  1320
tcaggaattc ttctgtgatg ttctcctcta agagctgctc tacgatgcgc acagctttcc  1380
tttcaaactc caccttcctt tgtatagcag cttccagttc tgcttgcctg aaattttaat  1440
```

```
gagaaagtta acccaattca agacttctcc taccttcaac actccatgct ttaaaagcca    1500
cctagtggcc tactattttg ccaataaatg agcttttaac tctccacctc tgatccaata    1560 cttttttggtc ttcccagtgt gtacatggaa gctggccacg aggacttact tctaggctca   1620
gagaacaagg aaacacttat agactccagt agaggagggc tgggcaggac atggtggtac    1680
atgccacagt tacacacttg ggaggaggca gtgggaagat tcagagtcta aggcaagtgt    1740
gaactacata aaatgaagtt atattttaa aaagagtat atatataaat tttataacaa      1800
aatttatata tataaatttt ccttttgtag ttttgccata catagtaaaa aaattttttt    1860
tctctgtcac ataagtaaac agaatgaagg gtgaagagat gatttctact tttctttcac    1920
tcaaaaaatt gtcaacagcc tagttgtggt agctcagctt actagaacag ttatgtctga    1980
aaagaagagc agcattttct caccttcatt ataaagtcct actaaataac tatcctgata    2040
tgtgaaatgc agtcgaggaa cccttgccat agccaccacg ggtcccatca gtgctctgtc    2100 cccccactc ccccaacaca cacacacaca cggaaggcaa aaatcgaagc tatctcagga    2160
aacagcctca ctgagctgca caccaagaac agacaccatg cccaggtccc acaacaggcc    2220
cagtcaacca gaataggaca gaagcacaga agggagattc actgtcacgc tcaggataca    2280
gtgctgtggt gacttactcg ctcttcttct aggttgggac ctaccagaac tacctctgtt    2340
ggtcaccagg tcttacccctt ctctctcaca tctggaacct agaaactttc atgtgttcac    2400
gtgaaggtag gaaccttcat taactttga gactttagac tctcgttctt tgcctagagc    2460
aatatgtccc ctcccaaccc ccataacttg ggactctggt acagattcac caacaattct    2520
tttttgcaaa atacatgaaa gtgagaagtt tgcaaccaaa cacctatttt tatcccatca    2580
agatcatttt attgttactt taagataccg gggctagaac ccagggcctc gtacatgcta    2640
agcaagcact ctactactga gctataacca ctaactccat aaagaccact tttgtatcaa    2700
agaaagtaaa aagatatgaa cacagattac attacaggtc tttatattaa atacgaaaag    2760
cttcatgaaa aataattttt ctcactttat gcccatcaat aaaggtgata tcatgtacta    2820
agatttatat acaatttgct ggctccaatt atcaagcaca ctgactgttt aaccattctc    2880
ctgactgaca gatatctaca gtaccttact atgttctctg tctgtcacaa atgatggcag    2940
tcaataatgt tgtcctggca gttttacatc aaactgacac acactaatgt cactggagag    3000
gagggaacct taagaatgcc tctatgagag ctcatgtctt tagctgcata tatagcagaa    3060
gatgtcctag tcagccatca ttgggcaaag aggcccttg gtcttgcaaa ctttatattc     3120
cccagtacag gggaatgcca gggccaagaa gtgggagtgg gtgggtaggg gagcagggtg    3180
gggggagggt atagagaact ttcgggatag gatttgaaat gtaaataaag aaaatattta    3240
attaaaaaaa aaaaaagaa tgcctctatg agttctagct acaggcaagc ctaaagagca     3300
ttttcttagt gattgatggg aaggacccag cccatttgtg gatgatgtta tcctagggc     3360 ttatgctgta tgaaagcagg ctgagcaagc catgctcaac aagcccgtaa ggagcactcc    3420
tccatggtat ctgcatcggc tcctgcccca aggttcctgc cctgcgtgag ttcctgacct    3480
gactgtcctt ccgtgatgag cagtgatacg gaagtgaaag ctcagttctt gtgagcaaaa    3540
ccgacttgtt caacaacaca tcctaagggc ctaactcaaa tacagacgat cttgtatttg    3600
gaaattatct tgcaagaaga gtcggtgagt cctgaagtga tgaatgttag tctcttcaga    3660
tgagttttgc tctagctatc tcctctgtga cacgagaggc catgactttt tggaagctct    3720
aaactgtaaa ggatgctttt ggttggtttg ttttttaagtt cctatttaac gttacaaaga    3780
agacaaaaac aaaataaaag aaaacaaaaa aacgggcagt ggtggagaac ggttttaatc    3840
```

```
ccagcacttg ggaggcagag gcaggcggat ttctgagttt gaggccagcc tggtctacag    3900
agtgagttcc aggacagcca gggctataca gagaaaccct gtctcgaaaa accaaagggg    3960
ggggggggag gggaaagaaa gaaaggaagg aagaaggaaa gaaagaaaag aaagaaaaaa    4020
gaaagaaaaa acaaaacaac aacagaacaa aaacccaga agacaaaagg tgccttgaag    4080
tgataaagaa agaacctgct tcagcgagct tggcacatac aacagtaata gtgtacctga    4140
agaaatggga aagattggtt aattcaggaa ctatgtcccc agaactttct acaggtgttc    4200
atgatagttt ccaacagcct aagcctccac attggttttc ctacagctga aggacagagc    4260
agtcttacgt gagaatcgac agtgcttcct gagtcttcag tattttctca agaaaggtat    4320
gcactatgct tttaaactat ttgggctgga gtatagctcg gtaaattaga caaagagctt    4380
cattagaatg tacaaagtct ttaagttcaa ttcccagatt gcaaaacag aaaacagaac    4440 atcaaaacaa aaaaccaaa accaaaaaga aaaagaaaa aaaaaaaaaa aaagaaaaaa    4500 aaaaagaaa agaaaaaaaa aaccaaatca gattgaatta atgagataaa agcaaagtga    4560
aatgcagatg cccacgtggt tctacctttt agatgcatct cctcgtttca gggctcgggt    4620
ctgtttagta cctacaattg aagagagaaa agtcaagtgc caatgcattt gatgtagcag    4680
agtagtcccc aaatatcaca ctgtaggcac catttccttt tctctcacac atctcatttc    4740
caacttcgat gtgtacaaaa aaagaaaaac aacccccccc cagaaaaaca aaacaaaag    4800 gggggctaa acaggaagca aattcaattg tttctgtaaa ttaattacat tttacatttt    4860
catgacggca gttcttcgag gactcttct catataccgg atgcgcttta atcaagtgct    4920
tttaaaacac tctctaaact gggttccttt agaataaaca ttgctcagtc tcccaaatgt    4980
ttgttccctt gcctaaagag aggagtctga gacctcagag accagatatc aaagcaatcc    5040
aaggttcaag gcaactgacc accacctgcc ttggccactt gttcccacgt acgggtagat    5100
cctaaaaccc ctgtgtaaga gtgtgggatt cctcccccga aggcactagg acagcctgcg    5160
ttgggaagct ctgggcctca tccacccgga gttctcgctc tccccggcgc agcctcagaa    5220
agaggtccgc gcgtgcgtgg tactcaaacc aaggtctcag ggtcccagcc tgggacggtg    5280
gctcttgttc gtaccggtag catctcggtg ggtgctggaa gcccgggtac ttgggcctag    5340
agagcaaggt acggcagagt cagccatggg gaaatgcggt cagaagaggg ggtcgggaca    5400
gcacatctac ctcctcacgc ttcgcccgga accgtgtggg ggcgggccca gggagggcgg    5460
ggcgagcggc ggaggggcg ggcccagggc ggggcgggc gagcggcgga gggggagggt    5520
ccggtccggg ggcggggcca ggagtgcggc ctgcgctacc tgaagtggag aaggaggagg    5580
aggtcaagag gcaggcgcgt ggatcggcgg gtaggtagac atgctaggtc gggcggatcg    5640
ggctcgccga acaggacctg cgccgcacgc ggctctcctg ctcggcctct ggaggtgctg    5700
gagcctggac accctgccct gcaggagcag ggagaaatgg cctcccttcg cctcagccag    5760
gcgcggtagg gtgtgatttt cctgttcgcg cctgcgggc aaggaccttc gctgctggcc    5820
tccttttcgt gatactcggt gatctcactg acgattgttt atgtgaggag ggagatcctg    5880
tggagaatgg ggtgggcggc atcggaatct tcaacttctt tgggtgactt aattatgttg    5940
gattccagtt tttgtcaatg gacatttaa aaaaattact taatgattag attttcatt    6000 ccaggtccac aatttggatt tttgttttcc ttttaaacaa aggcttttct agtagttctt    6060
tctagggctc ttttttatttt tttactcgtc attcttaaa aattactttc tttaggcatt    6120
atatcagggc ttttaaaaa tgcttcatta ggctaacaca gtaacgttca gtaatagcag    6180
ttaacctata aaactttaca ttgtgtttgt tgtcttgtct aataattcag aatgaaacgg    6240
```

```
tttatgaaac ataatttaca tggtatcaca caattaactg ggttttttg tattagttca    6300 ttacagcatc aaaattagga aaataattag gaatggctgt ggaggaactt cagagcataa    6360
taaaaagatg tgtaagtact tctccgaaaa caccttaaaa tatatgggaa gggcatagag    6420
tatctttact ttgtggtcac tcatgttatt tatcttaact aaattctgct tcttcttttt    6480
tgacttgtaa atatcaaaaa atcaggaaag tagattagat gataatgatg atggtggtgg    6540
tgactttcaa tcctagtact tttgggaggc aaaggcagag gggtctctga ttttgaggct    6600
ggcctggttt acatggtaaa tttccaggac agctcgggct atgaagagag agagacctct    6660
ctcacaaaag gggcataagg ggctagagag atggttcagt ggttaagagc acttgttctt    6720
gcggaggacc tgggttcatt tctcaaaacc caggccctgt tctggcccac aatgggcatc    6780
aggcacatgc atatgtatga aggtaaacgt tagtaaattg tatttaaaag catattaaat    6840
catgtacatg tctgtttatg tgtgttggta gggggtatat atgagtataa gtgcctggca    6900
tggaagccgt agcgttagga ccactcagag ctggagttac aggtggttgt gagccacctg    6960
atctgggtgc tgggaattga actcaggtcc tctgcaagga tagtatttgc tcttatctac    7020
caaaccactt ctctagtccc agtagtcttt aattttaaat ttcttattgt tttcataagt    7080
ttctctggta cagtaggttc aagatcactc cctaagccat actgattcat gcttatagac    7140
agcagtcagg agctgtgaca agaggacctg aaatttccag gtcagcctaa gcctcctcat    7200
gagagcccgt ctcaaaagcc aaaatgaata aagccaatca ttaaaatatt aggataattc    7260 taattttat ctgtgtctta gtcagggttt ctattcctgc acaaacatca tgaccaagaa    7320
acaagttggg gaggaaaggg tttattcggc ttatacttcc atactgcagt tcatcaccaa    7380
ggaagtcagg actggaagtc aagcaggtca gaaagcagga gctgatgcag aagccatgga    7440
gggatgttct ttactggctt cccctggctt gctcagcctg ctctcttata gaaccaagac    7500
taccagccca gagatggtcc cactcacaag gggcctttcc cccttgatca ctaattgaga    7560
aaatgcctta cagttggatc tcatggaggc atttcctcaa ctgaagttcc tttctctgtg    7620
ataactccgc tgtgtcaagt tgacacaacg agccagtaca attgacccct tgtcaacttg    7680
acacacaaac acatcactag taagcctcaa cccttgcatt cttattcatc cccaaggtct    7740
aaataacttt aaacgtctca aagtctttac atattcttaa aatttcaatc tctttaagat    7800
atccatctct tttaaaatcc aaagtctttt tacaattaaa agtctcttaa ctgtgggctc    7860
cactaaaata gtttcttcct ttaagaggga aaatatcagg gcacagtcac agtcaaaaac    7920
aaaaatcaat ctccaaccat ccaatgtctg ggatccaact caagatcttc tgggctcctc    7980
caagggcttg ggtcacttct ccagccatgc cctttgaagc acacgcgtca tcctctaggc    8040
tccagatgcc tgtactccac tgctgctgct cttggtggtc atctcatggt actggcatct    8100
ccaaaacact gcatgacccc ttcagtcctg ggccgtcaat tgcaactgag gctgcacctt    8160
caccaatggc cttccatggc ctctcacagt gccacgcctc agctgctctg tgtgaccccc    8220
tcatgccttc aaaaccagta ccacctgggt gacccttaca tattaccaag tcccgctgca    8280
gcaggagtac aaccttggcc atcttctgga ccacagcatc tttgtgcttt cagaaaacac    8340
ttcccagaag atgtcacctc aaagatgctg gtctcttttt aatcactgct aatttcttag    8400
ctccagctaa ccagcattaa tagtcccagt aatgcaaagt ttttgcttta gtagttctgg    8460
tatcttgtta atcacagctg attcttcagc cccagctaac cagaactaca gaatcttcac    8520
aatcaaaaac agcagtggcc ctgaaaagag gctttaattt tccctctgaa atttcacaag    8580
ccagacctac atcttctgca ctgttctcaa cattatcttc caagctccta cacaacatct    8640
```

```
gacagagctc ttaacaacga atggatcttc aagcccaaag ttccaaagtc cttccacagt    8700
cctccccaaa acaaggtcag gttgtcacag gaatacccca ctatgttggt accaatttgt    8760
cttagtcagg gtttctattc ctgcacaaac atcatgacca agaagcaagt tggggaggaa    8820
agggtttatt cagcttataa ttccatactg ctgtttatca ccaaggaagt caggactgga    8880
actcaaacag gtcaggaagc aggagctgat gcagaggcca tggagggatg ttctttactg    8940
gcttgcttcc cctggcttgc tcagcctgct ctcttataga accaagacta cctaccagcc    9000
cagagatggt cccacccaca agggccttt ccccttgat cactaattga gaaaatgcct      9060
tacagttgta tctcatgggc atttccttaa tggaagctcc tttctctgtg ataactccag    9120
ctgtgtcaag ttgacacaaa actagccagt acaatctctg taacatgttc attttttgcta  9180
caatttaaga tttcagtttt tttcctagag ataaaatcag gaagtcattt atattaaatc    9240
tatatttgca tctgtgtgaa ttttttattg tttacagcaa atcctagaag agcatgattt    9300
taaagaagaa gattttggcc tctttcagtt agcaggtcaa agatgcattg aagatggtta    9360
tataaaccag ctgctagaga ttattcaaga tgaaagaac aaggtaagcc caggctctgt     9420
gtccactctt cagtctttga gaaggaaata atacattgtt gttattactc atttggaagg   9480
ggaataatac attgttgtta ttacttattt gggaagggat aatacattga taatactcat   9540
ttgagaaggg aataatagat tgttgttgtt aaccatttat ccatcctctt agttactatt   9600
ctactgctgc agtgcgggag tatgaccatg tctcagcctt ccttagagaa ggaacagttc   9660
attgggcctt tcagggtcag aggatgaggt catggaggtc actcctgaga accatcaacc   9720
tagtgattac ctggtccttg aggctgggtg tctcagcagt cagcccagtc tacaatggct   9780
gtccccactg gggcagggct ggatgtctca gtggtcctgt ttgaacccag acatctaaaa   9840
tggctgtaga gctgccgatc ctaggtcaca atgaaagctt agaaactggt tctcatagca   9900
gggaaggagg tggcggcagc agcaccagct ggactgctat taaccaacca cacactgcag   9960
gagggaaggc caaggaacaa aggtgcagtc ttccttctcc cgtgcccttc ctacctgtac  10020
tgctacaaca atcaaagcag ttaggatccc agctgatgtt aagatcaact ataatatact  10080
cttatggcct ccaatacagt cagttttgtg gggttttga ggcagagtct tagcccatgc   10140
tgtcctggag ttcttaaact tactatgtgt ttttcgttgt ttgtgtgtgt gcgggtggag  10200
gagggaaggg agggagaggc gtgcttttgt gagtgtatat gcaggtgcat gccaaggcca  10260
ggggttgatg ttgattgtcc tcaatcactc cccatctttt gaaacaaggt ccctcatttg  10320
aacctgggac tcacacattc atctaggctg ggtggccaac aaattctaag cgacgtgcca  10380
tgatncttt ctagatgatt ttttaanagg nttctacctt tgaaaattag ctttgtgccc   10440
acaaggtntc tcggcctaaa tntaaaattc cnaaaagatg gtggaatcaa cacccttct   10500
cctatttngg caacctaaaa atttaaaatt nggtaagttt gtgtggttcg atgttgcaaa  10560
aattttcaac ccttgagaag gaaaattttt aaaattggaa aaacgtaaaa actcatttn   10620
ttaaaaagt ttatttttant tngaattncaa agtgtaaaaa aaatccttg gttattttta  10680
cacgttaggg gggggtttaa aacattttgg gttttttnttt aaaaccccc ttctttttt   10740
gngaaatttt tttctcttca caaacngccc ccgcgttttc tcctttgtcc ctcccaaaaa  10800
aatcctaatt tttccacttt cccttanttc aaaaagggaa gaaatttaaa tatatgncan  10860
agttcctgta ggataaatan natcgctatc tttatttta tatttttgt cgtgatgnaa    10920
ataaatacaa ataa                                                    10934
```

<210> SEQ ID NO 152
<211> LENGTH: 8427
<212> TYPE: DNA
<213> ORGANISM: Mus musculus

<400> SEQUENCE: 152

| | |
|---|---|
| accatcatta agtctatggg gtggaatctt gttggtccag ttgttcgatg cctcctgagg | 60 |
| ggcagagaag aggataaaag agaagagtgt tttctgatat ttgatttgct ggtgaaggta | 120 |
| agtcaggaaa gcttgttctg tctgtcatgc acacagcagc tccacaattc ccttccactt | 180 |
| ttaattcttg ttcttcggta agaaaatttt agtccaggaa attattccta gataatgccc | 240 |
| agttgtactt gactggatga gtgggcagct ccagctgagc atcatcaaca tttctagata | 300 |
| taagaattac ccagtctgag acccctaact cagtttccag taagaaagct acaaggtgat | 360 |
| ttaacaagtg ttctcattat ataggcgaag tcacttttag agaacttta atgccatgct | 420 |
| gacccttgtg tagcattaga gccagaatca aataccagat atgaaagtta agagagactg | 480 |
| aggggtggc agatcaacaa taacaactct tgtttgaaaa tgccatagta aaatctaata | 540 |
| taggaagatt ttgggatatt ggagattgtt gggatataca cagatgagta ctggatgag | 600 |
| aaagctcctc ccgggtaaca gcacttgatc atgaggactt ttaaagaggg aggcagtggc | 660 |
| tggggatgca gctctggtag aggcactgag aaagttaagc agattgaggc tttaagctga | 720 |
| gaaagaaatt agggaaacaa caccccttctc aatagtcaca aataatataa ataccttgg | 780 |
| cgtgactcta actaaggaag tgaaagatct gtatgataag aacttcaagt ctctaaagaa | 840 |
| agaaattaaa gaagatctca gaagatggaa agatctccca tgctcatgga ttggcaggat | 900 |
| caacattgta aaaatggcta ttttgccaaa agcaatctac agattcaatg caatccccat | 960 |
| caaaattcca actcaattct tcaacgaatt agaaagggca atcggcagat tcatctggaa | 1020 |
| taacaaaaaa ccgaggatag caaaaactct tctcaaggat aaaagaactt ctggtggaat | 1080 |
| caccatgccg gacctaaaac tgtactacag agcaattgtg atcaaaactg catggtactg | 1140 |
| gtatactgac agacaagtag accaatggaa cagaattgaa gacccagaga tgaatccaca | 1200 |
| cacctatggt cacttgatct tcgacaaggg agctaaaacc atccagtgga aaaagacag | 1260 |
| cattttcaac aaatggtgct ggcacaactg gttgttatca tgtagaagaa tgcgaattga | 1320 |
| tccatttcca tctccttgta ctaaggtcaa atctaagtgg attaaggaac tccacataaa | 1380 |
| accagagaca ctgaaactta tagaggagaa agtggggaaa agccttgaag atatgggtac | 1440 |
| aggggaaaaa ttcctgaata aacagcaat ggcttgtgct gtaagatcaa gaatcaataa | 1500 |
| atgggacctc ataaaattgc aaagcttctg caaagcaaaa gacaccgtca ataagacaaa | 1560 |
| aaggccacca acagattggg aaaggatctt tacctatccc aaatcagata ggggactaat | 1620 |
| atccaatata tataaagaac tcaagaaggt ggactccaga aaatcaaata accccattaa | 1680 |
| aaaatggggc tcagagctga acaaagaatt ctcacctgag gaataccgaa tggcagagaa | 1740 |
| gcacctgaaa aaatgttcaa catccttaat catcaggga atgcaaatca aaacaacact | 1800 |
| gagattccac ttcactccag tcagaatggc taagatcaaa gactcaggtg acagcagatg | 1860 |
| ctggcaagga tgtggagaag ggggaacact cctccattgt tggtgggatt gcaagcttgt | 1920 |
| acaaccactc tggaaatcag tctggcggtt cctcagaaaa ttggacatag tactaccgga | 1980 |
| agatcccgca atacctctcc tgggcatata tccagaagat gtcccaaccg gtaagaagaa | 2040 |
| cacatgctcc actatgttca tagcagcctt gtttataata gccagaagct ggaaagaacc | 2100 |
| cagatgcccc tcaacagagg aatggataca gaaaatggtg gtacatttac acaatggagt | 2160 |

```
actactcagc tattaaaaaa atgaatttat gaaattccta ggcaaatgga tggacctgga    2220
gggtatcatc ctgggtgaag taccccaatc acaaaggarc tcgcacaata tgtactcact    2280
gataagtgga tattagccca gaaacttagg atacccaaga tataagatac aacttgccaa    2340
acgcatgaaa ttcaagaaga acgaagaccc aaagtgtgga cactttaccc tttcttagaa    2400
atgggaacaa acacccata gaaggagtta cagagacaaa atttggagct gtgacgaaag    2460 gatgaccat ctagtgattg ccatatgcag ggatccatcc cataatcagc ttccaaatgc    2520
tgacaccatt gcataaaacta gcaagatttt gctgaaagga cccagatata gctctctctt    2580
gtgagactat gccggggcct agcaaacaca gaagtggatg atcacggtca gctattggat    2640
gggtcacacg ccccccaatg gaggagctag agaaattacc aaggagcta aagggaactg    2700 caaccctata ggtggaacaa caatatgaac taaccagtac cccggagctc ttgtctttag    2760
ctgcatatgt atcaaaagat ggcctagtcg gccatcactg caaagagagg cccattggac    2820
ttgcaaactt tatatgcccc agtacagggg aacgccatgg ccaaaaaggg ggagtgggtg    2880
ggtaggggat tgggggggtg ggtatgggaa actttggga tagcattgaa aatgtaaatg    2940
aggaaaatac ctaataaaaa aaaagatat ggcagtcagg acacactata gagcatctgt    3000
tgagaaaaca caagagacca gtggtgtcgc gtcagggcct tgcatggaga gtctgcagtc    3060
tacagtgaag aagcctgagt tctgaaaagc cttaacaact gaatagggca ttttacagtt    3120
agcaaataga actgtatttt ctcggtatgt cttcttttaaa atagtaatca tgtggcttta    3180
aatgcaactt gtattaaaca ggttcaattg tgaatatttt tatagttatg taatccaaag    3240
gaattgttgt tgggtttgct tgaactcatt gaagagccct ccggaaaaca gatttcccaa    3300
attattcttc ttttactgca accattacaa acaggtaatg agcattttga tatccaagta    3360
tttcttgttc tatttgcatt agtgtcttga tgtttaccct aagtatgaac tgtcaccaaa    3420
gtaaagtttg tgataagtta ctgcatgctc agcttttagg ctgtcccagc agcgccagtg    3480
tggatgctgc aggatgcctg gaagattggc tgctcagtaa atcccttgtt gtatgtcata    3540
ctgtttgcgt gtgtgtagct ctttggttag ctttcttttt gcatatatgt gtgttttgtc    3600
tgcatgcatg tttgtacatc acttgcatgc ctggtaccttt atcagatccc ctggagtttg    3660
agctgccata tgggttctgg gaactgaatc tgggtcctct gggagcagcc agtgctctta    3720
gccactgagc cgtctctctc tagcctccta gtaagcttct tatccacagc tatagttaga    3780
atttcccctc taagcatgtt tagtggctca gctgtggtac ctgcagcact cagtctaaca    3840
gcagtgtggt cgtcctgtag tttggttaag aaggatatga gacagggtgt tactcggcct    3900
ttgaattggg aggttggagt taaaaggttc aaccagaatg aaatgaggca tgaaaagaga    3960
gaaagcttca cagttcaata ttggcaaata atggctctca gcaaccaaca tagacacttt    4020
ccatgaaaga agctatttac tgtttgtgtg tatgtagcac atatatatgc ttcagaatat    4080
gatagacact tcttaaatat tcaaagtttt ctaaggacac aaaaagcttt ttaatactct    4140
tgtacactta tatggtgctt tgcaattttc cattcatatt ttgtgcttat aatcaaaaat    4200
aagggaaaga tgtaaccagt tataaaaata ctgtatttgt tggttttctt attgctgggc    4260
ctaagtgcct gacaactggc aatttaaaga agaactgttc atctggttag gatccgcagt    4320
ccaccatggt ggcgaggcat ggtggaagta gggtggcgaa gtacctggtc acattgtaat    4380
gacagtcaca gtagtgaggt caggctctac cgcctcagag cccacctcta gtgaccactt    4440
cctttagcaa ggctccacct gctaaggatc cagagccttg tcccatgtga agaagttctg    4500
tgtcacaggg tgacacagtt aactgtcacg cataagcaca ggtgaccact taagaggcga    4560
```

```
acacaggtga cagctcatac actgagcaca gtaaccactt atgcggtgag cagagggagt    4620
aactgcttgg tctctgttgc agttattcag aaacttccta caacaaggc atactccgtt     4680 ggactagcat tgtcaacact ttggagtcag ctgtctcttc ttcctgttcc acactcagaa    4740
gaacaaattc aggcagatga ttatggcctc tgtcagtgtt gtaaggcctt gatagagttc    4800
acgaaacctt ttgtggaaga agtaataagt gataaagaaa acaaagaaaa tgcaaaacta    4860
aaagatgaat tactgaaatt gtaagtatac cttgaggaac atttcaccgt ggagtgagta    4920
attagcagct cagttacctt atgtttctta tttgtacata caaatctagt ttcatatttt    4980
gaattttaga cgtagatgtt tggctgacac agcgtggtcg ttttctgagg cactgacagt    5040
acaaaaccaa ccttcactta attcactttc acccatcaca gcaagcaaac actgaaagtg    5100
ggggcagggg atgtactcaa ctcaagggac ttattactct gtctcgggga actcgtacct    5160
gaaaatagag accactagag agttgggctt ccaccctgac tgcagactca gcaaagtgct    5220
catccactct ctcacaccgt gggttctaac caaacatcca ccagtggtta gggtggctgc    5280
cgatccctaa gtatatggat ggtccaaact gaggtgctct cagtatgaca cagcctccgg    5340
acttgatggc tctcagtatg acacaggatt gtaagatcaa agctagagcc tcgattatag    5400
aataagttgt cccaaaaacc aaatcaacac aaaacctcca aaataaagga caaaataaag    5460
gaatttgtgt taaatttctc ttggacagta ctgaattttt tttttttaa aatttgggag     5520 actaatgcca ttcttacctt ttctattttt ctgggttaag gcatttaaag ttgttttta     5580 aaacaaaaaa aattgttttg aaaaaaaacg tcctaaagaa ctagaaaagg cttagttaca    5640
gaataaagtt agagtttaaa aaaatgcaac tctatgaaaa acatgactat attgtcctga    5700
attytccttg gaccagtgay ggtgacctct tggactagct ggccctcagg agacattcag    5760
catcaattgt aacactctag agattcaatt gaatctgagc tatgcagtct agcaaggcct    5820
tctcatgctt tcccagtact gtcacgagtg aggarggatt cagcctgtgt taccgtgctt    5880
gccttaggtc acgtctgtga catagtaaag tatcagrtga tttgtaatca aggcattgtg    5940
gcttgcagtt ctaggagttc tcaggctgga ctgaggctca ggttcgctga gctcatactt    6000
tgagaacagc atcttctttc ccatgagagt gaacccacct ttcaaaggtc tcacttgtta    6060
tactgtttta gcctgagttg aggggctgca ctcagttctc atgaaaagcc aggtatgaag    6120
aactacaggt gtcgtgcctt gggagtgttg actgcaaagt tacccatwtc ttatgccgta    6180
gttgtttcaa aggcttgaaa tgccctttgc tgacagcaca attcctcgaa cagtcagaag    6240
acgttggaaa tgacccttt cggtgttttg catctgaaat aatagtaagt acagccgatc     6300
taatctctaa tacttataac tttaaattta tcctgctata ttgtgatata tgaccagtta    6360
aactgttaat ttattaatag ggcagtatat agtttttttag aatacagata aacaacagga   6420
tggaaactaa gtagcagtaa tattatccaa agccttctaa atgtttctaa atgctaataa    6480
ataagaaaat gtatacatac atatacggtc ttgaaaatgt gtatattttc cattggtatt    6540
aatttcatat tattttttt agagagagag aatgtgtgtg agtgagtgtt gtgtgtatgt     6600
gttcatgtgt atctgacctg aatttatttg caccacatgc atgcagtacc tgtggaaacc    6660
agaagagacc atcagatctt agttgtcagc caacatgtgg atgctaggaa ttgaatttgg    6720
actctctaga agagcagcca gccccatct taagcatttt aaagtacagc attaagtgtg     6780
tttccattgc tgtgcaatca ccagcgctgc catctcaaga acatttcttt ctacctgaat    6840
tctctacttg ctaagcgctg ccccagcacc ctccccacac cctgtcctgt cactaactgg    6900
ctaagtgtgc atacatacac acacacaccc acacacacac acacacacac actgtcctgt    6960
```

-continued

```
cattgcctga ctaagcactc ctcccaggcc cctgcctgtc ctgtcactgc ctggcagctg    7020
ccacactgta ttggaaagca cttctattgt ttccatgcta aaatggtttt tctcttttta    7080
tttcggtatt ttgaagacaa ggtctctcta catagatctg gctattctgg aactctcttt    7140
gcagttcagg ctggccttga actcacagtg atccacttgt gtctgtctcc caaaatggtg    7200
ggattaaagg tgtgcccagc ttcatttgtg tttaaaactt actcatttta ttttatcaca    7260
gtgggtttgt gcatcacatg tgtatagtgg ccaaggagac cagaagaggg tattggatcc    7320
cttggaattg gagttgtaga tggttgtgag ctgccatgag ggtggtgaga accaaacctg    7380
ggtcttctgc aagagcagca agtactctta actgctaagt catctcttca gcccctgaaa    7440
tgacctgtct tagtttactc taaagccctc cctccagcaa ttgggtagtt tagctatcag    7500
caaaaactca atgtatgtgt gtgtgtgtat atgttgtgtc atgtgtgcgt gcacatgcgc    7560
ctttaattat gattttgagc gagatcatat caaggaagga aggaaggaaa gcagaaaccc    7620
tgcctgaata ggtaaggccc atccagtaat cttgaataac tcaaaatcaa ttgattcaag    7680
acctgcatta caccagcaga cttcctccgt ggcttagtca gtgtgctgtt gctatgcaga    7740
gacactgtga ctacagcaac tcttaggaaa ggaagtactg aattggggct tgcttacagt    7800
ttcagaagtt tggttcatta tctccatggt ggagagcatg gcagcacaca ggaagacatg    7860
gtgctggaga acagttgag tttccattca aacccacagg cagcaggaag agagagtctg    7920
ggtctggctt gggcttttga aacctcagag cccacccca ctgacatact tttaacaagg     7980
ccacacctcc tattccttct caagtagtgc cactccctgc cgaccaagca ttcaagtgtg    8040
tgatcccata gggccattct tattcagagc actgcattca cctttgccat ttaagagggc    8100
ctaacaatgg gggtgacatt caaagcaagt gccacaaatt gtatataccc tcaaagagaa    8160
gggatatgga cagagtatgg acatggaata agtgggtgat gtatgccaac agcttccttt    8220 ttaaaaccc atttcacagg gatttttatc aaaaattgga caccctgtcc cccaaattat     8280
tcttaatcat ggaaggaaaa aaaggacttg ggattaccttgaatttgaag aagaagaaga   8340 caaacaactg gcagagtctg tggcttctct gacatatcta gtatttgttc agggcatcgg    8400
tattgatcag ctgcccatgg tcttaag                                        8427
```

<210> SEQ ID NO 153
<211> LENGTH: 594
<212> TYPE: PRT
<213> ORGANISM: Human

<400> SEQUENCE: 153

```
Met Ala Val Glu Glu Leu Gln Ser Ile Ile Lys Arg Cys Gln Ile Leu
1               5                   10                  15

Glu Glu Gln Asp Phe Lys Glu Glu Phe Gly Leu Phe Gln Leu Ala
            20                  25                  30

Gly Gln Arg Cys Ile Glu Glu Gly His Thr Asp Gln Leu Leu Glu Ile
        35                  40                  45

Ile Gln Asn Glu Lys Asn Lys Val Ile Ile Lys Asn Met Gly Trp Asn
    50                  55                  60

Leu Val Gly Pro Val Val Arg Cys Leu Leu Cys Lys Asp Lys Glu Asp
65                  70                  75                  80

Ser Lys Arg Lys Val Tyr Phe Leu Ile Phe Asp Leu Leu Val Lys Leu
                85                  90                  95

Cys Asn Pro Lys Glu Leu Leu Leu Gly Leu Leu Glu Leu Ile Glu Glu
            100                 105                 110
```

-continued

```
Pro Ser Gly Lys Gln Ile Ser Gln Ser Ile Leu Leu Leu Gln Pro
        115                 120                 125

Leu Gln Thr Val Ile Gln Lys Leu His Asn Lys Ala Tyr Ser Ile Gly
        130                 135                 140

Leu Ala Leu Ser Thr Leu Trp Asn Gln Leu Ser Leu Leu Pro Val Pro
145                 150                 155                 160

Tyr Ser Lys Glu Gln Ile Gln Met Asp Asp Tyr Gly Leu Cys Gln Cys
                165                 170                 175

Cys Lys Ala Leu Ile Glu Phe Thr Lys Pro Phe Val Glu Glu Val Ile
                180                 185                 190

Asp Asn Lys Glu Asn Ser Leu Glu Asn Glu Lys Leu Lys Asp Glu Leu
                195                 200                 205

Leu Lys Phe Cys Phe Lys Ser Leu Lys Cys Pro Leu Leu Thr Ala Gln
        210                 215                 220

Phe Phe Glu Gln Ser Glu Glu Gly Gly Asn Asp Pro Phe Arg Tyr Phe
225                 230                 235                 240

Ala Ser Glu Ile Ile Gly Phe Leu Ser Ala Ile Gly His Pro Phe Pro
                245                 250                 255

Lys Met Ile Phe Asn His Gly Arg Lys Lys Arg Thr Trp Asn Tyr Leu
                260                 265                 270

Glu Phe Glu Glu Glu Asn Lys Gln Leu Ala Asp Ser Met Ala Ser
        275                 280                 285

Leu Ala Tyr Leu Val Phe Val Gln Gly Ile His Ile Asp Gln Leu Pro
        290                 295                 300

Met Val Leu Ser Pro Leu Tyr Leu Leu Gln Phe Asn Met Gly His Ile
305                 310                 315                 320

Glu Val Phe Leu Gln Arg Thr Glu Glu Ser Val Ile Ser Lys Gly Leu
                325                 330                 335

Glu Leu Leu Glu Asn Ser Leu Leu Arg Ile Glu Asp Asn Ser Leu Leu
                340                 345                 350

Tyr Gln Tyr Leu Glu Ile Lys Ser Phe Leu Thr Val Pro Gln Gly Leu
        355                 360                 365

Val Lys Val Met Thr Leu Cys Pro Ile Glu Thr Leu Arg Lys Lys Ser
        370                 375                 380

Leu Ala Met Leu Gln Leu Tyr Ile Asn Lys Leu Asp Ser Gln Gly Lys
385                 390                 395                 400

Tyr Thr Leu Phe Arg Cys Leu Leu Asn Thr Ser Asn His Ser Gly Val
                405                 410                 415

Glu Ala Phe Ile Ile Gln Asn Ile Lys Asn Gln Ile Asp Met Ser Leu
                420                 425                 430

Lys Arg Thr Arg Asn Asn Lys Trp Phe Thr Gly Pro Gln Leu Ile Ser
        435                 440                 445

Leu Leu Asp Leu Val Leu Phe Leu Pro Glu Gly Ala Glu Thr Asp Leu
450                 455                 460

Leu Gln Asn Ser Asp Arg Ile Met Ala Ser Leu Asn Leu Leu Arg Tyr
465                 470                 475                 480

Leu Val Ile Lys Asp Asn Glu Asn Asp Asn Gln Thr Gly Leu Trp Thr
                485                 490                 495

Glu Leu Gly Asn Ile Glu Asn Asn Phe Leu Lys Pro Leu His Ile Gly
                500                 505                 510

Leu Asn Met Ser Lys Ala His Tyr Glu Ala Glu Ile Lys Asn Ser Gln
        515                 520                 525
```

-continued

```
Glu Ala Gln Lys Ser Lys Asp Leu Cys Ser Ile Thr Val Ser Gly Glu
        530                 535                 540

Glu Ile Pro Asn Met Pro Pro Glu Met Gln Leu Lys Val Leu His Ser
545                 550                 555                 560

Ala Leu Phe Thr Phe Asp Leu Ile Glu Ser Val Leu Ala Arg Val Glu
                565                 570                 575

Glu Leu Ile Glu Ile Lys Thr Lys Ser Thr Ser Glu Glu Asn Ile Gly
            580                 585                 590

Ile Lys

<210> SEQ ID NO 154
<211> LENGTH: 20
<212> TYPE: PRT
<213> ORGANISM: Artificial Sequence
<220> FEATURE:
<223> OTHER INFORMATION: Description for artificial sequence: 6x
      histidine tag contained in a 20 amino acid hinge
<220> FEATURE:
<221> NAME/KEY: BINDING
<222> LOCATION: (20)...(20)
<223> OTHER INFORMATION: attached to glomulin

<400> SEQUENCE: 154

Met Gly Ser Ser His His His His His His Ser Ser Gly Leu Val Pro
1               5                   10                  15

Arg Gly Ser His
            20
```

VMGLOM GENE AND ITS MUTATIONS CAUSING DISORDERS WITH A VASCULAR COMPONENT

CROSS-REFERENCE TO RELATED APPLICATIONS

This is the U.S. National Phase under 35 U.S.C. §371 of International Application No. PCT/EP01/01760, filed Feb. 16, 2001, designating the United States and published in English, which claims priority to European Application No. 00870022.1, filed Feb. 16, 2000, U.S. Provisional Application No. 60/195,577, filed Apr. 6, 2000 and European Application No. 00870320.9, filed Dec. 22, 2000.

FIELD OF THE INVENTION

The present invention relates to the field of molecular biology. More particularly the present invention relates to the identification of new genes. More particularly to the detection and treatment of venous malformations with glomus cells. The present invention relates to the identification of genes residing in the VMGLOM locus, responsible for disorders with a vascular component, the identification of mutations in said genes and the detection of their sequences as well as methods of treatment for disorders with a vascular component based on said gene sequences

BACKGROUND OF THE INVENTION

Venous malformations (VMs) are bluish-purple lesions that can be single or multiple (Vikkula et al. 1998). They are most often localized on the skin and mucous membranes. In two families in which these lesions are inherited as an autosomal dominant trait, a locus (VMCM1) was identified on chromosome 9p21 that is linked to the phenotype (Boon et al. 1994; Gallione et al. 1995). It was found that the mutation in this locus is in the gene encoding the endothelial-specific receptor tyrosine kinase TIE-2. The R849W mutation in the intracellular kinase domain of TIE-2 leads to hyper-activation of the receptor in a ligand-independent manner (Vikkula et al. 1996). Another amino acid substitution, Y897S, identified in a separate family, seems to have a similar effect (Calvert et al. 1999).

Recently a second locus (VMGLOM) was identified on chromosome 1p21-22 for a subtype of VMs called "glomangiomas" because of the presence of undifferentiated smooth-muscle cells ("glomus cells") in histological slides (Boon et al. 1999). Three positional candidate genes: DR1 (depressor of transcription 1), TGFBR3 (transforming growth factor-β receptor, type 3) and TFA (tissue factor) were screened and excluded. The identification of a candidate gene in the 5 Mbp VMGLOM locus would allow detection of mutations involved with venous malformations. It is thus an aim of the present invention to provide nucleic acid sequences representing genes involved with disorders with a vascular component as well as methods for diagnosis and treatment of disorders with a vascular component.

SUMMARY OF THE INVENTION

The present invention relates to an isolated nucleic acid molecule selected from any of the following:
a) a nucleic acid molecule encoding a human polypeptide having a sequence which is more than 68%, preferably more than 70%, more preferably more than 80% homologous to the sequence as represented in SEQ ID NO 2,
b) a nucleic acid molecule encoding a human polypeptide having an amino acid sequence as represented in SEQ ID NO 2 or a shorter fragment thereof as represented in SEQ ID NO 4,
c) a nucleic acid molecule having a nucleotide sequence as represented in SEQ ID NO 1 or 3,
d) a nucleic acid molecule encoding a mammalian non-human polypeptide which is a biological equivalent of a human polypeptide as mentioned in a) or b),
e) a nucleic acid molecule encoding a mouse polypeptide having an amino acid sequence as represented in SEQ ID NO 6 or 8, and,
f) a nucleic acid molecule having a nucleotide sequence as represented in SEQ ID NO 5 or 7, or the complement thereof.

Said nucleic acid sequences represent the genes for venous malformations with glomus cells and for other disorders with a vascular component, or synthetic versions thereof.

The present invention further provides a nucleic acid molecule as defined above having a nucleotide sequence modification, with said modification resulting in patients bearing said modification in their genome having disorders with a vascular component.

The present invention further relates to a nucleic acid molecule as defined here above, wherein said nucleotide sequence modification is selected from the group of nucleotide mutations consisting of point mutations, deletions, insertions, rearrangements, translocations and other mutations and preferably selected from the mutations as indicated in Table 8 or 9, such that the resulting nucleic acid sequence is altered.

The present invention also relates to a probe or primer containing a sequence comprising at least 15 contiguous nucleotides of a nucleic acid sequence as defined above.

The present invention also relates to an isolated polypeptide selected from the following:
a) a human polypeptide having a sequence which is more than 68%, preferably more than 70%, more preferably more than 80% homologous to the sequence as represented in SEQ ID NO 2,
b) a human polypeptide having an amino acid sequence as represented in SEQ ID NO 2 or a shorter fragment thereof as represented in SEQ ID NO 4,
c) a mammalian non-human polypeptide which is a biological equivalent of a human polypeptide as mentioned in a) or b), and,
d) a mouse polypeptide having an amino acid sequence as represented in SEQ ID NO 6 or 8, or a functional part thereof.

The present invention also relates to a nucleic acid or polypeptide molecule as defined above for use as a medicament or a diagnostic kit.

The present invention also relates to the use of a molecule as defined above for the preparation of a medicament for preventing, treating or alleviating disorders with a vascular component or for the preparation of a diagnostic kit for detecting disorders with a vascular component.

The present invention further relates to a method for detecting the presence of mutations in a nucleic acid sequence as defined above in a sample containing nucleic acids.

The present invention also relates to a method for diagnosis of disorders with a vascular component in a patient comprising detecting a mutation in a nucleic acid sequence as defined above or detecting a nucleic acid as defined above.

The present invention also relates to a method for screening molecules for preventing, treating or alleviating disorders with a vascular component comprising the steps of:
   a) contacting the molecule to be screened with a nucleic acid as defined above, or with a polypeptide as defined above, and,
   b) detecting the formation of a complex or detecting the interaction between said molecule and said nucleic acid or said polypeptide.

The present invention relates to a molecule identifiable by a method as defined above.

The present invention relates to a method for the production of a composition comprising the steps of producing a compound identifiable by a method as defined above and mixing said identified compound with a pharmaceutically acceptable carrier.

The present invention also relates to an antibody characterized in that it specifically recognises a polypeptide as defined above, or an antigenic fragment thereof.

The present invention also relates to a DNA construct comprising at least part of a nucleic acid as defined above, wherein the coding sequence of said nucleic acid is operably linked to a control sequence enabling the expression of the coding sequence of said nucleic acid by a specific host.

The present invention also relates to a host cell transformed with a DNA construct as defined above.

The present invention also relates to a recombinant polypeptide encoded by a nucleic acid as defined above or part thereof, said recombinant polypeptide being produced by:
   a) culturing said transformed cellular host as defined above under conditions which allow the expression and possibly secretion of the encoded polypeptide, and
   b) optionally, recovering the expressed polypeptide from said culture.

The present invention also relates to a method for treating or alleviating disorders with a vascular component comprising the use of molecule which allows to interfere with the expression of a polypeptide as defined above in a patient.

The present invention also relates to a method for the diagnosis of disorders with a vascular component in a patient comprising the use of at least a nucleic acid sequence as defined above or a probe or primer as defined above or an antibody as defined above. The present invention also relates to a kit for the diagnosis of disorders with a vascular component in a patient comprising at least a probe or primer as defined above or an antibody as defined above.

DETAILED DESCRIPTION OF THE INVENTION

The practice of the present invention will employ, unless otherwise indicated, conventional techniques of molecular biology and recombinant DNA technology, which are within the skill of the art. Such techniques are explained fully in the literature.

All publications cited herein are hereby incorporated by reference in their entirety. In describing the present invention, the following terms will be employed, and are intended to be defined as indicated below.

The term "disorders with a vascular component" refers to disorders and diseases, in which there is altered vascular development, growth and/or maintenance or other abnormality, or altered size, structure, number etc. of blood vessels, such as in vascular anomalies (including several different types; for example hemangiomas, and arterial, capillary, lymphatic, venous and combined malformations), in other congenital and acquired vascular problems, such as aortic dilatation, coarctation of aorta, annuloaortic ectasia, angiopathies, occlusive vascular disorders, atherosclerotic vascular disease, ischemic heart disease, limb ischemia etc., as well as in disordres in which the vascular phenotype might not be the primary cause of the disease, such as in tumor induced angiogenesis, diabetic retinopathy, rheumatoid arthritis, etc.

The term "vascular" refers to the whole vascular system, i.e. venous, capillary, arterial and lymphatic vessels.

The term "nucleic acid" refers to genomic or complement DNA or RNA, amplified versions thereof, or the complement thereof. The term nucleic acid may refer to a complete gene or a part thereof and may refer to genes (including introns) or synthetic versions thereof.

The term "gene" as used herein refers to any DNA sequence comprising one to several operably linked DNA fragments such as a promoter and a 5' untranslated region (the 5'UTR), a coding region (which may or may not code for a protein), and an untranslated 3' region (3'UTR) comprising a polyadenylation site. Typically in mammalian cells, the 5'UTR, the coding region and the 3'UTR (together referred to as the transcribed DNA region) are transcribed into an RNA which, in the case of a protein encoding gene, is translated into a protein. A gene may include additional DNA fragments such as, for example, introns.

The preferred mutations in said genes are given in Table 8.

The term "complement" refers to a nucleotide sequence which is complementary to an indicated sequence and which is able to hybridize to the indicated sequence.

The term "primer" refers to a single stranded nucleotide sequence capable of acting as a point of initiation for synthesis of a primer extension product which is complementary to the nucleic acid strand to be copied. The length and the sequence of the primer must be such that they allow to prime the synthesis of the extension products. Preferably the primer is about 5-50 nucleotides. Specific length and sequence will depend on the complexity or the required DNA or RNA targets, as well as on the conditions of primer use such as temperature and ionic strength.

The fact that amplification primers do not have to match exactly with corresponding template sequence to warrant proper amplification is amply documented in the literature (see for instance Kwok et al., 1990).

The term "probe" according to the present invention refers to a single-stranded oligonucleotide sequence which is designed to specifically hybridize to any of the polynucleic acids of the invention. The probes used in the process of the invention can be produced by any method known in the art, such as cloning of recombinant plasmids containing inserts including the corresponding nucleotide sequences, if need be, by cleaving the latter out from the cloned plasmids upon using the appropriate nucleases and recovering them (e.g., by fractionation according to molecular weight). The probes can also be synthesized chemically, for instance, by the conventional phopho-triester method.

The probes of the invention can optionally be labelled using any conventional label. Primers and probes according to the present invention may also be directed against the introns of the nucleic acid sequences as defined above. The probes according to the present invention preferably hybridize to a region of a nucleic acid molecule according to the claims comprising a nucleotide sequence modification (mutation) resulting in patients bearing said modification in their genome having disorders with a vascular component.

The primers according to the present invention may specifically bind to a region of a nucleic acid molecule according to the claims comprising a nucleotide sequence modification (mutation) resulting in patients bearing said modification in their genome having disorders with a vascular component. By binding to said region, said primers are able to differentially amplify a wild-type and a mutated nucleic acid of the invention.

The term "mutation" in the context of the present invention refers to any change in the identity of a nucleotide or a change in the succession of nucleotides in the nucleic acid strand(s) which may occur, including nonsense, frameshift and missense mutations, small insertions (e.g. 1, 2, 3, 4, 5 or more nucleotides) or deletions (e.g. 1, 2, 3, 4, 5 or more nucleotides), large deletions encompassing substantial parts of the gene as well as encompassing the total gene, translocations, and any other change known to the person skilled in the art.

The term "translocation" means an event in which part of one chromosome has broken off and become attached to another chromosome or part thereof.

The present invention also relates to a method for detecting the presence of mutations in a nucleic acid according to the invention in a sample containing nucleic acids comprising the steps of:
a) possibly isolating and purifying the nucleic acids from said sample by means of methods known in the art,
b) contacting said nucleic acids of said sample with at least a probe or a primer as defined above,
c) detecting said wild-type or mutated nucleic acid of the invention by means of specific hybridization, or in the alternative,
d) detecting said wild-type or mutated nucleic acid of the invention by means of an amplification reaction such as PCR possibly combined with for instance a hybridization or sequencing reaction.

The term "amplification" used in the context of the present invention refers to polymerase chain reaction (PCR) or any other type of nucleic acid amplification method, such as ligase chain reaction (LCR; Landgren et al., 1988; Wu and Wallace, 1989; Barany, 1991), nucleic acid sequence based amplification (NASBA; Guatelli et al., 1990; Compton, 1991), transcription-based amplification system (TAS; Kwoh et al., 1989), strand displacement amplification (SDA; Duck, 1990; Walker et al., 1992) or amplification by means of Qss replicase (Lizardi et al., 1988; Lomeli et al., 1989) or any other suitable method to amplify nucleic acid molecules. The amplification reaction is preferably repeated between 20 and 70 times, advantageously between 25 and 45 times.

In another embodiment of the present invention, a molecule according to the invention can be used as a medicament or in a diagnostic kit.

In a more preferred embodiment, said medicament is used for the diagnosis, prevention, alleviation or treatment of disorders with a vascular component or for the preparation of a diagnostic kit for detecting disorders with a vascular component. In yet another preferred embodiment, said molecule according to the invention can be used for the preparation of a medicament for preventing, treating or alleviating disorders in which an alteration of vascular smooth muscle cell phenotype is needed. As illustrated in the examples, due to the known interaction between FKBP12 and the TGFβ type I receptor, it is likely that glomulin, via FKBP12, modulates TGFβ receptor signaling. Vascular smooth muscle cell differentiation has been shown to be induced by TGFβ. As "phenotypic modulation" of vascular smooth muscle cells has been shown in several conditions, such as in atherosclerotic plaque, it is also likely that glomulin, via TGFβ, modulates this phenotypic change. Thus, glomulin may have use as such or as a target, when alteration of (vascular) smooth muscle cell phenotype is needed.

According to yet another preferred embodiment, said molecule according to the invention can be used for the preparation of a medicament for preventing, treating or alleviating varicosities. This is again illustrated in the examples where Western blot data show glomulin expression in many veins, and varicose veins are encountered in families with inherited glomuvenous malformations.

According to another preferred embodiment, said molecule according to the invention can be used for the preparation of a medicament for preventing, treating or alleviating cardiopathies or cardiomyopathies. The inventors found high RNA expression levels supported by the glomulin protein detection by Western blot analysis in heart tissue, underlining the fact that glomulin is likely to have an important function in heart. Several clinical entities affecting the heart and associated tissues (cardiopathies or cardiomyopathies) are known, and may encounter alterations in glomulin function, which thus can serve as target for e.g. diagnosis, treatment and prevention.

According to another preferred embodiment, said molecule according to the invention can be used for the preparation of a medicament for preventing, treating or alleviating cerebral disorders. As illustrated in the examples, Northern blot analysis has also detected high expression of glomulin in the brain. As brain vessels are not specifically rich in smooth muscle cells, but rather pericytes, this expression may originate from the cerebral vascular endothelial cells and/or pericytes, and/or parenchymal cells. Glomulin is likely to have a special function in the brain, and thus serve in e.g. in the diagnosis, treatment and prevention of cerebral disorders.

Other related disorders with can be prevented and/or treated within the scope of this invention are disorders by modulation of the immune response. Due to the interaction of FAP48 with FKBP59 and FKBP12, glomulin is likely to have a similar action. Thus, glomulin may act as an immunomodulator, and have use in the treatment of various conditions in which modulation of immune response is needed, such as e.g. in atopic dermatitis.

Finally, said molecule according to the invention can also be used preventing, treating or alleviating cancer. Indeed, Northern blot analysis has detected expression of glomulin in cancers, such as cervical adenocarcinoma (Hela S3), lung carcinoma epithelial cell line (A549), leukemias (K-562, MOLT-4, and HL-60), Burkitt's lymphomas (Raji and Daudi) and colorectal adenocarcinoma, epithelial cell line (SW480). These cell lines are not vascular endothelial cells or vascular smooth muscle cells. Thus, glomulin may encounter alteration in e.g. expression or concentration in cancers, and thus serve as a target e.g. for diagnosis, treatment and prevention.

Also according to the invention, the identification of the presence or absence of said mutation in any of the methods of the invention can be done by direct sequencing or by micro array methods. Preferably, the present invention further relates to a method for detecting the presence of mutations in a nucleic acid sequence as defined above in a sample containing nucleic acids comprising the steps of:
a) contacting said nucleic acids of said sample with at least one probe or primer as defined above, with said probe or primer being preferably able to detect a nucleotide sequence modification as defined above,
b) detecting said wild-type or mutant nucleic acid of the invention by specific hybridisation or amplification, and,
c) possibly sequencing said amplification products of step c).

Also other methods can be used to identify such mutations including methods such as STS-PCR, countourclamped homogeneous electric field (CHEF) gel electrophoresis, restriction mapping, hybridization, Southern and Northern blotting, FISH analysis, mismatch cleavage, single strand conformation polymorhism (SSCP) or any other method known in the art. The diagnostic methods of the present invention also include segregation analysis, involving PCR-based genotyping and/or haplotyping methods. The diagnostic methods according to the present invention also include methods based on direct sequencing or CAS (coupled amplification and sequencing) optionally combined with additional analytic steps as known in the art, such as ligation analysis to detect and evaluate mutations.

The terms "protein" of the invention and "polypeptide" of the invention are equivalent and interchangeable. These terms also capture proteins substantially homologous and functionally equivalent to native proteins. Thus, the term encompasses modifications, such as deletions, additions and substitutions (generally conservative in nature), to the native sequences, as long as the biological activity of said polypeptide is not destroyed. Such modifications of the primary amino acid sequence may result in polypeptides which have enhanced activity as compared to the native sequence. These modifications may be deliberate, as through site-directed mutagenesis, or may be accidental, such as through mutations of hosts which produce the protein. All of these modifications are included, so long as biological activity is retained.

Two nucleotide or amino acid sequences are "substantially homologous" according to the present invention when at least about 65% (preferably at least about 80% to 90%, and most preferably at least about 95%) of the nucleotides or amino acids match over a defined length of the molecule. As used herein, substantially homologous also refers to sequences showing identity to the specified DNA or polypeptide sequence. DNA sequences that are substantially homologous can be identified in a Southern hybridization experiment under, for example, stringent conditions, as defined for that particular system.

The term "functionally equivalent" intends that the amino acid sequence of the subject protein is one that will give a defined biological activity, equivalent to or better than, the biological activity a non-mutated protein of the invention.

An "antigen" refers to a molecule containing one or more epitopes that will stimulate a host's immune system to make a humoral and/or cellular antigen-specific response. The term is also used interchangeably with "immunogen".

A "hapten" is a molecule containing one or more epitopes that does not stimulate a host's immune system to make a humoral or cellular response unless linked to a carrier.

The term "epitope" refers to the site on an antigen or hapten to which a specific antibody molecule binds. The term is also used interchangeably with "antigenic determinant" or "antigenic determinant site."

The term "functional part" of a polypeptide or protein refers to a (poly)peptide or amino acid sequence, respectively, which has at least one identical or at least one equivalent biological activity compared to the protein it is derived from. Such parts will usually be at least about 10 amino acids in length, and preferably at least about 15 or 20 amino acids in length. There is no critical upper limit to the length of the fragment, which could comprise nearly the full length of the protein sequence. The terms "polypeptide" and "protein" include oligopeptides, protein fragments, analogs, muteins, fusion proteins and the like.

By "isolated protein" is meant a protein separate and discrete from a whole organism (live or killed) with which the protein is normally associated in nature. Thus, a protein produced synthetically or recombinantly would constitute an isolated protein.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

The term "comprising" within the context of the present invention is to be understood as containing at least an item or step as claimed but possibly also containing more than that item or step. Comprising thus constitutes open language.

In order to identify additional genes encoding the proteins of the present invention and particularly proteins from other non-human mammals, recombinant techniques can be employed. These techniques are well known in the art and include DNA library screening or PCR cloning all well known in the art.

DNA sequences encoding proteins of the invention can be prepared synthetically rather than cloned. The DNA sequence can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence.

Once coding sequences for the desired proteins have been prepared or isolated, they can be cloned into any suitable vector or replicon. Numerous cloning vectors are known to those of skill in the art, and the selection of an appropriate cloning vector is a matter of choice.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. Leader sequences can be removed by the host in post-translational processing.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular antigen of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal. It may also be desirable to produce mutants or analogs of the antigens of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art.

Depending on the expression system and host selected, the proteins of the present invention are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art. The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides may be preferable if a small fragment of the antigen in question is capable of raising an immunological response in the subject of interest.

In particular, the inventors have expressed glomulin in bacteria as illustrated in the examples. Therefore they developed two prokaryotic glomulin expression constructs, one without and one with a Histidine tag facilitating the purification step.

Furthermore, they developed two constructs which can be used for the generation of transgenic animals, as illustrated in FIG. 36.

The proteins of the present invention or their fragments can be used to produce antibodies, both polyclonal and monoclonal. If polyclonal antibodies are desired, a selected mammal, (e.g., mouse, rabbit, goat, horse, pig etc.) is immunized with an antigen of the present invention, or its fragment, or a mutated antigen. Serum from the immunized animal is collected and treated according to known procedures. If serum containing polyclonal antibodies is used, the polyclonal antibodies can be purified by immunoaffinity chromatography, using known procedures.

Monoclonal antibodies to the proteins of the present invention, and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against the antigen of interest, or fragment thereof, can be screened for various properties; i.e., for isotype, epitope, affinity, etc. Monoclonal antibodies are useful in purification, using immunoaffinity techniques, of the individual antigens which they are directed against.

Animals can be immunized with the compositions of the present invention by administration of the protein of interest, or a fragment thereof, or an analog thereof. If the fragment or analog of the protein is used, it will include the amino acid sequence of an epitope which interacts with the immune system to immunize the animal to that and structurally similar epitopes.

As illustrated in the examples, the inventors have used peptides synthesized from two amino acid sequences (SEQ ID NO 138 and SEQ ID NO 139) of glomulin and created polyclonal antisera against said peptides and tested them in Western blotting. This polyclona antisera was used to detect the glomulin protein in vitro in the bacterial expression. In addition, it was used to detect the presence of glomulin protein in various human tissues and eukaryotic cell lines. They found that glomulin seems to be expressed in a variety of tissues ranging from cardiovascular tissues to brain parenchyma and carcinoma cell lines.

The present invention also relates to a method for treating or alleviating disorders with a vascular component comprising the use of a molecule which allows to interfere with the expression or activity of a protein as defined in the claims in a patient or with the expression levels of the RNA encoded by the nucleic acids of the invention. A preferred molecule according to this embodiment is an antisense RNA molecule which is capable of hybridizing to the nucleic acid according to the invention. Advantageously, an antisense RNA molecule according to the present invention may be used as medicament, or in the preparation of a medicament for the treatment of disorders with a vascular component (antisense RNA therapy). The present invention also provides a pharmaceutical composition comprising an antisense RNA molecule according to the invention together with a pharmaceutically acceptable carrier, diluent or excipient therefor.

A further aspect of the present invention provides a method for determining whether a compound is an inhibitor or an activator of expression or biological activity of the polypeptide of the invention which method comprises contacting a cell expressing the polypeptide of the invention or cell extracts thereof or purified polypeptide of the invention with said compound and comparing the level of expression of the protein of said cell or cell extract or comparing the level of activity of said purified polypeptide according to the invention against an equivalent amount which has not been contacted with said compound. Alternatively said compound may be determined to be an inhibitor or activator of expression of the RNA encoded by the nucleic acid of the invention. Any compounds identified as inhibitors may advantageously be used as a medicament or in the preparation of a medicament for treating disorders with a vascular component which are alleviated by reducing or increasing the expression or activity of a polypeptide of the invention or by reducing or increasing the expression of RNA encoded by a nucleic acid according to the invention. These polypeptides can be wild-type or mutant polypeptides.

In an alternative embodiment of the invention, the inhibitory compounds may comprise antibodies according to the invention capable of recognising an epitope of a protein according to the invention and binding thereto. In this embodiment, the pharmaceutical composition comprises an effective amount of said antibody. In the same manner as described above, compounds which are identified as activators or enhancers of activity or expression of a protein of the invention or activators or enhancers of the expression level of the RNA encoded by the nucleic acids of the invention may be utilised as a medicament or in the preparation of a medicament for treating disorders with a vascular component alleviated by overexpression or enhanced of said protein of the invention.

There is also provided by the present invention a method of screening to identify compounds which interact with and bind to a protein according to the invention of the invention, which method comprises contacting a host cell expressing said protein or cell extracts comprising said protein or purified protein of the invention with a selection of said compounds and identifying any compounds which interact with or bind to said protein. The compounds may, for example, be labelled with a marker such as biotin or the like or a radiolabel so as to facilitate detection of said binding. The invention further includes a method for producing a compound as defined here above, which involves steps known to the person skilled in the art. The present invention further includes methods for producing a composition comprising mixing such a compound with a suitable pharmaceutically acceptable carrier also know in the art.

According to a next embodiment, the present invention is related to a non-human transgenic animal transformed by a nucleic acid according to the invention, or a DNA construct according to v.

In a more preferred embodiment, the present invention relates to a method for the production of a genetically modified non-human animal in which this modification results in overexpression, underexpression or a knock-out of the nucleic acids of the invention, or the polypeptides of the invention.

Said animal is preferably a mammal such as a mouse or a rat, transformed by a vector according to the invention and overexpressing a protein according to the invention, or genetically modified by a partial or total deletion of its genomic sequence encoding the protein according to the invention (a knock-out non-human mammal) and obtained by methods well known by the person skilled in the art.

As illustrated in the examples, the present inventors have cloned genomic fragments of the mouse glomulin gene which could be used for homologous recombination to result e.g. in ES cells that are genetically modified and generation of transgenic animals. In particular, they developed two constructs, one which would lead to a glomulin null-allele, and a second one allowing a conditional knock-out of the glomulin gene.

Other examples of genetically modified non-human animals provided by the invention are for instance transgenic non-human animals comprising an antisense sequence as defined above and complementary to the nucleic acid sequences according to the invention, and placed in such a way that it is transcribed into antisense mRNA which is complementary to the nucleic acid sequences according to the invention and which hybridises to said nucleic acid sequences, thereby reducing or blocking their translation.

The present invention also relates to a transgenic non-human animal comprising in its genome a nucleic acid according to the invention for use a model system for testing treatments to disorders with a vascular component.

The present invention also relates method for treating disorders with a vascular component by means of gene therapy, comprising administering to a patient in need of a normal version of a nucleic acid or gene of the invention at least part of this nucleic acid of the present invention or in the alternative switching off or lowering the possible overexpression of a nucleic acid or gene of the invention in a disorder with a vascular component.

Known gene therapy protocols can consist of delivering nucleic acids, such as by means of expression vectors for transfection and expression of said nucleic acids as to reconstitute the function of the affected gene, or alternatively delivering a functional form of the affected gene or protein. Expression constructs may be administered in any biologically effective carrier as known in the art. Retrovirus vectors, adenovirus vectors and adeno-associated virus vectors are exemplary recombinant gene delivery system for the transfer of exogenous genes in vivo, particularly into humans.

In addition to viral transfer methods, non-viral methods can also be employed, such as liposomal derived systems, poly-lysine conjugates, and artificial viral envelopes.

In clinical settings, the gene delivery systems for therapeutic use can be introduced into a patient by any of a number of methods, each of which is familiar in the art.

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

The gene should be administrated in a manner which results in sufficient expression of the non-defective gene. The following examples are for the purpose of better understanding the present invention but are in no way to be considered as limiting the invention.

Figure 16:
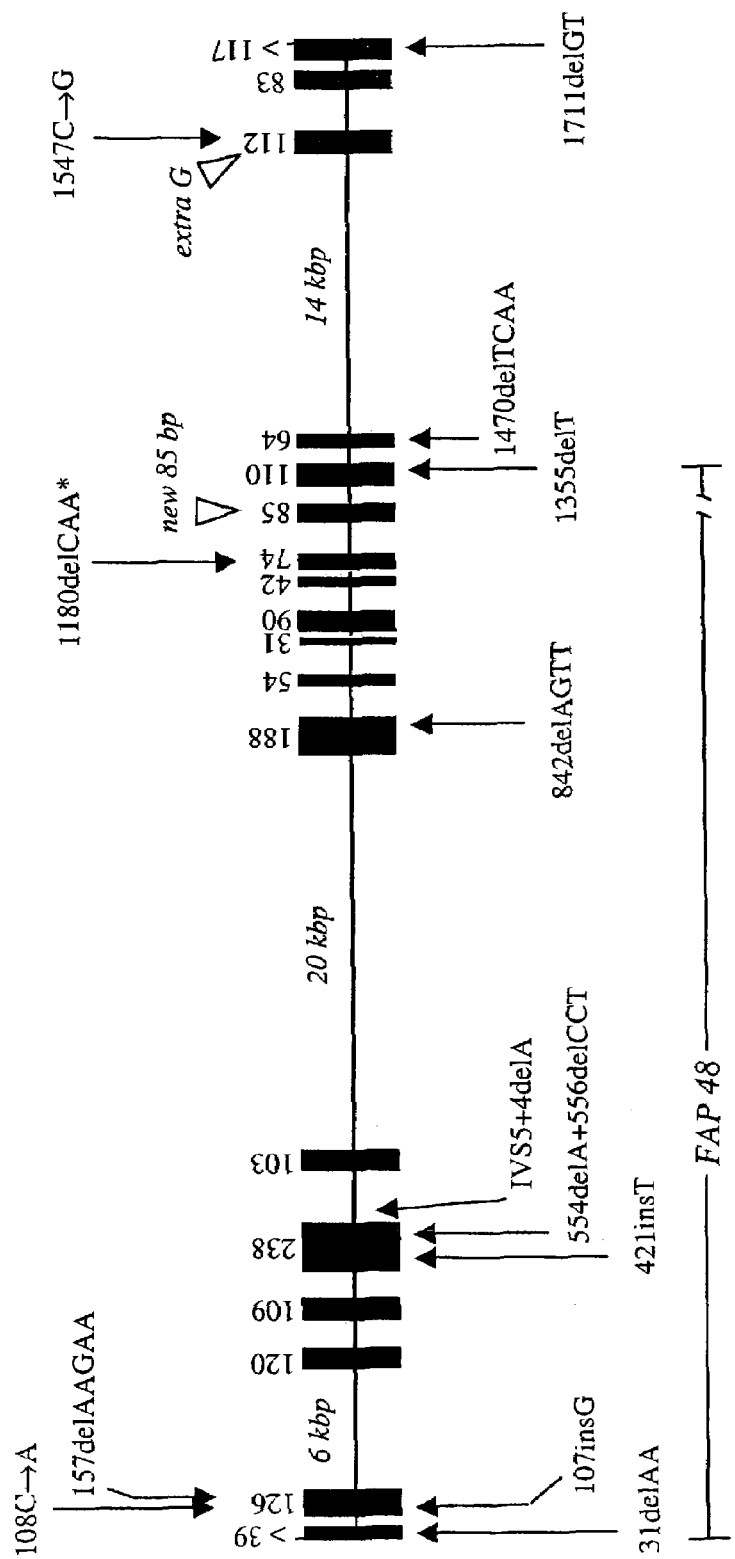

The present invention also relates to an isolated nucleic acid molecule having a nucleotide sequence as represented in SEQ ID NO 142 to 152. These SEQ ID NO's represent the sequences of inter-exonic fragments obtained when determining the genomic structure of the VMGLOM gene (FIGS. 19 to 29). The inventors also dedicated the name "glomulin" to the gene encoding the full length VMGLOM "long form". The genomic structure of human glomulin is shown in FIG. 16 and further described in the examples. The gene is composed of 19 exons, extends over 55 kbp and the complete cDNA sequence is given in FIG. 5.

The present invention further provides a nucleic acid molecule as defined in the previous paragraph and having a nucleotide sequence containing a modification, wherein said modification results in patients bearing said modification in their genome having disorders with a vascular component.

According to a further embodiment said modification is selected from the group of nucleotide mutations consisting of point mutations, deletions, insertions, rearrangements, translocations and other mutations and preferably selected from the mutations as indicated in Table 8, such that the resulting nucleic acid sequence is altered.

The inventors identified 13 different mutations in this glomulin gene in 19 families. Nine of the mutations were deletions or insertions that cause frame-shifts resulting in premature stop codons. Therefore, it is likely that the venous malformations present in said families are caused by loss-of-function of glomulin. This finding suggests that glomulin is important for the differentiation of vascular smooth muscle cells, and thus for vasculogenesis and angiogenesis.

According to another embodiment, the present invention relates to a probe or primer for use in the detection of a mutation occurring in a nucleic acid sequence according to the invention as defined above.

In particular, the inventors developed several sets of intronic primer pairs (Table 6) enabling the amplification of the 19 exons of the glomulin gene. These primers allow mutational screening via e.g. SSCP or Heteroduplex analysis, directly on genomic DNA. This method is less laborious compared to screening on cDNA produced from RNA extracted from resected venous malformations or from cultered lymphoblasts.

Therefore, the present invention also relates to a method for the diagnosis of disorders with a vascular component in a patient comprising detecting a mutation in a nucleic acid sequence as defined above or detecting a nucleic acid as defined above.

According to a further embodiment, the present invention relates to a method for diagnosis of disorders with a vascular component in a patient comprising:
(a) providing a sample containing nucleic acids from said patient,
(b) isolating and possibly purifying nucleic acids from said sample,
(c) amplifying said nucleic acids using primers as defined above,
(d) analysing said amplified DNA indicative for the presence or absence of a mutation in said nucleic acids.

According to a more preferred embodiment, the present invention relates to the method as defined above wherein the amplification is performed by means of the polymerase chain reaction (PCR) and the primers as defined above. Several methods can be used to analyse an amplified DNA or a mutation characteristic for said disorders of the invention. Said methods include for instance SSCP, heteroduplex analysis, sequencing or any other method as described earlier in the description.

According to another aspect, the identification of the presence or absence of said mutation of the invention as defined above can also be done by means of a hybridisation reaction with a probe as defined above.

According to yet another aspect, the invention relates to a method for the diagnosis of disorders with a vascular component comprising the use of at least a nucleic acid sequence of the invention as defined above or a probe or primer as defined above.

According to another embodiment, the present invention relates to a kit for the diagnosis of disorders with a vascular component in a patient comprising at least a probe or primer according to the invention as defined above.

Said kit can be based upon a technique selected from the group consisting of in situ hybridisation, Northern blot hybridisation, Southern blot hybridisation, isotopic or non-isotopic labelling (by immunofluorescence or biotinylated probes), genetic amplification (especially by PCR or LCR), STS-PCR, countourclamped homogeneous electric field (CHEF) gel electrophoresis, restriction mapping, FISH analysis, mismatch cleavage, single strand conformation polymorphism (SSCP) or any other method known in the art, or a mixture thereof.

FIGURE LEGENDS

FIG. 1.

Pedigrees of 7 additional families with venous malformations with glomus cells. Blackened symbols indicate affected persons and unblackened symbols indicate unaffected persons. A question mark (?) indicates a person for which the affection status is not known and a slash symbol (/) indicates a deceased person.

FIG. 2.

Schematic representation of the YAC map and STS localization. Genes are marked in bold italic and SNPs in small underlined capital letters (WIAF).

A) *=YAC clone reported to be chimeric. Results for marker WI-6020 are marked with an I and reflect database entries only. ?=unclear results for marker D1S2849 for YAC 896b3.

Figure 2:
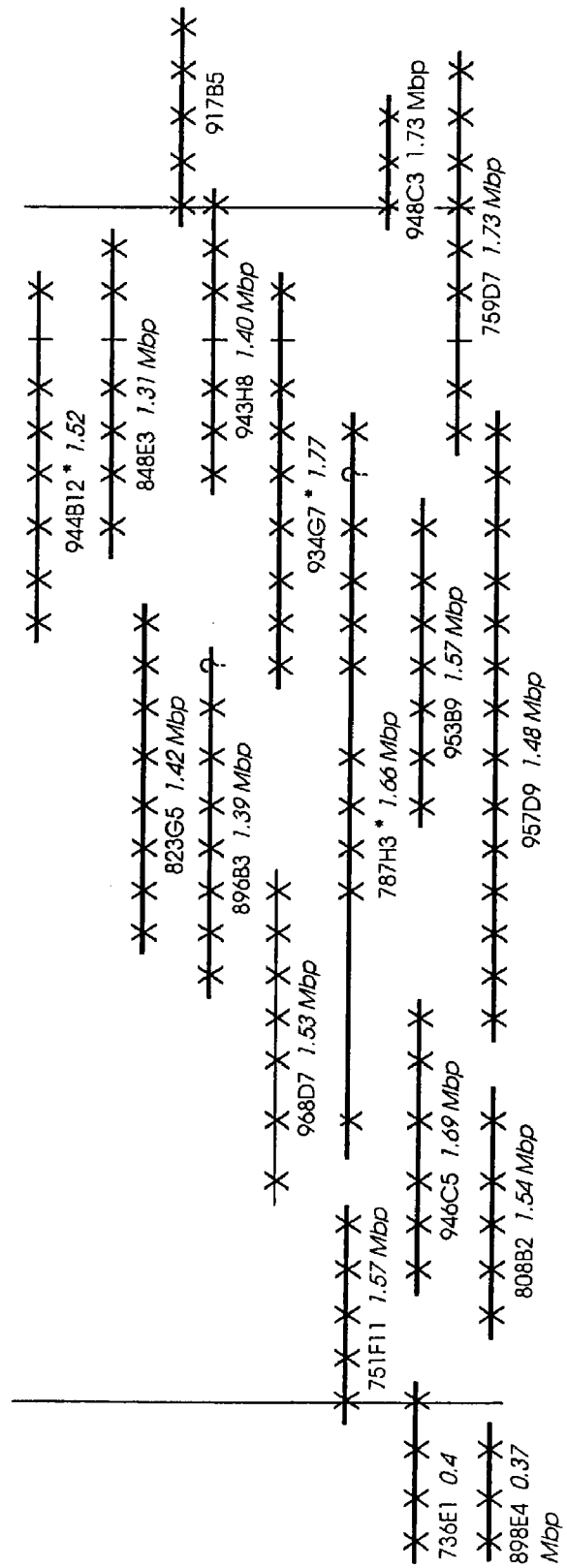
Figure 2:
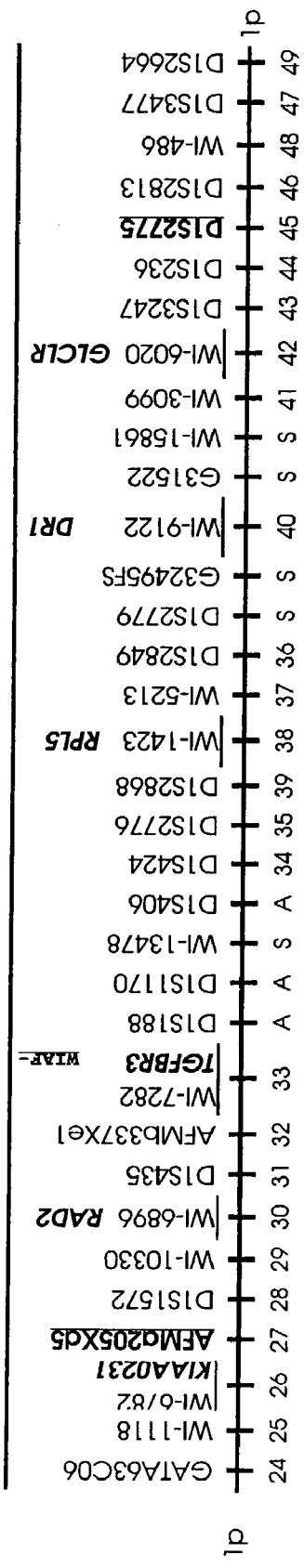
Figure 2:
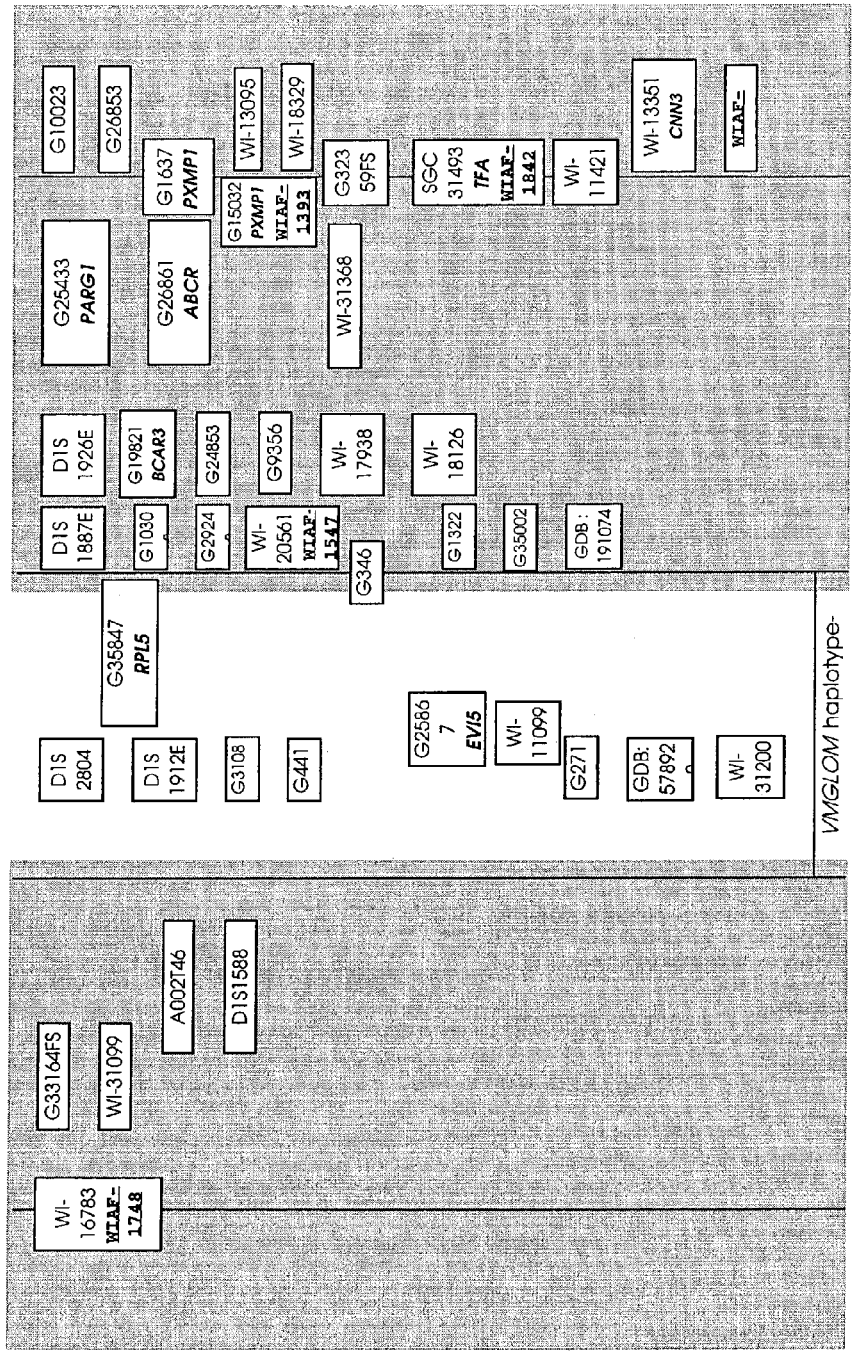

B) Numbers under the markers correspond to those in WC1.14 contig from Whitehead/MIT database. A=from (Allikmets et al. 1997). S=placed during the STSs localization. Order for markers #36 to #39 is inverted to reflect the order in the PAC-map (FIG. 2).

C) Boxes represent the areas of localization for the mapped or novel STSs. Vertical lines delimit the VMGLOM locus (unbroken lines) or the smaller, haplotype-shared area (dashed lines).

FIG. 3.

Schematic representation of the PAC based STS and transcript map of VMGLOM. Gene names are in bold italic and underlined. Polymorphic markers are in bold.

Novel CA-repeats are in bold, italic. Markers for which the order was impossible to define with the clones used are represented by gray boxes. The best annealing temperature for PCR is given for each STS. PAC clones forming the original four islands marked with bold lines. PAC with names in bold were used for fingerprinting. Underlined clones are selected for sequencing by The Sanger Center. X=positive PCR result, −=negative PCR result, ⊗=new end-of-clone STS.

FIG. 4.

Picture of an agarose electrophoresis result for Hind III fingerprinting of the selected PAC clones. 1 kb=1 Kb DNA Ladder (Gibco BRL); the smallest marker band on the picture is 1018 bp.

FIG. 5 cDNA sequence for the human VMGLOM "long form" (SEQ ID NO 1).

FIG. 6

Predicted amino acid sequence for the human VMGLOM "long form" (SEQ ID NO 2).

FIG. 7 cDNA sequence for the human VMGLOM "short form" (SEQ ID NO 3).

FIG. 8

Predicted amino acid sequence for the human VMGLOM "short form" (SEQ ID NO 4).

FIG. 9

Alignment of the cDNA sequences of human VMGLOM "short form" (SEQ ID NO 3), "long form" (SEQ ID NO 1) and FAP-48 (U73704).

FIG. 10

Alignment of the predicted amino acid sequences of human VMGLOM "long form" (SEQ ID NO 2), FAP-48 (U73704) and VMGLOM "short form" (SEQ ID NO 4).

FIG. 11 cDNA sequence for the mouse VMGLOM "long form" (SEQ ID NO 5).

FIG. 12

Predicted amino acid sequence for the mouse VMGLOM "long form" (SEQ ID NO 6).

FIG. 13 cDNA sequence for the mouse VMGLOM "short form" (SEQ ID NO 7).

FIG. 14

Predicted amino acid sequence for the mouse VMGLOM "short form" (SEQ ID NO 8).

FIG. 15

Pedigrees of 7 additional families with venous malformations with glomus cells. Black symbols are affected patients. Individuals with numbers were tested. *, no clinical examination.

FIG. 16

Glomulin gene structure and mutations. Size of exons and three largest introns are shown. Other introns are on scale. Top, mutations that cause an immediate stop codon or *, single amino acid deletion. Bottom, frame-shift mutations leading to premature stop codons. Line below represents the exons encoding FAP48. The open reading frame of "glomulin" is roughly 30% longer than that of FAP48. This was identified due to both an additional 85 by exon and an extra G in the gene encoding FAP48 (indicated by arrowheads in this figure). Both changes modify the open reading frame of "glomulin" resulting in a protein of 594 aa instead of 417 aa for FAP48.

FIG. 17

Glomulin northern blot analysis. Human multiple northern blot (Clontech) hybridized with a 482 by 5'-probe of glomulin. Similar results obtained with full-length glomulin probe. This figure shows that glomulin is expressed in a large variety of tissues, and not only in the skin and subcutaneous tissue in which glomuvenous malformations are encountered.

FIG. 18

Upper chromatogram, control sequence; lower profile, mutant sequence; arrows, sites of mutation; *, reverse strand chromatogram. Δ, deletion; ins, insertion; >, substitution. Insets show segregation of the mutation by size difference (1,4,7-9,11), restriction enzyme digestion (2,3,6,13), heteroduplex analysis (5,10) or allele-specific PCR (12). C, control; ND, non-digested.

FIG. 19

Human glomulin (VMGLOM) genomic sequence (SEQ ID NO 142), exons 1 and 2 (underlined) and intron 1 and partially intron 2.

FIG. 20

Human glomulin (VMGLOM) genomic sequence (SEQ ID NO 143), exons 3, 4 and 5 (underlined) and introns 3 and 4, and partially introns 2 and 5.

FIG. 21

Human glomulin (VMGLOM) genomic sequence (SEQ ID NO 144), exon 6 (underlined) and partially introns 5 and 6.

FIG. 22

Human glomulin (VMGLOM) genomic sequence (SEQ ID NO 145), exon 7 (underlined) and partially introns 6 and 7.

FIG. 23

Human glomulin (VMGLOM) genomic sequence (SEQ ID NO 146), exon 8 (underlined) and partially introns 7 and 8.

FIG. 24

Human glomulin (VMGLOM) genomic sequence (SEQ ID NO 147), exons 9, 10, 11 and 12 (underlined) and introns 9, 10, 11 and partially introns 8 and 12.

FIG. 25

Human glomulin (VMGLOM) genomic sequence (SEQ ID NO 148), exons 13, 14 and 15 (underlined) and introns 13, 14 and partially introns 12 and 15.

FIG. 26

Human glomulin (VMGLOM) genomic sequence (SEQ ID NO 149), exons 16, 17 and 18 (underlined) and introns 16 and 17 and partially introns 15 and 18.

FIG. 27

Human genomic sequence: partial promoter, exon −1, intron −1, exon 1 and the beginning of intron 1. The exons are underlined (SEQ ID NO 150).

FIG. 28

Murine genomic sequence: partial promoter, exon −1, intron −1, exon 1, intron 1, exon 2 and partial intron 2. The exons are underlined (SEQ ID NO 151).

FIG. 29

Murine genomic sequence: exon 3, intron 3, exon 4, intron 4, exon exon 5, intron 5, exon 6, intron 6 and exon 7. The exons are underlined (SEQ ID NO: 152).

FIG. 30

Human multiple tissue expression (MTE) dot blot (Clontech) hybridised with the full-length (1850 bp) glomulin cDNA probe (amplified from cloned fragment with primer 1: TCT GGC CGA TTT TAG CAT CG (SEQ ID NO 9) and primer 27: TAG TTT TTA TTT AGG AAA TGG AAC (SEQ ID NO 10). All tissues show a positive hybridisation signal.

FIG. 31

Glomulin RT-PCR results on several human tissues. Multiple tissue RT-PCR using primers specific to a region of approximately 500 by at the 5' (A) or 3' (B) end of the glomulin gene and covering multiple exon-intron boundaries. Control RT-PCR using primers specific to glyceraldehyde phosphate dehydrogenase, and glucose-6-phosphate dehydrogenase, demonstrated equal concentration of cDNA for every sample (results not shown). DNA size standards are indicated to the left. Lanes in A and B: 1, Artery cDNA; 2, Aorta cDNA; 3, Placenta cDNA; 4, Skeletal muscle cDNA; 5, Skin cDNA; 6, Smooth muscle cell cDNA; 7, Umbilical cord cDNA; 8, Umbilical vein cDNA; 9 Vena Cava cDNA. Lane 10: plasmid containing glomulin insert (positive control), lane 11: water (negative control). (C) and (D): Lanes: 1, Artery cDNA; 2, Heart cDNA; 3, Placenta cDNA; 4, Skeletal muscle cDNA; 5, Umbilical cord 1 cDNA; 6, Umbilical cord 2 cDNA; 7, Umbilical vein cDNA. VA's Lane 8, Glomuvenous malformation cDNA extracted from a patient with known 5 by mutation in the glomulin gene leading to a premature stop codon. Lane 9: Kaposiform hemangioendothelioma (KHE) cDNA. Lane 10: Venous malformation with know mutation in Tie 2/Tek gene. Lane 11: plasmid containing glomulin insert (positive control), lane 12: water (negative control). DNA size standards are indicated to the left. Control RT-PCR using primers specific to glyceraldehyde phosphate dehydrogenase, and glucose-6-phosphate dehydrogenase demonstrated equal concentration of cDNA for every sample (results not shown).

FIG. 32

Glomulin amino acid sequence (SEQ ID NO 153) showing in bold the sequences of the two synthesized peptides (207: SEQ ID NO 138; and 208: SEQ ID NO 139) used for polyclonal antisera production.

FIG. 33

ELISA results in triplicate for antiserum 455 against peptide 208 for preimmune serum, as well as for $1^{st}$ and $2^{nd}$ test samples at 43 and 71 days of the injection program.

FIG. 34

Western dot blot showing hybridisation immunoreactivity of the antiserum 452 and 453, 454 and 455 in concentration 1:500 against the synthetized peptides 207 and 208 in between 1-100 mg (A). In B: higher dilutions of 455 was tested.

FIG. 35

Prokaryotic glomulin expression constructs. pET-15b introduces a Histidine-tag to the aminoterminus of the glomulin, pET-3a encodes the wild-type, non-tagged, glomulin.

FIG. 36

Knock-out constructs. A) The lacZ knock-out construct leading to lacZ transcription under the control of endogenous glomulin promoter after homologous recombination in ES cells; B) The conditional knock-out construct creates a glomulin allele that can be made deficient at a given tissue or time point by the introduction of Cre-recombinase.

FIG. 37

Glomulin RT-PCR results on four murine embryos: From Left to right: embryonic day (E) 10, 14, 16 and 18. Lane 5, plasmid DNA containing the 5' end of the glomulin gene as insert. On the right of the diagram Low Range marker (Fermentas) is shown with the alongside corresponding DNA sizes in base pairs.

FIG. 38

Western blot using glomulin anti-peptide antibody 452 shows binding to a 67 kDa and roughly 100 kDa protein in lysates from expression constructs of pET15b-glomulin. Binding to a protein of 58 kDa is observed in human tissue. Lanes 1 & 2, pET-15b-glomulin (His-tagged) transformed BL21 bacterial lysate at 8 hours post-induction from supernatant and pellet fractions respectively. Lane 3, same bacterial strain as 1 & 2 at time 0. Lane 4, lysate from hek293T cells. Lane 5, protein extract from vena cava tissue. Lane 6, Nickel column purified His-tagged glomulin. Lanes 7 & 8, pET-15b transformed BL21 bacterial strains following IPTG induction of an unrelated gene. Protein standards are indicated to the left of the diagram in kDa.

FIG. 39

Western blot using glomulin antiserum 453 shows binding to a 67 kDa and roughly 100 kDa protein to lysates from expression constructs. Lanes 1 & 2, pET-15b-glomulin (His-tagged) transformed BL21 bacterial lysate at 8 hours post-induction from supernatant and pellet fractions respectively. Lane 3, same bacterial strain as 1 & 2, at time 0. Lane 4 lysate from hek293T cells. Lane 5, protein extract from vena cava tissue. Lane 6, Nickel column purified His-tagged glomulin. Lanes 7 & 8, pET-15b transformed BL21 bacterial strains following IPTG induction of an unrelated gene. Protein standards are indicated to the left of the diagram in kDa.

FIG. 40

A) Western blot using anti-glomulin antiserum 455 shows specific binding to a 67 kDa protein in the supernatant of bacterial cell lysates. Lanes 1-9: pET-15b-glomulin transformed BL21 bacterial lysates at 0-8 hours after IPTG induction. Lanes 10 and 11: lysates from uninduced lysates at 5 and 7 hours respectively. Lane 12: control lysate from BL21 bacteria transformed with pET-15b—human glucokinase regulatory protein expression construct (used as a negative control). Protein standards are indicated to the left of the diagram in kDa. Each lane contains 27 µg of total protein as determined by the BCA-200 assay (Pierce). B) Western blot using anti-histidine tag antibody (Amersham-Pharmacia) shows specific binding to a 67 kDa protein in the supernatant of bacterial cell lysates form BL21 bacteria transformed with pET-15b-glomulin construct. Lanes 1-9: pET-transformed BL21 bacterial lysates at 0-8 hours after IPTG induction. Lanes 10 and 11: lysates from uninduced lysates at 5 and 7 hours respectively. Lane 12: control lysate from BL21 bacteria transformed with pET-15b—human glucokinase regulatory protein expression construct. Protein standards are indicated to the left of the diagram in kDa. Each lane contains 54 µg of total protein as determined by the BCA-200 assay (Pierce).

FIG. 41

Western blots from bacterial cell lysates expressing glomulin as a transgene, and tissues in which endogenous glomulin is present. A) Note the difference in size between glomulin expressed in pET-3a (lane 3), purified glomulin from pET-15b—histidine-tagged (lane 1), and endogenous glomulin from heart tissue (lane 2). B) Various human tissues in which protein was extracted and glomulin expression assessed. Lanes 1-6: vena cava, umbilical cord, placenta, heart, aorta, and umbilical vein. Equal loading of all samples was confirmed by the Pierce BCA-200 protein absorbance assay. Protein standards are marked in kDa to the left of the two figures.

FIG. 42

Western blots from tissues taken from an autopsy from a normal individual. Fifty micrograms of total protein was loaded in each lane unless otherwise stated. Protein size standards are indicated to the left in kDa. Tissues from A are: 1) aorta, 2) vena cava, 3) uninduced pET-15b-glomulin lysate, 4) 7 µg column-purified glomulin, 5) protein isolated from the lesion of a patient with Maffucci syndrome, 6) renal artery, 7) atrium, 8) splenic artery, 9) pulmonary artery, 10) sub-clavial artery, and 11) primitive carotid artery. Tissues in B are: 1) vena cava, 2) 7 µg column purified glomulin, 3) protein isolated from a lesion of a patient with Maffucci syndrome, 4) skin, 5) liver, 6) testicle, 7) left ventricle, 8) right ventricle, 9) supra-renal vena cava, 10) portal vein, 11) inferior vena cava.

TABLE 1A+B

Haplotypes A and B sharing in VMGLOM. Numbers indicate sizes of alleles that segregate with the disease in each family. At the top, symbol and geographic origin of family. USA:The United States of America; Bel:Belgium; Sco:Scotland; It&Italy; Fra:France; Ger:Germany; Yug:Yugoslavia. +:tetranucleotide repeat microsatellite. R: a recombinant individual in the family for this marker. X/Y: data not informative for linked allele. Alleles with a probable ancestral mutation differ from shared haplotype: white background; n/N: number of the shared allele on total number of alleles; fam: families linked to VMGLOM; con: control individuals from the Belgian population. P: P-value for the uncorrected chi-square test in a 2×2 table; *:significant P-value (p<0.01).

Table 2

Sixty-four control haplotypes, deduced from 16 father-mother-child triplets. Alleles of haplotype A have been boxed and shaded in gray. F: inferred haplotypes of father. M: inferred haplotypes of mother. T: haplotype transmitted to child. NT: haplotype not transmitted to child.

Table 3

Sixty-four control haplotypes, deduced from 16 father-mother-child triplets. Alleles of haplotype B have been boxed and shaded in gray. F: inferred haplotypes of father. M: inferred haplotypes of mother. T: haplotype transmitted to child. NT: haplotype not transmitted to child.

Table 4

Primer sequences for the 22 new end-of-clone STSs with fragment sizes in base pairs.

Table 5

Primer sequences for nine novel CA-repeats with number of heterozygotes identified in 16 controls.

Table 6

Primer sequences for 18 intronic primer pairs enabling the amplification of 18 exons of the human VMGLOM gene.

Table 7

Exon-intron structure of the human VMGLOM gene with exonic and intronic sizes.

Table 8

Identified mutations in the VMGLOM gene. The numbering of said mutations refers to the nucleotide numbering as used in FIG. 5, where +1 is the A of the ATG codon at positions 39 to 41.

EXAMPLES

Materials and Methods

Families

In addition to the families already described in Boon et al., 1999, 7 new families were identified. After informed consent, a clinical history was taken and physical examination was performed on all family members participating in the study. Venous blood samples were drawn for extraction of DNA. An additional sample was drawn for lymphocytic transformation from individuals Bln12, Bln100, Bln102, Sch12, Sch100, Sch102, Del101, Ad3, Ad12, Lml145, Lml181 and Lm1183. The pedigrees are shown in FIG. 1.

Linkage Analysis

Genomic DNA was extracted from the buffy coat (QIAGEN DNA extraction kit). Genotyping of individuals was performed as described elsewhere (Boon et al., 1994). All microsatellite markers located in the VMGLOM region on the basis of various databases (CEPH, CHLC, MIT/Whitehead; see the electronic database information below) were used. In addition to published polymorphic markers in the region, additional CA repeat microsatellites were isolated as part of the construction of a physical map of the region (33CA1, 50CA1, 69CA1 and 75CA1, Brouillard et al., unpublished). Linkage calculations were performed using the MLINK program of the LINKAGE package (Lathrop, 1984). The parameters were for an autosomal dominant disease with 90%, 80% and 70% penetrance, for individuals older than 16 years, between 10 and 16 years, and younger than 10 years, respectively, a disease allele frequency of $10^{-5}$ and 10 marker alleles with egal frequencies 0.1. The LOD scores were calculated for a recombination fraction 0 equal to 0.01, 0.05, 0.1, 0.2, 0.3 or 0.4.

Haplotype Sharing

In order to detect haplotype sharing, 3 affected individuals from each family were genotyped for every available microsatellite marker in the VMGLOM locus, except for families Ba and Al, where only 2 affected individuals are present. The radioactive PCR products for each marker were resolved on a separate polyacrylamide gel to allow a consistent scoring of the alleles across the families. The slowest allele was assigned number 1, with allele numbers increasing with mobility in the gel. Unscorable alleles were assigned number 0 (see Table 1).

To assess the degree of linkage disequilibrium of the shared haplotypes in the affected families, the frequencies of these haplotypes in the general population were estimated (see Table 2 and 3). 16 triplets (father-mother-child) belonging to the genetically heterogeneous belgian population were genotyped for the markers. Two triplets of affected individuals from the families were included as controls to provide an internal reference for the size of the alleles. Each marker was resolved on a separate gel. Haplotypes were constructed by eye based on the inheritance of parental alleles to child, assuming no recombination. When a marker was uninformative because the father, the mother and the child have the same genotype, we always tried to maximize the occurrence of the shared haplotypes.

YAC Clones

Yeast strains containing YAC clones were ordered from *Research Genetics* or from *C.E.P.H.* (clones 736E1, 751F11, 848E3, 898E4, 917B5 and 948C3). They were grown in YPD (yeast extract/peptone/D-glucose) media and DNA was extracted according to the Current protocols in molecular biology (Unit 6.10.2).

STS Markers

STSs markers were selected on the basis of their localization in databases (Sanger, Unigene, Science maps '96, '98 & '99) close to VMGLOM (a205xD5-D1S2775). Primers for the STSs were synthesized by Gibco BRL on the basis of the sequence information from various databases (Genbank, GDB, dbSNP). Novel STSs were created from our PAC-end sequences (Table 4) and from the sequences of the (GT)16-positive clones (Table 5). All markers were amplified by PCR in 10 µl reaction volume using 10 ng of DNA. The amplification conditions were: [95° C., 3'; (95° C., 30"; 55-65° C., 30"; 72° C., 30")×35; 72° C., 10'] using 0.25 units of the Biotools DNA polymerase™ (Labsystems).

PAC Clones

*E. coli* strains containing PAC clones were provided by The Sanger Centre (UK) except for the clones 103d10, 10406 and 226k2 that were ordered from HGMP. Colonies were isolated on LB-agar plates containing 30 µg/ml kanamycin (ICN). DNA extractions from 1.5 ml overnight cultures were carried according to a protocol from BACPAC resources, except that, at the end, the DNA pellets were resuspended in 200 µl of 10 mM Tris-HCl, pH=7.5, containing 0.1 mM EDTA.

PAC End-sequencing

Selected PAC clones were purified with the QIAGEN Plasmid Midi Kit using the QIAGEN protocol with slight modifications. Briefly, 100 ml of an overnight bacterial culture was divided into two tubes and the bacteria were pelleted by centrifugation. For each tube, 10 ml of P1, P2 and P3 were used. After the two steps of centrifugation, the supernatants were pooled and applied to the columns. Elution was done with 5 times 1 ml of QF buffer, pre-warmed to 65° C. DNA was precipitated as mentioned in the kit and resuspended into 200 µl of 10 mM Tris-HCl, pH=7.5, containing 0.1 mM EDTA.

Sequencing reactions were done using the Thermo SEQUENASE kit RPN2538 (Amersham). A 24 µl pre-mix containing 2 µg of purified PAC DNA and 3 µmol of IRD-800 fluorescent primer was divided into four tubes, each containing 2 µl of the appropriate nucleotide mix. The SP6 and T7 primers were synthesized by MWG Biotech. Cycle-sequencing program used was: [95° C., 5'; (95°, 30"; 54° C. for primer T7 (5'-TAA TAC GAC TCA CTA TAG GG-3') (SEQ ID NO 111) or at 50° C. for primer SP6 (5'-CAT TTA GGT GAC ACT ATA G-3') (SEQ ID NO 112), 30"; 70° C., 1')×50]. 5 µl of the loading buffer were added and samples were denatured 5 min before separation on a 66 cm 4% Long Ranger gel with the DNA4000L™ sequencer (LI-COR).

PAC-library Screening

To identify new PAC clones, the Human RPCI-1 PAC library filters (Ioannou and de Jong 1996), provided by HGMP, were screened by Southern blot hybridizations using PCR-amplified end-of-clone STSs as probes (Table 1). PCR products were purified with QIAQUICK PCR purification kit™ (QIAGEN) prior to radiolabelling with [$\alpha^{32}$P]-dCTP (Amersham). Hybridizations were performed as previously described (Boon et al. 1999).

Isolation of Novel CA-repeats

Isolation of novel CA-repeats from genomic DNA clones was performed as described (Klockars et al. 1996; Paavola et al. 1999). Briefly, 350 ng of PAC DNA was digested with Sau3A I, ligated to BamH I-digested pBLSK+, transformed in XL1-blue cells and plated on LB media containing 100 µg/ml ampicilin. The colonies were transferred on HYBOND-N membranes (Amersham) according to the manufacturer's protocol. A $(GT)_{16}$ oligonucleotide, synthesized by Gibco BRL was end-labeled with $[\alpha^{32}P]$-ATP (Amersham) and hybridization was carried out as described (Boon et al. 1999). Positive colonies were picked and plasmid DNA was isolated with the QUANTUM PREP plasmid miniprep kit (Bio-Rad). The clones were sequenced with the M13 forward and reverse primers using the CEQ DTCS kit (Beckman), and an 8-capillary CEQ2000 sequencer (Beckman). The degree of polymorphism for the novel markers was tested by genotyping 16 unrelated control individuals as previously described (Boon et al. 1994).

Fingerprinting

44 µl of the mini-prep DNA extractions of the selected clones were digested with 18 units of Hind III in a final volume of 50 µl, for 2 hours. Digests were loaded on a 0.9% agarose gel (18 cm long), containing 0.8 µg/ml ethidium bromide. The gels were run at 70V (2.4 V/cm) for 15-20 hr. Pictures taken were manually analyzed.

Cloning of the VMGLOM Genes

The PAC end sequence 33SP6 (unpublished) identified ESTs homologous to FAP48, as well as the published FAP48 cDNA, in nBLAST searches. To clone the gene, primers were synthesized from the beginning and the end of the published FAP48 sequence (primers: VMGLOM-1: 5'-TCTGGC-CGATTTTAGCATCG-3' (SEQ ID NO 113) and VMGLOM-27: 5'-TAGTTTTTATTTAGGAAATGGAAC-3' (SEQ ID NO 114)). Using total RNA extracted from EBV-transformed lymphoblasts the gene was amplified and cloned into pBLSK+ vector by T/A cloning. For this, pBLSK+ vector was digested with EcoRV and thymidines were added with Tth DNA polymerase (Labsystems). Inserts were sequenced through using vector primers (M13 F and R), using the Thermo SEQUENASE kit RPN2538™ (Amersham,). A 24 µl pre-mix containing 2 µg of purified DNA and 3 µmol of IRD-800 fluorescent primer was divided into four tubes, each containing 2 µl of the appropriate nucleotide mix. Cycle-sequencing program used was: [95° C., 5'; (95°, 30"; 55° C., 30"; 70° C., 1')×35]. 5 µl of the loading buffer were added and samples were denatured 5 min before separation on a 66 cm 4% LONG RANGER gel (FMC BioProducts, Rockland, Me.) with the DNA4000L sequencer (LI-COR).

The obtained sequences were compiled to obtain full-length sequences (FIGS. 5 and 7), which were compared to the published FAP48 sequence (FIG. 9). The corresponding predicted amino acid sequences are 594 and 98 residues long (FIGS. 6 and 8).

To clone the human gene (including the introns), several exonic primer pairs were synthesized and used for PCR with genomic DNA as template. Gradually all introns were amplified. The ends of these amplified fragments were sequenced either directly or after cloning the PCR products. 18 separate exons were identified (Table 6) and the intronic sizes could be estimated (Table 7). Further below the sequence of the exon/intron boundaries is given (See Further determination of genomic structure of the VMGLOM genes)

To clone the mouse cDNA, the human VMGLOM cDNA sequence was aligned with identified mouse EST sequences. On the basis of these mouse ESTs, primers were selected from the 5' end (before the putative ATG codon in the mouse sequences) and from the 3' end (after the putative STOP codon in the mouse sequences): mVMGLOM-1,5'-AATG-GCTGTGGAGGAACTTC-3' (SEQ ID NO 11) and mVM-GLOM-5,5'-GCATTTTGTTGGTTTTTATTTATG-3' (SEQ ID NO 12). These primers were used to amplify the full-length murine cDNA, which was cloned to pBLSK+ vector by T/A cloning. As above, inserts were sequenced using vector primers M13 F and R on the DNA4000L sequencer (LI-COR). The obtained sequences were compiled to obtain full-length sequences (FIGS. 11 and 13). The corresponding predicted amino acid sequences are 573 and 98 residues long (FIGS. 12 and 14). A separate paragraph relating to the cloning of genomic fragments of the mouse glomulin gene is incorporated further below.

Identification of Mutations

Patient cDNA or DNA was amplified using exonic or intronic primer pairs. The size of the amplification products varied roughly between 200-350 by (Table 6). For single stranded conformation polymorphism (SSCP) and heteroduplex analysis, both PCR primers were end-labeled with $\alpha^{32}P$ using polynucleotide kinase (TAKARA), according to manufacturer's recommendations. The PCR reactions were divided into two aliquots before loading onto non-denaturing polyacrylamide gels (MDE gel solution, FMC). EDTA (final concentration 5 mM) and non-denaturing loading buffer (according to FMC) was added to the reactions for heteroduplex analysis, whereas a denaturing loading buffer (according to FMC) was added to the SSCP samples. After heat-denaturation, the samples for SSCP analysis were immediately loaded onto SSCP gels. The samples for heteroduplex analysis were first cooled from 95° C. to 37° C. at one centigrade per minute to increase the formation of heteroduplexes. Both gels were run for 14-16 hours, SSCP gels at constant power (6-8W), and heteroduplex gels at constant potential (700V). Gels were vacuum-dried and exposed for 12-24 hours to KODAK X-OMAT™ film. Fragments showing abnormal migration were reamplified, purified (Qiagen PCR columns), and cycle-sequenced using Beckman fluorescent dye-terminator technology (CEQ DTCS™ kit) and the Beckman CEQ 2000™ capillary sequencer.

Seven New Families with Glomuvenous Malformations

Figure 15:
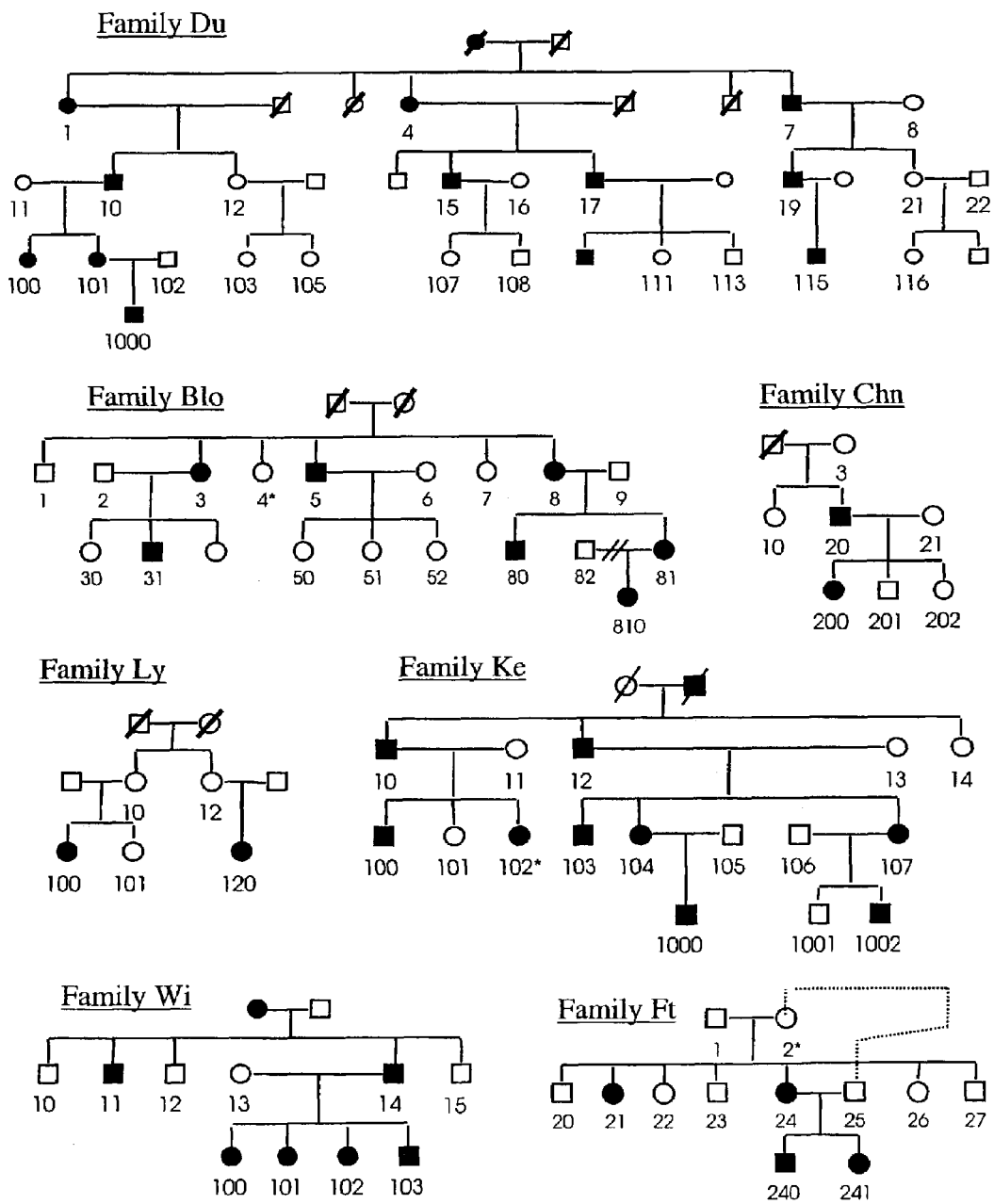

The inventors studied seven additional families (FIG. 15), one patient with familial history of the disorder (R1), and one sporadic case (BG). For genomic DNA extraction, buccal-cell brushes were obtained from individuals Blo-52 and Blo-810. Venous blood samples were drawn for others. A second blood sample was obtained from some individuals for lymphocytic transformation with Epstein-Barr virus. Immunohistochemistry was performed as described (Boon et al., 1999).

Northern Blots

Hybridizations of the Human Multiple Tissue Northern (MTN)® Blot were carried out according to the protocol for Human Multiple Tissue Expression (MTE)™ Dot Blot (Clontech Laboratories, CA, USA). Two different probes that were radiolabelled by random-priming with $^{32}\alpha$-dCTP were used: full-length glomulin coding sequence and a 482 by 5'-fragment (nt −23 to +459). The filters were exposed to Biomax films (Kodak) or analysed by phosphorimager (Molecular Dynamics). 5' RACE, using gene-specific primers 5'-GCT GAT TCC AAA GGG TAG AC-3' (SEQ ID NO 115), 5'-TGG GAT ATC TGT TTT CCA GAG-3' (SEQ ID NO 116) and 5'-CTA TCC TCT TTA TCT TTA CAC-3' (SEQ ID NO 117), was done with 5'RACE System for Rapid Amplification of cDNA Ends (Life Technologies).

Human Multiple Tissue Expression Dot Blot

Hybridizations of the Human Multiple Tissue Expression Dot Blot (MTE)™ (Clontech Laboratories, CA, USA) were carried out according to the protocol for Human Multiple Tissue Expression Dot Blot™ (Clontech Laboratories, CA, USA). The full-length coding sequence of human glomulin, radioactively labelled by $\gamma P^{32}$ and amplified using exonic primers Primer 1: TCT GGC CGA TTT TAG CAT CG (SEQ ID NO 118) and Primer 27: TAG TTT TTA TTT AGG AAA TGG AAC (SEQ ID NO 119), was used as a probe (FIG. 30). The analysis was done as for MTN® hybridisations.

Human Multiple Tissue RT-PCR Analysis

For testing glomulin expression in human tissues by RT-PCR, cDNAs were prepared by reverse-transcription using the SUPERSCRIPT™ kit according to the recommendations of the manufacturer (Gibco-BRL). Tissues tested included: an artery, aorta, heart, placenta, skeletal muscle, skin, cultured smooth muscle cells (a gift from Dr. B. Kraling, Heidelberg, Germany), umbilical cord, umbilical vein, vena cava, glomuvenous malformation resected from a patient with a known 5 by mutation in the glomulin gene, kaposiform hemangioendothelioma (KHE), and a venous malformation with as of yet no known mutation in TIE2/TEK gene. A plasmid containing glomulin cDNA was used as a positive control, and water as negative control. 5 µg of total RNA was used for cDNA synthesis. 1 µl out of the 20 µl reverse transcription product was used as template for PCR. Primer pairs "15": GCA CAC AGA CCA GCT ATT AG (SEQ ID NO 120) and "8": TCA AAG AAT TGT GCT GTC AGC (SEQ ID NO 121) from exons 2 and 6, and "25": AGT TTA GCT ATG CTT CAG CTG (SEQ ID NO 122) and "19": GGA GGC ATA TTA GGG ATC TC (SEQ ID NO 123) from exons 12 and 17 are specific to regions of 561 by and 503 bp, respectively, at the 5' (FIGS. 31B and D) and 3' (FIGS. 31A and C) ends of the glomulin gene. Both cover multiple exon-intron boundaries. PCRs were performed in standard conditions with cycling conditions: 95° C., 4' for initial denaturation followed by 35 cycles of 95° C., 30", 60° C., 30", 72° C., 40", followed by a 10' final extension at 72° C. (FIG. 31). Control RT-PCR using primers specific to glyceraldehyde phosphate dehydrogenase (TTG GTA TCG TGG AAG TAC TCA (SEQ ID NO 124) and TGT CAT CAT ATT TGG CAG GTT T (SEQ ID NO 15)), and glucose-6-phosphate dehydrogenase (ATC GAC CAC TAC CTG GGC AA (SEQ ID NO 126) and TTC TGC ATC ACG TCC CGG A (SEQ ID NO 127)) were used as positive controls for all the cDNAs (results not shown).

Mouse Developmental Stage RT-PCR Analysis cDNAs were prepared on total RNAs extracted from murine embryos of embryonic days (E) 10, 14, 16 and 18 (a gift from Dr. P Chomez, Ludwig Institute for Cancer Research, Brussels, Belgium). cDNAs were prepared by reverse-transcription using the SUPERSCRIPT™ kit (Gibco-BRL) using 2 µg of total RNA extracted from total murine embryos. 1 µl out of 20 µl of the prepared cDNA was used as template for PCR using primers AAT GGC TGT GGA GGA ACT TC (SEQ ID NO 128) for the forward primer and CAT CGA ACA ACT GGA CCA AC (SEQ ID NO 129) for the reverse primer. The amplified DNA product was 196 base pairs in length and covered 2 exon-intron boundaries, from exon 1 to exon 3. PCRs were performed in standard conditions with cycling conditions as follows: 95° C., 4' for initial denaturation followed by 37 cycles of 95° C., 30", 60° C., 30", 72° C., 40", followed by a 10' final extension at 72° C. Control RT-PCR using primers specific to glyceraldehyde phosphate dehydrogenase (TTG GTA TCG TGG AAG TAC TCA (SEQ ID NO 130) and TGT CAT CAT ATT TGG CAG GTT T (SEQ ID NO 131)) were used as positive control for all cDNAs (results not shown).

Further Determination of the Genomic Structure of the VMGLOM Gene

Exon/intron boundaries for exon 3 were identified by sequencing the SP6-end of the PAC clone 775d17 (Brouillard et al., 2000). To define the remainder of the genomic structure, 36 primers were designed based on the glomulin cDNA sequence. Different combinations of these exonic primers were used for PCR on PAC clones 775d15 and 1090n11. Inter-exonic fragments obtained were partially sequenced to identify exon/intron boundaries (FIG. 16), using a DNA4000 (Li-Cor) or a CEQ2000 (Beckman) fluorescent sequencer.

Cloning of the VMGLOM Genes

To further study the structure of the 5' end of the glomulin gene, the glomulin cDNA sequences obtained from 5' RACE experiments and the 3' sequences obtained during the cloning of the full-length glomulin cDNA, were used to screen against public sequence databases, especially dbEST and Unigene, and the human genome draft sequence database, to see whether the exon-intron structure of the glomulin gene was complete regarding the ends of the glomulin cDNA sequences. Part of the 5' cDNA sequence (the 8 first nucleotides in FIG. 5) was not covered by the genomic sequences of the investigators, but was identified in a PAC sequence in the human draft sequences. This sequence is located 894 by upstream of exon 1, thus creating a new intron and exon (a $19^{th}$ exon named exon −1). The sequence of exon—1 and the surrounding intronic and promoter sequences are given in FIG. 27. Primers TAC CTG CGG CTT TTC GAG AG (SEQ ID NO 132) and ACC CTG AAC CTC TCC ACA AC (SEQ ID NO 133) were synthesized allowing the amplification of this exon for mutational screening using genomic DNA as template, as described for other exons. In addition, a new intronic forward primer CTT AAG TGT AAT ATC ACG GAT AG (SEQ ID NO 134), was synthesized for exon 1 genomic amplification, and replaced the forward primer in Table 6.

Cloning of Genomic Fragments of the Mouse Glomulin Gene

To allow the construction of glomulin null-alleles, which would be introduced into murine embryonic stem cells (ES cells) by homologous recombination, large fragments of the murine glomulin gene were cloned and sequenced. To do this, several exonic primer pairs were synthesized and used for PCR, with murine genomic DNA from a female of the strain 12956/ScEvTac as template. Gradually all introns were amplified between exons 1 and 7. The ends of these amplification products were sequenced either directly or after cloning the PCR products into the pBLSK+ (Stratagene) vector. To get the full-length sequences of the introns, except for intron 2, which is about 10 kbp, additional primers were synthesized on the basis of the already obtained intronic sequences, and thus by "genomic walking" the complete sequences were obtained (FIGS. 28 and 29).

The 5' end of intron 1 and the sequences upstream of murine exon 1, were obtained by subcloning and sequencing a murine PAC clone, known to contain exon 1. Briefly, PAC clone 587o16 was digested with BamHI and the fragments were ligated into pBLSK+ (Stratagene). The products were tranformed into *E. coli* and the bacteria were plated to obtain isolated colonies. These 'libraries' were transferred onto nylon membranes that were hybridized with a probe corresponding to murine exon 1 and beginning of intron 1. One subclone containing a BamHIH/BamHI insert of about 8 kbp was identified. This clone contained sequences up to 6 kbp upstream of exon 1. Ends of this clone were sequenced with universal F and R primers as well as with a reverse primer of exon 1. To speed up the sequencing, the 8 kbp insert was further subcloned using EcoRV, PstI, PvuII and Sau3aI restriction enzyme cutting sites. Several of these subclones were sequenced, and this shotgun sequencing provided pieces covering altogether about 4 kbp. New primers were designed at the ends of these pieces of sequences and by 'walking', the gaps were closed. The ordered consensus sequences are shown in FIG. 28.

Mutational Screening on Genomic DNA 34 additional intronic primers were synthesized from the obtained genomic sequences to amplify the 18 exons of the human glomulin gene. Genomic DNA was screened by radio-active SSCP and Heteroduplex analysis for Ad-3, Al-14, Ba-10, BG, Chn-200, Del-2, Du-10, Ft-21, Ke-10, Ly-100, R1, Wi-14 and several control individuals, as described (Boon et al., 1999). Amplified fragments were also loaded on denaturing 5% acrylamide sequencing gels to identify potential insertions or deletions. Fragments presenting abnormal migration were re-amplified, purified, and sequenced on a CEQ2000 capillary sequencer (Beckman) (FIG. 18). Furthermore, the novel exon-1 was screened for additional mutation, as described below.

Mutational Screening of the Novel Exon −1

With the forward and reverse primer pair (a fragment with the size of 254 bp), exon −1 can be amplified by PCR using genomic DNA extracted e.g. from patients blood samples or from resected tissues, as template. With SSCP, heteroduplex analysis, sequencing gel size analysis, and sequencing, this fragment was screened in a set of new DNA samples from additional families with vascular phenotypes, glomuvenous malformations, venous malformations and blue rubber bleb nevus syndrome (BRBN), as well as from 2 glomuvenous malformation lesions of the same patient.

Co-segregation of Point Mutations

As most mutations create size differences, sequencing gels were used to assess inheritance in the families. Mutations 107insG, 554del4+556delCCT and 1711delGT were also checked by appropriate digestion (FIG. 18). To identify carriers of the 108C→A mutation (Ba family) that destroys an NsiI cutting site, exon 2 was amplified by PCR and digested with the enzyme. As the mutation 1547C→G (Ft family) does not change any restriction site, a wild-type and a mutant primer for allele-specific PCR (5'-CTG CTT CAT AAT GTG CTT TT(C/G)-3') (SEQ ID NO 135) were synthesized. These were used in combination with the forward primer of exon 16 (5'-AGT AGG CAA TCA ATC ATT GTT G-3') (SEQ ID NO 136). Annealing temperature was 58° C. A reverse primer of exon 16 (5'-AAT GGC TTA GCT GTT ATG GTC-3') (SEQ ID NO 137) was added to the reaction to serve as an internal positive control and as competitor to improve the specificity of the reaction.

Polyclonal Antisera Against Human Glomulin Peptides

Peptides

On the basis of the deduced amino acid sequence of human glomulin, two 16 amino acid peptides were synthesized by Eurogentec (Seraing, Belgium); CVPYSKEQIQMDDYGL (SEQ ID NO 138) and CEIKTKSTSEENIGIK (SEQ ID NO 139) (called 207 and 208, respectively, FIG. 32). The peptides were coupled to a BSA carrier (Eurogentec, Seraing, Belgium). Each peptide was injected into two rabbits, following the antibody production program of Eurogentec, (Seraing, Belgium). It consists of immunisation of 4 rabbits, with booster injections given every 28 days over a 3 month (84 day) period. Negative serum controls were obtained before injections, and altogether three serum samples were obtained at 43, 71 and 100 days of the program. Final bleeds were obtained at 3.5 months after the beginning of the injections. Titers of the four polyclonal rabbit antisera (452, 453, 454 and 455) were determined by Elisa against the synthesised peptides. Results for 455 shown in FIG. 33 (Eurogentec, Seraing, Belgium).

Purification of IgG Fractions from Antisera

Aliquots of the antisera were purified using a Protein G Sepharose HITRAP® column (Amersham-Pharmacia). Briefly, the columns were washed with water and equilibrated with supplied binding buffer. Subsequently 5 mL of the serum sample was applied and the columns were washed with the supplied binding buffer until no material appeared in the effluent. The IgG fractions were eluted using the supplied elution buffer (Amersham-Pharmacia). Working dilutions for the antisera were determined by dot blot Western hybridisation. 1, 10 and 100 ng of the synthesised peptides were spotted on nitrosellulose membranes (Amersham) and antisera dilutions 1:500 (FIG. 34A) or 1:4500, 1:13500 and 1:27000 (FIG. 34B) were tested.

Western Blotting

Western blots were done according to the NOVEX WESTERN BREEZE™ protocol of the chemiluminescent Western blotting and immunodetection system (Invitrogen, Germany). Briefly, bacterial or tissue extracts were run in a 24 cm 10% denaturing SDS-PAGE gel at 60 V for 16 hours. Following SDS-PAGE the proteins were transferred to nitrosellulose membranes by electrophoresis at 150 mAmps for 2 hours.

The immunostainings were performed using 1:5000 dilution of the purified 455 antiserum or the antisera from 452 and 453. Nonspecific hybridization was blocked by incubating the nitrocellulose membranes for 30 min in a supplied concentrated buffered saline solution containing detergent and concentrated Hammersten casein solution (Invitrogen, Germany). Alkaline phosphatase-conjugated, affinity purified anti-rabbit IgG was used as the secondary antibody (Invitrogen, Germany). A ready-to-use supplied solution of CDP-START™ (Invitrogen, Germany) mixed with supplied NITRO-BLOCK-II™ (Tropix Inc.) was used as the chemiluminescent substrate for alkaline phosphatase (Invitrogen, Germany). Exposure were done on Kodak Biomax™ films (Amersham-Pharmacia) for 30"-10'.

COOMASSIE Stains

For COOMASSIE staining of the protein size standards, gels were incubated in COOMASSIE BRILLIANT BLUE™ 250R (Sigma, USA) for 45 minutes and washed 2 times in decolouring agent (13% alcohol, 13% methanol and 4% acetic acid) for 1 hour, followed by a third wash performed overnight. The following day, the gels were rinsed for a minimum of 3 hours in water.

Bacterial Expression Constructs, Expression, and Extractions

The full-length human glomulin cDNA was cloned in fragments into the multiple cloning site (MCS) of the high-copy plasmid pBLSK+ between the Sal I and Bgl II restriction sites (Stratagene, Belgium). The integrity of the sequences was confirmed by sequencing. The glomulin cDNA was then modified by PCR, using this clone as template, with specific primers to create 5' Nde I (GGA GAA ATA CAT ATG GCT GTA G) (SEQ ID NO 140) and 3' Bam HI (AAC CCT ATT TCA CTT TCA CCT AGG AC) (SEQ ID NO 141) restriction sites. The purified PCR product was ligated into the Eco RV blunt end restriction site in the MCS of pBLSK+ vector (Stratagene, Belgium). After sequencing the insert, to ensure that the open reading frame of glomulin was free of mutations, glomulin cDNA was excised using the introduced Nde I and Bam HI sites, and ligated into the Nde I and Bam HI sites in the MCS of the low-copy pET-3a and pET-15b expression vectors (Novagen, USA). These vectors have the advantage of having the start "ATG" codon directly in the Nde I restriction site, and contain upstream the T7 promoter site for transgene activation. Furthermore, pET-15b possesses a histidine-tag, located on the 5' (N-terminal) end of the encoded protein (FIG. 35).

For expressing transgenic glomulin, E. coli strain BL21 transformed with pET-15b, containing recombinant glomulin, was plated on LB-agar (1% Tryptone, 0.5% Yeast extract, 1% NaCl, 1.5% Agar, pH 7.4) containing the antibiotics chloramphenicol (25 µg/ml) and ampicillin (100 µg/ml). Fresh colonies were selected and 20 mL of LB (1% Tryptone, 0.5% Yeast extract, 1% NaCl, pH 7.4) precultures were grown overnight. The following day, 100 mL of LB or M9 minimal salt medium (5×M9 salts [6.4% $Na_2HPO_4$, 1.5% $KH_2PO_4$, 0.25% NaCl, 0.5% $NH_{4]}$, $_1M$ $MgSO_4$, 20% glucose, 1M $CaCl_2$) containing chloramphenicol and ampicillin, was innoculated with 4 mL from the preculture. Preliminary expression experiments with this system demonstrated that LB growth medium produced bacteria expressing greater amounts of glomulin, which convinced the investigators to abandon the use of M9 growth medium for all subsequent experiments.

A plasmid miniprep (BioRad, USA), followed by Nde I/Bam HI double digestion and agarose gel electrophoresis, was performed on the precultures in order to ensure that the glomulin insert was still present. Positive cultures were grown at 37° C. for roughly 2 hours to obtain an absorbance at 600 nm of 0.5, at which point the cultures were cooled on ice for 20 minutes and separated into 2 flasks, one containing 15 mL and the other 85 mL. At this point, the 85 mL culture was induced with Isopropyl-β-D-thiogalactopyranoside (IPTG), and the 15 mL culture was used as an uninduced control. Both culture flasks were then returned to an incubator to grow. Various temperatures (37° C., 22° C., and 16° C.) were assayed, and it was observed that glomulin production was best at 22° C. Thus, 22° C. was the temperature focused upon for the remaining experiments.

Four (4) mL aliquots were taken at various time points (Eg. 0, 3, 5, 8 hours) to assess the expression level of the glomulin construct. Cells were pelleted and resuspended in lysing buffer (20 mM potassium phosphate pH7.4, 5 mM EDTA, 1 mM dithiothreitol, 1 mg/mL lysozyme, 2.5 µg/mL leupeptin, 2.5 µg/mL antipain, and 0.5 mM phenylmethylsulfonylfluoride PMSF). Cells were then lysed by freeze thawing, then 3 times, between liquid nitrogen and 37° C. heating block. Bacterial DNA was removed by DNase digestion for 1 hour at 4C (5 µg/mL DNase with 0.1M $MgSO_4$). Cell debris and inclusion bodies were then removed by centrifugation at 13,000 g for 30 minutes at 4° C. in an Eppendorf microcentrifuge. Supernatant and pellet fractions were stored at −20° C. Protein levels were quantitated using the BCA-200™ kit from Pierce (Rockford, USA).

Eukaryotic Protein Extraction

Proteins were extracted from tissues frozen and stocked at −80° C. First, the chosen tissues were transferred to liquid nitrogen. Tissues were then crunched in a sub-zero metal cylinder with a mallet, and weighed out on a scale. Filter sterilized Camiolo extraction buffer pH 7.4 (0.0075M potassium acetate, 0.3M sodium chloride, 0.1M L-arginine basic salt, 0.01M EDTA and 0.25% Triton X-100) was added in the amount of 1 mL per 100 mg crunched tissue, and homogenized for 1 minute with a ULTRA-TURRAX™ T25 (Janke & Kunkel, Germany) tissue homogenizer. After being placed on ice for a minimum of 5 minutes, the homogenized tissue was spun at 3000 rpm for 15 minutes at 4° C. Supernatant and pellet fractions were then separated and protein levels quantitated using the BCA-200 kit from Pierce.

Determination of Protein Concentration

Protein concentration from prokaryotic and eukaryotic cell and tissue extracts were determined using the BCA-200 Protein Assay Kit from Pierce (Rockford, USA). Briefly, a fresh set of protein standards was made using BSA at concentrations of 2000, 1500, 1000, 750, 500, 250, 125, and 25 µg/mL. Next, 25 µL of each of the protein samples and BSA standards were mixed with 200 µL of the supplied BCA (bicinchoninic acid) working reagent on a microwell plate. The plate was covered and mixed on a vortex, and incubated at 37° C. for 30 minutes. At this point, a colorimetric reaction occurred, in which the copper in the working reagent was reduced from $Cu^{+2}$ to $Cu^{+1}$ by the proteins in the samples. This reaction occurs in a protein concentration dependent manner. Subsequently, the plate was cooled to room temperature and the absorbance at 562 nm was measured on a plate reader. A response curve for BSA was generated (net absorbance at 562 nm vs. protein concentration in µg/mL). The measured absorbance of the test samples was then plotted onto the response curve and unknown protein concentrations were determined.

Affinity Column Purification of Glomulin

Glomulin that was expressed in the pET-15b vector containing a histidine tag was column purified using HITRAP® affinity columns (Amersham-Pharmacia), owing to the histidine tag's affinity for metal ions. Briefly, as a washing step, 5 mL distilled water was let through the HITRAP® column dropwise using a syringe. The column was subsequently loaded with 0.5 mL of 0.1M $NiSO_4$ metal salt solution and washed with distilled water. The column was then equilibrated with 5 mL of start buffer (0.02M sodium phosphate, 0.5M NaCl, pH 7.4), and 5 mL of the sample was applied. The column was then re-washed with 5 mL of start buffer, before applying 2 mL of elution buffer (0.02M sodium phosphate, 0.5M NaCl, 0.5M imidazole, pH 7.4). This led to competitive elution of the histidine-tagged glomulin protein by imidazole, which has a higher affinity for the nickel ions than histidine. Alternatively, pH gradient purifications were performed with less success (results not shown).

Results

Families

The number of affected males in the 12 families is 35 and the number of affected females is 40. This is consistent with the data in Boon et al., 1999, showing no significant sex bias. 59% (26/44) of children from an affected person are also affected, a figure compatible with a dominant disease.

Linkage

The highest observed two-point LOD scores for the new families were 4.05 for marker D1S2804 (family Lml), 1.69 for marker D1S2776 (family Sch), 0.75 for marker D1S188 (family Bln), 0.56 for marker D1S188 (family Del), 0.56 for marker D1S2776 (Family Ad), 0.52 for marker D1S2776 (family Ba), and −0.18 for marker D1S188 (family Al), all at θ=0.0. For marker D1S188, the LOD scores at θ=0.0 for the families were 3.78 (family Lml), 1.28 (family Sch), 0.75 (family Bln), 0.56 (family Del), 0.32 (family Ba), −0.52 (family Ad) and –0.18 (family Al). The maximum combined LOD score for D1S188 for these seven families is thus 5.99, and, for all 12 families, 18.41 (θ=0.0).

The number of affected males and females in the 12 families is 35 and 40, respectively, and 59% (26/44) of children from an affected person are affected. Visual examination of the pedigrees reveals that the disease seems to skip a generation twice (individuals De15 and Bln104). However, individual Bln104 has not inherited the haplotype linked with the disease, suggesting that he is not a carrier and that his daughter Bln1040, with a single small ventral lesion, is a phenocopy. In contrast, Del5 is an unaffected person who has inherited the haplotype associated with the disease in his family, and she has an affected son. Thus, she is an obligatory carrier and the mutated gene has a reduced penetrance. Similarly, individuals Lml223, Sch1020, Al12 and Bln1070 were recombinant throughout the VMGLOM region and are likely to be unaffected carriers. This could be explained by their age: Lm1223 is 14 years old, A112 is 10 years old, Sch1020 is 2 years old, and Bln1070 is 1 year old. Thus, 5 unaffected carriers are observed among 43 individuals with the disease haplotype in these seven families. Combined with the data in the 5 initial families, where all 38 carriers of the disease haplotype were affected, a penetrance of ~94% (76/81) can be calculated.

Haplotypic analysis of the seven families defined new obligatory recombination events within VMGLOM between markers AFMB337XE1 and D1S188 (affected individual Lm122) on the telomeric part of VMGLOM, and between markers D1S236 and D1S2779 (affected individuals Sch3 and Bln100, and unaffected individual Bln1020) on the centromeric part of the region. This reduces the locus by 2 cM from AFMA205XD5-D1S236 (Boon et al. 1999) to AFMB337XE1-D1S236, a region of about 3 cM.

Haplotype Sharing in VMGLOM

When the linked haplotypes of the 12 families were compared, two distinct haplotypes, haplotype A, shared by 7 families (BI, Bt, Sh, F, T, Bln, Sch), and haplotype B, shared by 4 families (Al, Ba, Del, Ad) were revealed. Haplotype A is shared from D1S2804 to D1S2849, and, in a subset of families, even more telomerically or centromerically (Table 1A). Haplotype B is shared between markers D1S2804 and D1S2868, and, again, telomeric and centromeric extensions are observed in a subset of the families (Table 1B). Family Lml presents a unique haplotype. Within the shared haplotypes, non-shared marker alleles were occasionally observed in some families for markers D1S2804, D1S424, D1S406, 69CA1, 50CA1 and 75CA1 (Table 1A+B).

Control haplotypes were constructed on the basis of the genotypes of 16 father-mother-child triplets, with the assumption that no crossovers have occurred between the markers. Within these haplotypes, the presence of haplotype A, haplotype B, and portions thereof, was looked for (Table 2). Haplotype A (from D1S2804 to D1S2849) was not seen in controls, although three haplotypes may be considered closely related to it (F1-NT, M2-NT, and F14-T). Haplotype B (from D1S2804 to D1S2868) was not seen in controls either, even if the alleles composing this haplotype seem more frequent than those of Haplotype A (Table 2).

Statistical significance of the apparent linkage disequilibrium was assessed using the chi-square independence test. The frequency bias is significant (P<0.01) for seven out of nine markers in the core of the first haplotype (between D1S2804 and D1S2849, Table 1A). This supports the hypothesis of a founder effect for this haplotype, and allowed to refine the locus further by inferring ancestral recombinations. In contrast, alleles of the second haplotype do not show statistically significant enrichment from the general population, and thus the second haplotype is probably due to co-occurrence of frequent alleles by chance (Table 1B). Thus, based on apparent ancestral crossovers in family T for the first haplotype, the VMGLOM locus can be delineated between marker_33CA1 and marker D1S2779. These two makers, and all intervening markers, have been localised on the same non-chimeric 1.48 Mbp YAC 957D9 (Whitehead/MIT database). Naturally, the possiblility that the apparent crossovers in markers 33CA1 and D1S1170 in family T are actually the consequence of marker mutations cannot be ruled out, as such mutations were observed inside the core of the first haplotype for markers D1S424, D1S406, 50CA1 and 75CA1 (Table 1A). Taking this possibility into consideration, a very conservative analysis of the data delineates the locus between markers D1S188 and D1S2779.

YAC Physical Map

The positional cloning strategy was initiated by creating a YAC-based physical map on the basis of information collected from the Whitehead Institute/MIT database. Eighteen overlapping YAC clones were selected that cover the 5 Mbp area between the polymorphic markers AFMa205xD5 and D1S2775 that define the VMGLOM locus (Boon et al. 1999). The integrity of the clones was checked by PCR amplification of markers #24 to #49 from the contig WC1.14 of the Whitehead/MIT database (FIGS. 2A and 2B). These clones were used for the precise localization of additional STSs selected from various databanks (FIG. 2C) and created from our end-of-clones (FIG. 3 and Table4). We also identified the position of three polymorphic markers (D1S188, D1S406 and D1S1170) known to localize to this region (Allikmets et al. 1997). In contrast to Allikmets et al. (1997), marker WI-7719 could not be localised to our YAC-map and the order for markers D1S2849 to D1S286 as well as for D1S424 and D1S406 was inverted (FIG. 2). These results were later confirmed with the PAC-map (FIG. 3). For the integrity of the map, each YAC clone was tested for several markers assumed to be located outside the extremities of the clone. Although clones 934G7 and 944B12 are reported to be chimeras, no gaps were found with the marker set used. However, YAC 784H3, also reported to be a chimera, shows at least two gaps (FIG. 2A). Based on the known sizes of the YAC clones, the size of the VMGLOM locus was estimated to be approximately 5 Mbp (751F11, 946C5, 957D9 and 943H8 cover altogether 6.14 Mbp with overlapping parts).

YAC-based STS and Transcript Map

Having previously excluded as the mutated gene three known genes in VMGLOM (Boon et al. 1999), new positional candidate genes needed to be indentified. Therefore, more than 80 STSs were selected from several databases (Sanger, Unigene, Science maps '96, '98 & '99) on the basis of their localization by radiation hybrid mapping to the vicinity of the VMGLOM locus. Every marker was first amplified by PCR on six overlapping YACs covering the whole region (736E1, 751F11, 946C5, 957D9, 944B12 and 759D7, FIG. 1A), with a genomic DNA as positive control. 48 positive markers were identified. Finer localization of these 48 markers was performed by testing all the YAC clones in the vicinity of the positive ones. Each negative result allowed the exclusion of the area covered by the corresponding clone. Using this strategy, five markers, WI-13478, D152779, G32495FS, G31522 and WI-15861 were precisely localized inbetween existing markers of the YAC-map (FIG. 2B), whereas the 43 other STSs were only roughly localized (FIG. 2C). Six of the STSs correspond to SNPs (WIAF-1748, WIAF-1230, WIAF-1547, WIAF-1393, WIAF-1842 and WIAF-1642). In addition, to identify novel genes in the region, a homology search was done for each marker by Blast analysis and several genes were retrieved: EVI5, breast cancer anti-estrogen resistance 3 (BCAR3), PTPL1-associated RhoGAP (PARG1), peroxisomal 70 kD membrane protein (PXMP1), KIAA0231, RAD2 and Acidic Calponin (FIGS. 2B and 2C).

The identification of haplotype sharing in VMGLOM among 12 families having reduced the candidate region from AFMa205xD5-D1S2775 to D1S1170-D1S2779, the resolution of our YAC map became too low for precise localisation of candidate genes and polymorphic markers. Based on the size of the YAC 957D9 containing both D1S1170 and D1S2779, and thus the whole region showing haplotype sharing, the VMGLOM locus should be less than 1.48 Mbp (FIG. 2). We undertook the creation of a more precise physical map of this locus, using PAC clones.

PAC Map

The Sanger Center, as part of the Human Genome Project, is sequencing the human chromosome 1, and thus, they have already identified several PAC clones from this human chromosome. To create a map, their database was first searched for PAC clones with the STSs in the VMGLOM haplotype-shared area. This way, twenty clones were found possibly localizing to VMGLOM. Each clone was tested by PCR for all the markers in the VMGLOM YAC map between D1S1170 and D1S2779 (FIG. 3). A manual analysis of the results allowed the clustering of the PACs in four contigs (FIG. 3). With a second search in the Sanger database, we picked twenty-three additional PACs. None closed the gaps between the PAC clusters. To join the different PAC-islands, altogether 21 new STSs were generated from the sequences obtained by direct sequencing of the ends of the protruding PAC clones (Table 4). Marker 33SP6, from the centromeric end of clone 775d17, closed the first gap, being positive for the PAC 1090n11 (FIG. 3). Similarly, marker 21SP6 enabled to bridge clone 981e3 with clone 606m5. However, the novel markers 47SP6 and 17T7 inside the last gap, did not reach any clone from the other cluster. Thus, a PAC library screening, using the amplified 17T7 as probe was performed. This resulted in the identification of two new PACs: 104o6 and 226k2. These clones bridged the two contigs, what was also confirmed with three new STSs generated from the ends of these clones (70SP6, 70T7 and 75SP6, Table 1). To obtain double coverage for the single-linked point in the map around marker 21SP6, new clones were screened for from the PAC library with 21SP6. Clone 103d10, which overlaps with clones 606 m5 and 981e3, was identified. This overlap was confirmed with the novel STS 69SP6. All other novel STSs created were located inside the contigs (FIG. 3).

Novel CA-repeats

To identify new polymorphic markers for linkage and haplotypic analyses, nine PAC clones were selected for CA-repeat screening. Seven of these were not positive for a known CA-repeat (PACs 976013, 606 m5, 775d17, 828k3, 617o13, 103d10 and 226k2, FIG. 3) and two (612c19 and 981e3) contained one (D1S2776 or D1S2779, respectively). These PACs were subcloned and the libraries were screened by hybridization with a radiolabelled (GT)16 probe. More than forty positive subclones were sequenced. This enabled the identification of nine different CA-repeats (Table 5). The sub-library from clone 828k3 did not show any clone containing a putative repeat and the eight positive ones from clone 981e3 only revealed the known D1S2776. Three out of 12 from PAC 612c19 were identical to D1S2779. The nine novel markers were tested by PCR for their specificity on genomic DNA. All except 25CA1 gave a unique signal. To know if these eight specific STSs were polymorphic, 16 unrelated control individuals were genotyped. Seven markers showed variable allele sizes and heterozygosities (Table 5).

To integrate additional published information into our map, the PAC contig was analyzed for the ten novel markers reported by Roberts et al. (1998) (FIG. 3). Two of these markers, D1S2868 and D1S1870E, were identified to have an inverted localization. The whole map is now covered by 46 clones and 69 STSs of which four are known genes: the Ribosomal protein L5, KIAA0231, the EVI5, from which is derived the NB4S chimerical gene (Roberts et al. 1998), and GFI1, a growth factor independence gene (Roberts and Cowell 1997). In addition, some STSs (G4415; D1S1887E; G35002; GDB:191074, G29243 and WI-20561) represent four putative genes as they correspond to a cDNA or to an EST-cluster.

Selection of Clones for Sequencing

Figure 4:
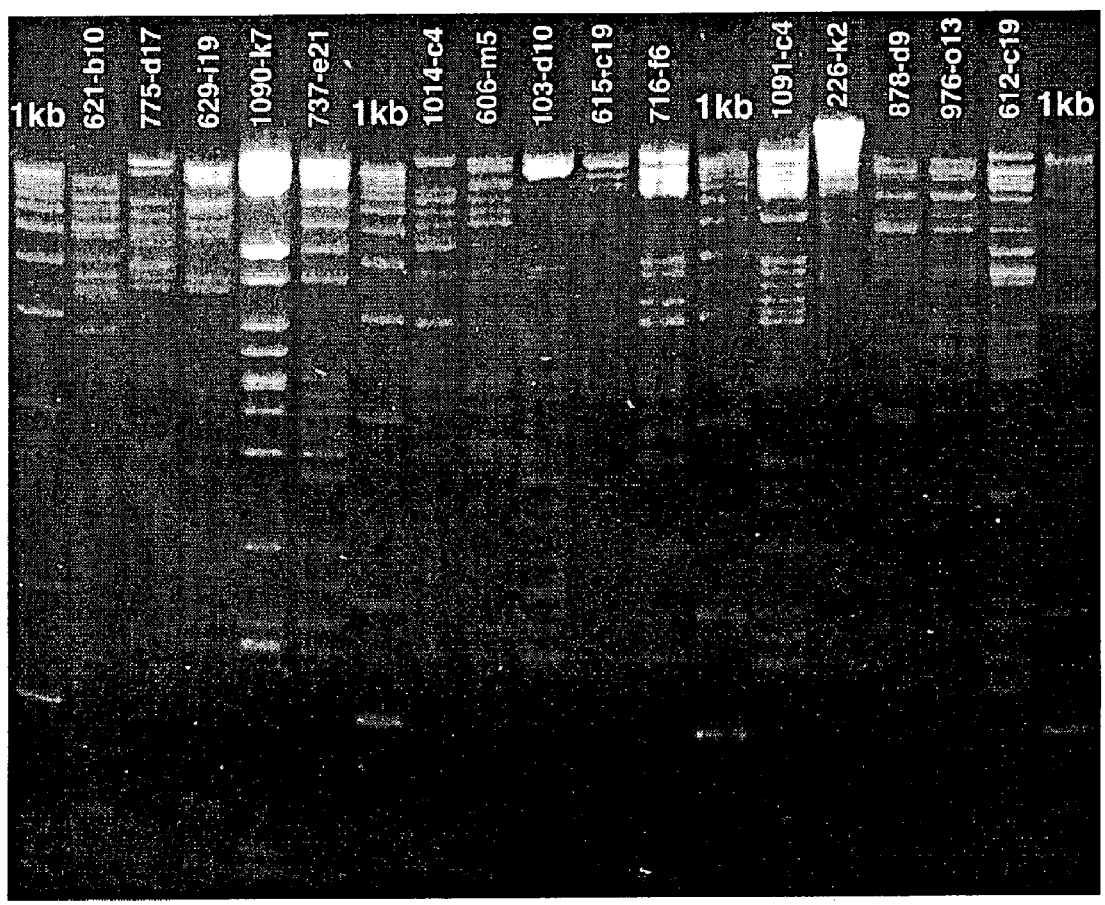

The most efficient way to sequence through the area covered by the PAC-map is to select clones presenting a minimum of overlap. Seven of the 46 clones already exist in the Sanger contig maps and have been selected for sequencing (621b10, 629119, 1014c4, 716f6, 878d9, 976013, and 612c19). To cover the whole region, clones 775d17, 1090k7 or 737e21, 606 m5, 103d10, 615c19, 1091c4 and 226k2 should also be selected. To confirm the overlaps, we fingerprinted these 15 clones by Hind III restriction digestion. Fragments of the same size were identified in overlapping clones (FIG. 4).

Cloning of the VMGLOM Gene:

On the basis of the PAC end sequence 33SP6 (unpublished), ESTs homologous to FAP48, as well as the published FAP48 cDNA, the human VMGLOM gene was cloned and sequenced. Sequences obtained from clones were aligned with the published FAP48 sequences and several differences were identified (FIG. 9). Most remarkably, the open reading frame of VMGLOM "long form" was roughly 30% longer than that of FAP48, extending from the published TAG stop codon at position 1339 in the FAP48 sequence to a STOP codon at position 1785 in the VMGLOM "long form" sequence (FIG. 6). This was identified to be due to two mistakes in the published sequence: 1) an extra guanine at position 1565 in FAP 48 sequence, and 2) a missing 85 by at position 1215-1300.

Figure 17:
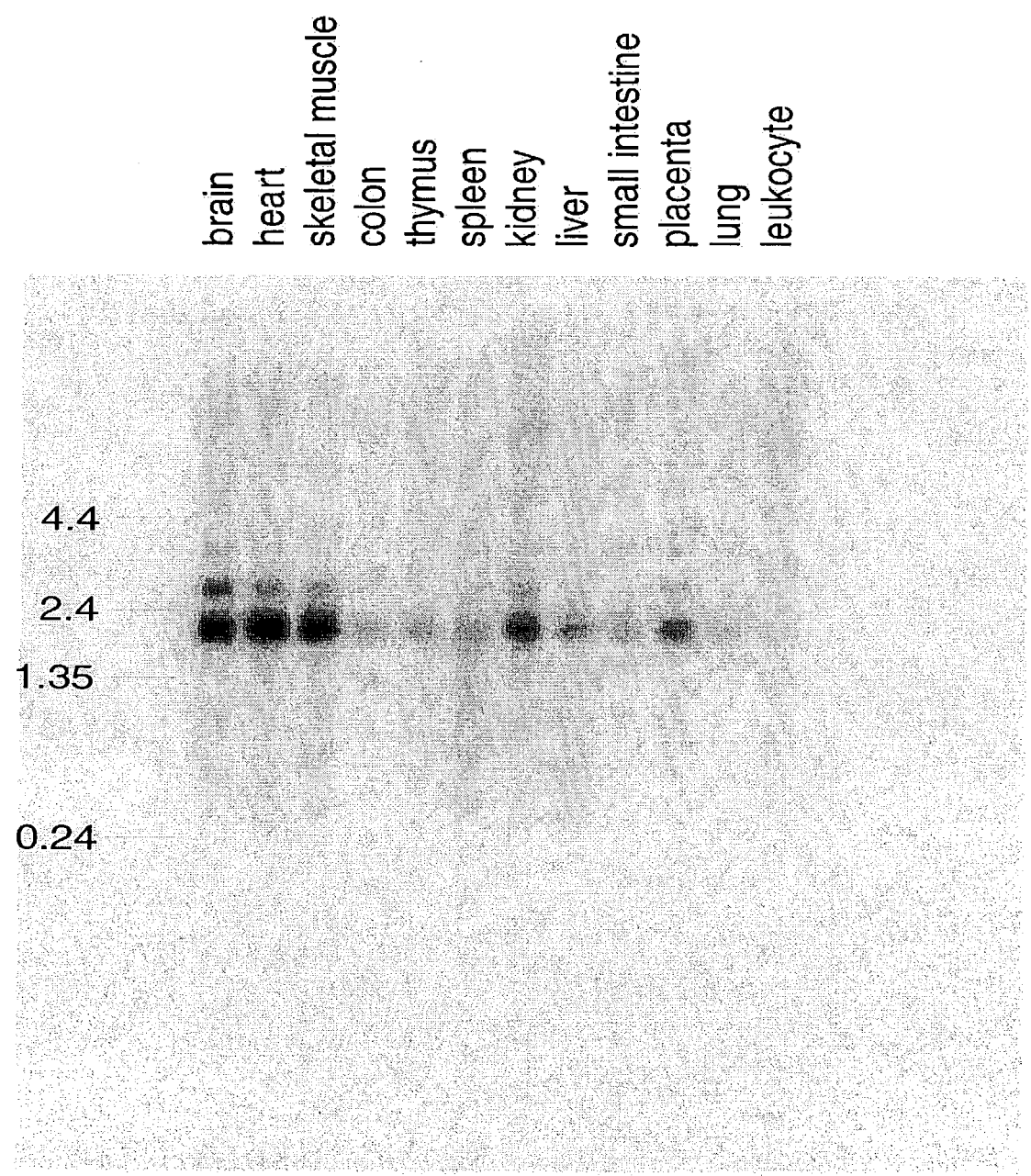

The gene encoding the VMGLOM "long form" has been named "glomulin" by the inventors. Its genomic structure is further illustrated in FIG. 16. The gene is composed of 18 exons and extends over 55 kbp; exon 1 contains the translation start site and exon 18 the TGA stop codon. The sequence of the unique 5' RACE product obtained was in accordance with the published FAP48 5'-sequence and confirmed the presence of an in frame STOP codon, 81 by before ATG. Northern blot hybridization (FIG. 17) showed one major transcript around 2 kbp (glomulin coding sequence=1785 bp) in 12 human tissues of a Multiple Tissue Northern filter (Clontech). An additional band of ~3 kbp was observed in most of the tissues. However, the identity of this transcript remains unclear, as the 5' RACE resulted in a single product.

In addition to the VMGLOM "long form", another VMGLOM cDNA form, with an extra 24 nucleotides in the 5' end of exon 4, creating a STOP codon at position 295, was identified among the clones (FIG. 7). This VMGLOM "short form" encodes a predicted protein of only 98 amino acids (FIG. 8). In mouse, both forms were also cloned (FIGS. 11 and 13).

Further analyses of the genomic structure of the 5' end of the glomulin gene led to the identification of an additional (19$^{th}$ exon) that was named exon −1 (FIG. 27). This exon was identified using the human genome draft sequences and the investigator's glomulin cDNA 5' sequences. It was observed that the cDNA sequence, 31 by upstream of the ATG codon, was not located 31 by upstream of exon 1 in the genomic draft sequences, but rather 925 by upstream. This fragment (exon −1) of the cDNA had a consensus splice site at its 3' end of the genomic sequence and consists of at least 57 by (the exact transcription start site being currently unknown, thus the exact number may be higher). As the translation start codon (ATG) is located in exon one, this newly identified exon −1 does not contain coding sequences for amino acids of glomulin.

Identification of Mutations

To screen the VMGLOM cDNA for possible mutations by SSCP and heteroduplex analyses, several overlapping fragments were amplified from patients from whom we had total RNA extracted from EBV-transformed lymphoblasts. Fragments showing abnormal migration in either of these gels, were reamplified and sequenced using Beckman fluorescent dye-terminator technology and the Beckman CEQ 2000 capillary sequencer. Mutations 1-4 (Table 8; VMGLOM$^{\Delta A431,32}$, VMGLOM$^{insG107}$, VMGLOM$^{\Delta AAGAA157-161}$, and VMGLOM$^{\Delta CAA1180-1182}$) were identified.

To screen patients from whom we did not have RNA for mutations in the VMGLOM gene, intronic primers (Table 6) were used. With these primer pairs, all 18 exons were amplified and analysed by SSCP, heteroduplex and sequencing gels. Nine additional mutations 5-10 were identified (Table 8).

Most of the mutations lead to frame shift and thereafter to premature STOP codons, and thus, may cause loss-of-function or dominant-negative effects. As the most 5' mutation creating a premature STOP occurs already in exon 2, it is very likely that the effect of all the identified mutations is loss-of-function.

All mutations were tested by PCR on genomic DNA from all family members, and were shown to co-segregate with venous malformations with glomus cells. Interestingly, the VMGLOM$^{\Delta AAGAA157-161}$ mutation was found in seven of the families with a shared haplotype. Thus, the hypothesis that this haplotype sharing reflects identity by descent, and thus relatedness of these families and sharing of the same mutation, was true for these seven families.

Overview of Identified Glomulin Mutations and Penetrance of these Mutations

Mutational screening of glomulin was performed on cDNA produced either from RNA extracted from resected GVMs (glomuvenous malformations) or from cultured lymphoblasts, or alternatively on genomic DNA. Thirteen different mutations were identified in 18 families and in 1 sporadic patient FIGS. 16 & 18). Nine of the mutations were deletions or insertions that cause frame-shifts resulting in premature stop codons. Mutation 157delAAGAA was present in all seven families in which the inventors previously found strong evidence for linkage disequilibrium (Irrthum et al., in press), proving the ancestral origin of the identified haplotype. An additional deletion was found in family Chn. It affects an adenine at the +4 position of the consensus donor site sequence of intron 5, and should, thus, interfere with splicing of exon 5, resulting in exonic skipping. Loss of this 238 by exon would also modify the reading frame and result in a premature stop codon. In addition, two nonsense mutations were detected: a substitution of 108C by an A in a TGC codon (family Ba) and the replacement of 1547C by a G in a TCA codon (family Ft). The only mutation that would not cause a premature stop codon was a deletion of 3 nt (family Du), equivalent to the removal of an asparagine at position 394. Since no mutations were found in previously published families Ad and Al (Irrthum et al., in press), and the mutations in families Ba and Del are different, the sharing-by-chance of a similar haplotype in these four families was confirmed (Irrthum et al., in press).

The co-segregation experiments (FIG. 18) allowed the detection of altogether 19 unaffected carriers and 5 phenocopies. The penetrance of the different mutations varied from 50 to 100%. The combined penetrance for the most common mutation, 157delAAGAA, was 95.6%, whereas the overall penetrance for all mutations was 88.2%. Penetrance increased by age, as the onset of the first lesion varied from birth to puberty. Thus, at 20 years of age, the overall penetrance rose to 96.5%. The fact that the disorder can be expressed as only a single tiny blue lesion anywhere on the body (Boon et al., 1999), creates difficulties in the determination of affecteds, a partial explanation for the observed penetrance below 100%.

Cloning of Genomic Fragments of the Mouse Glomulin Gene

The amplification and/or subcloning of genomic fragments of the murine glomulin gene led to the decoding of altogether about 18 kbp of murine genomic sequences. Exon-intron structure of the murine gene was revealed between exons 1 and 7 (FIGS. 28 and 29). Because of the large size of the second intron (about 10 kbp), only partial sequences were obtained (altogether 2.5 kbp) for this intron. From exon 3 until exon 7, all introns were completely sequenced (FIG. 29). Their sizes varied between 1301 by to over 10 kbp. In addition, using homology based search, a novel murine exon −1 was identified based on the novel human exon −1 sequences (FIGS. 27 and 28).

These sequences allow, among others, the construction of precise restriction digestion maps of these parts of the murine glomulin gene. These maps are important, among others, for the in vitro construction of fragments of the murine glomulin gene that could be used for homologous recombination to result e.g. in ES cells that are genetically modified.

Two constructs for such experimenst were designed (FIG. 36). The first construct, which contains the LacZ marker gene positioned at the ATG start codon of the glomulin gene, would lead to a glomulin null-allele. In addition, it would allow to study the marker gene expression in vivo under the normal control of the endogenous glomulin promoter, especially in the heterozygous mice, in case homozygotes would be lethal.

The second construct was designed to allow conditional knock-out of the glomulin gene. Using the Cre-loxP system, the DNA fragment between the inserted loxP sites can be excised by introduction of the Cre-recombinase. Thus, in mice or murine embryos or ES cells, homozygous for this construct, a deficiency of glomulin can be introduced in a given time point. This should be especially helpful for the study of the function of glomulin in various organs, developmental time points, and various pathogenic as well as physiologic processes.

Human Multiple Tissue Expression Dot Blot

All the tissues on the Human Multiple Tissue Expression Dot Blot (MTE™) showed a positive hybridisation signal (FIG. 30). Thus, glomulin seems to be expressed in all the human tissues examined ranging from cardiovascular tissues to brain parenchyma and carcinoma cell lines. This may reflect the fact that glomulin is widely expressed in several cell types, or that, as blood vessels are present in most tissues, the positive signals are due to the glomulin present in blood vessels. In that case, the detected expression of glomulin in cancers, such as cervical adenocarcinoma (Hela S3), lung carcinoma epithelial cell line (A549), leukemias (K-562, MOLT-4, and HL-60), Burkitt's lymphomas (Raji and Daudi) and colorectal adenocarcinoma, epithelial cell line (SW480), would be due to inappropriate expression, and glomulin could serve as a marker for transformed cells. It may also be that glomulin is expressed by a variety of cell types, and its expression in cancer only encounters qualitative or quantitative alteration in e.g. expression or concentration, and thus serves as a target e.g. for diagnosis, treatment and prevention. As the embryonic tissues were also positive for glomulin, expression of glomulin occurs already during human embryogenesis.

Human Multiple Tissue RT-PCR Analysis

Multiple human tissues were studied by RT-PCR for the expression of the glomulin gene. The amplified fragments were designed so that a distinction could be made between the amplification product originating from cDNA and the one from contaminating genomic DNA. The primers synthesized were from exons 2 and 6 (primers 15 and 8) for fragment A from the 5' end of the cDNA (FIGS. 31A and C), and from exon 9 and 12 (FIGS. 31B and D) for fragment B, from the 3' end of the cDNA. Thus, the size of amplified cDNA is 561 bp, whereas the corresponding genomic fragment would be about 11.5 kbp. Analogously, for fragment B, the size amplified from cDNA is 503 bp, whereas the genomic amplification product has a size about 17 kbp (see FIG. 15). As both amplification products correspond to the expected size of cDNA, they reflect the expression of glomulin in the corresponding tissue (FIG. 32). Tissues tested included: an artery, aorta, heart, placenta, skeletal muscle, skin, cultured smooth muscle cells, umbilical cord, umbilical vein, vena cava, glomuvenous malformation resected from a patient with a known 5 by mutation resulting in a premature STOP codon in the glomulin gene, kaposiform hemangioendothelioma (KHE), and a venous malformation with as of yet no known mutation in the TIE2/TEK gene (FIG. 31). A plasmid containing glomulin cDNA was used as a positive control, and water as negative control. All tissues showed an amplification product of the expected size of 561 or 503 bp, thus revealing that glomulin is expressed in all the studied tissues. As cultured smooth muscle cells express glomulin, and GVMs with glomulin mutations show altered differentiation of smooth muscle cells (replaced by glomus cells), glomulin is likely to be an important factor for smooth muscle development. As vascular smooth muscle cell phenotypic modulation ("synthetic" versus "contractile") has been reported during vascular development and disease states (such as in atherosclerotic plaque formation), glomulin may serve as a new target for altering such changes.

Control RT-PCR, using primers specific to glyceraldehyde phosphate dehydrogenase, and glucose-6-phosphate dehydrogenase demonstrated equal concentration of cDNA for every sample (results not shown).

Mouse Developmental Stage RT-PCR Analysis

Figure 37:
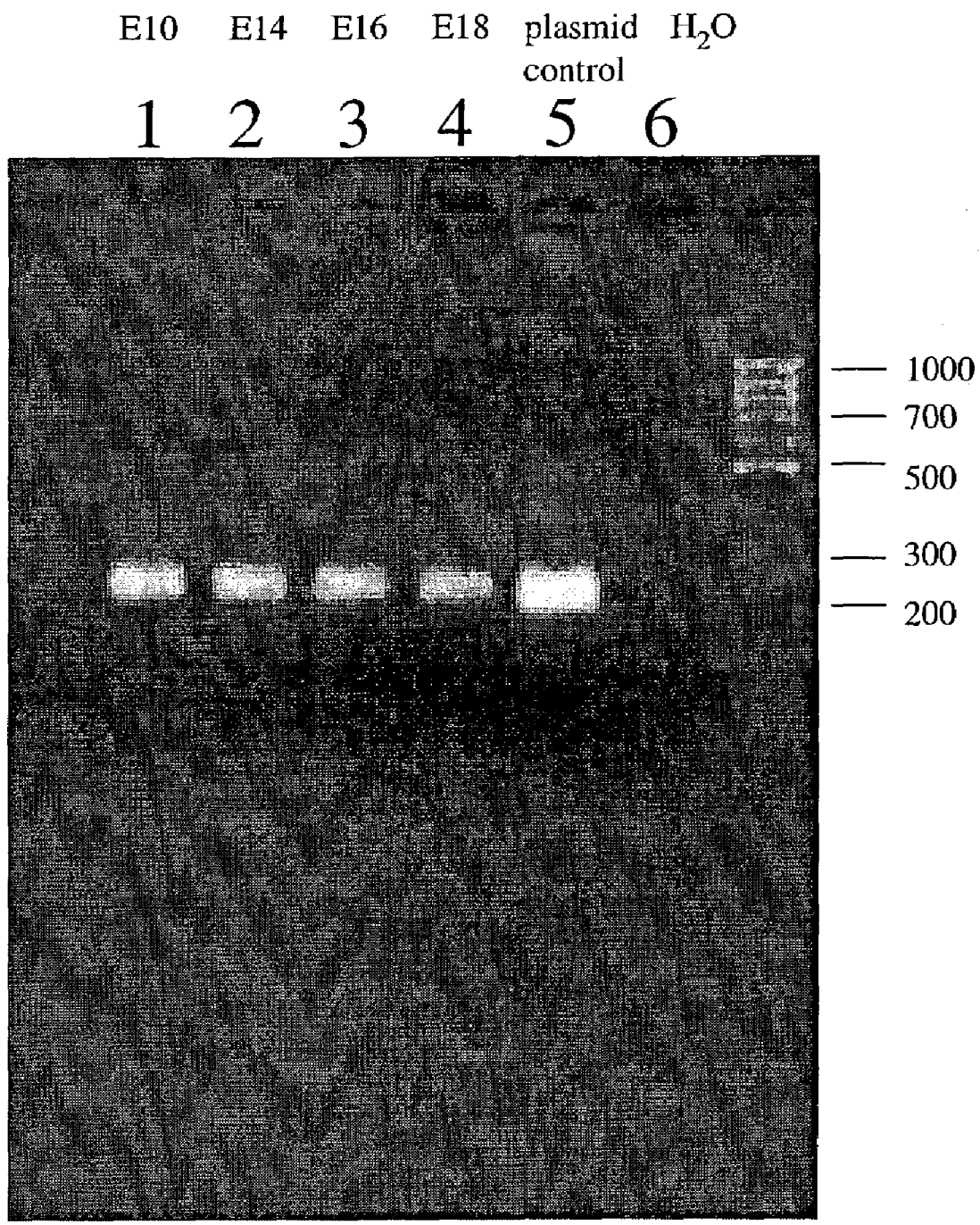

Glomulin expression was also studied during mouse development by RT-PCR analysis. Total RNAs were extracted from total murine embryos of 10, 14, 16 and 18 days postcoitum. cDNAs were created using the SUPERSCRIPT™ kit (Gibco-BRL) according to the protocol of the manufacturer. Primers used in the amplification were from exons 1 and 3, in the 5' end of the gene, amplifying a cDNA fragment of 196 base pairs. This fragment covers two exon-intron boundaries. All embryonic time points show an amplification product of the expected size of 196 by (FIG. 37). Thus, glomulin is expressed already during embryogenesis in the mouse, at least from embryonic day 10 until 18.

Polyclonal Antisera Against Human Glomulin Peptides

Two (#454 and 455) of the four polyclonal antisera created against the two synthesized peptides of glomulin (207 and 208) showed increases in titers on ELISA assays. Both of these antisera were induced with the peptide 208 from the C-terminal end of the glomulin polypeptide sequence. As the titer increase was the best for antiserum #455, this was mainly used in the subsequent assays (FIG. 33).

An estimate for working dilution for the purified IgG fraction was obtained by Western dot blots using the synthesized peptides in varying concentrations as template. Even at dilution 1:4500, the antiserum 455 gave specific results for the low antigen amounts of 10 ng (FIG. 34). All subsequent experiments were performed using 455 in 1:5000 dilution.

Figure 38:
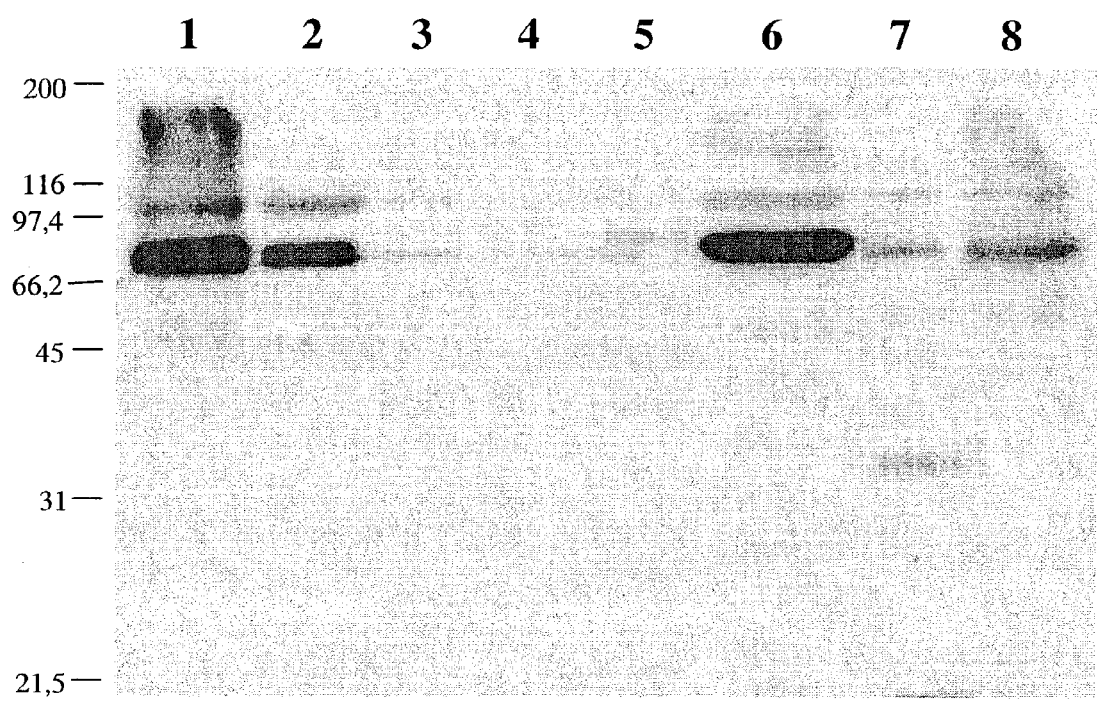
Figure 39:
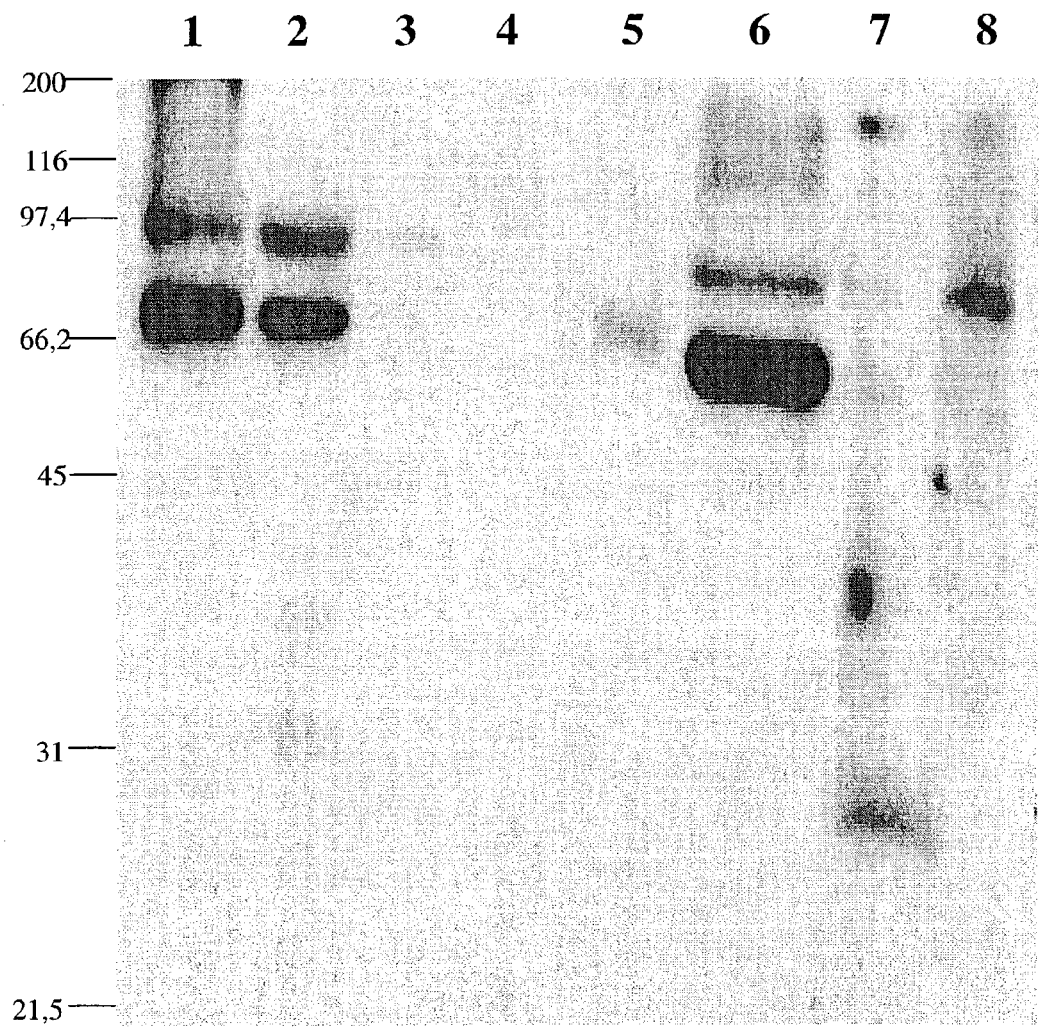
Figure 40:
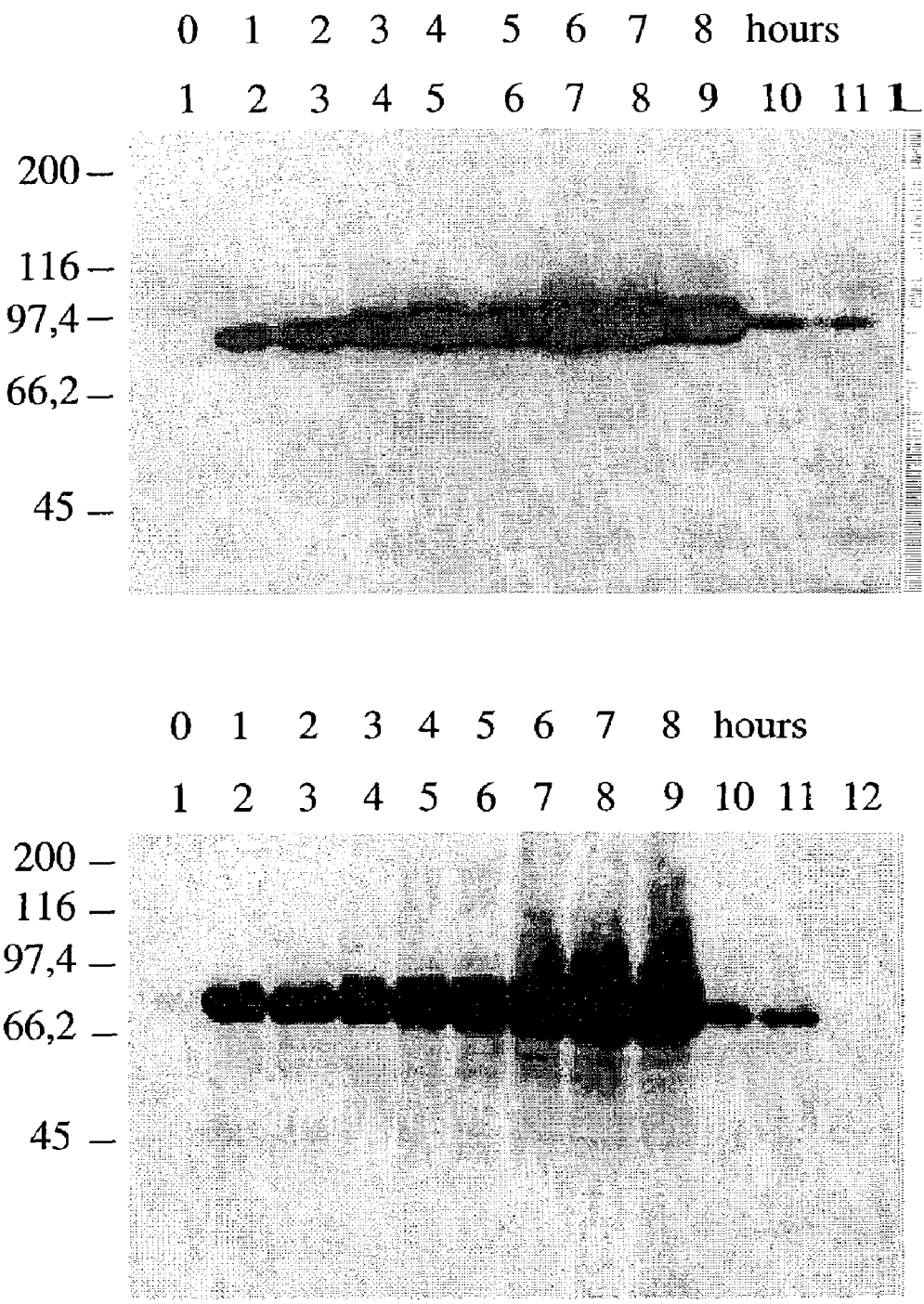

The decision to concentrate on 455 was further influenced by the observation that purified IgG fractions obtained from the other 3 antisera showed consistent cross hybridization to an assumed non-specific band at roughly 97 kDa (FIGS. 38-40).

Bacterial Expression Constructs, Expressions and Extractions

To study the glomulin protein in vitro, it was overexpressed in *E. coli* using pET-3a or pET-15b bacterial expression vectors (Invitrogen BV, The Netherlands) containing a T7 promoter (FIG. 35). These plasmids were transformed into *E. coli* strain BL21 (donated by the group of Emile Van Schaftingen, Brussels, Belgium) containing a native plasmid pLysS harbouring the gene encoding T7 lysosyme that causes the lysis of endogenous T7 RNA polymerase. By adding IPTG to the culture medium, the production of T7 RNA polymerase is increased to such an extent that T7 lysosyme can no longer lyse all the native T7 RNA polymerase. This resulting increased production of T7 RNA polymerase leads to increased expression of the downstream glomulin gene in pET-3a and 15b vector constructs.

The bacterial expressions were performed at LB medium and in M9 low salt medium and at 16° C., 22° C. and at 37° C., to identify the best expression conditions. LB at 22° C. gave the largest amount of protein expressed in the soluble fraction, and was thus chosen as the condition for further experiments.

The expressions made it possible to study the specificity of the created antisera to the protein created by both construct. The pET-15b "Histidine-tag" construct produces a protein corresponding to the open reading frame of glomulin plus a 6× histidine tag contained in a 20 amino acid hinge (MGSS-HHHHHH-SSGLVPRGSH-glomulin) (SEQ ID NO: 154), whereas the pET-3a "wild-type" construct produces a protein corresponding to the open reading frame of glomulin alone. The advantage of the pET-15b construct is that it is possible to screen the protein product by both the polyclonal antisera (452, 453, 454, or 455) and an antibody against histidine.

Expression Analysis by Western Blotting

The presence of glomulin protein in various human tissues and eukaryotic cell lines, as well as bacteria expressing the introduced glomulin constructs were tested by Western blot analysis. These tissues and cell extracts were analyzed with three of the four available antisera, 452, 453 and 455.

Western blots using the purified IgG fraction from the antiserum of 452 and 453 showed a band of 67 kDa in lanes with protein lysates from pET-15b transformed bacteria over-expressing glomulin. This corresponds to the expected size of glomulin with 6×HIS tag (FIGS. 38 and 39). All lanes were loaded with 7 µg of protein as calculated by the BCA-200 assay (Pierce).

Western blots using the purified IgG fraction from the antiserum 455 also showed a 67 kDa protein in lysates from the supernatant fraction of pET-15b transformed bacteria over-expressing glomulin. The concentration of this protein increased in conjunction with increasing growth periods (FIG. 40A). All lanes were loaded with 27 µg of protein as calculated by the BCA-200 assay (Pierce).

Western blot using anti-histidine tag antibody showed specific binding to a 67 kDa protein in lysates from the supernatant fraction of pET-15b transformed bacteria over-expressing glomulin, which increased in concentration in conjunction with increasing growth periods (FIG. 40B). This result confirmed the identity of the protein detected with the polyclonal antisera. All lanes were loaded with 54 µg of protein as calculated by the BCA-200 assay (Pierce).

Figure 41:
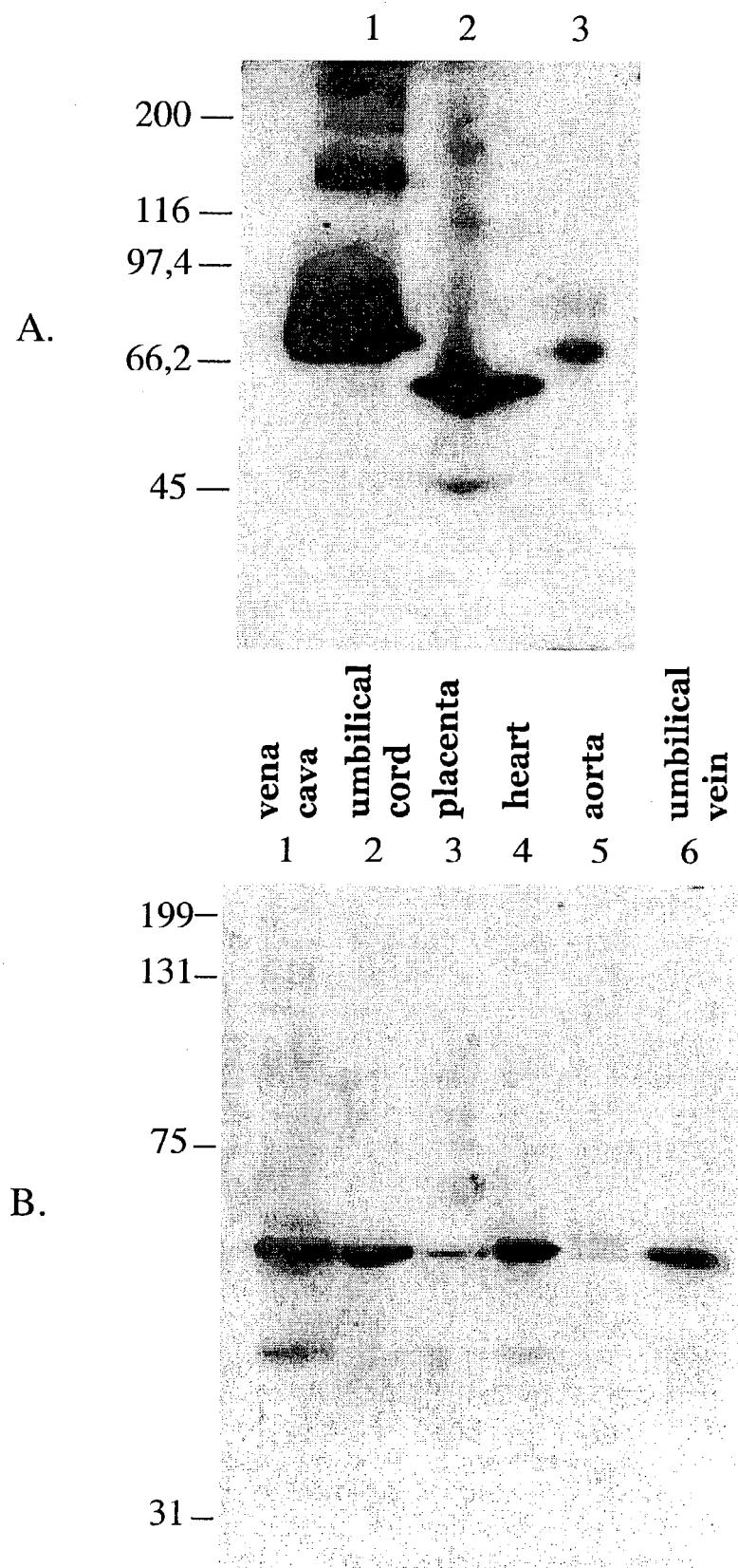

Western blots with purified 455 show a clear difference between the bacterially expressed, His-tagged, column purified 67 kDa pET-15b protein and the 65 kDa pET-3a protein; and the 58 kDa protein extracted from human tissues (FIG. 42 A). The 58 kDa glomulin protein was observed in vena cava, umbilical cord, placenta, heart, aorta, umbilical vein, renal artery, atrium, splenic artery, testicle, left ventricle, right ventricle, supra-renal vena cava, portal vein and inferior vena cava (FIGS. 41B and 42). Also apparent in FIG. 42B is an double band of about 58 and 60 kDa, observed only in aorta. All lanes were loaded with 60 µg of eukaryotic, and 12 µg of prokaryotic protein for A, 45 µg of protein for B, and 50 µg of protein for 43, as calculated by the BCA-200 assay (Pierce).

Interestingly, all these Western blot results revealed that the glomulin protein, although 67 kDa, as expected in the bacterial histidine-tagged expressions, and 65 kDa, as expected in the bacterial non-histidine tagged expression, only had the size of around 58 kDa in the human tissue extracts. This suggests that it undergoes either post-translational processing, such as proteolytic cleavage, or that in eukaryotic cells, a shorter protein is translated. As the Western blot analysis identified glomulin protein in vena cava, umbilical cord, placenta, heart, aorta, and umbilical vein, it is clear that it is not only present in veins, but in other vessels, too. Especially elevated quantities were observed in heart structures. In addition, veins seems to contain more glomulin than other vessels. Thus, glomulin may have a specific function in vein morphogenesis and/or maintenance.

REFERENCES

Allikmets, R., N. Singh, H. Sun, N. F. Shroyer, A. Hutchinson, A. Chidambaram, B. Gerrard, L. Baird, D. Stauffer, A. Peiffer, A. Rattner, P. Smallwood, Y. Li, K. L.

Anderson, R. A. Lewis, J. Nathans, M. Leppert, M. Dean, and J. R. Lupski. 1997. A photoreceptor cell-specific ATP-binding transporter gene (ABCR) is mutated in recessive Stargardt macular dystrophy. Nat Genet. 15: 236-246.

Boon, L. M., P. Brouillard, A. Irrthum, L. Karttunen, M. L. Warman, R. Rudolph, J. B. Mulliken, B. R. Olsen, and M. Vikkula. 1999. A gene for inherited cutaneous venous anomalies ("glomangiomas") localizes to chromosome 1p21-22. Am J Hum Genet. 65: 125-133.

Boon, L. M., J. B. Mulliken, M. Vikkula, H. Watkins, J. Seidman, B. R. Olsen, and M. L. Warman. 1994. Assignment of a locus for dominantly inherited venous malformations to chromosome 9p. Hum Mol Genet. 3: 1583-1587.

Brouillard, P., Olsen, B. R. & Vikkula, M. 2000 High resolution physical and transcript map of the locus for venous malformations with glomus cells (VMGLOM) on chromosome 1p21-22. Genomics 67, 96-101.

Calvert, J. T., T. J. Riney, C. D. Kontos, E. H. Cha, V. G. Prieto, C. R. Shea, J. N. Berg, N. C. Nevin, S. A. Simpson, K. A. Pasyk, M. C. Speer, K. G. Peters, and D. A. Marchuk. 1999. Allelic and locus heterogeneity in inherited venous malformations. Hum Mol Genet. 8: 1279-1289.

Gallione, C. J., K. A. Pasyk, L. M. Boon, F. Lennon, D. W. Johnson, E. A. Helmbold, D. S. Markel, M. Vikkula, J. B. Mulliken, M. L. Warman, et al. 1995. A gene for familial venous malformations maps to chromosome 9p in a second large kindred. J Med Genet. 32: 197-199.

Ioannou, P. A. and P. J. de Jong. 1996. Construction of bacterial artificial chromosome libraries using the modified P1 (PAC) system. In Current Protocols in Human Genetics (eds. Dracopoli et al.) Unit 5.15. John Wiley and Sons, NY.

Irrthum, A. et al. Linkage disequilibrium narrows locus for venous malformation with glomus cells (VMGLOM) to a single 1.48 MBP YAC. Eur J Hum Genet, in press.

Klockars, T., M. Savukoski, J. Isosomppi, M. Laan, I. Jarvela, K. Petrukhin, A. Palotie, and L. Peltonen. 1996. Efficient construction of a physical map by fiber-FISH of the CLN5 region: refined assignment and long-range contig covering the critical region on 13q22. Genomics 35: 71-78.

Lathrop, G. M., Lalouel, J. M., Julier, C., Ott, J. 1984. Strategies for multilocus linkage in humans. Proc. Natl. Acad. Sci. USA 81: 3443-3446.

Lee, W. C., B. Balsara, Z. Liu, S. C. Jhanwar, and J. R. Testa. 1996. Loss of heterozygosity analysis defines a critical region in chromosome 1p22 commonly deleted in human malignant mesothelioma. Cancer Res 56: 4297-4301.

Paavola, P., K. Avela, N. Horelli-Kuitunen, M. Barlund, A. Kallioniemi, N. Idanheimo, M. Kyttala, A. de la Chapelle, A. Palotie, A. E. Lehesjoki, and L. Peltonen. 1999. High-resolution physical and genetic mapping of the critical region for Meckel syndrome and Mulibrey Nanism on chromosome 17q22-q23. Genome Res 9: 267-276.

Roberts, T., O. Chemova, and J. K. Cowell. 1998. NB4S, a member of the TBC1 domain family of genes, is truncated as a result of a constitutional t(1;10)(p22;q21) chromosome translocation in a patient with stage 4S neuroblastoma. Hum Mol Genet. 7: 1169-1178.

Roberts, T. and J. K. Cowell. 1997. Cloning of the human Gfi-1 gene and its mapping to chromosome region 1p22. Oncogene 14: 1003-1005.

Sheffield, V. C., M. E. Pierpont, D. Nishimura, J. S. Beck, T. L. Burns, M. A. Berg, E. M. Stone, S. R. Patil, and R. M. Lauer. 1997. Identification of a complex congenital heart defect susceptibility locus by using DNA pooling and shared segment analysis. Hum Mol Genet. 6: 117-121.

Vikkula, M., L. M. Boon, K. L. Carraway, 3rd, J. T. Calvert, A. J. Diamonti, B. Goumnerov, K. A. Pasyk, D. A. Marchuk, M. L. Warman, L. C. Cantley, J. B. Mulliken, and B. R. Olsen. 1996. Vascular dysmorphogenesis caused by an activating mutation in the receptor tyrosine kinase TIE2. Cell 87: 1181-1190.

Vikkula, M., L. M. Boon, J. B. Mulliken, and B. R. Olsen. 1998. Molecular basis of vascular anomalies. Trends in Cardiovascular Medicine 8: 281-292.

Barany, F (1991). Genetic disease detection and DNA amplification using cloned thermostable ligase. Proc. Natl. Acad. Sci. USA, 88, 189-193.

Compton, J (1991). Nucleic acid sequence-based amplification. Nature, 350, 91-92.

Duck, P. (1990) Probe amplifier system based on chimeric cycling oligonucleotides. *Biotechniques,* 9, 142-147.

Guatelli, J C; Whitfield, K M; Kwoh, D Y; Barringer, K J, Richman, D D; Gingeras, T R (1990). Isothermal, in vitro amplification of nucleic acids by a multienzyme reaction modeled after retroviral replication. *Proc. Natl. Acad. Sci. USA,* 87, 1874-1878.

Kwoh, D; Davis, G; Whitfield, K; Chappelle, H; Dimichele, L; Gingeras, T. (1989). Transcription-based amplification system and detection of amplified human immunodeficiency virus type 1 with a bead-based sandwich hybridization format. *Proc. Natl. Acad. Sci. USA,* 86, 1173-1177.

Kwok, S., Kellog, D., McKinney, N., Spasic, D., Goda, L., Levenson, C. and Sinisky, J. (1990). Effects of primer-template mismatches on the polymerase chain reaction: Human immunodeficiency views type 1 model studies. Nucl. Acids Res., 18: 999.

Landgren, U; Kaiser, R; Sanders, J; Hood, L. (1988). A ligase-mediated gene detection technique. *Science* 241, 1077-1080

Lizardi, P; Guerra, C; Lomeli, H; Tussie-Luna, I; Kramer, F (1988). Exponential amplification of recombinant RNA hybridization probes. *Bio/Technology* 6, 1197-1202.

Lomeli, H; Tyagi, S; Printchard, C; Lisardi, P; Kramer, F (1989). Quantitative assays based on the use of replicatable hybridization probes. *Clin. Chem.,* 35, 1826-1831.

Walker, G; Little, M; Nadeau, J; Shank, D (1992). Isothermal in vitro amplification of DNA by a restriction enzyme/DNA polymerase system. *Proc. Natl. Acad. Sci. USA,* 89, 392-396.

Wu, D; Wallace, B. (1989). The ligation amplification reaction (LAR)—amplification of specific DNA sequences using sequential rounds of template-dependent ligation. *Genomics,* 4, 560-569.

The invention claimed is:

1. An isolated nucleic acid molecule selected from the group consisting of:
   (a) a nucleic acid molecule encoding a human polypeptide having the sequence of SEQ ID NO 2,
   (b) a nucleic acid molecule encoding a human polypeptide having the amino acid sequence of amino acid position 405 to 594 in SEQ ID NO 2,
   (c) a nucleic acid molecule encoding a human polypeptide consisting of the amino acid sequence of SEQ ID NO 4,
   (d) a nucleic acid molecule having the nucleotide sequence of SEQ ID NO 1 or 3, and
   (e) a nucleic acid molecule consisting of the 85 bp nucleotide sequence of position 1253 to 1337 in SEQ ID NO 1,
   (f) a modified SEQ ID NO: 1 having a mutation selected from the group consisting of deletion of 2 nucleotides, positions 31-32; insertion of a G, position 107; substitution of a C by an A, position 108; deletion of 5 nucleotides, positions 157-161; insertion of an A, position 423; deletion of 4 nucleotides, positions 554+556–558; deletion of the 5th nucleotide (G) in the splice-site consensus in intron 5 (5' end of intron); deletion of 4 nucleotides, positions 842-845; deletion of 3 nucleotides, positions 1179-1181; deletion of a T, position 1355; deletion of 4 nucleotides, positions 1470-1473; substitution of a C by a G, position 1547; and deletion of GT, positions 1711-1712, wherein numbering of said mutations refers to the nucleotide numbering as used in SEQ ID NO: 1, where +1 is the A of the ATG codon at positions 39 to 41, and
   (g) a nucleic acid molecule comprising the nucleotide sequence set forth by SEQ ID NO: 143 with a deletion of the TA at position 3800-3801 and the full length complement thereof.

2. A molecule comprising the isolated nucleic acid according to claim 1 wherein said molecule is incorporated into a diagnostic kit.

3. A composition comprising the molecule according to claim 2.

4. A method for detecting the presence of mutations of claim 1 associated with venous malformations of glomus cells in a nucleic acid sequence comprising obtaining a sample containing nucleic acids, and determining the presence of mutations in a nucleic acid sequence wherein the nucleic acid sequence is a nucleic acid sequence according to claim 1.

5. An isolated DNA construct comprising a nucleic acid consisting of the nucleic acid according to claim 1.

6. An isolated host cell transformed in vitro with a DNA construct according to claim 5.

* * * * *

UNITED STATES PATENT AND TRADEMARK OFFICE
CERTIFICATE OF CORRECTION

PATENT NO. : 7,700,748 B2  
APPLICATION NO. : 10/204254  
DATED : April 20, 2010  
INVENTOR(S) : Miikka Vikkula It is certified that error appears in the above-identified patent and that said Letters Patent is hereby corrected as shown below:

Column 4, Line 55, "phopho-triester method." should be changed to --phospho-triester method.--

Column 6, Line 67, "countourclamped" should be changed to --contourclamped--

Column 7, Line 4, "polymorhism (SSCP)" should be changed to --polymorphism (SSCP)--

Column 10, Line 12, "This polyclona antisera" should be changed to --This polyclonal antisera--

Column 15, Line 9, "additional 85 by exon" should be changed to --additional 85 bp exon--

Column 15, Line 16, "a 482 by 5'-probe" should be changed to --a 482 bp 5'-probe--

Column 16, Line 15, "500 by at the" should be changed to --500 bp at the--

Column 16, Line 31, "known 5 by mutation" should be changed to --known 5 bp mutation--

Column 16, Line 34, "know mutation in" should be changed to --known mutation in--

Column 19, Line 47, "exept for families Ba" should be changed to --except for families Ba--

Column 20, Line 25, "10406 and" should be changed to --104o6 and--

Column 21, Line 7, "µg/ml ampicilin." should be changed to --µg/ml ampicillin.--

Column 22, Line 19, "between 200-350 by" should be changed to --between 200-350 bp--

Column 22, Line 59, "and a 482 by" should be changed to --and a 482 bp--

Column 23, Line 22, "known 5 by mutation" should be changed to --known 5 bp mutation--

Column 23, Line 34, "regions of 561 by" should be changed to --regions of 561 bp--

Column 24, Line 28, "is located 894 by" should be changed to --is located 894 bp--

Column 24, Line 62, "tranformed into *E. coli*" should be changed to --transformed into *E. coli*--

Column 26, Line 21, "on nitrosellulose" should be changed to --on nitrocellulose--

Column 26, Line 31, "to nitrosellulose" should be changed to --to nitrocellulose--

Column 27, Line 24, "innoculated with" should be changed to --inoculated with--

Signed and Sealed this

Seventh Day of September, 2010

David J. Kappos  
*Director of the United States Patent and Trademark Office*

CERTIFICATE OF CORRECTION (continued)
U.S. Pat. No. 7,700,748 B2

Column 30, Line 10, "the possiblility that" should be changed to --the possibility that--

Column 30, Line 51, "to be indentified." should be changed to --to be identified.--

Column 32, Line 45, "missing 85 by at" should be changed to --missing 85 bp at--

Column 32, Line 54, "81 by before ATG." should be changed to --81 bp before ATG.--

Column 33, Line 6, "31 by upstream" should be changed to --31 bp upstream--

Column 33, Line 7, "located 31 by" should be changed to --located 31 bp--

Column 33, Line 8, "but rather 925 by" should be changed to --but rather 925 bp--

Column 33, Line 10, "at least 57 by" should be changed to --at least 57 bp--

Column 33, Line 65, "238 by exon" should be changed to --238 bp exon--

Column 34, Line 30, "(altogether 2.5 kbp)" should be changed to --(altogether 2,5 kbp)--

Column 34, Line 32, "between 1301 by to" should be changed to --between 1301 bp to--

Column 34, Line 42, "such experimenst were" should be changed to --such experiments were--

Column 35, Line 35, "a known 5 by" should be changed to --a known 5 bp--

Column 36, Line 1, "size of a 196 by" should be changed to --size of a 196 bp--

Column 36, Line 32, "T7 lysosyme that" should be changed to --T7 lysozyme that--

Column 38, Line 40, "O. Chemova," should be changed to --O. Chernova,--